United States Patent
Afroze et al.

(10) Patent No.: US 10,202,389 B2
(45) Date of Patent: Feb. 12, 2019

(54) PYRAZOLOPYRIMIDINYL INHIBITORS OF UBIQUITIN-ACTIVATING ENZYME

(71) Applicant: Millennium Pharmaceuticals, Inc., Cambridge, MA (US)

(72) Inventors: Roushan Afroze, Lexington, MA (US); Indu T. Bharathan, Cambridge, MA (US); Jeffrey P. Ciavarri, Reading, MA (US); Paul E. Fleming, Natick, MA (US); Jeffrey L. Gaulin, Londonderry, NH (US); Mario Girard, Waltham, MA (US); Steven P. Langston, N. Andover, MA (US); Francois Soucy, Stoneham, MA (US); Tzu-Tshin Wong, Belmont, MA (US); Yingchun Ye, Belmont, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/699,818

(22) Filed: Sep. 8, 2017

(65) Prior Publication Data

US 2017/0369499 A1    Dec. 28, 2017

Related U.S. Application Data

(62) Division of application No. 15/488,800, filed on Apr. 17, 2017, now Pat. No. 9,796,725, which is a division of application No. 15/048,007, filed on Feb. 19, 2016, now Pat. No. 9,663,525, which is a division of application No. 13/767,314, filed on Feb. 14, 2013, now Pat. No. 9,290,500.

(60) Provisional application No. 61/600,070, filed on Feb. 17, 2012.

(51) Int. Cl.
C07D 487/04    (2006.01)

(52) U.S. Cl.
CPC ................. C07D 487/04 (2013.01)

(58) Field of Classification Search
None
See application file for complete search history.

(56) References Cited

U.S. PATENT DOCUMENTS

| | | |
|---|---|---|
| 7,078,525 B2 | 7/2006 | Guzi et al. |
| 7,196,092 B2 | 3/2007 | Guzi et al. |
| 7,563,798 B2 | 7/2009 | Guzi et al. |
| 7,642,266 B2 | 1/2010 | Guzi et al. |
| 7,951,810 B2 | 5/2011 | Critchley et al. |
| 8,008,307 B2 | 8/2011 | Claiborne et al. |
| 8,207,177 B2 | 6/2012 | Langston et al. |
| 8,481,550 B2 | 7/2013 | Claiborne et al. |
| 8,809,356 B2 | 8/2014 | McCarron et al. |
| 8,901,136 B2 | 12/2014 | Critchley et al. |
| 9,150,525 B2 | 10/2015 | Claiborne et al. |
| 9,290,500 B2 | 3/2016 | Afroze et al. |
| 9,663,525 B2 | 5/2017 | Afroze et al. |
| 2004/0102451 A1 | 5/2004 | Guzi et al. |
| 2007/0082901 A1 | 4/2007 | Guzi et al. |
| 2007/0191293 A1 | 8/2007 | Langston et al. |
| 2008/0051404 A1 | 2/2008 | Claiborne et al. |
| 2011/0021544 A1 | 1/2011 | Armitage et al. |
| 2012/0077814 A1 | 3/2012 | Wang et al. |
| 2012/0258927 A1 | 10/2012 | Langston et al. |
| 2013/0217682 A1 | 8/2013 | Afroze et al. |
| 2015/0011572 A1 | 1/2015 | McCarron et al. |
| 2015/0210700 A1 | 7/2015 | Amidon et al. |

(Continued)

FOREIGN PATENT DOCUMENTS

| | | |
|---|---|---|
| JP | 2005008581 A | 1/2005 |
| WO | WO 2003/073989 A2 | 9/2003 |

(Continued)

OTHER PUBLICATIONS

Brownell et al., "Substrate-Assisted Inhibition of Ubiquitin-Like Protein-Activating Enzymes: The NEDD8 E1 Inhibitor MLN4924 Forms A NEDD8-AMP Mimetic In Situ," *Mol. Cell* 37:102-111, Elsevier, The Netherlands (2010).

(Continued)

*Primary Examiner* — Alicia L Otton
(74) *Attorney, Agent, or Firm* — Sterne, Kessler, Goldstein & Fox P.L.L.C.

(57) ABSTRACT

Disclosed are chemical entities that inhibit ubiquitin-activating enzyme (UAE), each of which is a compound of Formula I:

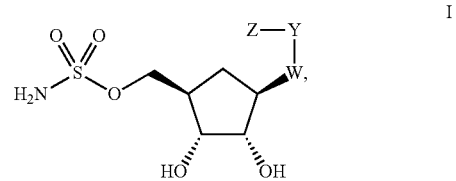

or a pharmaceutically acceptable salt thereof, wherein Y is

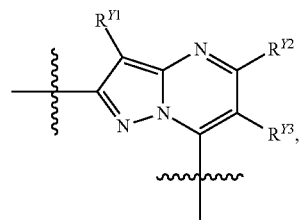

and W, Z, $X^Y$, $R^{Y1}$, $R^{Y2}$ and $R^{Y3}$ are defined herein; pharmaceutical compositions comprising the chemical entities; and methods of using the chemical entities. These chemical entities are useful for treating disorders, particularly cell proliferation disorders, including cancers.

7 Claims, 11 Drawing Sheets

(56) References Cited

U.S. PATENT DOCUMENTS

| | | |
|---|---|---|
| 2016/0009744 A1 | 1/2016 | Duffey et al. |
| 2016/0039761 A1 | 2/2016 | Claiborne et al. |
| 2017/0217968 A1 | 8/2017 | Afroze et al. |

FOREIGN PATENT DOCUMENTS

| | | |
|---|---|---|
| WO | WO 2004/022559 A1 | 3/2004 |
| WO | WO 2004/026229 A2 | 4/2004 |
| WO | WO 2004/087707 A1 | 10/2004 |
| WO | WO 2005/037845 A1 | 4/2005 |
| WO | WO 2006/002284 A1 | 1/2006 |
| WO | WO 2007/044401 A2 | 4/2007 |
| WO | WO 2007/092213 A2 | 8/2007 |
| WO | WO 2008/154642 A2 | 12/2008 |
| WO | WO 2009/082691 A1 | 7/2009 |
| WO | WO 2010/086040 A1 | 8/2010 |
| WO | WO 2010/088518 A2 | 8/2010 |
| WO | WO 2010/132110 A1 | 11/2010 |
| WO | WO 2011/109059 A1 | 9/2011 |
| WO | WO 2013/123169 A1 | 8/2013 |
| WO | WO 2015/002994 A2 | 1/2015 |

OTHER PUBLICATIONS

International Search Report and Written Opinion PCT/US07/017463 dated Nov. 23, 2007 corresponding to U.S. Appl. No. 11/890,338.

Notice of Allowability dated Apr. 3, 2015 in U.S. Appl. No. 13/767,314.

Notice of Allowability dated Jul. 13, 2015, in U.S. Appl. No. 13/767,314.

Notice of Allowability dated Nov. 16, 2015, in U.S. Appl. No. 13/767,314.

PCT Notification of Transmittal of the International Search Report and the Written Opinion of the International Searching Authority, or the Declaration for International Application No. PCT/US2013/026113 dated Apr. 11, 2013.

Restriction Requirement dated Dec. 19, 2014, in U.S. Appl. No. 13/767,314.

Supplementary European Search Report of European Application No. EP 13748707, dated Jun. 9, 2015.

Pearce et al., "Failure modes in anticancer drug discovery and development, Cancer Drug Design and Discovery," Edited by Stephen Neidle, Chapter 18, pp. 424-435, Elsevier, The Netherlands, (2008).

Gura, "Systems for Identifying New Drugs Are Often Faulty," Cancer Models, *Science* 278(5340): 1041-1042, AAAS, The United States (Nov. 1997).

Johnson et al. "Relationships between drug activity in NCI preclinical in vitro and in vivo models and early clinical trials," British Journal of Cancer 84(10):1424-1431, Cancer Research Campaign, England (2001).

Simone, Oncology: Introduction, Cecil Textbook of Medicine, 20th Edition, vol. 1, pp. 1004-1010, W.B. Saunders Company, United states (1996).

Xu et al.. "The ubiquitin-activating enzyme E1 as a therapeutic target for the treatment of leukemia and multiple myeloma," *Blood* 115(11): 2251-2259, The American Society of Hematology, United States (Mar. 2010).

Extended European Search Report for EP Application No. 16205139.5, Munich, Germany, dated Mar. 10, 2017, 9 pages.

PYRAZOLOPYRIMIDINYL INHIBITORS OF UBIQUITIN-ACTIVATING ENZYME

This application claims the benefit of U.S. patent application Ser. No. 15/488,800, filed Apr. 17, 2017, U.S. patent application Ser. No. 15/048,007, filed Feb. 19, 2016, U.S. patent application Ser. No. 13/767,314, filed Feb. 14, 2013, and U.S. Provisional Patent Application No. 61/600,070, filed on Feb. 17, 2012, all of which are hereby incorporated by reference in their entirety.

BACKGROUND

Ubiquitin is a small 76-amino acid protein that is the founding member of a family of posttranslational modifiers known as the ubiquitin-like proteins (Ubls). Ubls play key roles in controlling many biological processes including cell division, cell signaling and the immune response. Ubls are small proteins that are covalently attached to a lysine on a target protein via an isopeptide linkage with a C-terminal glycine of the ubl. The Ubl molecule alters the molecular surface of the target protein and can affect such properties as protein-protein interactions, enzymatic activity, stability and cellular localization of the target.

There are 8 known human Ubl activating enzymes (known as E1s) (Schulman, B. A., and J. W. Harper, 2009, Ubiquitin-like protein activation by E1 enzymes: the apex for downstream signalling pathways, *Nat Rev Mol Cell Biol* 10:319-331). Ubiquitin and other ubls are activated by a specific E1 enzyme which catalyzes the formation of an acyl-adenylate intermediate with the C-terminal glycine of the ubl. The activated ubl molecule is then transferred to the catalytic cysteine residue within the E1 enzyme through formation of a thioester bond intermediate. The E1-ubl intermediate and an E2 interact, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein. Eukaryotic cells possess ~35 ubiquitin E2 enzymes and >500 ubiquitin E3 enzymes. The E3 enzymes are the specificity factors of the ubiquitin pathway which mediate the selective targeting of specific cellular substrate proteins (Deshaies, R. J., and C. A. Joazeiro, 2009, RING domain E3 ubiquitin ligases, *Annu Rev Biochem* 78:399-434; Lipkowitz, S., and A. M. Weissman, 2011, RINGs of good and evil: RING finger ubiquitin ligases at the crossroads of tumour suppression and oncogenesis, *Nat Rev Cancer* 11:629-643; Rotin, D., and S. Kumar, 2009, Physiological functions of the HECT family of ubiquitin ligases, *Nat Rev Mol Cell Biol* 10:398-409).

Two E1 enzymes have been identified for ubiquitin, UAE (ubiquitin-activating enzyme) and UBA6 (Jin, J., et al., 2007, Dual E1 activation systems for ubiquitin differentially regulate E2 enzyme charging, *Nature* 447:1135-1138). UAE is the E1 responsible for the majority of ubiquitin flux within the cell. UAE is capable of charging each of the approximately ~35 E2 enzymes with the exception of Use1, which is the only E2 known to exclusively work with UBA6 (Jin et al., 2007). Inhibition of UAE is sufficient to dramatically impair the great majority of ubiquitin-dependent cellular processes (Ciechanover, A., et al., 1984, Ubiquitin dependence of selective protein degradation demonstrated in the mammalian cell cycle mutant ts85, *Cell* 37:57-66; Finley, D., A. et al., 1984, Thermolability of ubiquitin-activating enzyme from the mammalian cell cycle mutant ts85, *Cell* 37:43-55).

The cellular signals generated by ubiquitin are diverse. Ubiquitin can be attached to substrates as a single entity or as polyubiquitin polymers generated through isopeptide linkages between the C-terminus of one ubiquitin and one of the many lysines on a second ubiquitin. These varied modifications are translated into a variety of cellular signals. For example, conjugation of a lysine 48-linked polyubiquitin chain to a substrate protein is predominantly associated with targeting the protein for removal by the 26S proteasome. A single ubiquitin modification, or monoubiquination, typically affects protein localization and/or function. For example, monoubiquitination modulates the function of Histones 2a and 2b (Chandrasekharan, M. B., et al., 2010, Histone H2B ubiquitination and beyond: Regulation of nucleosome stability, chromatin dynamics and the trans-histone H3 methylation, *Epigenetics* 5:460-468), controls the nucleocytoplasmic shuttling of PTEN (Trotman, L. C., et al., 2007, Ubiquitination regulates PTEN nuclear import and tumor suppression, *Cell* 128:141-156), drives localization of the FANCD2 protein to sites of DNA damage (Gregory, R. C., et al., 2003, Regulation of the Fanconi anemia pathway by monoubiquitination, *Semin Cancer Biol* 13:77-82) and promotes the internalization and endosomal/lysosomal turnover of some cell surface receptors like EGFR (Mosesson, Y., and Y. Yarden, 2006, Monoubiquitylation: a recurrent theme in membrane protein transport. *Isr Med Assoc J* 8:233-237). Other forms of polyubiquitination include lysine 11, 29 and 63 chains which play various roles in the cell including the cell cycle, DNA repair and autophagy (Behrends, C., and J. W. Harper, 2011, Constructing and decoding unconventional ubiquitin chains, *Nat Struct Mol Biol* 18:520-528; Bennett, E. J., and J. W. Harper, 2008, DNA damage: ubiquitin marks the spot, *Nat Struct Mol Biol* 15:20-22; Komander, D., 2009, The emerging complexity of protein ubiquitination, *Biochem Soc Trans* 37:937-953).

UAE-initiated ubiquitin conjugation plays an important role in protein homeostasis, cell surface receptor trafficking, transcription factor turnover and cell cycle progression. Many of these processes are important for cancer cell survival and it is believed that tumor cells may have increased sensitivity to UAE inhibition as a result of their rapid growth rate, increased metabolic demands and oncogene fueled protein stress. Disruption of protein homeostasis is a validated therapeutic approach for the treatment of cancer. VELCADE® (bortezomib), disrupts cellular protein homeostasis and is approved for the treatment of multiple myeloma and mantle cell lymphoma. MLN4924, an E1 inhibitor of the Nedd8-activating enzyme (NAE) is currently in clinical oncology trials (Soucy, T. A., et al., 2009, An inhibitor of NEDD8-activating enzyme as a new approach to treat cancer, *Nature* 458:732-736; Soucy, T. A., et al., 2009, Targeting NEDD8-activated cullin-RING ligases for the treatment of cancer, *Clin Cancer Res* 15:3912-3916) and numerous other targets within the ubiquitin/protein homeostasis arena are of interest for oncology (Nalepa, G., et al., 2006, Drug discovery in the ubiquitin-proteasome system, *Nat Rev Drug Discov* 5:596-613). Preclinical studies with PYZD-4409, a UAE inhibitor, showed that it induced cell death in both leukemia and myeloma cell lines and demonstrated anti-tumor activity in a mouse acute myeloid leukemia (AML model). (Xu, W. G., et al., 2010, The ubiquitin-activating enzyme E1 as a therapeutic target for the treatment of leukemia and multiple myeloma, *Blood,* 115: 2251-59). Thus, UAE represents a novel protein homeostasis target opportunity for the treatment of cancer.

It is believed that UAE inhibitors would also be applicable for the treatment of other diseases and conditions outside of oncology due to the vast role of ubiquitin in cellular process; for example, proteasome inhibitors, which like UAE inhibitors alter cellular protein homeostasis, show promise for the treatment of antibody mediated transplant rejection (Woodle, E. S., et al., 2011, Proteasome inhibitor treatment of antibody-mediated allograft rejection, *Curr Opin Organ Transplant* 16:434-438), ischemic brain injury, infection, and autoimmune disorders (Kisselev, A. F., et al., 2012, Proteasome inhibitors: an expanding army attacking a unique target, *Chem Biol* 19:99-115). Ubiquitin-dependent signaling and degradation are important for the activation of pro-inflammatory pathways such as the NF-kB pathway implicating UAE inhibitors as potential anti-inflammatory agents Wertz, I. E., and Dixit, V. M., 2010, Signaling to NF-kappaB: regulation by ubiquitination, *Cold Spring Harb Perspect Biol*, 2:a003350).

SUMMARY

In one aspect, the invention relates to chemical entities, each of which is a compound of Formula I:

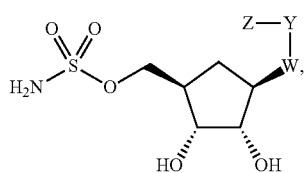

or a pharmaceutically acceptable salt thereof, wherein W, Y and Z are defined as below.

In one aspect, the invention relates to compositions comprising one or more of the chemical entities and one or more pharmaceutically acceptable carriers.

In one aspect, the invention relates to methods of treating cancer comprising administering to a patient in need of such treatment one or more of the chemical entities.

DESCRIPTION

Definitions

Figure 1:
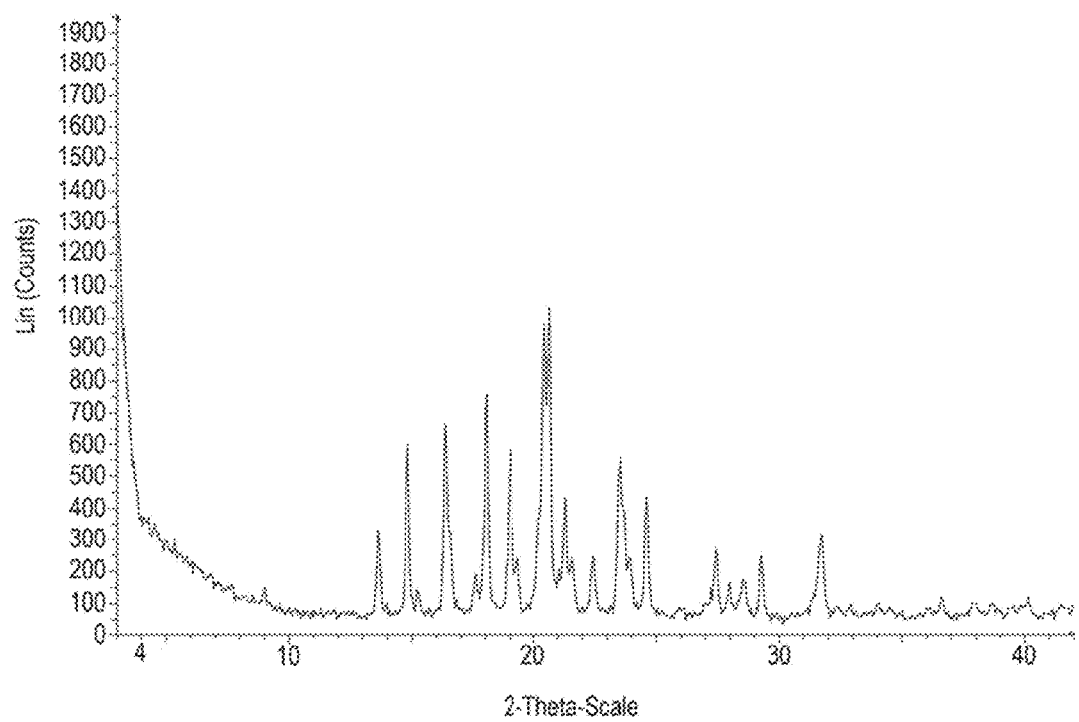
FIG. 1 shows an x-ray powder diffraction (XRPD) pattern for crystalline Form 1 anhydrous (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.

Unless otherwise specified, as used herein, alone or as part of another group, "halo" or "halogen" refers to fluoro, chloro, bromo or iodo.

Unless otherwise specified, as used herein, alone or as part of another group, "alkyl" refers to a straight-chain or branched saturated hydrocarbyl group having from 1 to 8 carbon atoms. In some embodiments, an alkyl group can have from 1 to 6 carbon atoms. In some embodiments, an alkyl group can have from 1 to 4 carbon atoms. In some embodiments, an alkyl group can have from 1 to 3 carbon atoms. Examples of $C_{1-3}$ alkyl groups include methyl, ethyl, propyl and isopropyl. Examples of $C_{1-4}$ alkyl groups include the aforementioned $C_{1-3}$ alkyl groups as well as butyl, isobutyl, sec-butyl and tert-butyl. Examples of $C_{1-6}$ alkyl groups include the aforementioned $C_{1-4}$ alkyl groups as well as pentyl, isopentyl, neopentyl, hexyl and the like. Additional examples of alkyl groups include heptyl, octyl and the like.

Unless otherwise specified, as used herein, alone or as part of another group, "alkenyl" refers to a straight-chain or branched hydrocarbyl group having from 2 to 8 carbon atoms and one or more carbon-carbon double bonds. In some embodiments, an alkenyl group can have from 2 to 6 carbon atoms. In some embodiments, an alkenyl group can have from 2 to 4 carbon atoms. The one or more carbon-carbon double bonds can be internal (such as in 2-butenyl) or terminal (such as in 1-butenyl). Examples of $C_{2-4}$ alkenyl groups include ethenyl, 1-propenyl, 2-propenyl, 1-butenyl, 2-butenyl, butadienyl and the like. Examples of $C_{2-6}$ alkenyl groups include the aforementioned $C_{2-4}$ alkenyl groups as well as pentenyl, pentadienyl, hexenyl and the like. Additional examples of alkenyl include heptenyl, octenyl, octatrienyl and the like.

Unless otherwise specified, as used herein, alone or as part of another group, "alkynyl" refers to a straight-chain or branched hydrocarbyl group having from 2 to 8 carbon atoms and one or more carbon-carbon triple bonds. In some embodiments, an alkynyl group can have from 2 to 6 carbon atoms. In some embodiments, an alkynyl group can have from 2 to 4 carbon atoms. The one or more carbon-carbon triple bonds can be internal (such as in 2-butynyl) or terminal (such as in 1-butynyl). Examples of $C_{2-4}$ alkynyl groups include ethynyl, propyn-1-yl, propyn-3-yl, 1-butyn-1-yl, 1-butyn-4-yl, 2-butyn-1-yl and the like. Examples of $C_{2-6}$ alkenyl groups include the aforementioned $C_{2-4}$ alkynyl groups as well as pentynyl, hexynyl and the like. Additional examples of alkynyl include heptynyl, octynyl and the like.

Unless otherwise specified, as used herein, alone or as part of another group, "aliphatic" refers to alkyl, alkenyl and alkynyl groups as defined above. For example, if a moiety can be substituted with "$C_{1-6}$ aliphatic", it can be substituted with $C_{1-6}$ alkyl, $C_{2-6}$ alkenyl or $C_{2-6}$ alkynyl.

Unless otherwise specified, each instance of "optionally substituted" alkyl, alkenyl or alkynyl (collectively, "optionally substituted" aliphatic) is independently unsubstituted or substituted with 1-3, 1-2 or 1 substituent(s):

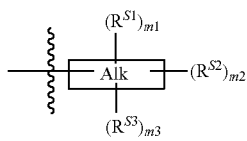

wherein

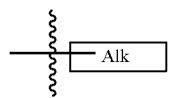

represents the alkyl, alkenyl or alkynyl group, respectively,
and
each of m1, m2 and m3 is independently 0 (i.e., $R^{S[1,2,3]}$ is —H) or 1.

In some embodiments, m1+m2+m3≤2. In some embodiments, m1+m2+m3≤1.

Unless otherwise specified, as used herein, alone or as part of another group, "alkylene" refers to a diradical of a straight-chain or branched saturated hydrocarbon group having from 1 to 6 carbon atoms. In some embodiments, an alkylene group can have from 1 to 4 carbon atoms. In some embodiments, an alkylene group can have from 1 to 2 carbon atoms. Examples of $C_{1-2}$ alkylene groups include methylene and ethylene. Examples of $C_{1-4}$ alkylene groups include the aforementioned $C_{1-2}$ alkylene groups as well as trimethylene (1,3-propanediyl), propylene (1,2-propanediyl), tetramethylene (1,4-butanediyl), butylene (1,2-butanediyl), 1,3-butanediyl, 2-methyl-1,3-propanediyl and the like. Examples of $C_{1-6}$ alkylene groups include the aforementioned $C_{1-4}$ alkylene groups as well as pentamethylene (1,5-pentanediyl), pentylene (1,2-pentanediyl), hexamethylene (1,6-hexanediyl), hexylene (1,2-hexanediyl), 2,3-dimethyl-1,4-butanediyl and the like. In some embodiments ("α,ω-alkylene"), an alkylene group is an α,ω-diradical. Examples of α,ω-alkylene groups include methylene, ethylene, trimethylene, tetramethylene, pentamethylene and hexamethylene.

Unless otherwise specified, as used herein, alone or as part of another group, "alkenylene" refers to a diradical of a straight-chain or branched hydrocarbon group having from 2 to 6 carbon atoms and one or more carbon-carbon double bonds. In some embodiments, an alkenylene group can have from 2 to 4 carbon atoms. In some embodiments, an alkenylene group can have 2 carbon atoms, i.e., ethenediyl. The one or more carbon-carbon double bonds can be internal (such as in 1,4-but-2-enediyl) or terminal (such as in 1,4-but-1-enediyl). Examples of $C_{2-4}$ alkenylene groups include ethenediyl, 1,2-propenediyl, 1,3-propenediyl, 1,4-but-1-enediyl, 1,4-but-2-enediyl and the like. Examples of $C_{2-6}$ alkenylene groups include the aforementioned $C_{2-4}$ alkenylene groups as well as 1,5-pent-1-enediyl, 1,4-pent-2-enediyl, 1,6-hex-2-enediyl, 2,5-hex-3-enediyl, 2-methyl-1,4-pent-2-enediyl and the like. In some embodiments ("α,ω-alkenylene"), an alkenylene group is an α,ω-diradical. Examples of α,ω-alkenylene groups include ethenediyl, 1,3-propenediyl, 1,4-but-2-enediyl, 1,5-pent-1-enediyl, 1,6-hex-3-enediyl and the like.

Unless otherwise specified, as used herein, alone or as part of another group, "alkynylene" refers to a diradical of a straight-chain or branched hydrocarbon group having from 2 to 6 carbon atoms and one or more carbon-carbon triple bonds. In some embodiments, an alkynylene group can have from 2 to 4 carbon atoms. In some embodiments, an alkynylene group can have 2 carbon atoms, i.e., ethynediyl. The one or more carbon-carbon triple bonds can be internal (such as in 1,4-but-2-ynediyl) or terminal (such as in 1,4-but-1-ynediyl). Examples of $C_{2-4}$ alkynylene groups include ethynediyl, 1,3-propynediyl, 1,4-but-1-ynediyl, 1,4-but-2-ynediyl and the like. Examples of $C_{2-6}$ alkynylene groups include the aforementioned $C_{2-4}$ alkynylene groups as well as 1,5-pent-1-ynediyl, 1,4-pent-2-ynediyl, 1,6-hex-2-ynediyl, 2,5-hex-3-ynediyl, 3-methyl-1,5-hex-1-ynediyl and the like. In some embodiments ("α,ω-alkynylene"), an alkynylene group is an α,ω-diradical. Examples of α,ω-alkynylene groups include ethynediyl, 1,3-propynediyl, 1,4-but-2-ynediyl, 1,5-pent-1-ynediyl, 1,6-hex-3-ynediyl and the like.

Unless otherwise specified, as used herein, alone or as part of another group, "heteroalkylene" refers to a diradical having the structure $C_{n1}$ alkylene[ψ]$C_{n2}$ alkylene, wherein n1 and n2 are whole numbers, at least one of which is other than zero ($C_0$ alkylene is a covalent bond), and ψ is —O—, —NH—, —N(CH$_3$)— or —S—. $C_{0-3,0-3}$ heteroalkylene refers to $C_{n1}$ alkylene[ψ]$C_{n2}$ alkylene, wherein each of n1 and n2 is independently 0, 1, 2 or 3, provided that n1+n2 is 1, 2, 3 or 4. $C_{0-2,0-2}$ heteroalkylene refers to $C_{n1}$ alkylene[ψ]$C_{n2}$ alkylene, wherein each of n1 and n2 is independently 0, 1 or 2, provided that n1+n2 is 1, 2, 3 or 4. Examples of heteroalkylene groups include —OCH$_2$—, —NHCH$_2$CH$_2$—, SCH$_2$CH$_2$CH$_2$, —OCH(CH$_3$)CH$_2$—, —CH$_2$N(CH$_3$)—, —CH$_2$OCH$_2$—, —CH$_2$NHCH$_2$CH$_2$—, —CH$_2$SCH$_2$CH$_2$CH$_2$—, CH$_2$OCH(CH$_3$)CH$_2$—, —CH$_2$CH$_2$NH—, —CH$_2$CH$_2$N(CH$_3$)CH$_2$—, —CH$_2$CH$_2$OCH$_2$CH$_2$—, —CH(CH$_3$)CH$_2$S—, CH(CH$_3$)CH$_2$OCH$_2$— and the like.

Unless otherwise specified, as used herein, alone or as part of another group, "haloalkyl" refers to an alkyl group, wherein one or more of the hydrogen atoms are each independently replaced with halo. In some embodiments ("perhaloalkyl"), all of the hydrogen atoms are each replaced with fluoro or chloro. In some embodiments ("perfluoroalkyl"), all of the hydrogen atoms are each replaced with fluoro. Examples of perfluoroalkyl groups include —CF$_3$, —CF$_2$CF$_3$, —CF$_2$CF$_2$CF$_3$ and the like. Examples of perhaloalkyl groups include the aforementioned perfluoroalkyl groups as well as —CCl$_3$, —CFCl$_2$, —CF$_2$Cl, —CCl$_2$CCl$_3$ and the like. Examples of haloalkyl groups include the aforementioned perhaloalkyl groups as well as —CH$_2$F, —CHF$_2$, —CH$_2$Cl, —CH$_2$Br, —CH(Cl)CH$_2$Br, —CH$_2$CH(F)CH$_2$Cl and the like.

Unless otherwise specified, as used herein, alone or as part of another group, "alkoxy" or "alkyloxy" refers to an —O-alkyl group having from 1 to 8 carbon atoms. In some embodiments, an alkoxy group can have from 1 to 6 carbon atoms. In some embodiments, an alkoxy group can have from 1 to 4 carbon atoms. Examples of $C_{1-4}$ alkoxy groups include methoxy, ethoxy, propoxy, isopropoxy, butoxy, tert-butoxy and the like. Examples of $C_{1-6}$ alkoxy groups include the aforementioned $C_{1-4}$ alkoxy groups as well as pentyloxy, isopentyloxy, neopentyloxy, hexyloxy and the like. Additional examples of alkoxy groups include heptyloxy, octyloxy and the like.

Unless otherwise specified, as used herein, alone or as part of another group, "haloalkoxy" refers to an alkoxy group, wherein one or more of the hydrogen atoms are each independently replaced with halo. In some embodiments ("perhaloalkoxy"), all of the hydrogen atoms are each replaced with fluoro or chloro. In some embodiments ("perfluoroalkoxy"), all of the hydrogen atoms are each replaced with fluoro. Examples of perfluoroalkoxy groups include —OCF$_3$, —OCF$_2$CF$_3$, —OCF$_2$CF$_2$CF$_3$ and the like. Examples of perhaloalkoxy groups include the aforementioned perfluoroalkoxy groups as well as —OCCl$_3$, —OCFCl$_2$, —OCF$_2$Cl, —OCCl$_2$CCl$_3$ and the like. Examples of haloalkoxy groups include the aforementioned perhaloalkoxy groups as well as —OCH$_2$F, —OCHF$_2$, —OCH$_2$Cl, —OCH$_2$Br, —OCH(Cl)CH$_2$Br, —OCH$_2$CH(F)CH$_2$Cl and the like.

Unless otherwise specified, as used herein, alone or as part of another group, "alkylthio" refers to an —S-alkyl group having from 1 to 8 carbon atoms. In some embodiments, an alkylthio group can have from 1 to 6 carbon atoms. In some embodiments, an alkylthio group can have from 1 to 4 carbon atoms. Examples of $C_{1-4}$ alkylthio groups include methylthio, ethylthio, propylthio, isopropylthio, butylthio, isobutylthio and the like. Examples of $C_{1-6}$ alkylthio groups include the aforementioned $C_{1-4}$ alkylthio groups as well as pentylthio, isopentylthio, hexylthio and the like. Additional examples of alkylthio groups include heptylthio, octylthio and the like.

Unless otherwise specified, as used herein, alone or as part of another group, "haloalkylthio" refers to an alkylthio group, wherein one or more of the hydrogen atoms are each independently replaced with halo. In some embodiments ("perhaloalkylthio"), all of the hydrogen atoms are each replaced with fluoro or chloro. In some embodiments ("perfluoroalkylthio"), all of the hydrogen atoms are each replaced with fluoro. Examples of perfluoroalkylthio groups include —SCF$_3$, —SCF$_2$CF$_3$, —SCF$_2$CF$_2$CF$_3$ and the like. Examples of perhaloalkylthio groups include the aforementioned perfluoroalkylthio groups as well as —SCCl$_3$, —SCFCl$_2$, —SCF$_2$Cl, —SCCl$_2$CCl$_3$ and the like. Examples of haloalkylthio groups include the aforementioned perhaloalkylthio groups as well as —SCH$_2$F, —SCHF$_2$, —SCH$_2$Cl, —SCH$_2$Br, —SCH(Cl)CH$_2$Br, —SCH$_2$CH(F)CH$_2$Cl and the like.

Illustrative examples of aryl, carbocyclyl, heteroaryl, heterocyclyl, fused aryl, fused carbocyclyl, fused heteroaryl and fused heterocyclyl are shown in the table below, in which X represents a heteroatom such as N, O or S. These examples are intended merely to illustrate the differences between the radicals and are not in any way intended to limit any other feature shown, e.g., position of attachment (except in the fused rings, where the point of attachment must be on the ring type shown), position of the heteroatom(s), number of heteroatoms, size of rings, number of rings, etc.

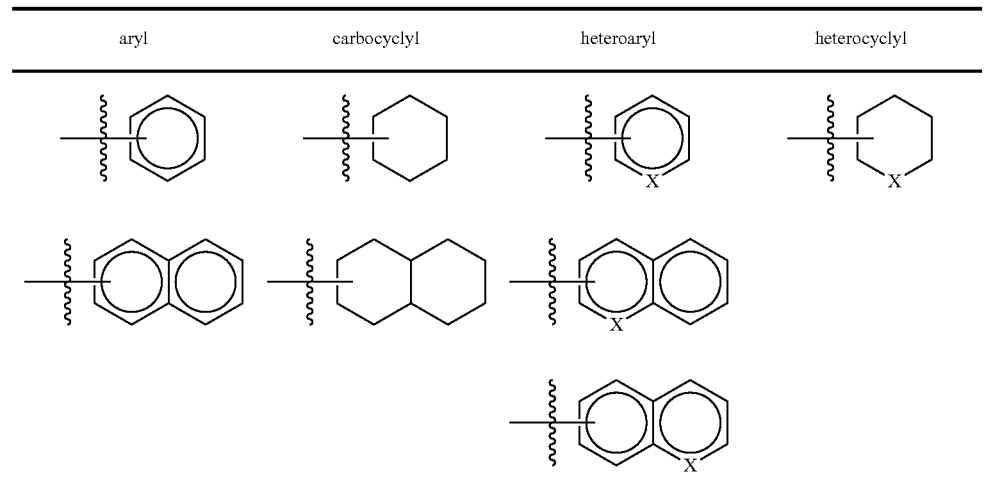

-continued

| fused aryl | fused carbocyclyl | fused heteroaryl | fused heterocyclyl |
| --- | --- | --- | --- |

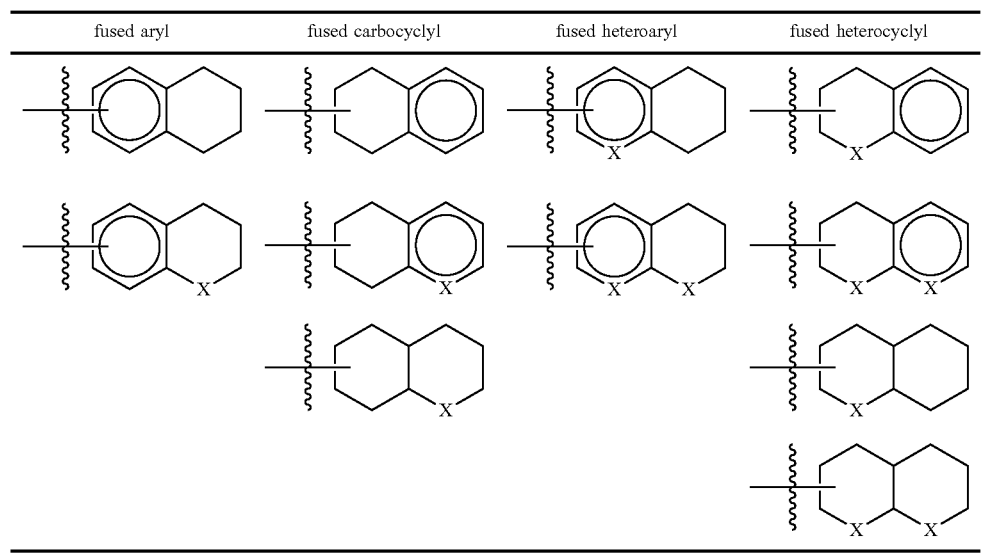

Unless otherwise specified, as used herein, alone or as part of another group, "aryl" refers to a radical of an aromatic monocyclic or bicyclic ring system having from 6 to 10 ring carbon atoms. Examples of such aryl groups include phenyl, 1-naphthyl and 2-naphthyl and the like.

Unless otherwise specified, each instance of an "optionally substituted" aryl group is independently unsubstituted or substituted with 1-4, 1-3, 1-2 or 1 substituent(s):

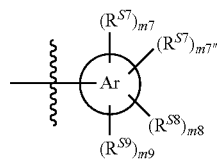

wherein

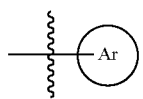

represents the aryl group, and
each of m7, m7", m8 and m9 is independently 0 (i.e., $R^{S[7,8,9]}$ is —H) or 1.
In some embodiments, m7+m7"+m8+m9≤3. In some embodiments, m7+m7"+m8+m9≤2. In some embodiments, m7+m7"+m8+m9≤1.

Unless otherwise specified, as used herein, alone or as part of another group, "carbocyclyl" refers to a radical of a non-aromatic cyclic hydrocarbon group having from 3 to 10 ring carbon atoms. In some embodiments ("$C_{3-8}$ carbocyclyl"), a carbocyclyl group has from 3 to 8 ring carbon atoms. In some embodiments ("$C_{3-6}$ carbocyclyl"), a carbocyclyl group has from 3 to 6 ring carbon atoms. Examples of $C_{3-6}$ carbocyclyl groups include cyclopropyl, cyclobutyl, cyclopentyl, cyclopentenyl, cyclohexyl, cyclohexenyl, cyclohexadienyl and the like. Examples of $C_{3-8}$ carbocyclyl groups include the aforementioned $C_{3-6}$ carbocyclyl groups as well as cycloheptyl, cycloheptadienyl, cycloheptatrienyl, cyclooctyl, bicyclo[2.2.1]heptanyl, bicyclo[2.2.2]octanyl and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl and the like. As the foregoing examples illustrate, a carbocyclyl group can be monocyclic or bicyclic (e.g., containing a fused, bridged or spiro ring system), and can be saturated or can contain one or more carbon-carbon double or triple bonds.

In some embodiments ("cycloalkyl"), a carbocyclyl group is monocyclic, saturated, and has 3 to 8 ring carbon atoms. In some embodiments ("$C_{3-6}$ cycloalkyl"), a cycloalkyl group has 3 to 6 ring carbon atoms. In some embodiments ("$C_{5-6}$ cycloalkyl"), a cycloalkyl group has 5 or 6 ring carbon atoms. Examples of $C_{5-6}$ cycloalkyl groups include cyclopentyl and cyclohexyl. Examples of $C_{3-6}$ cycloalkyl groups include the aforementioned $C_{5-6}$ cycloalkyl groups as well as cyclopropyl and cyclobutyl. Examples of $C_{3-8}$ cycloalkyl groups include the aforementioned $C_{3-6}$ cycloalkyl groups as well as cycloheptyl and cyclooctyl.

Unless otherwise specified, each instance of an "optionally substituted" carbocyclyl group is independently unsubstituted or substituted with 1-3, 1-2 or 1 substituent(s):

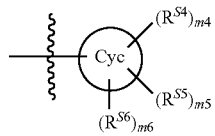

wherein

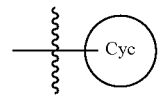

represents the carbocyclyl group, and each of m4, m5 and m6 is independently 0 (i.e., $R^{S[4,5,6]}$ is —H) or 1.

In some embodiments, m4+m5+m6≤2. In some embodiments, m4+m5+m6≤1.

Unless otherwise specified, as used herein, alone or as part of another group, "heteroaryl" refers to a radical of a 5- to 10-membered aromatic ring system having ring carbon atoms and 1 to 4 ring heteroatoms, each heteroatom independently selected from N, O and S. Examples of such heteroaryl groups include pyrrolyl, furanyl (furyl), thiophenyl (thienyl), pyrazolyl, imidazolyl, oxazolyl, isoxazolyl, thiazolyl, triazolyl, oxadiazolyl, thiadiazolyl, tetrazolyl, pyridinyl (pyridyl), pyridazinyl, pyrimidnyl, pyrazinyl, triazinyl, indolyl, benzofuranyl, benzothiophenyl (benzothienyl), indazolyl, benzimidazolyl, benzoxazolyl, benzisoxazolyl, benzothiazolyl, quinolinyl, isoquinolinyl, cinnolinyl, quinazolinyl, quinoxalinyl, phthalazinyl, naphthyridinyl and the like.

As the foregoing examples illustrate, a heteroaryl group can be monocyclic or bicyclic. In some embodiments the heteroaryl group is monocyclic and has 5 to 6 ring atoms. In some embodiments the heteroaryl group is monocyclic and has 5 to 6 ring atoms, 1 or 2 of which are heteroatoms. In some embodiments the heteroaryl group is bicyclic and has 8 to 10 ring atoms. In some embodiments the heteroaryl group is bicyclic and has 9 to 10 ring atoms, 1-3 of which are heteroatoms. In some embodiments the heteroaryl group is bicyclic and has 9 to 10 ring atoms, 1 or 2 of which are heteroatoms.

Unless otherwise specified, each instance of an "optionally substituted" heteroaryl group is independently unsubstituted or substituted with 1-4, 1-3, 1-2 or 1 substituent(s):

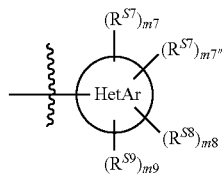

wherein

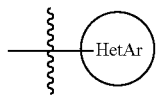

represents the heteroaryl group,
and each of m7, m7", m8 and m9 is independently 0 (i.e., $R^{S[7,8,9]}$ is —H) or 1.

In some embodiments, m7+m7"+m8+m9≤3. In some embodiments, m7+m7"+m8+m9≤2. In some embodiments, m7+m7"+m8+m9≤1.

Unless otherwise specified, as used herein, alone or as part of another group, "heterocyclyl" refers to a radical of a monocyclic 3- to 7-membered non-aromatic ring system having ring carbon atoms and 1 to 3 ring heteroatoms, each heteroatom independently selected from N, O and S, wherein each ring carbon atom that is bonded to a ring heteroatom can also be bonded to an oxo (=O) group (such that the ring carbon atom is the carbon atom of a carbonyl (—C(=O)— group). Examples of heterocyclyl groups include oxiranyl, aziridinyl, oxetanyl, azetidinyl, pyrrolidinyl, dihydropyrrolyl, tetrahydrofuranyl, dihydrofuranyl, tetrahydrothiophenyl, dihydrothiophenyl, pyrazolidinyl, imidazolidinyl, oxazolidinyl, isoxazolidinyl, thiazolidinyl, triazolidinyl, oxadiazolidinyl, piperidinyl, tetrahydropyridinyl, dihydropyridinyl, piperazinyl, tetrahydropyranyl, dioxanyl, morpholinyl, triazinanyl, azepanyl, diazepanyl, diazepinyl, oxepanyl, dioxepanyl, oxazepanyl, oxazepinyl and the like. In some embodiments, the heterocyclyl group has 1 or 2 ring heteroatoms. In some embodiments, the heterocyclyl group has from 5 to 6 ring atoms, 1 or 2 of which are heteroatoms.

Unless otherwise specified, each instance of an "optionally substituted" heterocyclyl group is independently unsubstituted or substituted with 1-3, 1-2 or 1 substituent(s):

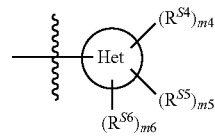

wherein

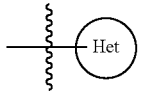

represents the heterocyclyl group,
and each of m4, m5 and m6 is independently 0 (i.e., $R^{S[4,5,6]}$ is —H) or 1.

In some embodiments, m4+m5+m6≤2. In some embodiments, m4+m5+m6≤1.

Unless otherwise specified, as used herein, alone or as part of another group, "fused aryl" refers to an aryl group in which two adjacent ring atoms, together with additional atoms, form a carbocycle or heterocycle (as defined with reference to "carbocyclyl" and "heterocyclyl", respectively). Examples of fused aryl groups include 1,2,3,4-tetrahydronaphthalen-5-yl, 1,2,3,4-tetrahydronaphthalen-6-yl, 2,3-dihydro-1H-inden-4-yl, 2,3-dihydro-1H-inden-5-yl, 1H-inden-4-yl, 2,2-dimethyl-2,3-dihydrobenzofuran-7-yl, 1,1-dimethyl-1,3-dihydroisobenzofuran-4-yl, benzo[d][1,3]dioxol-4-yl, 1,2,3,4-tetrahydroquinoxalin-5-yl, 2,2-dimethyl-3,4-dihydro-2H-benzo[b][1,4]oxazin-6-yl and the like.

Unless otherwise specified, each instance of an "optionally substituted" fused aryl group is independently unsubstituted or substituted with 1-4, 1-3, 1-2 or 1 substituent(s):

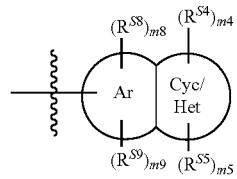

wherein

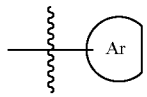

represents the aryl group, and

represents the and carbocycle or heterocycle, and each of m4, m5, m8 and m9 is independently 0 (i.e., $R^{S[4,5,8,9]}$ is —H) or 1.

In some embodiments, m4+m5+m8+m9≤3. In some embodiments, m4+m5+m8+m9≤2. In some embodiments, m4+m5+m8+m9≤1.

Unless otherwise specified, as used herein, alone or as part of another group, "fused carbocyclyl" refers to a carbocyclyl group in which two adjacent ring atoms, together with additional atoms, form an aromatic or heteroaromatic ring (as defined with reference to "aryl" and "heteroaryl", respectively), or in which two ring atoms, together with additional atoms, form a heterocycle (as defined with reference to "heterocyclyl"). Examples of fused carbocyclyl groups include 1,2,3,4-tetrahydronaphthalen-1-yl, 1,2,3,4-tetrahydronaphthalen-2-yl, 2,3-dihydro-1H-inden-1-yl, 2,3-dihydro-1H-inden-2-yl, 1H-inden-1-yl, 5,6,7,8-tetrahydroquinolin-5-yl, 5,6,7,8-tetrahydroquinolin-7-yl, 4,5,6,7-tetrahydro-1H-indol-4-yl, 4,5,6,7-tetrahydro-1H-indol-6-yl, 4,5,6,7-tetrahydrobenzofuran-7-yl and the like.

Unless otherwise specified, as used herein, alone or as part of another group, "fused heteroaryl" refers to a heteroaryl group in which two adjacent ring atoms, together with additional atoms, form a carbocycle or heterocycle (as defined with reference to "carbocyclyl" and "heterocyclyl", respectively). Examples of fused heteroaryl groups include 4,5,6,7-tetrahydro-1H-indol-2-yl, 4,5,6,7-tetrahydro-1H-indol-3-yl, 4,5,6,7-tetrahydrobenzofuran-2-yl, 4,5,6,7-tetrahydrobenzofuran-3-yl, 4,5,6,7-tetrahydrobenzothiophen-2-yl, 4,5,6,7-tetrahydrobenzothiophen-3-yl, 4,5,6,7-tetrahydro-1H-pyrrolo[2,3-b]pyridin-2-yl, 4,5,6,7-tetrahydro-1H-pyrrolo[2,3-b]pyridin-3-yl, 1,4,5,7-tetrahydropyrano[3,4-b]pyrrol-2-yl, 1,4,5,7-tetrahydropyrano[3,4-b]pyrrol-3-yl, 4,5,6,7-tetrahydrofuro[3,2-c]pyridin-2-yl, 4,5,6,7-tetrahydrofuro[3,2-c]pyridin-3-yl, 6,7-dihydro-5H-furo[3,2-b]pyran-2-yl, 6,7-dihydro-5H-furo[3,2-b]pyran-3-yl, 4,5,6,7-tetrahydrothieno[3,2-b]pyridin-2-yl, 4,5,6,7-tetrahydrothieno[3,2-b]pyridin-3-yl, 5,7-dihydro-4H-thieno[2,3-c]pyran-2-yl, 5,7-dihydro-4H-thieno[2,3-c]pyran-3-yl and the like.

Unless otherwise specified, as used herein, alone or as part of another group, "fused heterocyclyl" refers to a heterocyclyl group in which two adjacent ring atoms, together with additional atoms, form an aromatic or heteroaromatic ring (as defined with reference to "aryl" and "heteroaryl", respectively), or in which two ring atoms, together with additional atoms, form a carbocycle or heterocycle (as defined with reference to "carbocyclyl" and "heterocyclyl", respectively). Examples of fused heterocyclyl groups include indolin-1-yl, indolin-2-yl, indolin-3-yl, tetrahydroisoindol-1-yl, tetrahydroisoindol-2-yl, dihydrobenzofuran-2-yl, dihydrobenzofuran-3-yl, dihydrobenzothien-2-yl, dihydrobenzothien-3-yl, 1,2,3,4-tetrahydroquinolin-1-yl, 1,2,3,4-tetrahydroquinolin-2-yl, 1,2,3,4-tetrahydroquinolin-3-yl, 1,2,3,4-tetrahydroquinolin-4-yl, chroman-2-yl, chroman-3-yl, chroman-4-yl, chromen-2-yl, chromen-3-yl, chromen-4-yl, thiochroman-3-yl, isochroman-4-yl, 1H-benzo[e][1,4]diazepin-2-yl, 2,3-dihydro-1H-pyrrolo[2,3-b]pyridin-1-yl, 2,3-dihydro-1H-pyrrolo[2,3-b]pyridin-2-yl, 2,3-dihydro-1H-pyrrolo[2,3-b]pyridin-3-yl, 2,3-dihydrofuro[2,3-b]pyridin-3-yl, 5,6-dihydro-4H-furo[3,2-b]pyrrol-6-yl, 1,2,3,4-tetrahydro-1,6-naphthyridin-3-yl, decahydroquinolinyl, decahydroisoquinolinyl, octahydrochromenyl, octahydroisochromenyl, decahydronaphthyridinyl, 2-azabicyclo[2.2.2]octan-2-yl, 2-azabicyclo[2.2.2]octan-3-yl, 2,5-diazabicyclo[2.2.2]octan-2-yl, 2,5-diazabicyclo[2.2.2]octan-6-yl, 3,3-dimethyl-1,3-dihydroisobenzofuran-1-yl, 2,3-dihydrobenzofuran-3-yl, 6-((trifluoromethyl)thio)-2,3-dihydrobenzofuran-3-yl, 2,3-dihydronaphtho[1,2-b]furan-3-yl, 2,3,4,5-tetrahydrobenzo[b]oxepin-5-yl and the like.

Unless otherwise specified— each instance of $R^{S1}$ is independently selected from —H, (a) halo, (c) —OR*², (d) —N(R*²)₂ and (e) —SR†²;

each instance of $R^{S2}$ is independently selected from —H, (a) halo, (c) —OR*⁴, (d) —N(R*⁴)₂, (e) —SR†⁴, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;

each instance of $R^{S3}$ is independently selected from (a) halo, (c) —OR*⁴, (d) —N(R*⁴)₂, (e) —SR†⁴, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴, (r) —N(R*⁴)—C(O)—N(R*⁴)₂, (aa) $C_{3-6}$ carbocyclyl, (cc) 5- to 6-membered heterocyclyl, (ee) $C_6$ aryl and (gg) 5- to 6-membered heteroaryl; wherein each of (aa) and (cc) is optionally substituted with 1-3 groups independently selected from (a) halo, (b1) $C_{1-2}$ aliphatic, (b2) $R^{\#2-1}$, (c) —OR*², (d) —N(R*²)₂ and (e) —SR†²; and wherein each of (ee) and (gg) is optionally substituted with 1-3 groups independently selected from (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S4}$ is independently selected from —H, (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S5}$ is independently selected from —H, (a) halo, (b1) $C_{1-4}$ aliphatic, (b2) $R^{4-2}$, (c) —OR*⁴, (d) —N(R*⁴)₂, (e) —SR†⁴, (f) $C_{1-3}$ haloalkyl, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;

each instance of $R^{S6}$ is independently selected from (a) halo, (b1) $C_{1-6}$ aliphatic, (b2) $R^{6-3}$, (c) —OR*⁶, (d) —N(R*⁶)₂, (e) —SR†⁶, (f) $C_{1-3}$ haloalkyl, (h) —NO₂, (i) —CN, (j) —C(O)—R†⁶, (k) —C(O)—OR*⁶, —C(O)—N(R*⁶)₂, (m) —O—C(O)—R†⁶, (n) —N(R*⁶)—C(O)—R†⁶, (o) —O—C(O)—OR*⁶, (p) —O—C(O)—N(R*⁶)₂, (q) —N(R*⁶)—C(O)—OR*⁶ (r) —N(R*⁶)—C(O)—N(R*⁶)₂, (aa) $C_{3-6}$ carbocyclyl, (bb) -A-($C_{3-6}$ carbocyclyl), (cc) 5- to 6-membered heterocyclyl, (dd) -A-(5- to 6-membered heterocyclyl), (ee) $C_6$ aryl, (ff) -A-($C_6$ aryl), (gg) 5- to 6-membered heteroaryl and (hh) -A-(5- to 6-membered heteroaryl); wherein each instance of A is independently selected from $C_{1-3}$ alkylene, $C_{0-2,0-2}$ heteroalkylene, —O—, —S—, —N(R*¹)— and —C(O)—; and wherein each of (aa)-(dd) is optionally substituted with 1-3 groups independently selected from (a) halo, (b1) $C_{1-2}$ aliphatic, (b2) $R^{\#2-1}$, (c) —OR*², (d) —N(R*²)₂ and (e) —SR†²; and wherein each of (ee)-(hh) is optionally substituted with 1-3 groups independently selected from (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S7}$ is independently selected from —H, (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S8}$ is independently selected from —H, (a) halo, (b1) $C_{1-4}$ aliphatic, (b2) $R^{\#4-2}$, (c) —OR*⁴, (d) —N(R*⁴)₂, (e) —SR†⁴, (f) $C_{1-3}$ haloalkyl, (g1) $C_{1-3}$ haloalkoxy, (g2) $C_{1-3}$ haloalkylthio, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂; and each instance of $R^{S9}$ is independently selected from —H, (a) halo, (b1) $C_{1-6}$ aliphatic, (b2) $R^{\wedge 6-3}$, (c) —OR*⁶, (d) —N(R*⁶)₂, (e) —SR†⁶, (f) $C_{1-3}$ haloalkyl, (g1) $C_{1-3}$ haloalkoxy, (g2) $C_{1-3}$ haloalkylthio, (h) —NO₂, (i) —CN, (j) —C(O)—R†⁶, (k) —C(O)—OR*⁶, (l) —C(O)—N(R*⁶)₂, (m) —O—C(O)—R†⁶, (n) —N(R*⁶)—C(O)—R†⁶, (o) —O—C(O)—OR*⁶, (p) —O—C(O)—N(R*⁶)₂, (q) —N(R*⁶)—C(O)—OR*⁶, (r) —N(R*⁶)—C(O)—N(R*⁶)₂, (s) —Si(R†²)₃, (aa) $C_{3-8}$ carbocyclyl, (bb) -A-($C_{3-8}$ carbocyclyl), (cc) 5- to 10-membered heterocyclyl, (dd) -A-(5- to 10-membered heterocyclyl), (ee) $C_{6-10}$ aryl, (ff) -A-($C_{6-10}$ aryl), (gg) 5- to 10-membered heteroaryl and (hh) -A-(5- to 10-membered heteroaryl); wherein each instance of A is independently selected from $C_{1-3}$ alkylene, $C_{0-3,0-3}$ heteroalkylene, —O—, —S—, —N(R*¹)— and —C(O)—; and wherein each of (aa)-(dd) is optionally substituted with 1-3 groups independently selected from (a) halo, (b1) $C_{1-2}$ aliphatic, (b2) $R^{\#2-1}$, (c) —OR*², (d) —N(R*²)₂ and (e) —SR†²; and wherein each of (ee)-(hh) is optionally substituted with 1-3 groups independently selected from (a) halo, (b1) $C_{1-4}$ aliphatic, (b2) $R^{\#4-2}$, (c) —OR'', (d) —N(R*⁴)₂ and (e) —SR†⁴.

Each instance of

| | | |
|---|---|---|
| {R*⁶} | is independently —H or | {$C_{1-6}$ alkyl} |
| {R*⁴} | | {$C_{1-4}$ alkyl} |
| {R*³} | | {$C_{1-3}$ alkyl} |
| {R*²} | | {$C_{1-2}$ alkyl} |
| {R*¹} | | {methyl. |

Each instance of

| | | |
|---|---|---|
| {R†⁶} | is independently | {$C_{1-6}$ alkyl} |
| {R†⁴} | | {$C_{1-4}$ alkyl} |
| {R†³} | | {$C_{1-3}$ alkyl} |
| {R†²} | | {$C_{1-2}$ alkyl. |

As prescribed in the following table, each instance of

| | | | | |
|---|---|---|---|---|
| {$R^{\wedge 6-3}$} | is independently | {$C_{1-6}$ alkyl} | unsubstituted or substituted with | {1-3 substituent(s): |
| {$R^{\wedge 6-2}$} | | {$C_{1-6}$ alkyl} | | {1-2 |
| {$R^{\wedge 6-1}$} | | {$C_{1-6}$ alkyl} | | {1 |
| {$R^{\wedge 4-2}$} | | {$C_{1-4}$ alkyl} | | {1-2 |
| {$R^{\wedge 4-1}$} | | {$C_{1-4}$ alkyl} | | {1 |
| {$R^{\wedge 2-1}$} | | {$C_{1-2}$ alkyl} | | {1 |

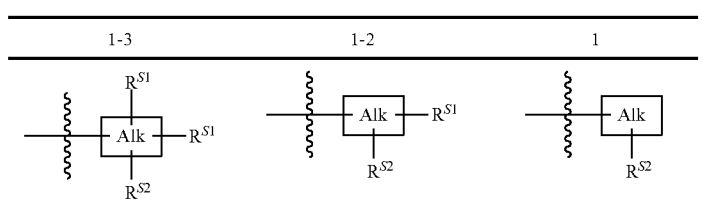

wherein

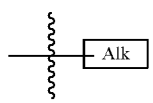

represents the alkyl group.

As prescribed in the following table, each instance of

| | | | | |
|---|---|---|---|---|
| {$R^{\#6-3}$} | is independently | {$C_{1-6}$ alkyl} | unsubstituted or substituted with | {1-3 substituent(s): |
| {$R^{\#6-2}$} | | {$C_{1-6}$ alkyl} | | {1-2 |
| {$R^{\#6-1}$} | | {$C_{1-6}$ alkyl} | | {1 |
| {$R^{\#4-2}$} | | {$C_{1-4}$ alkyl} | | {1-2 |
| {$R^{\#4-1}$} | | {$C_{1-4}$ alkyl} | | {1 |
| {$R^{\#2-1}$} | | {$C_{1-2}$ alkyl} | | {1 |

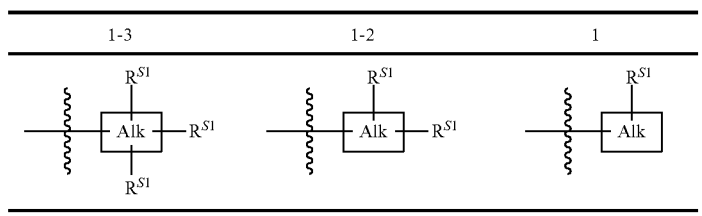

wherein

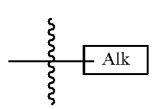

represents the alkyl group.

In each of these groups, when a subgroup is designating with a multiple occurrence, each occurrence is selected independently. For example, in —N(R*⁶)₂, the R*⁶ groups can be the same or different.

The following common names and abbreviations for various radicals are employed throughout.

| methyl | Me | —CH₃ |
| ethyl | Et | —CH₂CH₃ |
| propyl | Pr | —CH₂CH₂CH₃ |
| isopropyl | ⁱPr | CH₃CHCH₃ |
| butyl | Bu | —CH₂CH₂CH₂CH₃ |
| isobutyl | ⁱBu | —CH₂CHCH₃ with CH₃ |
| sec-butyl | ˢBu | CH₃CHCH₂CH₃ |
| tert-butyl | ᵗBu | —CCH₃ with CH₃ and CH₃ |
| phenyl | Ph | 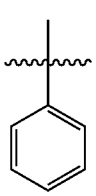 |
| benzyl | Bn | 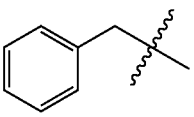 [SMILES: *Cc1ccccc1] |

Chemical Entities

Unless otherwise stated, structures depicted herein are meant to include chemical entities which differ only in the presence of one or more isotopically enriched atoms. For example, chemical entities having the present structure except for the replacement of a hydrogen atom by a deuterium or tritium, or the replacement of a carbon atom by a ¹³C- or ¹⁴C-enriched carbon are within the scope of the invention.

Unless stereochemical configuration is denoted, structures depicted herein are meant to include all stereochemical forms of the structure, i.e., the R and S configurations for each asymmetric center. Therefore, unless otherwise indicated, single stereochemical isomers as well as enantiomeric, racemic and diastereomeric mixtures of the present chemical entities are within the scope of the invention. As further clarification of the nomenclature used to describe the compounds exemplified in the invention, a compound such as the one with the name "(rac)-((1R,2R,3S,4R)-2,3-dihydroxy-4-(2-(naphthalen-2-yl)pyrazolo[1,5-a]pyrimidin-7-ylamino)cyclopentyl)methyl rel-sulfamate" describes a racemic mixture of both "((1R,2R,3S,4R)-2,3-dihydroxy-4-(2-(naphthalen-2-yl)pyrazolo[1,5-a]pyrimidin-7-ylamino)cyclopentyl)methyl rel-sulfamate" and "((1S,2S,3R,4S)-2,3-dihydroxy-4-(2-(naphthalen-2-yl)pyrazolo[1,5-a]pyrimidin-7-ylamino)cyclopentyl)methyl rel-sulfamate" whereas, for example "(s.e.)-((1R,2R,3S,4R)-2,3-dihydroxy-4-{[2-(1-naphthyl)pyrazolo[1,5-a]pyrimidin-7-yl]amino}cyclopentyl)methyl sulfamate" denotes the single enantiomer of the compound with the specified stereochemical assignment.

As used herein, "crystalline" refers to a solid in which the constituent atoms, molecules, or ions are packed in a regularly ordered, repeating three-dimensional pattern having a highly regular chemical structure. In particular, a crystalline compound or salt might be produced as one or more crystalline forms. For the purposes of this application, the terms "crystalline form" and "polymorph" are synonymous; the terms distinguish between crystals that have different properties (e.g., different XRPD patterns, different DSC scan results). Pseudopolymorphs are typically different solvates of a material, and thus the properties of pseudopolymorphs differ from one another. Thus, each distinct polymorph and pseudopolymorph is considered to be a distinct crystalline form herein.

"Substantially crystalline" refers to compounds or salts that are at least a particular weight percent crystalline. In some embodiments, the compound or salt is substantially crystalline. Examples of a crystalline form or substantially crystalline form include a single crystalline form or a mixture of different crystalline forms. Particular weight percentages include 50%, 60%, 70%, 75%, 80%, 85%, 87%, 88%, 89%, 90%, 91%, 92%, 93%, 94%, 95%, 96%, 97%, 98%, 99%, 99.5% and 99.9%. In some embodiments, substantially crystalline refers to compounds or salts that are at least 70% crystalline. In some embodiments, substantially crystalline refers to compounds or salts that are at least 80% crystalline. In some embodiments, substantially crystalline refers to compounds or salts that are at least 85% crystalline. In some embodiments, substantially crystalline refers to compounds or salts that are at least 90% crystalline. In some embodiments, substantially crystalline refers to compounds or salts that are at least 95% crystalline.

Representative solvates include, for example, hydrates, ethanolates, and methanolates.

The term "hydrate" refers to a solvate wherein the solvent molecule is H₂O that is present in a defined stoichiometric amount, and includes, for example, hemihydrates, monohydrates, dihydrates, and trihydrates.

The term "seeding" refers to the addition of crystalline material to a solution or mixture to initiate crystallization.

Some embodiments of the invention are directed to compounds or salts wherein at least a particular percentage by weight of the compound or salt is crystalline. Some embodiments of the invention are directed to a compound or salt wherein at least a particular percentage by weight of the compound or salt is crystalline. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. When a particular percentage by weight of the compound or salt is crystalline, the remainder of the compound or salt is the amorphous form of the compound or salt. When a particular percentage by weight of the compound or salt is a designated crystalline form, the remainder of the compound or salt is some combination of the amorphous form of the compound or salt, and one or more crystalline forms of the compound or salt excluding the designated crystalline form.

When a crystalline form of a compound or salt is identified using one or more XRPD peaks given as angles 2θ, each of the 2θ values is understood to mean the given value±0.2 degrees, unless otherwise expressed, for example as the given value±0.3.

When a crystalline form of a compound or salt is identified using one or more temperatures from a DSC profile (e.g., onset of endothermic transition, melt, etc.), each of the temperature values is understood to mean the given value±2° C.

When a crystalline form of a compound or salt is identified using one or more peaks from a raman pattern expressed as cm$^{-1}$, it is understood to mean the given value±0.2 cm$^{-1}$, unless otherwise expressed.

Each chemical entity of the present invention is a compound of Formula I:

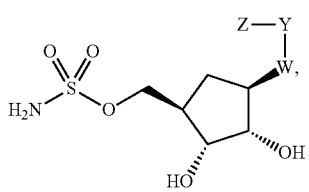

I or a pharmaceutically acceptable salt thereof, wherein:
W is —N(R*$^3$)—;
Y is

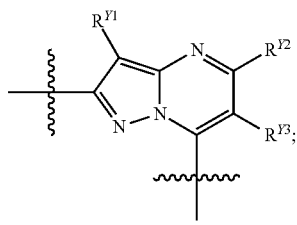

each of R$^{Y1}$, R$^{Y2}$ and R$^{Y3}$ is independently selected from —H, (a) halo, (b1) C$_{1-3}$ aliphatic, (b2) R$^{\#2-1}$, (c) —OR*$^3$, (d) —N(R*$^3$)$_2$, (e) —SR$^{\dagger 3}$, (f) C$_{1-2}$ haloalkyl and (g) C$_{1-2}$ haloalkoxy;
Z is
(1) optionally substituted aryl:

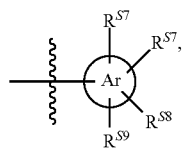

wherein

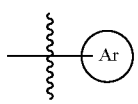

represents the aryl group;

(2) optionally substituted fused aryl:

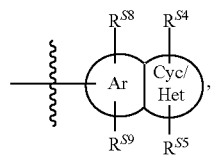

wherein

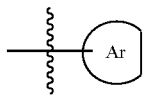

represents the aryl group, and

represents the carbocycle or heterocycle;
(3) optionally substituted heteroaryl:

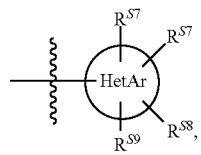

wherein

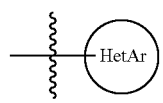

represents the heteroaryl
or
(4)

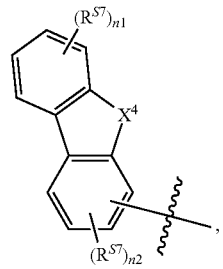

wherein
X$^4$ is —O—, —N(R*$^3$)—, —S— or —C(O)—; and
each of n1 and n2 is independently 0, 1 or 2, provided that n1+n2=0, 1 or 2.
In some embodiments, W is —N(R*$^1$)—. In some embodiments, W is —NH—.
In some embodiments, each of R$^{Y1}$, R$^{Y2}$ and R$^{Y3}$ is independently selected from —H, (a) halo and (b1) C$_{1-3}$ alkyl. In some embodiments, each of $R^{Y1}$, $R^{Y2}$ and $R^{Y3}$ is independently selected from —H, (a) —F, —Cl and (b1) methyl. In some embodiments, each of $R^{Y1}$, $R^{Y2}$ and $R^{Y3}$ is —H.

In some embodiments, Z is optionally substituted aryl.

In some embodiments, Z is optionally substituted phenyl:

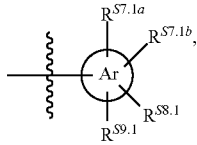

wherein

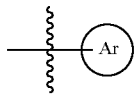

represents phenyl, each of $R^{S7.1a}$ and $R^{S7.1b}$ is independently selected from —H, (a) halo, (b1) $C_{1-4}$ aliphatic, (b2) $R^{\#4-2}$, (c) —OR$^{*4}$, (d) —N(R$^{*4}$)$_2$ and (e) —SR$^{\dagger4}$;

$R^{S8.1}$ is selected from —H, (a) halo, (b1) $C_{1-4}$ aliphatic, (b2) $R^{\#4-2}$, (c) —OR$^{*4}$, (d) —N(R$^{*4}$)$_2$, (e) —SR$^{\dagger4}$, (f) $C_{1-3}$ haloalkyl, (g1) $C_{1-3}$ haloalkoxy, (g2) $C_{1-3}$ haloalkylthio, (h) —NO$_2$, (i) —CN, (j) —C(O)—R$^{\dagger4}$, (k) —C(O)—OR$^{*4}$, (l) —C(O)—N(R$^{*4}$)$_2$, (m) —O—C(O)—R$^{\dagger4}$, (n) —N(R$^{*4}$)—C(O)—R$^{\dagger4}$, (o) —O—C(O)—OR$^{*4}$, (p) —O—C(O)—N(R$^{*4}$)$_2$, (q) —N(R$^{*4}$)—C(O)—OR$^{*4}$ and (r) —N(R$^{*4}$)—C(O)—N(R$^{*4}$)$_2$;

$R^{S9.1}$ is selected from —H, (a) halo, (b1) $C_{1-6}$ aliphatic, (b2) $R^{\#6-3}$, (c) —OR$^{*6}$, (d) —N(R$^{*6}$)$_2$, (e) —SR$^{\dagger6}$, (f) $C_{1-3}$ haloalkyl, (g1) $C_{1-3}$ haloalkoxy, (g2) $C_{1-3}$ haloalkylthio, (h) —NO$_2$, (i) —CN, (j) —C(O)—R$^{\dagger6}$, (k) —C(O)—OR$^{*6}$, (l) —C(O)—N(R$^{*6}$)$_2$, (m) —O—C(O)—R$^{\dagger6}$, (n) —N(R$^{*6}$)—C(O)—R$^{\dagger6}$, (o) —O—C(O)—OR$^{*6}$, (p) —O—C(O)—N(R$^{*6}$)$_2$, (q) —N(R$^{*6}$)—C(O)—OR$^{*6}$, (r) —N(R$^{*6}$)—C(O)—N(R$^{*6}$)$_2$, (s) —Si(R$^{\dagger2}$)$_3$, (aa) $C_{3-8}$ carbocyclyl, (bb) -A-($C_{3-8}$ carbocyclyl), (cc) 5- to 10-membered heterocyclyl, (dd) -A-(5- to 10-membered heterocyclyl), (ee) $C_{6-10}$ aryl, (ff) -A-($C_{8-10}$ aryl), (gg) 5- to 10-membered heteroaryl and (hh) -A-(5- to 10-membered heteroaryl); wherein A is selected from $C_{1-3}$ alkylene, $C_{0-3,0-3}$ heteroalkylene, —O—, —S—, —N(R$^{*1}$)— and —C(O)—; and wherein each of (aa)-(dd) is optionally substituted with 1-3 groups independently selected from (a) halo, (b1) $C_{1-2}$ aliphatic, (b2) $R^{\#2-1}$, (c) —OR$^{*2}$, (d) —N(R$^{*2}$)$_2$ and (e) —SR$^{\dagger2}$; and wherein each of (ee)-(hh) is optionally substituted with 1-3 groups independently selected from (a) halo, (b1) $C_{1-4}$ aliphatic, (b2) $R^{\#4-2}$, (c) —OR$^{*4}$, (d) —N(R$^{*4}$)$_2$ and (e) —SR$^{\dagger4}$.

In some embodiments, at least 1 of $R^{S7.1a}$, $R^{S7.1b}$, $R^{S8.1}$ and $R^{S9.1}$ is —H. In some embodiments, at least 2 of $R^{S7.1a}$, $R^{S7.1b}$, $R^{S9.1}$ and $R^{S9.1}$ are —H.

In some embodiments, $R^{S9.1}$ is selected from —H, (a) halo, (b1) $C_{1-6}$ aliphatic, (b2) $R^{\#6-3}$, (c) —OR$^{*6}$, (d) —N(R$^{*6}$)$_2$, (e) —SR$^{\dagger6}$, (f) $C_{1-3}$ haloalkyl, (g1) $C_{1-3}$ haloalkoxy, (g2) $C_{1-3}$ haloalkylthio, (h) —NO$_2$, (i) —CN, (j) —C(O)—R$^{\dagger6}$, (k) —C(O)—OR$^{*6}$, (l) —C(O)—N(R$^{*6}$)$_2$, (m) —O—C(O)—R$^{\dagger6}$, (n) —N(R$^{*6}$)—C(O)—R$^{\dagger6}$, (o) —O—C(O)—OR$^{*6}$, (p) —O—C(O)—N(R$^{*6}$)$_2$, (q) —N(R$^{*6}$)—C(O)—OR$^{*6}$, (r) —N(R$^{*6}$)—C(O)—N(R$^{*6}$)$_2$, (s) —Si(R$^{\dagger2}$)$_3$, (aa) $C_{3-6}$ carbocyclyl, (bb) -A-($C_{3-6}$ carbocyclyl), (cc) 5- to 6-membered heterocyclyl, (dd) -A-(5- to 6-membered heterocyclyl), (ee) $C_{6-10}$ aryl, (ff) -A-($C_{6-10}$ aryl), (gg) 5- to 10-membered heteroaryl and (hh) -A-(5- to 10-membered heteroaryl); wherein A is selected from $C_{1-3}$ alkylene, $C_{0-2,0-2}$ heteroalkylene, —O—, —S—, —N(R$^{*1}$)— and —C(O)—; and wherein each of (aa)-(dd) is optionally substituted with 1-2 groups independently selected from (a) halo, (b1) $C_{1-2}$ aliphatic, (b2) $R^{\#2-1}$, (c) —OR$^{*2}$, (d) —N(R$^{*2}$)$_2$ and (e) —SR$^{\dagger2}$; and wherein each of (ee)-(hh) is optionally substituted with 1-3 groups independently selected from (a) halo, (b1) $C_{1-4}$ aliphatic, (b2) $R^{\#4-2}$, (c) —OR$^{*4}$, (d) —N(R$^{*4}$)$_2$ and (e) —SR$^{\dagger4}$.

In some embodiments, each of (aa)-(dd) is optionally substituted with 1 group selected from (a) halo, (b1) $C_{1-2}$ aliphatic, (b2) $R^{\#2-1}$, (c) —OR$^{*2}$, (d) —N(R$^{*2}$)$_2$ and (e) —SR$^{\dagger2}$; and each of (ee)-(hh) is optionally substituted with 1-2 groups independently selected from (a) halo, (b1) $C_{1-4}$ aliphatic, (b2) $R^{\#4-2}$, (c) —OR$^{*4}$, (d) —N(R$^{*4}$)$_2$ and (e) —SR$^{\dagger4}$.

In some embodiments, each of $R^{S8.1}$ and $R^{S9.1}$ is independently selected from —H, (a) —F, —Cl, (b1) $C_{1-2}$ alkyl, (c) —OR$^{*2}$, (d) —N(R$^{*2}$)$_2$, (e) —SR$^{\dagger2}$, (f) —CF$_3$, (g1) —O—CF$_3$ and (g2) —S—CF$_3$. In some embodiments, each of $R^{S8.1}$ and $R^{S9.1}$ is independently selected from —H, (a) —F, —Cl, (b1) —CH$_3$, (c) —OMe, (f) —CF$_3$, (g1) —O—CF$_3$ and (g2) —S—CF$_3$.

In some embodiments, $R^{S7.1b}$ is —H. In some embodiments, each of $R^{S7.1a}$ and $R^{S7.1b}$ is —H.

In some embodiments, $R^{S9.1}$ is selected from —H, (a) halo, (b1) $C_{1-4}$ aliphatic, (b2) $R^{\#6-3}$, (c) —OR$^{*4}$, (d) —N(R$^{*4}$)$_2$, (e) —SR$^{\dagger4}$, (f) $C_{1-3}$ haloalkyl, (g1) $C_{1-3}$ haloalkoxy, (g2) $C_{1-3}$ haloalkylthio, (h) —NO$_2$, (i) —CN, (j) —C(O)—R$^{\dagger4}$, (k) —C(O)—OR$^{*4}$, (l) —C(O)—N(R$^{*4}$)$_2$, (m) —O—C(O)—R$^{\backslash4}$, (n) —N(R$^{*4}$)—C(O)—R$^{\dagger4}$, (o) —O—C(O)—OR$^{*4}$, (p) —O—C(O)—N(R$^{*4}$)$_2$, (q) —N(R$^{*4}$)—C(O)—OR$^{*4}$, (r) —N(R$^{*4}$)—C(O)—N(R$^{*4}$)$_2$, (s) —Si(R$^{\dagger2}$)$_3$, (aa) $C_{3-6}$ carbocyclyl, (bb) -A-($C_{3-6}$ carbocyclyl), (cc) 5- to 6-membered heterocyclyl, (dd) -A-(5- to 6-membered heterocyclyl), (ee) $C_6$ aryl, (ff) -A-($C_6$ aryl), (gg) 5- to 6-membered heteroaryl and (hh) -A-(5- to 6-membered heteroaryl); wherein A is selected from $C_{1-3}$ alkylene, $C_{0-2,0-2}$ heteroalkylene, —O—, —S—, —N(R$^{*1}$)— and —C(O)—; and wherein each of (aa)-(dd) is optionally substituted with 1 group selected from (a) halo, (b1) $C_{1-2}$ aliphatic, (b2) $R^{\#2-1}$, (c) —OR$^{*2}$, (d) —N(R$^{*2}$)$_2$ and (e) —SR$^{\dagger2}$; and wherein each of (ee)-(hh) is optionally substituted with 1-2 groups independently selected from (a) halo, (b1) $C_{1-4}$ aliphatic, (b2) $R^{\#4-2}$, (c) —OR$^{*4}$, (d) —N(R$^{*4}$)$_2$ and (e) —SR$^{t4}$; and $R^{\#6-3}$ is

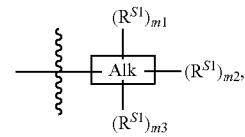

wherein

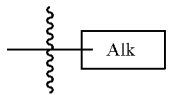

represents $C_{1-6}$ alkyl; and each of m1, m2 and m3 is independently 0 or 1.

In some embodiments, $R^{S9.1}$ is selected from —H, (a) halo, (b1) $C_{1-4}$ aliphatic, (b2) $R^{\#6-3}$, (c) —OR*$^4$, (f) $C_{1-3}$ haloalkyl, (g1) $C_{1-3}$ haloalkoxy, (g2) $C_{1-3}$ haloalkylthio, (s) —Si(R$^{†2}$)$_3$, (aa) $C_{3-6}$ carbocyclyl, (bb) -A-($C_{3-6}$ carbocyclyl), (cc) 5- to 6-membered heterocyclyl, (ee) $C_6$ aryl, (ff) -A-($C_6$ aryl) and (gg) 5- to 6-membered heteroaryl; wherein A is selected from —CH$_2$—, $C_{0-1,0-1}$ heteroalkylene, —O—, —S—, —NH— and —C(O)—; and wherein each of (aa)-(cc) is optionally substituted with 1 group selected from (a) halo, (b1) $C_{1-2}$ aliphatic, (b2) $R^{\#2-1}$, (c) —OR*$^2$, (d) —N(R*$^2$)$_2$ and (e) —SR$^{†2}$; and wherein each of (ee)-(gg) is optionally substituted with 1 group selected from (a) halo, (b1) $C_{1-2}$ aliphatic, (b2) $R^{\#2-1}$, (c) —OR*$^2$, (d) —N(R*$^2$)$_2$ and (e) —SR$^{†2}$. In some embodiments, $R^{S9.1}$ is selected from —H, (a) —Cl, —Br, (b1) $^t$Bu, —C≡C, (b2) —C(CH$_3$)$_2$—CF$_3$, —C(CH$_3$)$_2$—O-Me, —C(CH$_3$)$_2$—O-Et, —C(CH$_3$)$_2$—O—Pr, —C(CH$_3$)(CH$_2$—OH)(CH$_2$—Cl), (c) —OMe, (f) —CF$_3$, (g1) —O—CHF$_2$, —O—CF$_3$, (g2) —S—CF$_3$, (s) —Si(CH$_3$)$_3$, (aa) cyclopentyl, cyclopenten-1-yl, (bb) —S-cyclopropylmethyl, (cc) pyrrolidin-1-yl, piperidin-1-yl, pyrrolidin-2-on-1-yl, morpholin-4-yl, (ee) phenyl, (ff) benzyl, —O-Ph, —C(O)-Ph, (gg) pyridin-2-yl and 1-methyl-1H-pyrazol-2-yl.

In some embodiments, $R^{S8.1}$ is selected from —H, (a) halo, (b1) $C_{1-2}$ aliphatic, (b2) $R^{\wedge 2-1}$, (c) —OR*$^2$, (d) —N(R*$^2$)$_2$, (e) —SR$^{†2}$, (f) $C_{1-3}$ haloalkyl, (g1) $C_{1-3}$ haloalkoxy, (g2) $C_{1-3}$ haloalkylthio, (h) —NO$_2$, (i) —CN, (j) —C(O)—R$^{†2}$, (k) —C(O)—OR*$^2$, (l) —C(O)—N(R*$^2$)$_2$, (m) —O—C(O)—R$^{†2}$, (n) —N(R*$^2$)—C(O)—R$^{†2}$, (o) —O—C(O)—OR*$^2$, (p) —O—C(O)—N(R*$^2$)$_2$, (q) —N(R*$^2$)—C(O)—OR*$^2$ and (r) —N(R*$^2$)—C(O)—N(R*$^2$)$_2$. In some embodiments, $R^{S8.1}$ is —H.

In some embodiments, $R^{S7.1b}$ is —H; and $R^{S8.1}$ is —H. In some embodiments, each of $R^{S7.1a}$ and $R^{S7.1b}$ is —H; and $R^{S8.1}$ is —H.

In some embodiments, Z is optionally substituted naphthyl:

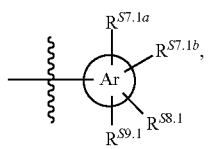

wherein

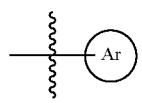

represents naphthyl;

each of $R^{S7.1a}$ and $R^{S7.1b}$ is independently selected from (a) halo, (b1) $C_{1-4}$ aliphatic, (b2) $R^{\#4-2}$, (c) —OR*$^4$, (d) —N(R*$^4$)$_2$ and (e) —SR$^{†4}$;

$R^{S8.1}$ is selected from (a) halo, (b1) $C_{1-4}$ aliphatic, (b2) $R^{\wedge 4-2}$, (c) —OR", (d) —N(R*$^4$)$_2$, (e) —SR$^{†4}$, (f) $C_{1-3}$ haloalkyl, (g) $C_{1-3}$ haloalkoxy, (h) —NO$_2$, (i) —CN, (j) —C(O)—R$^{†4}$, (k) —C(O)—OR*$^4$, (l) —C(O)—N(R*$^4$)$_2$, (m) —O—C(O)—R$^{†4}$, (n) —N(R*$^4$)—C(O)—R$^{†4}$, (o) —O—C(O)—OR*$^4$, (p) —O—C(O)—N(R*$^4$)$_2$, (q) —N(R*$^4$)—C(O)—OR*$^4$ and (r) —N(R*$^4$)—C(O)—N(R*$^4$)$_2$;

$R^{S9.1}$ is selected from (a) halo, (b1) $C_{1-4}$ aliphatic, (b2) $R^{\wedge 4-2}$, (c) —OR*$^4$, (d) —N(R*$^4$)$_2$, (e) —SR$^{†4}$, (f) $C_{1-3}$ haloalkyl, (g) $C_{1-3}$ haloalkoxy, (h) —NO$_2$, (i) —CN, (j) —C(O)—R$^{†4}$, (k) —C(O)—OR*$^4$, (l) —C(O)—N(R*$^4$)$_2$, (m) —O—C(O)—R$^{\setminus 4}$, (n) —N(R*$^4$)—C(O)—R$^{†4}$, (o) —O—C(O)—OR*$^4$, (p) —O—C(O)—N(R*$^4$)$_2$, (q) —N(R*$^4$)—C(O)—OR*$^4$ and (r) —N(R*$^4$)—C(O)—N(R*$^4$)$_2$, (aa) $C_{3-6}$ carbocyclyl, (cc) 5- to 6-membered heterocyclyl, (ee) $C_6$ aryl and (gg) 5- to 6-membered heteroaryl; wherein each of (aa) and (cc) is optionally substituted with 1-2 groups independently selected from (a) halo, (b1) $C_{1-2}$ aliphatic, (b2) $R^{\#2-1}$, (c) —OR*$^2$, (d) —N(R*$^2$)$_2$ and (e) —SR$^{†2}$; and wherein each of (ee) and (gg) is optionally substituted with 1-3 groups independently selected from (a) halo, (b1) $C_{1-2}$ aliphatic, (b2) $R^{\#2-1}$, (c) —OR*$^2$, (d) —N(R*$^2$)$_2$ and (e) —SR$^{†2}$;

provided that at least 1 of $R^{S7.1a}$, $R^{S7.1b}$, $R^{S8.1}$ and $R^{S9.1}$ is —H.

In some embodiments, at least 2 of $R^{S7.1a}$, $R^{S7.1b}$, $R^{S8.1}$ and $R^{S9.1}$ are —H.

In some embodiments, $R^{S9.1}$ is selected from (a) halo, (b1) $C_{1-4}$ aliphatic, (b2) $R^{\wedge 4-2}$, (c) —OR*$^4$, (d) —N(R*$^4$)$_2$, (e) —SR$^{†4}$, (f) $C_{1-3}$ haloalkyl, (g) $C_{1-3}$ haloalkoxy, (h) —NO$_2$, (i) —CN, (j) —C(O)—R$^{†4}$, (k) —C(O)—OR*$^4$, (l) —C(O)—N(R*$^4$)$_2$, (m) —O—C(O)—R$^{†4}$, (n) —N(R*$^4$)—C(O)—R$^{†4}$, (o) —O—C(O)—OR*$^4$, (p) —O—C(O)—N(R*$^4$)$_2$, (q) —N(R*$^4$)—C(O)—OR*$^4$ and (r) —N(R*$^4$)—C(O)—N(R*$^4$)$_2$.

In some embodiments, $R^{S7.1a}$ is —H; and $R^{S7.1b}$ is selected from —H, (a) halo and (b1) $C_{1-2}$ aliphatic.

In some embodiments, each of $R^{S7.1a}$ and $R^{S7.1b}$ is —H; $R^{S8.1}$ is selected from —H, (a) halo and (b1) $C_{1-2}$ aliphatic; and $R^{9.1}$ is selected from (a) halo, (b1) $C_{1-4}$ aliphatic, (b2) $R^{\wedge 4-2}$, (c) —OR*$^4$, (d) —N(R*$^4$)$_2$, (e) —SR$^{†4}$, (f) $C_{1-3}$ haloalkyl, (g) $C_{1-3}$ haloalkoxy, (h) —NO$_2$, (i) —CN, (j) —C(O)—R$^{†4}$, (k) —C(O)—OR*$^4$, (l) —C(O)—N(R*$^4$)$_2$, (m) —O—C(O)—R$^{†4}$, (n) —N(R*$^4$)—C(O)—R$^{†4}$, (o) —O—C(O)—OR*$^4$, (p) —O—C(O)—N(R*$^4$)$_2$, (q) —N(R*$^4$)—C(O)—OR*$^4$ and (r) —N(R*$^4$)—C(O)—N(R*$^4$)$_2$. In some embodiments, each of $R^{S7.1a}$ and $R^{S7.1b}$ is —H; $R^{S8.1}$ is —H; and $R^{S9.1}$ is selected from (a) —F, —Cl, (b1) $C_{1-2}$ alkyl, (c) —OR*$^4$, (d) —N(R*$^2$)$_2$, (f) $C_{1-2}$ haloalkyl, (g) $C_{1-2}$ haloalkoxy and (k) —C(O)—OR*$^2$. each of $R^{S7.1a}$ and $R^{S7.1b}$ is —H; and each of $R^{S8.1}$ and $R^{S9.1}$ is independently selected from —H, (a) halo and (b1) $C_{1-2}$ aliphatic. In some embodiments, each of $R^{S7.1a}$ and $R^{S7.1b}$ is —H; and each of $R^{S8.1}$ and $R^{S9.1}$ is independently selected from —H, (a) —F and —Cl.

In some embodiments, Z is optionally substituted fused aryl:

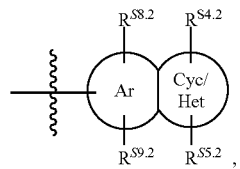

wherein

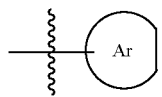

represents the aryl group, and

represents the carbocycle or heterocycle;
$R^{S4.2}$ is selected from —H, (a) halo, (b1) $C_{1-4}$ aliphatic, (b2) $R^{\#4-2}$, (c) —OR*⁴, (d) —N(R*⁴)₂ and (e) —SR†⁴;
$R^{S5.2}$ is selected from —H, (a) halo, (b1) $C_{1-4}$ aliphatic, (b2) $R^{\char"0234-2}$, (c) —OR*⁴, (d) —N(R*⁴)₂, (e) —SR†⁴, (f) $C_{1-3}$ haloalkyl, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;
$R^{S8.2}$ is selected from —H, (a) halo, (b1) $C_{1-4}$ aliphatic, (b2) $R^{\char"0234-2}$, (c) —OR*⁴, (d) —N(R*⁴)₂, (e) —SR†⁴, (f) $C_{1-3}$ haloalkyl, (g) $C_{1-3}$ haloalkoxy, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;
$R^{S9.2}$ is selected from —H, (a) halo, (b1) $C_{1-4}$ aliphatic, (b2) $R^{\char"0234-2}$, (c) —OR*⁴, (d) —N(R*⁴)₂, (e) —SR†⁴, (f) $C_{1-3}$ haloalkyl, (g) $C_{1-3}$ haloalkoxy, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂, (aa) $C_{3-6}$ carbocyclyl, (cc) 5- to 6-membered heterocyclyl, (ee) $C_6$ aryl and (gg) 5- to 6-membered heteroaryl; wherein each of (aa) and (cc) is optionally substituted with 1-2 groups independently selected from (a) halo, (b1) $C_{1-2}$ aliphatic, (b2) $R^{\#2-1}$, (c) —OR*², (d) —N(R*²)₂ and (e) —SR†²; and wherein each of (ee) and (gg) is optionally substituted with 1-3 groups independently selected from (a) halo, (b1) $C_{1-4}$ aliphatic, (b2) $R^{\#4-2}$, (c) —OR*⁴, (d) —N(R*⁴)₂ and (e) —SR†⁴.

In some embodiments, the aryl group is a $C_6$ aryl group; the carbocycle is a $C_{5-6}$ carbocycle; and the heterocycle is a 5- to 6-membered heterocycle having one ring heteroatom selected from —O—, —N(R*¹)— and —S—. In some embodiments, the carbocycle is a saturated $C_{5-6}$ carbocycle; and the heterocycle is a saturated 5- to 6-membered heterocycle wherein the ring heteroatom is —O—. In some embodiments, Z is optionally substituted indanyl, 2,3-dihydrobenzofuranyl or 1,3-dihydroisobenzofuranyl.

In some embodiments, $R^{S4.2}$ is selected from —H, (a) —F, Cl, (b1) $C_{1-2}$ aliphatic, (b2) $R^{\char"02-1}$, (c) —OR*², (d) —N(R*²)₂ and (e) —SR†²; $R^{S8.2}$ is selected from —H, (a) halo, (b1) $C_{1-2}$ aliphatic, (b2) $R^{\char"02-1}$, (c) —OR*², (d) —N(R*²)₂, (e) —SR†² and (f) —CF₃; $R^{S8.2}$ is —H; and $R^{S9.2}$ is selected from —H, (a) —F, Cl, (b1) $C_{1-2}$ aliphatic, (b2) $R^{\char"02-1}$, (c) —OR*², (d) —N(R*²)₂, (e) —SR†², (f) —CF₃ and (g) —OCF₃. In some embodiments, each of $R^{S4.2}$ and $R^{S5.2}$ is independently selected from —H, (b1) $C_{1-2}$ aliphatic and (b2) $R^{\char"02-1}$; and each of $R^{S8.2}$ and $R^{S9.2}$ is —H. In some embodiments, each of $R^{S4.2}$ and $R^{S5.2}$ is methyl; and each of $R^{S8.2}$ and $R^{S9.2}$ is —H.

In some embodiments, wherein Z is optionally substituted heteroaryl:

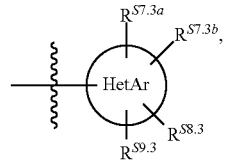

wherein

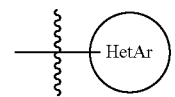

represents the heteroaryl group;
each of $R^{S7.3a}$ and $R^{S7.3b}$ is independently selected from (a) halo, (b1) $C_{1-4}$ aliphatic, (b2) $R^{\#4-2}$, (c) —OR*⁴, (d) —N(R*⁴)₂ and (e) —SR†⁴;
$R^{S8.3}$ is selected from (a) halo, (b1) $C_{1-4}$ aliphatic, (b2) $R^{\char"0234-2}$, (c) —OR*⁴, (d) —N(R*⁴)₂, (e) —SR†⁴, (f) $C_{1-3}$ haloalkyl, (g) $C_{1-3}$ haloalkoxy, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;
$R^{9.3}$ is selected from (a) halo, (b1) $C_{1-4}$ aliphatic, (b2) $R^{\char"0234-2}$, (c) —OR*⁴, (d) —N(R*⁴)₂, (e) —SR†⁴, (f) $C_{1-3}$ haloalkyl, (g) $C_{1-3}$ haloalkoxy, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂, (aa) $C_{3-6}$ carbocyclyl, (cc) 5- to 6-membered heterocyclyl, (ee) $C_6$ aryl and (gg) 5- to 6-membered heteroaryl; wherein each of (aa) and (cc) is optionally substituted with 1-2 groups independently selected from (a) halo, (b1) $C_{1-2}$ aliphatic, (b2) $R^{\#2-1}$, (c) —OR*², (d) —N(R*²)₂ and (e) —SR†²; and wherein each of (ee) and (gg) is optionally substituted with 1-3 groups independently selected from (a) halo, (b1) $C_{1-2}$ aliphatic, (b2) $R^{\#2-1}$, (c) —OR*², (d) —N(R*²)₂ and (e) —SR†²;
provided that at least 1 of $R^{S7.3a}$, $R^{S7.3b}$, $R^{S8.3}$ and $R^{S9.3}$ is —H.

In some embodiments, Z is optionally substituted 5- to 10-membered heteroaryl having 1 or 2 ring heteroatoms, each independently selected from O, S and NR*³. In some embodiments, Z is optionally substituted thienyl, oxazolyl, thiazolyl, pyridyl, pyrimidinyl, benzo[b]thiophenyl, benzofuranyl, 1H-indolyl, quinolinyl or isoquinolinyl.

In some embodiments, at least 2 of $R^{S7.3a}$, $R^{S7.3b}$, $R^{S8.3}$ and $R^{S9.3}$ are —H.

In some embodiments, $R^{S7.3a}$ is —H; and $R^{S8.3}$ is selected from —H, (a) halo, (b1) $C_{1-4}$ aliphatic and (f) $C_{1-3}$ haloalkyl.

In some embodiments, $R^{S7.3a}$ is —H; $R^{S7.3b}$ is —H; $R^{S8.3}$ is selected from —H, (a) halo, (b1) $C_{1-4}$ aliphatic and (f) $C_{1-3}$ haloalkyl; and $R^{S9.3}$ is selected from —H, (a) halo, (b1) $C_{1-4}$ aliphatic, (f) $C_{1-3}$ haloalkyl and (ee) phenyl. In some embodiments, $R^{S8.3}$ is selected from —H, (a) halo, (b1) $C_{1-2}$ alkyl and (f) —$CF_3$. In some embodiments, $R^{S7.3a}$ is —H; $R^{S7.3b}$ is —H; $R^{S8.3}$ is —H or (b1) methyl; and $R^{S9.3}$ is selected from —H, (a) halo, (b1) $C_{1-4}$ alkyl, (f) $C_{1-3}$ haloalkyl and (ee) phenyl. In some embodiments, $R^{S9.3}$ is selected from —H, (a) —F, —Cl, (b1) methyl, ethyl, $^tBu$ (f) —$CF_3$ and (ee) phenyl.

In some embodiments, each of $R^{S7.3a}$ and $R^{S7.3b}$ is —H; and $R^{S8.3}$ is —H.

In some embodiments, Z is

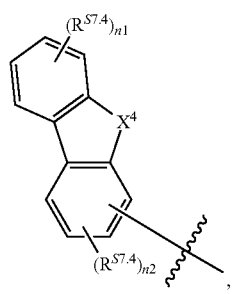

wherein
$X^4$ is —O—, —N($R^{*2}$)—, —S— or —C(O)—;
each of n1 and n2 is independently 0, 1 or 2, provided that n1+n2=0, 1 or 2; and
each instance of $R^{S7.4}$ is independently selected from (a) halo, (IA) $C_{1-2}$ aliphatic, (b2) $R^{\#2-1}$, (c) $OR^{*2}$, (d) —N($R^{*2}$)$_2$ and (e) —$SR^{\dagger 2}$.

In some embodiments, each instance of $R^{S7.4}$ is independently selected from (a) —F, —Cl, —Br, (b1) $C_{1-2}$ aliphatic, (b2) $R^{\#2-1}$, (c) —$OR^{*2}$ and (d) —N($R^{*2}$)$_2$, wherein each instance of $R^{\#2-1}$ is independently $C_{1-2}$ alkyl unsubstituted or substituted with 1 substituent selected from (a) —F, —Cl, (c) —$OR^{*2}$ and (d) —N($R^{*2}$)$_2$.

In some embodiments, $X^4$ is —O—, —NH—, —S— or —C(O)—.

In some embodiments, n1+n2=1. In some embodiments, each of n1 and n2 is 0.

Examples of compounds of the chemical entities of the present invention include those listed in the following tables.

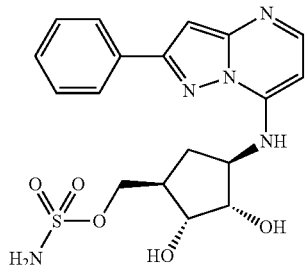
I-001

-continued

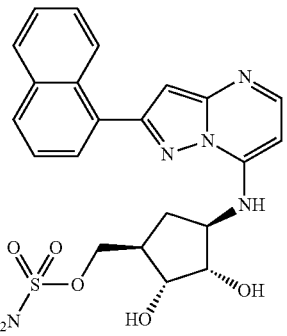
I-002

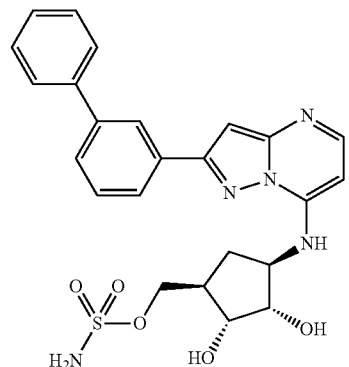
I-003

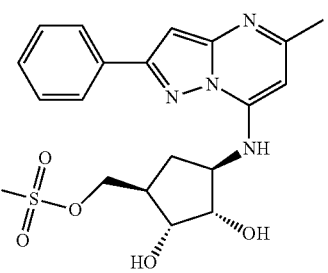
I-004

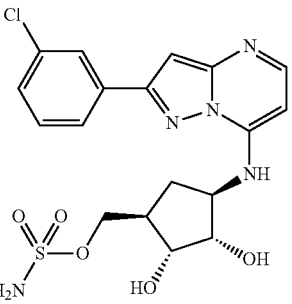
I-005

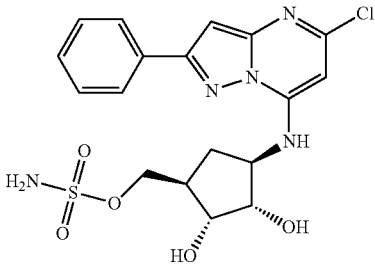 [SMILES: NS(=O)(=O)OC[C@H]1C[C@@H](Nc2cc(Cl)nc3cc(-c4ccccc4)nn23)[C@H](O)[C@@H]1O]
I-006

-continued
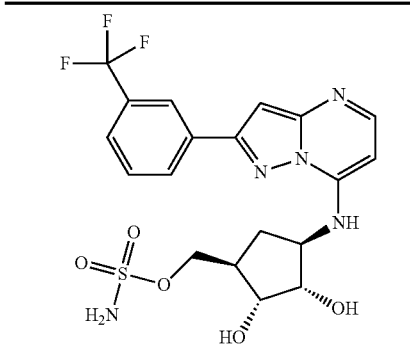
I-007
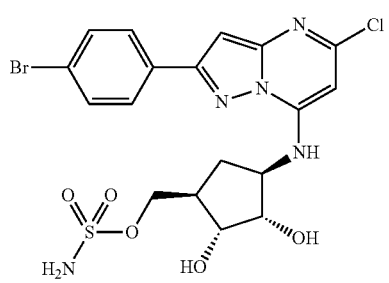 [SMILES: NS(=O)(=O)OC[C@H]1C[C@@H](Nc2cc(Cl)nc3cc(-c4ccc(Br)cc4)nn23)[C@H](O)[C@@H]1O]
I-008
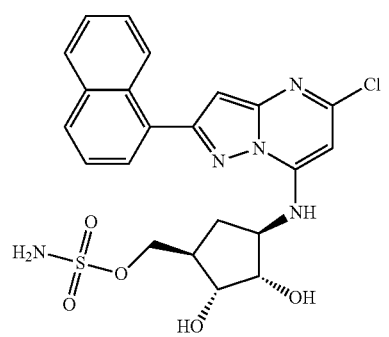 [SMILES: NS(=O)(=O)OC[C@H]1C[C@@H](Nc2cc(Cl)nc3cc(-c4cccc5ccccc45)nn23)[C@H](O)[C@@H]1O]
I-009
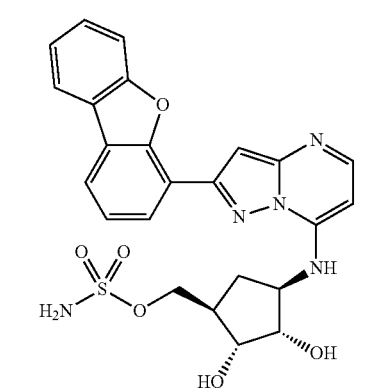 [SMILES: NS(=O)(=O)OC[C@H]1C[C@@H](Nc2ccnc3cc(-c4cccc5c4oc4ccccc45)nn23)[C@H](O)[C@@H]1O]
I-010
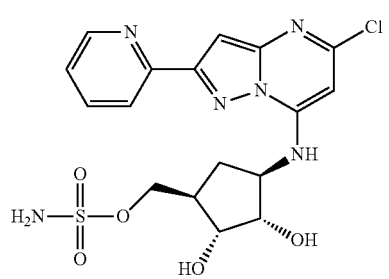 [SMILES: NS(=O)(=O)OC[C@H]1C[C@@H](Nc2cc(Cl)nc3cc(-c4ccccn4)nn23)[C@H](O)[C@@H]1O]
I-011
-continued
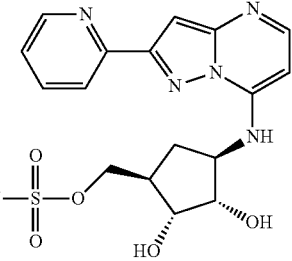
I-012
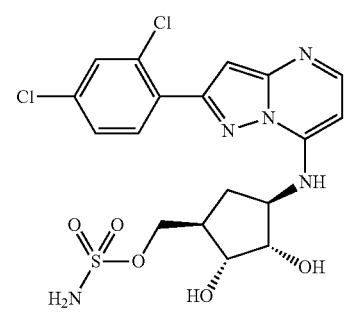 [SMILES: NS(=O)(=O)OC[C@H]1C[C@@H](Nc2ccnc3cc(-c4ccc(Cl)cc4Cl)nn23)[C@H](O)[C@@H]1O]
I-013
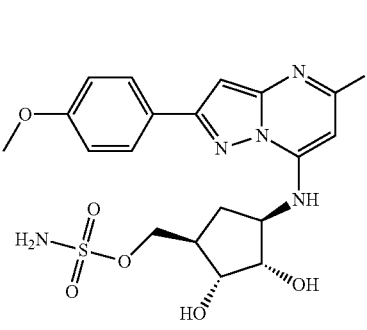
I-014
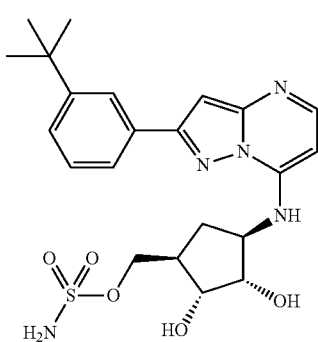 [SMILES: CC(C)(C)c1cccc(-c2cc3nccc(N[C@@H]4C[C@H](COS(N)(=O)=O)[C@@H](O)[C@H]4O)n3n2)c1]
I-015
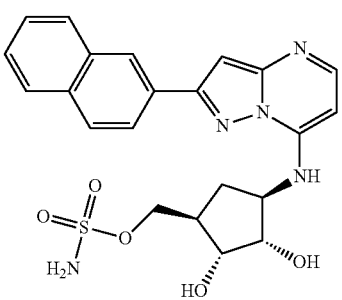 [SMILES: NS(=O)(=O)OC[C@H]1C[C@@H](Nc2ccnc3cc(-c4ccc5ccccc5c4)nn23)[C@H](O)[C@@H]1O]
I-016

31
-continued
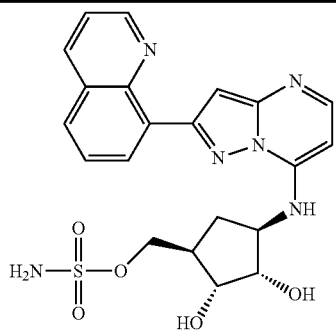
I-017
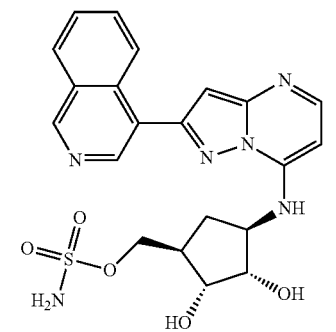 [SMILES: NS(=O)(=O)OC[C@H]1C[C@@H](Nc2ccnc3cc(-c4cncc5ccccc45)nn23)[C@H](O)[C@@H]1O]
I-018
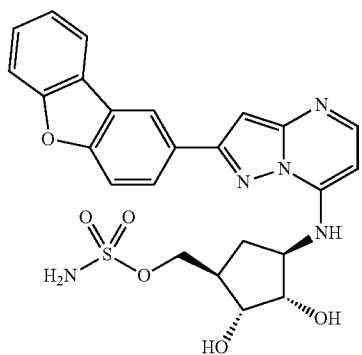 [SMILES: NS(=O)(=O)OC[C@H]1C[C@@H](Nc2ccnc3cc(-c4ccc5oc6ccccc6c5c4)nn23)[C@H](O)[C@@H]1O]
I-019
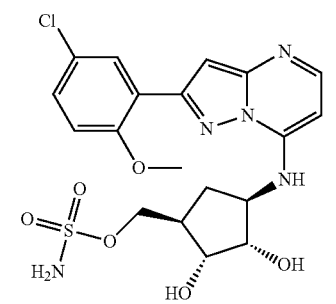 [SMILES: COc1ccc(Cl)cc1-c1cc2nccc(N[C@@H]3C[C@H](COS(N)(=O)=O)[C@@H](O)[C@H]3O)n2n1]
I-020
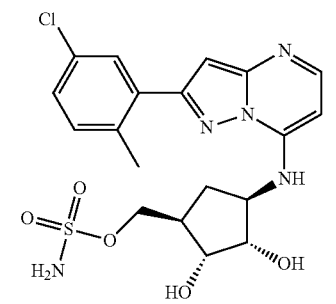 [SMILES: Cc1ccc(Cl)cc1-c1cc2nccc(N[C@@H]3C[C@H](COS(N)(=O)=O)[C@@H](O)[C@H]3O)n2n1]
I-021
32
-continued
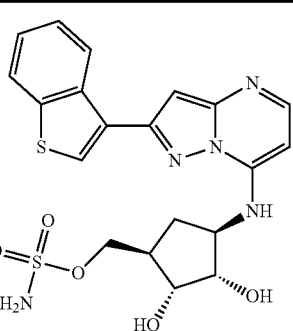
I-022
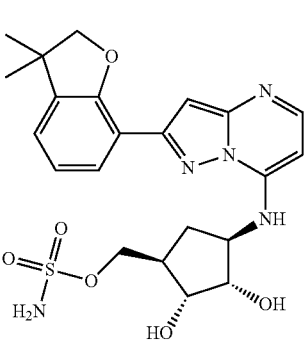 [SMILES: CC1(C)COc2c(-c3cc4nccc(N[C@@H]5C[C@H](COS(N)(=O)=O)[C@@H](O)[C@H]5O)n4n3)cccc21]
I-023
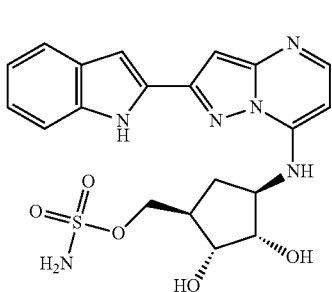 [SMILES: NS(=O)(=O)OC[C@H]1C[C@@H](Nc2ccnc3cc(-c4cc5ccccc5[nH]4)nn23)[C@H](O)[C@@H]1O]
I-024
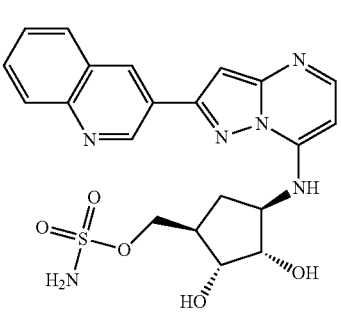 [SMILES: NS(=O)(=O)OC[C@H]1C[C@@H](Nc2ccnc3cc(-c4cnc5ccccc5c4)nn23)[C@H](O)[C@@H]1O]
I-025
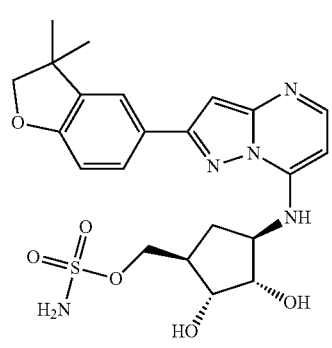 [SMILES: CC1(C)COc2ccc(-c3cc4nccc(N[C@@H]5C[C@H](COS(N)(=O)=O)[C@@H](O)[C@H]5O)n4n3)cc21]
I-026

-continued
I-027
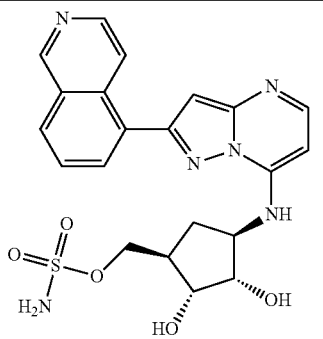
I-028
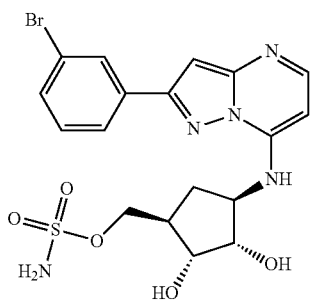 [SMILES: NS(=O)(=O)OC[C@H]1C[C@@H](Nc2ccnc3cc(-c4cccc(Br)c4)nn23)[C@H](O)[C@@H]1O]
I-029
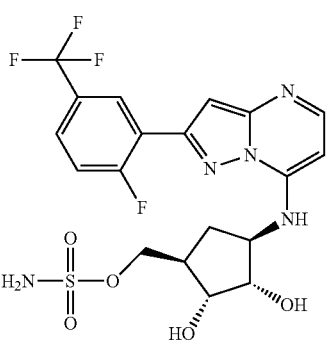
I-030
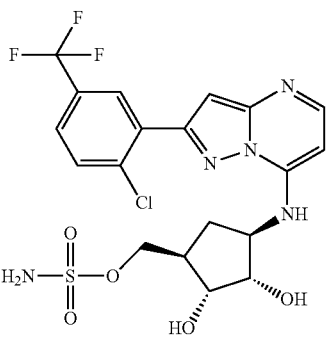 [SMILES: NS(=O)(=O)OC[C@H]1C[C@@H](Nc2ccnc3cc(-c4cc(C(F)(F)F)ccc4Cl)nn23)[C@H](O)[C@@H]1O]
I-031
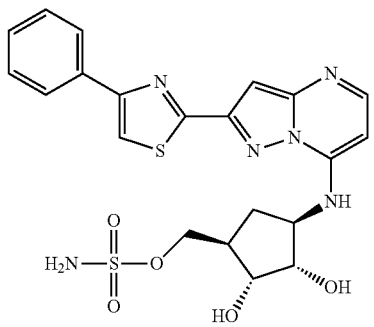 [SMILES: NS(=O)(=O)OC[C@H]1C[C@@H](Nc2ccnc3cc(-c4nc(-c5ccccc5)cs4)nn23)[C@H](O)[C@@H]1O]
-continued
I-032
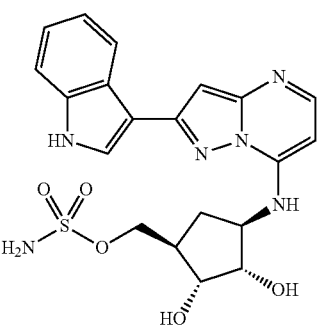 [SMILES: NS(=O)(=O)OC[C@H]1C[C@@H](Nc2ccnc3cc(-c4c[nH]c5ccccc45)nn23)[C@H](O)[C@@H]1O]
I-033
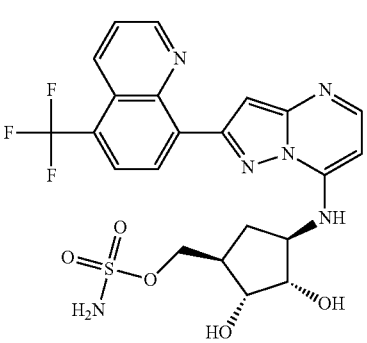 [SMILES: NS(=O)(=O)OC[C@H]1C[C@@H](Nc2ccnc3cc(-c4ccc(C(F)(F)F)c5cccnc45)nn23)[C@H](O)[C@@H]1O]
I-034
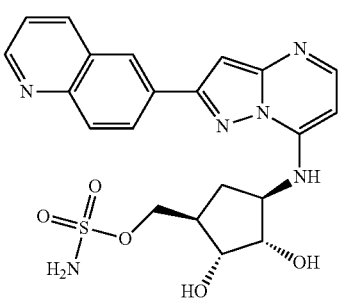
I-035
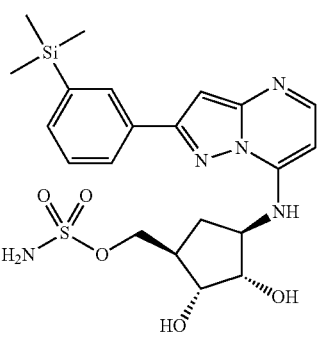 [SMILES: C[Si](C)(C)c1cccc(-c2cc3nccc(N[C@@H]4C[C@H](COS(N)(=O)=O)[C@@H](O)[C@H]4O)n3n2)c1]

TABLE-continued
| | |
|---|---|
| I-036 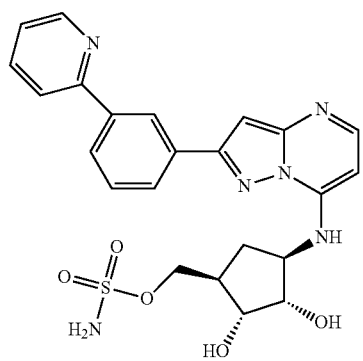 [SMILES: NS(=O)(=O)OC[C@H]1C[C@@H](Nc2ccnc3cc(-c4cccc(-c5ccccn5)c4)nn23)[C@H](O)[C@@H]1O] | I-040 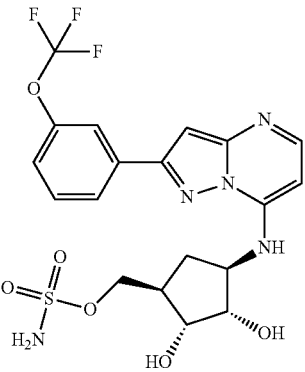 |
| I-037 | I-041 |
| I-038 | I-042 |
| I-039 | I-043 |
| | I-044 |

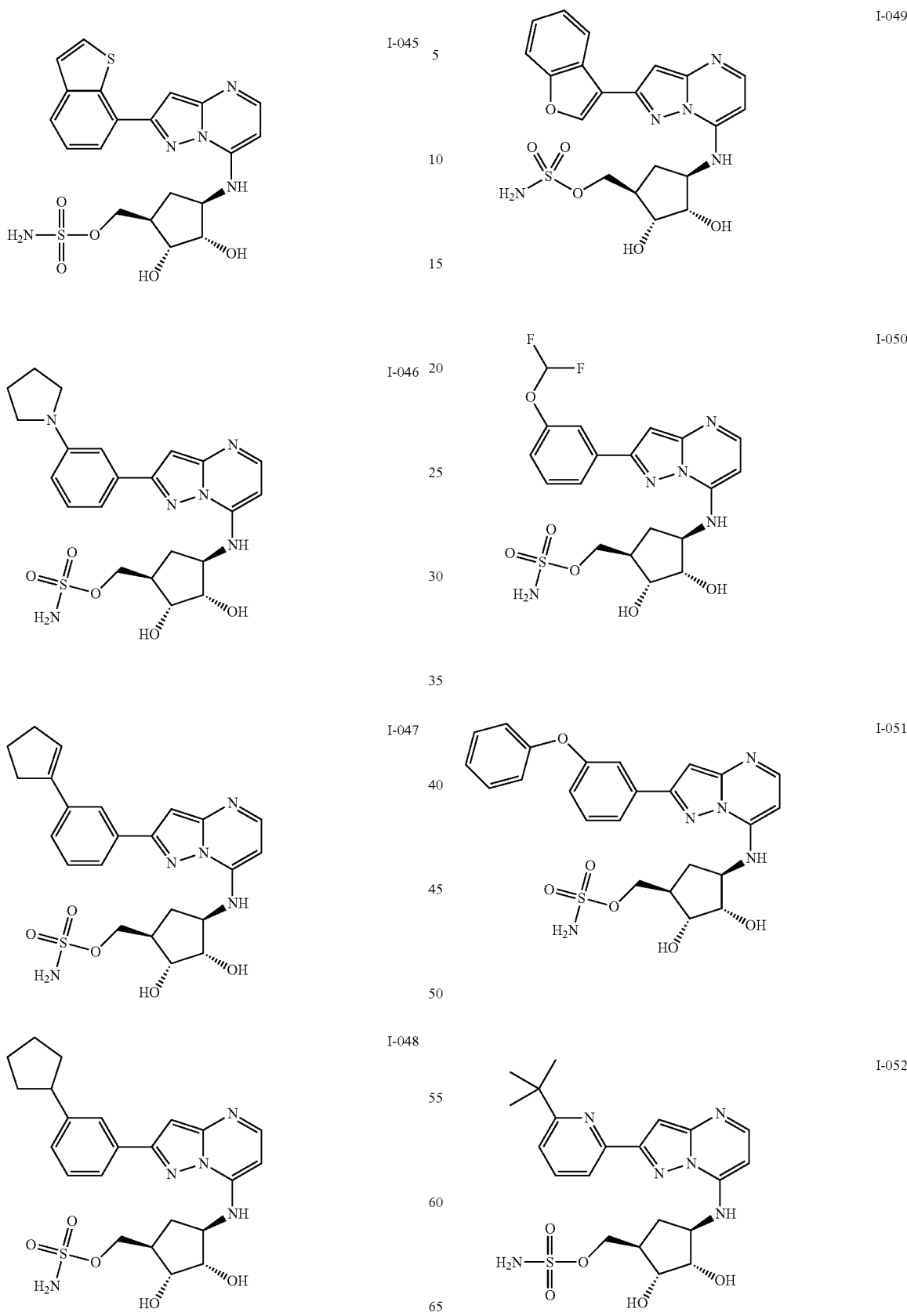

| 39 -continued | | 40 -continued | |
|---|---|---|---|
| 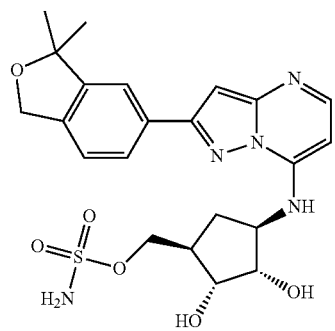 [SMILES: CC1(C)OCc2ccc(-c3cc4nccc(N[C@@H]5C[C@H](COS(N)(=O)=O)[C@@H](O)[C@H]5O)n4n3)cc21] | I-053 | 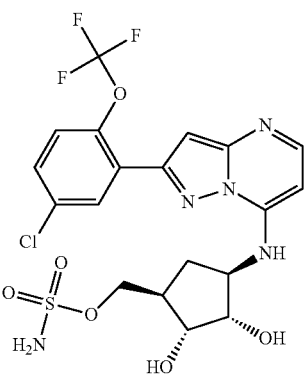 | I-057 |
| 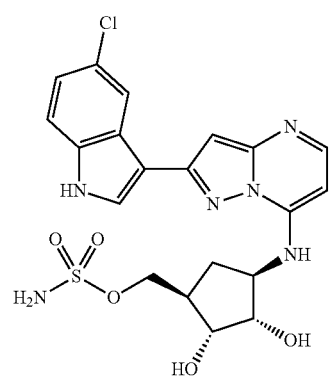 [SMILES: NS(=O)(=O)OC[C@H]1C[C@@H](Nc2ccnc3cc(-c4c[nH]c5ccc(Cl)cc45)nn23)[C@H](O)[C@@H]1O] | I-054 | 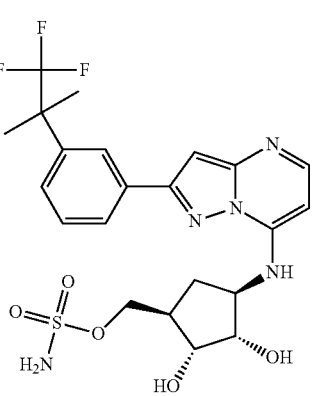 | I-058 |
| 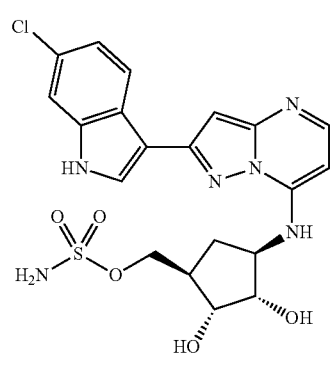 [SMILES: NS(=O)(=O)OC[C@H]1C[C@@H](Nc2ccnc3cc(-c4c[nH]c5cc(Cl)ccc45)nn23)[C@H](O)[C@@H]1O] | I-055 | 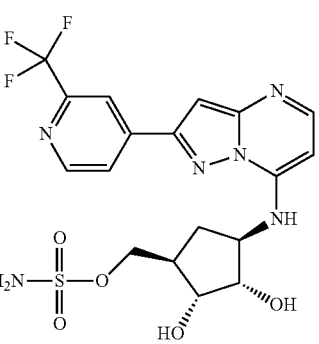 | I-059 |
| 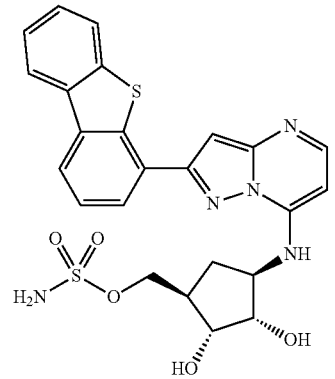 [SMILES: NS(=O)(=O)OC[C@H]1C[C@@H](Nc2ccnc3cc(-c4cccc5c4sc4ccccc45)nn23)[C@H](O)[C@@H]1O] | I-056 | 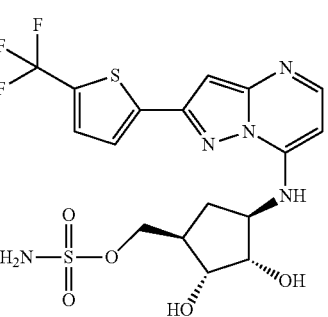 | I-060 |

-continued
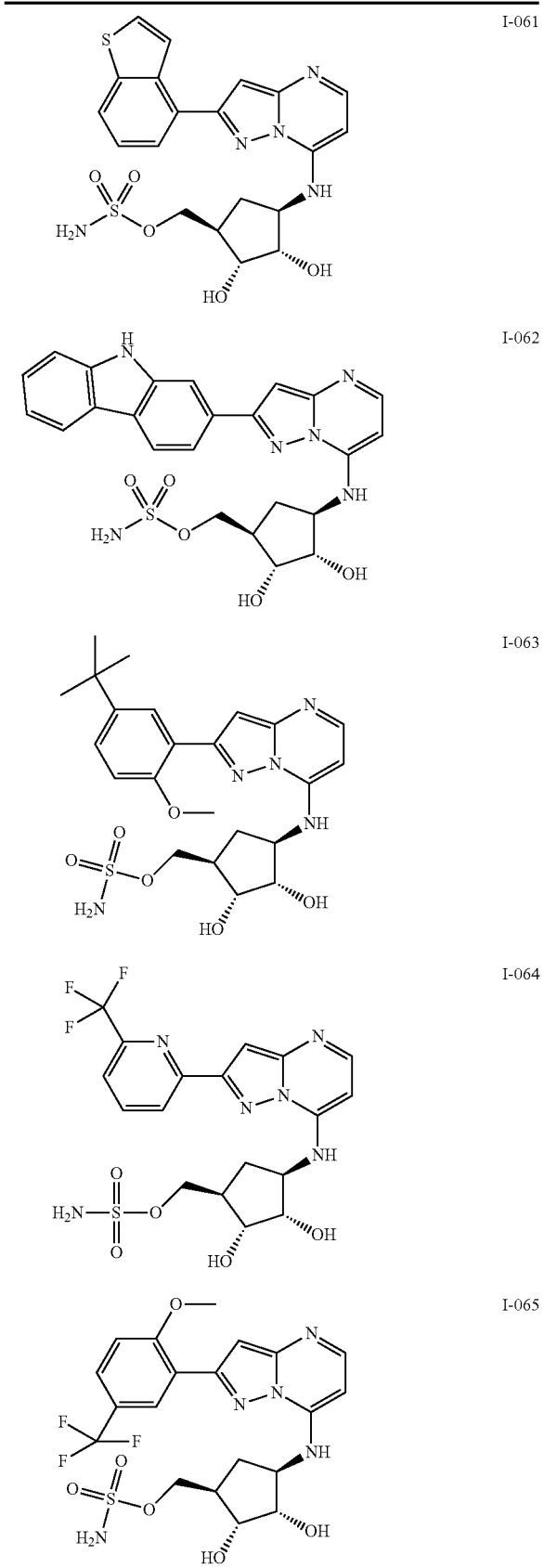
I-061
I-062
I-063
I-064
I-065
-continued
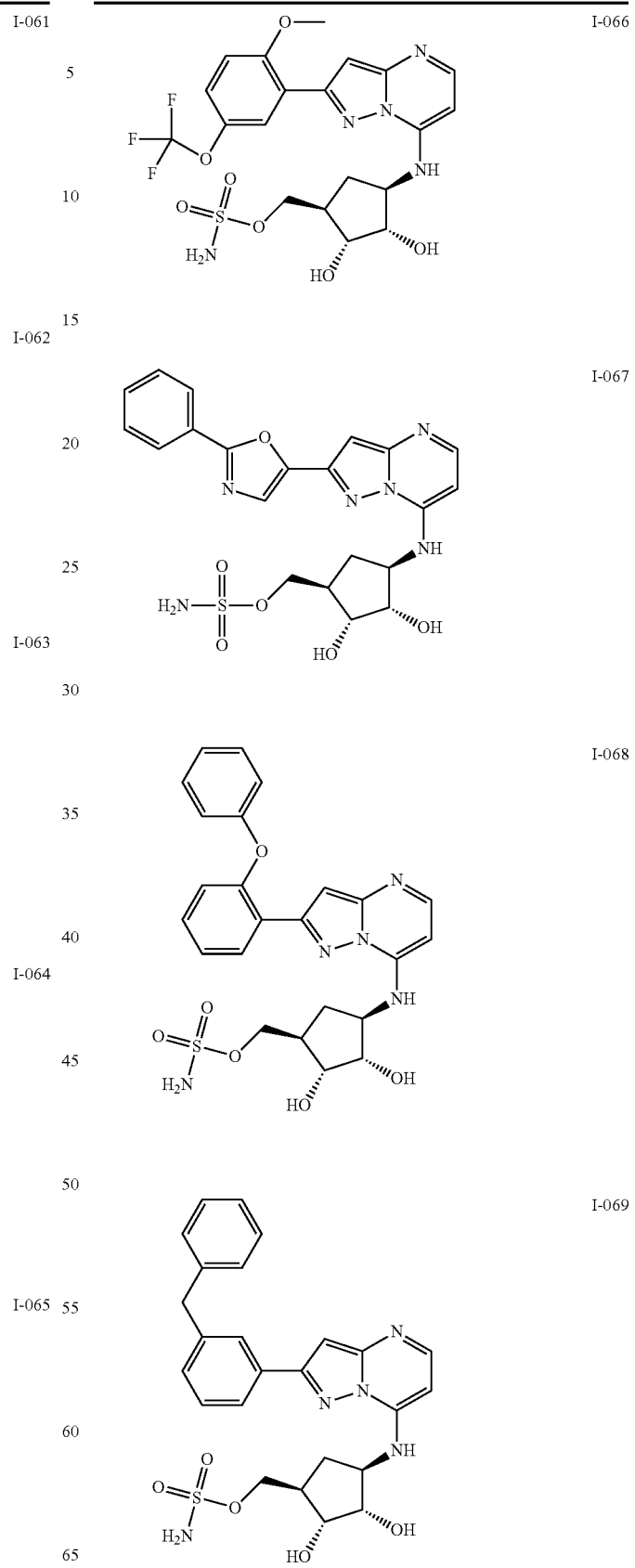
I-066
I-067
I-068
I-069

-continued
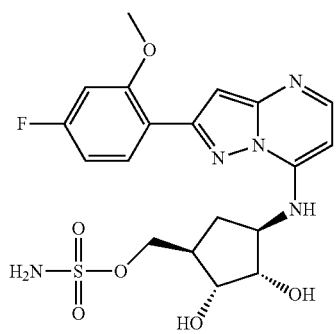 [SMILES: COc1cc(F)ccc1-c1cc2nccc(N[C@@H]3C[C@H](COS(N)(=O)=O)[C@@H](O)[C@H]3O)n2n1]
I-070
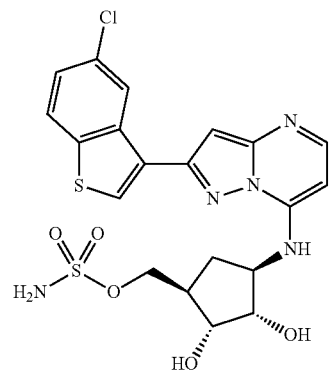 [SMILES: NS(=O)(=O)OC[C@H]1C[C@@H](Nc2ccnc3cc(-c4csc5ccc(Cl)cc45)nn23)[C@H](O)[C@@H]1O]
I-071
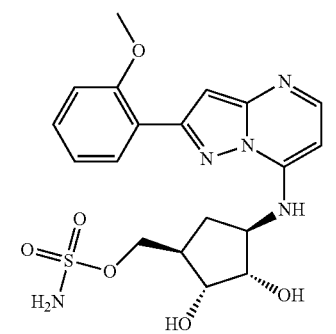 [SMILES: COc1ccccc1-c1cc2nccc(N[C@@H]3C[C@H](COS(N)(=O)=O)[C@@H](O)[C@H]3O)n2n1]
I-072
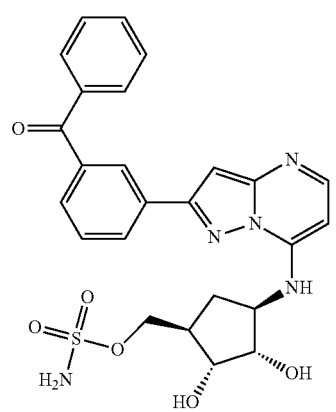 [SMILES: NS(=O)(=O)OC[C@H]1C[C@@H](Nc2ccnc3cc(-c4cccc(C(=O)c5ccccc5)c4)nn23)[C@H](O)[C@@H]1O]
I-073
-continued
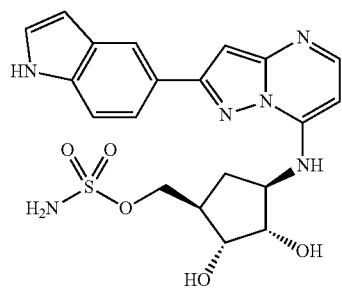 [SMILES: NS(=O)(=O)OC[C@H]1C[C@@H](Nc2ccnc3cc(-c4ccc5[nH]ccc5c4)nn23)[C@H](O)[C@@H]1O]
I-074
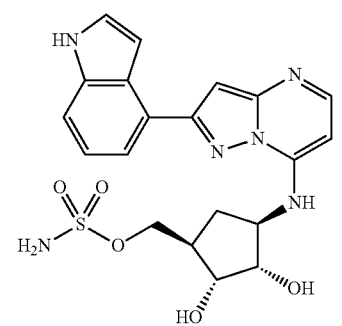 [SMILES: NS(=O)(=O)OC[C@H]1C[C@@H](Nc2ccnc3cc(-c4cccc5[nH]ccc45)nn23)[C@H](O)[C@@H]1O]
I-075
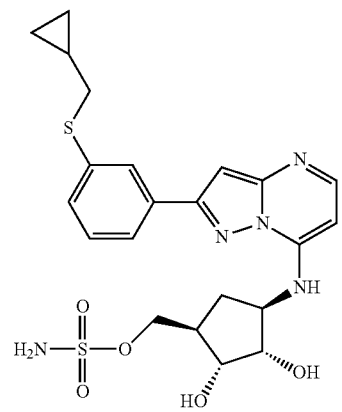 [SMILES: NS(=O)(=O)OC[C@H]1C[C@@H](Nc2ccnc3cc(-c4cccc(SCC5CC5)c4)nn23)[C@H](O)[C@@H]1O]
I-076
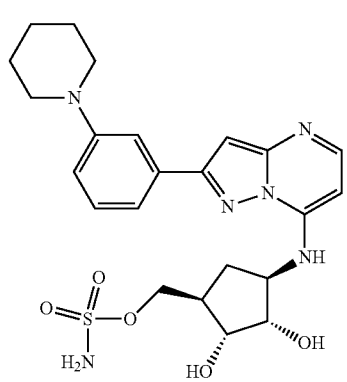 [SMILES: NS(=O)(=O)OC[C@H]1C[C@@H](Nc2ccnc3cc(-c4cccc(N5CCCCC5)c4)nn23)[C@H](O)[C@@H]1O]
I-077

I-078 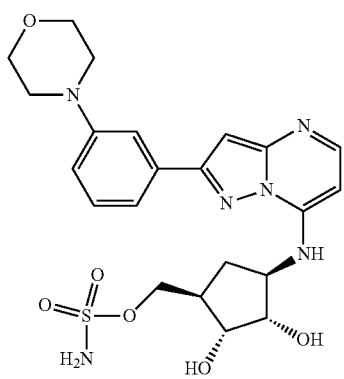 [SMILES: NS(=O)(=O)OC[C@H]1C[C@@H](Nc2ccnc3cc(-c4cccc(N5CCOCC5)c4)nn23)[C@H](O)[C@@H]1O]
I-079 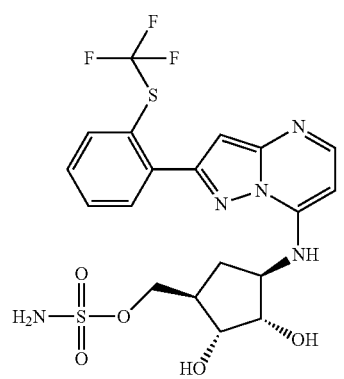 [SMILES: NS(=O)(=O)OC[C@H]1C[C@@H](Nc2ccnc3cc(-c4ccccc4SC(F)(F)F)nn23)[C@H](O)[C@@H]1O]
I-080 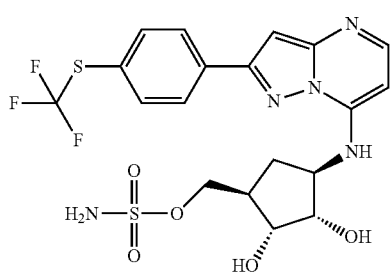 [SMILES: NS(=O)(=O)OC[C@H]1C[C@@H](Nc2ccnc3cc(-c4ccc(SC(F)(F)F)cc4)nn23)[C@H](O)[C@@H]1O]
I-081 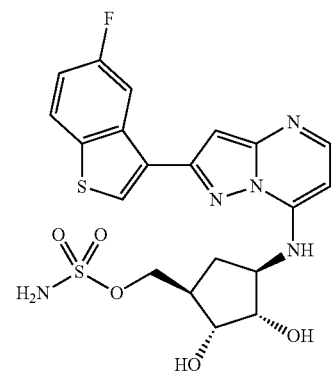 [SMILES: NS(=O)(=O)OC[C@H]1C[C@@H](Nc2ccnc3cc(-c4csc5ccc(F)cc45)nn23)[C@H](O)[C@@H]1O]
I-082 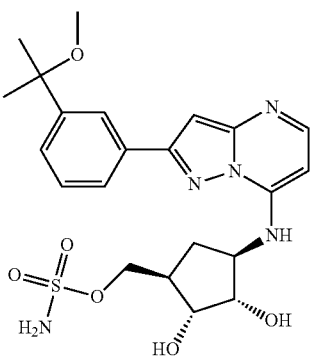 [SMILES: COC(C)(C)c1cccc(-c2cc3nccc(N[C@@H]4C[C@H](COS(N)(=O)=O)[C@@H](O)[C@H]4O)n3n2)c1]
I-083 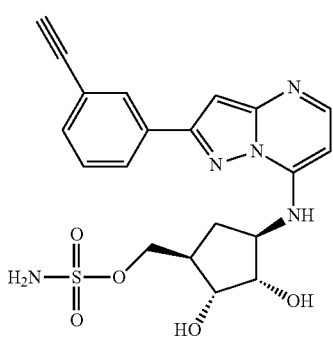 [SMILES: C#Cc1cccc(-c2cc3nccc(N[C@@H]4C[C@H](COS(N)(=O)=O)[C@@H](O)[C@H]4O)n3n2)c1]
I-084 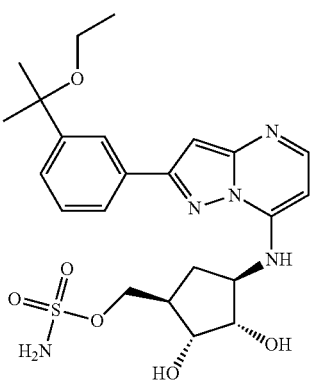 [SMILES: CCOC(C)(C)c1cccc(-c2cc3nccc(N[C@@H]4C[C@H](COS(N)(=O)=O)[C@@H](O)[C@H]4O)n3n2)c1]
I-085 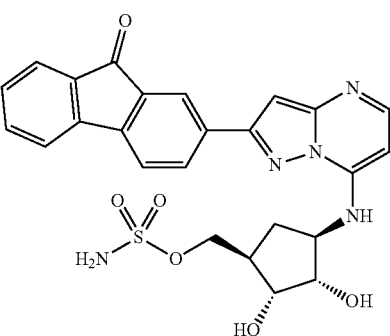 [SMILES: NS(=O)(=O)OC[C@H]1C[C@@H](Nc2ccnc3cc(-c4ccc5c(c4)C(=O)c4ccccc4-5)nn23)[C@H](O)[C@@H]1O]

-continued
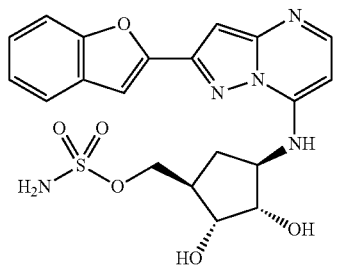 [SMILES: NS(=O)(=O)OC[C@H]1C[C@@H](Nc2ccnc3cc(-c4cc5ccccc5o4)nn23)[C@H](O)[C@@H]1O]
I-086
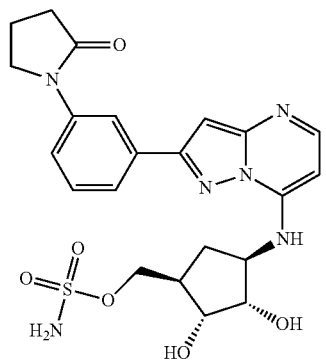 [SMILES: NS(=O)(=O)OC[C@H]1C[C@@H](Nc2ccnc3cc(-c4cccc(N5CCCC5=O)c4)nn23)[C@H](O)[C@@H]1O]
I-087
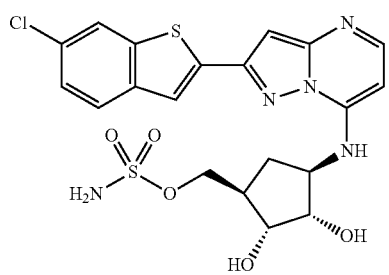 [SMILES: NS(=O)(=O)OC[C@H]1C[C@@H](Nc2ccnc3cc(-c4cc5ccc(Cl)cc5s4)nn23)[C@H](O)[C@@H]1O]
I-088
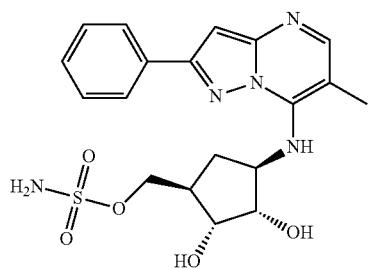 [SMILES: Cc1cnc2cc(-c3ccccc3)nn2c1N[C@@H]1C[C@H](COS(N)(=O)=O)[C@@H](O)[C@H]1O]
I-089
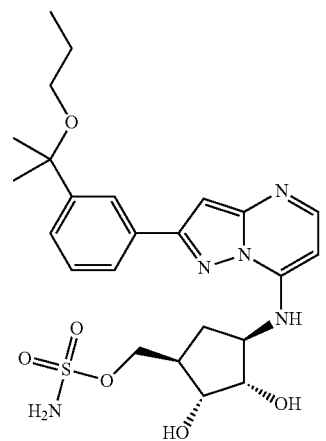 [SMILES: CCCOC(C)(C)c1cccc(-c2cc3nccc(N[C@@H]4C[C@H](COS(N)(=O)=O)[C@@H](O)[C@H]4O)n3n2)c1]
I-090
-continued
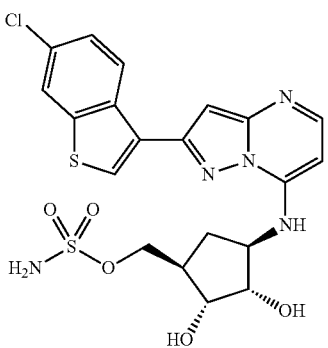 [SMILES: NS(=O)(=O)OC[C@H]1C[C@@H](Nc2ccnc3cc(-c4csc5cc(Cl)ccc45)nn23)[C@H](O)[C@@H]1O]
I-091
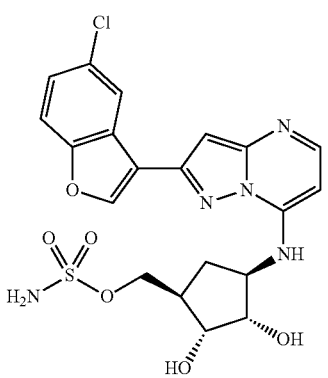
I-092
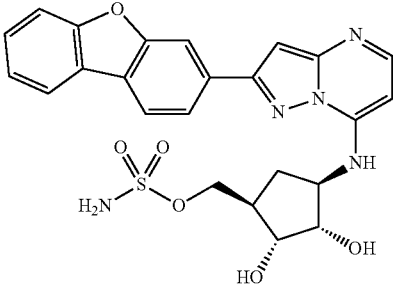 [SMILES: NS(=O)(=O)OC[C@H]1C[C@@H](Nc2ccnc3cc(-c4ccc5c(c4)oc4ccccc45)nn23)[C@H](O)[C@@H]1O]
I-093
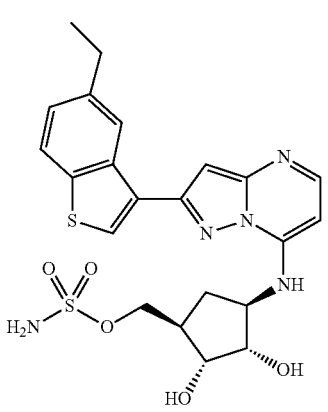 [SMILES: CCc1ccc2scc(-c3cc4nccc(N[C@@H]5C[C@H](COS(N)(=O)=O)[C@@H](O)[C@H]5O)n4n3)c2c1]
I-094

I-095 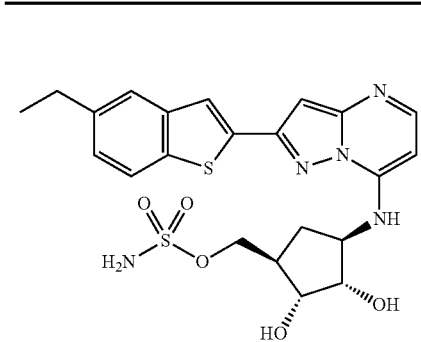
I-096 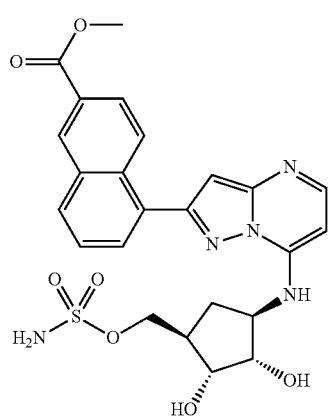 [SMILES: COC(=O)c1ccc2c(-c3cc4nccc(N[C@@H]5C[C@H](COS(N)(=O)=O)[C@@H](O)[C@H]5O)n4n3)cccc2c1]
I-097 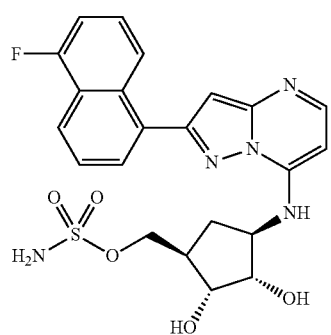 [SMILES: NS(=O)(=O)OC[C@H]1C[C@@H](Nc2ccnc3cc(-c4cccc5c(F)cccc45)nn23)[C@H](O)[C@@H]1O]
I-098 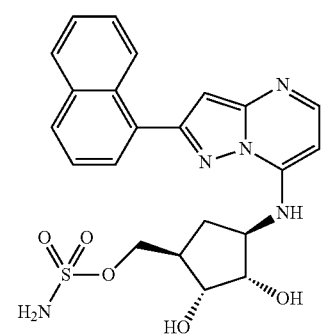 [SMILES: NS(=O)(=O)OC[C@H]1C[C@@H](Nc2ccnc3cc(-c4cccc5ccccc45)nn23)[C@H](O)[C@@H]1O]
I-099 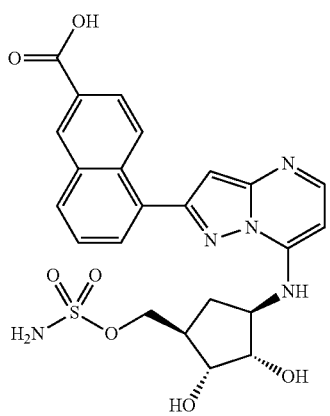
I-100 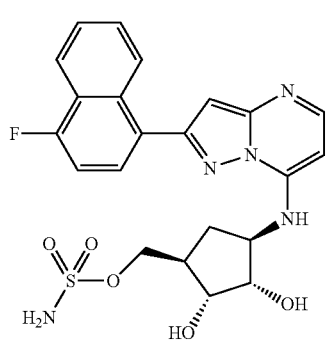 [SMILES: NS(=O)(=O)OC[C@H]1C[C@@H](Nc2ccnc3cc(-c4ccc(F)c5ccccc45)nn23)[C@H](O)[C@@H]1O]
I-101 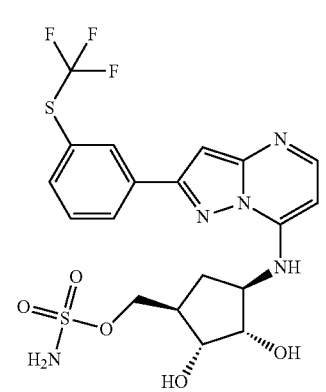
I-102 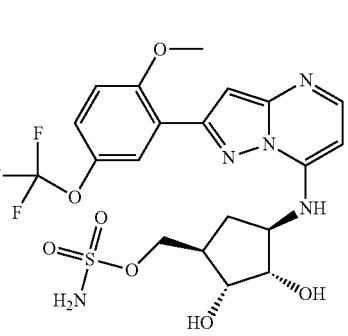

| | |
|---|---|
| I-103 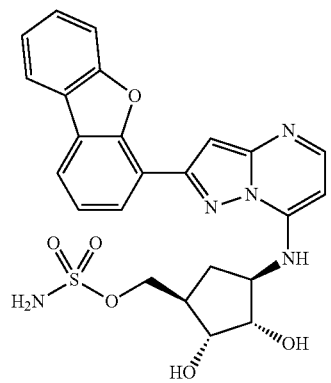 [SMILES: NS(=O)(=O)OC[C@H]1C[C@@H](Nc2ccnc3cc(-c4cccc5c4oc4ccccc45)nn23)[C@H](O)[C@@H]1O] | I-107 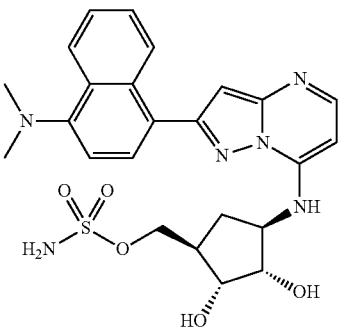 |
| I-104 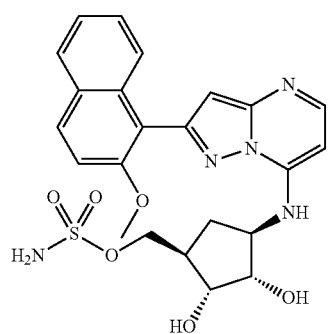 [SMILES: COc1ccc2ccccc2c1-c1cc2nccc(N[C@@H]3C[C@H](COS(N)(=O)=O)[C@@H](O)[C@H]3O)n2n1] | I-108 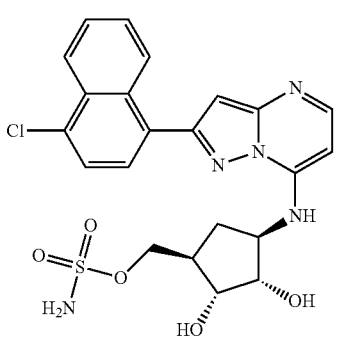 |
| I-105 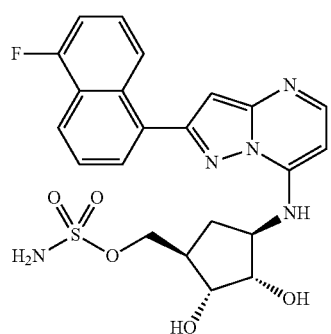 [SMILES: NS(=O)(=O)OC[C@H]1C[C@@H](Nc2ccnc3cc(-c4cccc5c(F)cccc45)nn23)[C@H](O)[C@@H]1O] | I-109 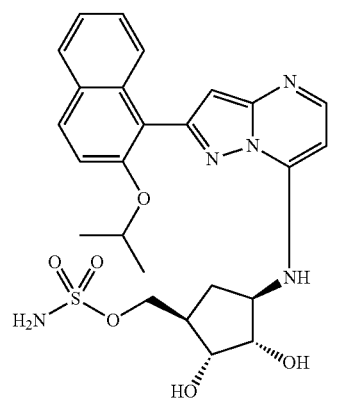 |
| I-106 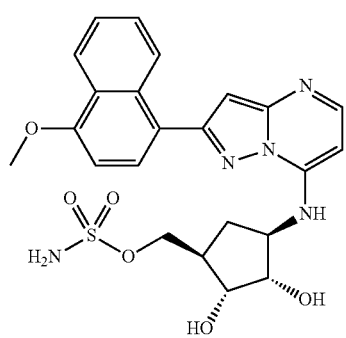 [SMILES: COc1ccc(-c2cc3nccc(N[C@@H]4C[C@H](COS(N)(=O)=O)[C@@H](O)[C@H]4O)n3n2)c2ccccc12] | I-110 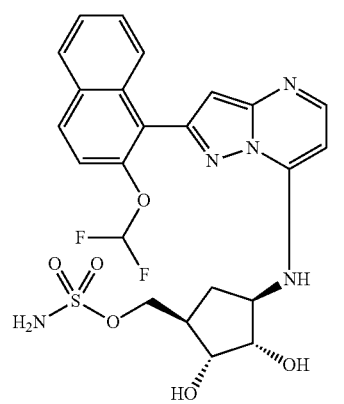 [SMILES: NS(=O)(=O)OC[C@H]1C[C@@H](Nc2ccnc3cc(-c4c(OC(F)F)ccc5ccccc45)nn23)[C@H](O)[C@@H]1O] |

I-111
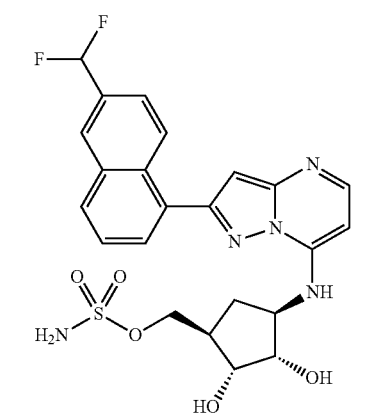 [SMILES: NS(=O)(=O)OC[C@H]1C[C@@H](Nc2ccnc3cc(-c4cccc5cc(C(F)F)ccc45)nn23)[C@H](O)[C@@H]1O]
I-112
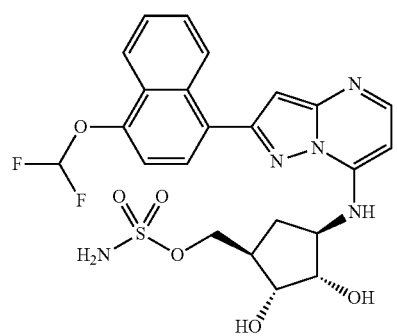 [SMILES: NS(=O)(=O)OC[C@H]1C[C@@H](Nc2ccnc3cc(-c4ccc(OC(F)F)c5ccccc45)nn23)[C@H](O)[C@@H]1O]
I-113
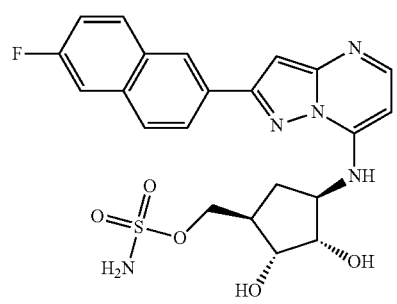 [SMILES: NS(=O)(=O)OC[C@H]1C[C@@H](Nc2ccnc3cc(-c4ccc5cc(F)ccc5c4)nn23)[C@H](O)[C@@H]1O]
I-114
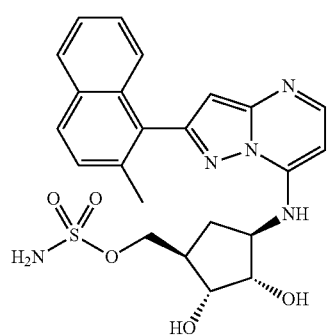 [SMILES: Cc1ccc2ccccc2c1-c1cc2nccc(N[C@@H]3C[C@H](COS(N)(=O)=O)[C@@H](O)[C@H]3O)n2n1]
I-115
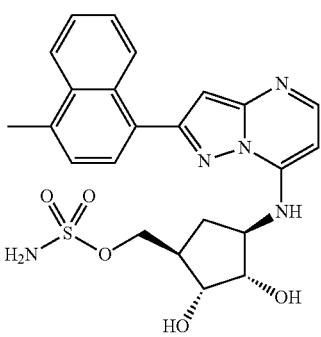 [SMILES: Cc1ccc(-c2cc3nccc(N[C@@H]4C[C@H](COS(N)(=O)=O)[C@@H](O)[C@H]4O)n3n2)c2ccccc12]
I-116
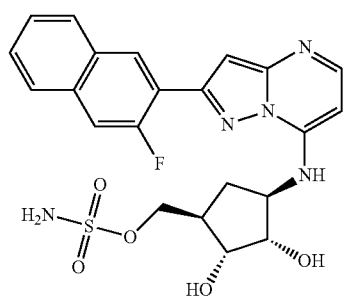 [SMILES: NS(=O)(=O)OC[C@H]1C[C@@H](Nc2ccnc3cc(-c4cc5ccccc5cc4F)nn23)[C@H](O)[C@@H]1O]
I-117
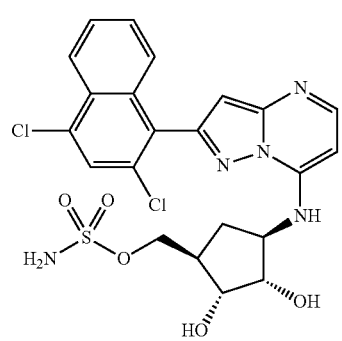 [SMILES: NS(=O)(=O)OC[C@H]1C[C@@H](Nc2ccnc3cc(-c4c(Cl)cc(Cl)c5ccccc45)nn23)[C@H](O)[C@@H]1O]
I-118
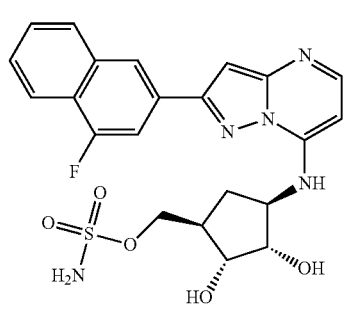 [SMILES: NS(=O)(=O)OC[C@H]1C[C@@H](Nc2ccnc3cc(-c4cc(F)c5ccccc5c4)nn23)[C@H](O)[C@@H]1O]
I-119
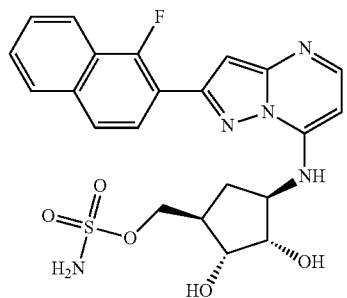 [SMILES: NS(=O)(=O)OC[C@H]1C[C@@H](Nc2ccnc3cc(-c4ccc5ccccc5c4F)nn23)[C@H](O)[C@@H]1O]

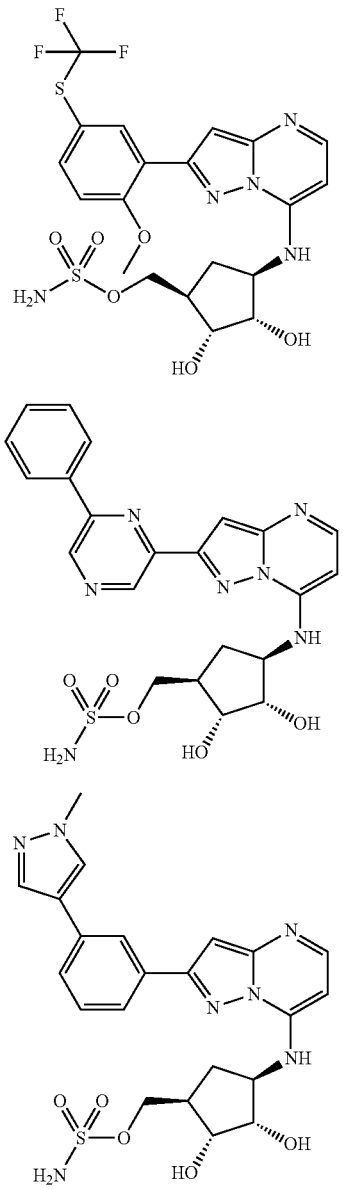

I-120

I-121

I-122

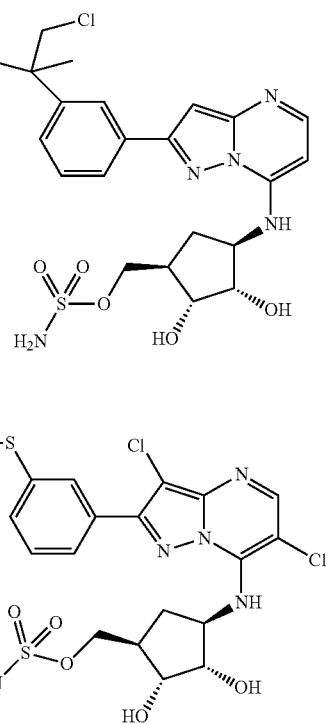

I-123

I-124

I-125

| cpd no. | compound name |
|---|---|
| I-001 | (rac)-((1R,2R,3S,4R)-2,3-dihydroxy-4-(2-phenylpyrazolo[1,5-a]pyrimidin-7-ylamino)cyclopentyl)methyl rel-sulfamate |
| I-002 | (rac)-((1R,2R,3S,4R)-2,3-dihydroxy-4-{[2-(1-naphthyl)pyrazolo[1,5-a]pyrimidin-7-yl]amino}cyclopentyl)methyl rel-sulfamate |
| I-003 | (rac)((1R,2R,3S,4R)-4-(2-(biphenyl-3-yl)pyrazolo[1,5-a]pyrimidin-7-ylamino)-2,3-dihydroxycyclopentyl)methyl rel-sulfamate |
| I-004 | (rac)-{(1R,2R,3S,4R)-2,3-dihydroxy-4-[(5-methyl-2-phenylpyrazolo[1,5-a]pyrimidin-7-yl)amino]cyclopentyl}methyl rel-sulfamate |
| I-005 | (rac)-((1R,2R,3S,4R)-4-((2-(3-Chlorophenyl)pyrazolo[1,5-a]pyrimidin-7-yl)amino)-2,3-dihydroxycyclopentyl)methyl rel-sulfamate |
| I-006 | (rac)-{(1R,2R,3S,4R)-4-[(5-chloro-2-phenylpyrazolo[1,5-a]pyrimidin-7-yl)amino]-2,3-dihydroxycyclopentyl}methyl rel-sulfamate |
| I-007 | (rac)-((1R,2R,3S,4R)-2,3-Dihydroxy-4-((2-(3-(trifluoromethyl)phenyl)pyrazolo[1,5-a]pyrimidin-7-yl)amino)cyclopentyl)methyl rel-sulfamate |
| I-008 | (rac)-((1R,2R,3S,4R)-4-(2-(4-bromophenyl)-5-chloropyrazolo[1,5-a]pyrimidin-7-ylamino)-2,3-dihydroxycyclopentyl)methyl rel-sulfamate |
| I-009 | (rac)-((1R,2R,3S,4R)-4-{[5-chloro-2-(1-naphthyl)pyrazolo[1,5-a]pyrimidin-7-yl]amino}-2,3-dihydroxycyclopentyl)methyl rel-sulfamate |

-continued

| cpd no. | compound name |
| --- | --- |
| I-010 | (rac)-((1R,2R,3S,4R)-4-(2-(dibenzo[b,d]furan-4-yl)pyrazolo[1,5-a]pyrimidin-7-ylamino)-2,3-dihydroxycyclopentyl)methyl rel-sulfamate |
| I-011 | (rac)-((1R,2R,3S,4R)-4-(5-chloro-2-(pyridin-2-yl)pyrazolo[1,5-a]pyrimidin-7-ylamino)-2,3-dihydroxycyclopentyl)methyl rel-sulfamate |
| I-012 | (rac)-[(1R,2R,3S,4R)-2,3-dihydroxy-4-{2-(pyridin-2-yl)pyrazolo[1,5-a]pyrimidin-7-yl]amino}cyclopentyl]methyl rel-sulfamate |
| I-013 | (rac)-[(1R,2R,3S,4R)-4-{[2-(2,4-dichlorophenyl)pyrazolo[1,5-a]pyrimidin-7-yl]amino}-2,3-dihydroxycyclopentyl]methyl rel-sulfamate |
| I-014 | (rac)-[(1R,2R,3S,4R)-4-{[5-chloro-2-(4-methoxyphenyl)pyrazolo[1,5-a]pyrimidin-7-yl]amino}-2,3-dihydroxycyclopentyl]methyl rel-sulfamate |
| I-015 | (rac)-((1R,2R,3S,4R)-4-((2-(3-(tert-Butyl)phenyl)pyrazolo[1,5-a]pyrimidin-7-yl)amino)-2,3-dihydroxycyclopentyl)methyl rel-sulfamate |
| I-016 | (rac)-((1R,2R,3S,4R)-2,3-dihydroxy-4-(2-(naphthalen-2-yl)pyrazolo[1,5-a]pyrimidin-7-ylamino)cyclopentyl)methyl rel-sulfamate |
| I-017 | (rac)-((1R,2R,3S,4R)-2,3-Dihydroxy-4-((2-(quinolin-8-yl)pyrazolo[1,5-a]pyrimidin-7-yl)amino)cyclopentyl)methyl rel-sulfamate |
| I-018 | (rac)-((1R,2R,3S,4R)-2,3-dihydroxy-4-(2-(isoquinolin-4-yl)pyrazolo[1,5-a]pyrimidin-7-ylamino)cyclopentyl)methyl rel-sulfamate |
| I-019 | (rac)-((1R,2R,3S,4R)-4-(2-(dibenzo[b,d]furan-2-yl)pyrazolo[1,5-a]pyrimidin-7-ylamino)-2,3-dihydroxycyclopentyl)methyl rel-sulfamate |
| I-020 | (rac)-((1R,2R,3S,4R)-4-(2-(5-chloro-2-methoxyphenyl)pyrazolo[1,5-a]pyrimidin-7-ylamino)-2,3-dihydroxycyclopentyl)methyl rel-sulfamate |
| I-021 | (rac)-((1R,2R,3S,4R)-4-(2-(5-chloro-2-methylphenyl)pyrazolo[1,5-a]pyrimidin-7-ylamino)-2,3-dihydroxycyclopentyl)methyl rel-sulfamate |
| I-022 | (rac)-((1R,2R,3S,4R)-4-(2-(benzo[b]thiophen-3-yl)pyrazolo[1,5-a]pyrimidin-7-ylamino)-2,3-dihydroxycyclopentyl)methyl rel-sulfamate |
| I-023 | (rac)-((1R,2R,3S,4R)-4-(2-(3,3-dimethyl-2,3-dihydrobenzofuran-7-yl)pyrazolo[1,5-a]pyrimidin-7-ylamino)-2,3-dihydroxycyclopentyl)methyl rel-sulfamate |
| I-024 | (rac)-((1R,2R,3S,4R)-4-(2-(1H-indol-2-yl)pyrazolo[1,5-a]pyrimidin-7-ylamino)-2,3-dihydroxycyclopentyl)methyl rel-sulfamate |
| I-025 | (rac)-((1R,2R,3S,4R)-2,3-dihydroxy-4-(2-(quinolin-3-yl)pyrazolo[1,5-a]pyrimidin-7-ylamino)cyclopentyl)methyl rel-sulfamate |
| I-026 | (rac)-((1R,2R,3S,4R)-4-(2-(3,3-dimethyl-2,3-dihydrobenzofuran-5-yl)pyrazolo[1,5-a]pyrimidin-7-ylamino)-2,3-dihydroxycyclopentyl)methyl rel-sulfamate |
| I-027 | (rac)-((1R,2R,3S,4R)-2,3-dihydroxy-4-(2-(isoquinolin-5-yl)pyrazolo[1,5-a]pyrimidin-7-ylamino)cyclopentyl)methyl rel-sulfamate |
| I-028 | (rac)-((1R,2R,3S,4R)-4-((2-(3-Bromophenyl)pyrazolo[1,5-a]pyrimidin-7-yl)amino)-2,3-dihydroxycyclopentyl)methyl rel-sulfamate |
| I-029 | (rac)-((1R,2R,3S,4R)-4-((2-(2-Fluoro-5-(trifluoromethyl)phenyl)pyrazolo[1,5-a]pyrimidin-7-yl)amino)-2,3-dihydroxycyclopentyl)methyl rel-sulfamate |
| I-030 | (rac)-((1R,2R,3S,4R)-4-((2-(2-Chloro-5-(trifluoromethyl)phenyl)pyrazolo[1,5-a]pyrimidin-7-yl)amino)-2,3-dihydroxycyclopentyl)methyl rel-sulfamate |
| I-031 | (rac)-[(1R,2R,3S,4R)-2,3-dihydroxy-4-{[2-(4-phenyl-1,3-thiazol-2-yl)pyrazolo[1,5-a]pyrimidin-7-yl]amino}cyclopentyl]methyl rel-sulfamate |
| I-032 | (rac)-[(1R,2R,3S,4R)-2,3-dihydroxy-4-{[2-(1H-indol-3-yl)pyrazolo[1,5-a]pyrimidin-7-yl]amino}cyclopentyl]methyl rel-sulfamate |
| I-033 | (rac)-((1R,2R,3S,4R)-2,3-dihydroxy-4-(2-(5-(trifluoromethyl)quinolin-8-yl)pyrazolo[1,5-a]pyrimidin-7-ylamino)cyclopentyl)methyl rel-sulfamate |
| I-034 | (rac)-((1R,2R,3S,4R)-2,3-dihydroxy-4-(2-(quinolin-6-yl)pyrazolo[1,5-a]pyrimidin-7-ylamino)cyclopentyl)methyl rel-sulfamate |
| I-035 | (rac)-((1R,2R,3S,4R)-2,3-dihydroxy-4-(2-(3-(trimethylsilyl)phenyl)pyrazolo[1,5-a]pyrimidin-7-ylamino)cyclopentyl)methyl rel-sulfamate |
| I-036 | (rac)-((1R,2R,3S,4R)-2,3-Dihydroxy-4-((2-(3-(pyridin-2-yl)phenyl)pyrazolo[1,5-a]pyrimidin-7-yl)amino)cyclopentyl)methyl rel-sulfamate |
| I-037 | (rac)-[(1R,2R,3S,4R)-4-{[2-(9H-carbazol-3-yl)pyrazolo[1,5-a]pyrimidin-7-yl]amino}-2,3-dihydroxycyclopentyl]methyl rel-sulfamate |
| I-038 | (rac)-[(1R,2R,3S,4R)-2,3-dihydroxy-4-{[2-(5-methyl-2-phenyl-1,3-thiazol-4-yl)pyrazolo[1,5-a]pyrimidin-7-yl]amino}cyclopentyl]methyl rel-sulfamate |
| I-039 | (rac)-((1R,2R,3S,4R)-4-(2-(7-chloroquinolin-4-yl)pyrazolo[1,5-a]pyrimidin-7-ylamino)-2,3-dihydroxycyclopentyl)methyl rel-sulfamate |
| I-040 | (rac)-((1R,2R,3S,4R)-2,3-Dihydroxy-4-((2-(3-(trifluoromethoxy)phenyl)pyrazolo[1,5-a]pyrimidin-7-yl)amino)cyclopentyl)methyl rel-sulfamate |
| I-041 | (rac)-((1R,2R,3S,4R)-4-(2-(3,3-dimethyl-2,3-dihydro-1H-inden-5-yl)pyrazolo[1,5-a]pyrimidin-7-ylamino)-2,3-dihydroxycyclopentyl)methyl rel-sulfamate |
| I-042 | (rac)-((1R,2R,3S,4R)-2,3-dihydroxy-4-(2-(quinolin-2-yl)pyrazolo[1,5-a]pyrimidin-7-ylamino)cyclopentyl)methyl rel-sulfamate |
| I-043 | (rac)-((1R,2R,3S,4R)-2,3-dihydroxy-4-(2-(quinolin-7-yl)pyrazolo[1,5-a]pyrimidin-7-ylamino)cyclopentyl)methyl rel-sulfamate |
| I-044 | (rac)-((1R,2R,3S,4R)-2,3-dihydroxy-4-(2-(3-(trifluoromethylthio)phenyl)pyrazolo[1,5-a]pyrimidin-7-ylamino)cyclopentyl)methyl rel-sulfamate |
| I-045 | (rac)-((1R,2R,3S,4R)-4-(2-(Benzo[b]thiophen-7-yl)pyrazolo[1,5-a]pyrimidin-7-yl)amino)-2,3-dihydroxycyclopentyl)methyl rel-sulfamate |
| I-046 | (rac)-((1R,2R,3S,4R)-2,3-dihydroxy-4-(2-(3-(pyrrolidin-1-yl)phenyl)pyrazolo[1,5-a]pyrimidin-7-ylamino)cyclopentyl)methyl rel-sulfamate |
| I-047 | (rac)-(1R,2R,3S,4R)-4-(2-(3-cyclopentenylphenyl)pyrazolo[1,5-a]pyrimidin-7-ylamino)-2,3-dihydroxycyclopentyl)methyl rel-sulfamate |

| cpd no. | compound name |
|---|---|
| I-048 | (rac)-[(1R,2R,3S,4R)-4-{[2-(3-cyclopentylphenyl)pyrazolo[1,5-a]pyrimidin-7-yl]amino}-2,3-dihydroxycyclopentyl]methyl rel-sulfamate |
| I-049 | (rac)-((1R,2R,3S,4R)-4-(2-(benzofuran-3-yl)pyrazolo[1,5-a]pyrimidin-7-ylamino)-2,3-dihydroxycyclopentyl)methyl rel-sulfamate |
| I-050 | (rac)-((1R,2R,3S,4R)-4-((2-(3-(Difluoromethoxy)phenyl)pyrazolo[1,5-a]pyrimidin-7-yl)amino)-2,3-dihydroxycyclopentyl)methyl rel-sulfamate |
| I-051 | (rac)-((1R,2R,3S,4R)-2,3-Dihydroxy-4-((2-(3-phenoxyphenyl)pyrazolo[1,5-a]pyrimidin-7-yl)amino)cyclopentyl)methyl rel-sulfamate |
| I-052 | (rac)-((1R,2R,3S,4R)-4-(2-(6-tert-butylpyridin-2-yl)pyrazolo[1,5-a]pyrimidin-7-ylamino)-2,3-dihydroxycyclopentyl)methyl rel-sulfamate |
| I-053 | (rac)-((1R,2R,3S,4R)-4-(2-(3,3-dimethyl-1,3-dihydroisobenzofuran-5-yl)pyrazolo[1,5-a]pyrimidin-7-ylamino)-2,3-dihydroxycyclopentyl)methyl rel-sulfamate |
| I-054 | (rac)-[(1R,2R,3S,4R)-4-{[2-(5-chloro-1H-indol-3-yl)pyrazolo[1,5-a]pyrimidin-7-yl]amino}-2,3-dihydroxycyclopentyl]methyl rel-sulfamate |
| I-055 | (rac)-[(1R,2R,3S,4R)-4-{[2-(6-chloro-1H-indol-3-yl)pyrazolo[1,5-a]pyrimidin-7-yl]amino}-2,3-dihydroxycyclopentyl]methyl rel-sulfamate |
| I-056 | (rac)-((1R,2R,3S,4R)-4-((2-(Dibenzo[b,d]thiophen-4-yl)pyrazolo[1,5-a]pyrimidin-7-yl)amino)-2,3-dihydroxycyclopentyl)methyl rel-sulfamate |
| I-057 | (rac)-((1R,2R,3S,4R)-4-(2-(5-chloro-2-(trifluoromethoxy)phenyl)pyrazolo[1,5-a]pyrimidin-7-ylamino)-2,3-dihydroxycyclopentyl)methyl rel-sulfamate |
| I-058 | (rac)-((1R,2R,3S,4R)-2,3-dihydroxy-4-(2-(3-(1,1,1-trifluoro-2-methylpropan-2-yl)phenyl)pyrazolo[1,5-a]pyrimidin-7-ylamino)cyclopentyl)methyl rel-sulfamate |
| I-059 | (rac)-((1R,2R,3S,4R)-2,3-dihydroxy-4-(2-(2-(trifluoromethyl)pyridin-4-yl)pyrazolo[1,5-a]pyrimidin-7-ylamino)cyclopentyl)methyl rel-sulfamate |
| I-060 | (rac)-((1R,2R,3S,4R)-2,3-Dihydroxy-4-((2-(5-(trifluoromethyl)thiophen-2-yl)pyrazolo[1,5-a]pyrimidin-7-yl)amino)cyclopentyl)methyl rel-sulfamate |
| I-061 | (rac)-((1R,2R,3S,4R)-4-((2-(Benzo[b]thiophen-4-yl)pyrazolo[1,5-a]pyrimidin-7-yl)amino)-2,3-dihydroxycyclopentyl)methyl rel-sulfamate |
| I-062 | (rac)-[(1R,2R,3S,4R)-4-{[2-(9H-carbazol-2-yl)pyrazolo[1,5-a]pyrimidin-7-yl]amino}-2,3-dihydroxycyclopentyl]methyl rel-sulfamate |
| I-063 | (rac)-((1R,2R,3S,4R)-4-{[2-(5-tert-butyl-2-methoxyphenyl)pyrazolo[1,5-a]pyrimidin-7-yl]amino}-2,3-dihydroxycyclopentyl)methyl rel-sulfamate |
| I-064 | (rac)-((1R,2R,3S,4R)-2,3-dihydroxy-4-(2-(6-(trifluoromethyl)pyridin-2-yl)pyrazolo[1,5-a]pyrimidin-7-ylamino)cyclopentyl)methyl rel-sulfamate |
| I-065 | (rac)-((1R,2R,3S,4R)-2,3-Dihydroxy-4-((2-(2-methoxy-5-(trifluoromethyl)phenyl)-pyrazolo[1,5-a]pyrimidin-7-yl)amino)cyclopentyl)methyl rel-sulfamate |
| I-066 | (rac)-((1R,2R,3S,4R)-2,3-Dihydroxy-4-((2-(2-methoxy-5-(trifluoromethoxy)-phenyl)pyrazolo[1,5-a]pyrimidin-7-yl)amino)cyclopentyl)methyl rel-sulfamate |
| I-067 | (rac)-[(1R,2R,3S,4R)-2,3-dihydroxy-4-{[2-(2-phenyl-1,3-oxazol-5-yl)pyrazolo[1,5-a]pyrimidin-7-yl]amino}cyclopentyl]methyl rel-sulfamate |
| I-068 | (rac)-((1R,2R,3S,4R)-2,3-dihydroxy-4-(2-(2-phenoxyphenyl)pyrazolo[1,5-a]pyrimidin-7-ylamino)cyclopentyl)methyl rel-sulfamate |
| I-069 | (rac)-((1R,2R,3S,4R)-4-(2-(3-benzylphenyl)pyrazolo[1,5-a]pyrimidin-7-ylamino)-2,3-dihydroxycyclopentyl)methyl rel-sulfamate |
| I-070 | (rac)-((1R,2R,3S,4R)-4-(2-(4-fluoro-2-methoxyphenyl)pyrazolo[1,5-a]pyrimidin-7-ylamino)-2,3-dihydroxycyclopentyl)methyl rel-sulfamate |
| I-071 | (rac)-((1R,2R,3S,4R)-4-(2-(5-chlorobenzo[b]thiophen-3-yl)pyrazolo[1,5-a]pyrimidin-7-ylamino)-2,3-dihydroxycyclopentyl)methyl rel-sulfamate |
| I-072 | (rac)-((1R,2R,3S,4R)-2,3-dihydroxy-4-(2-(2-methoxyphenyl)pyrazolo[1,5-a]pyrimidin-7-ylamino)cyclopentyl)methyl rel-sulfamate |
| I-073 | (rac)-((1R,2R,3S,4R)-4-(2-(3-benzoylphenyl)pyrazolo[1,5-a]pyrimidin-7-ylamino)-2,3-dihydroxycyclopentyl)methyl rel-sulfamate |
| I-074 | (rac)-[(1R,2R,3S,4R)-2,3-dihydroxy-4-{[2-(1H-indol-5-yl)pyrazolo[1,5-a]pyrimidin-7-yl]amino}cyclopentyl]methyl rel-sulfamate |
| I-075 | (rac)-((1R,2R,3S,4R)-4-(2-(1H-indol-4-yl)pyrazolo[1,5-a]pyrimidin-7-ylamino)-2,3-dihydroxycyclopentyl)methyl rel-sulfamate |
| I-076 | (rac)-((1R,2R,3S,4R)-4-(2-(3-(cyclopropylmethylthio)phenyl)pyrazolo[1,5-a]pyrimidin-7-ylamino)-2,3-dihydroxycyclopentyl)methyl rel-sulfamate |
| I-077 | (rac)-((1R,2R,3S,4R)-2,3-dihydroxy-4-(2-(3-(piperidin-1-yl)phenyl)pyrazolo[1,5-a]pyrimidin-7-ylamino)cyclopentyl)methyl rel-sulfamate |
| I-078 | (rac)-((1R,2R,3S,4R)-2,3-dihydroxy-4-(2-(3-morpholinophenyl)pyrazolo[1,5-a]pyrimidin-7-ylamino)cyclopentyl)methyl rel-sulfamate |
| I-079 | (rac)-((1R,2R,3S,4R)-2,3-dihydroxy-4-(2-(2-(trifluoromethylthio)phenyl)pyrazolo[1,5-a]pyrimidin-7-ylamino)cyclopentyl)methyl rel-sulfamate |
| I-080 | (rac)-((1R,2R,3S,4R)-2,3-dihydroxy-4-(2-(4-(trifluoromethylthio)phenyl)pyrazolo[1,5-a]pyrimidin-7-ylamino)cyclopentyl)methyl rel-sulfamate |
| I-081 | (rac)-((1R,2R,3S,4R)-4-(2-(5-fluorobenzo[b]thiophen-3-yl)pyrazolo[1,5-a]pyrimidin-7-ylamino)-2,3-dihydroxycyclopentyl)methyl rel-sulfamate |
| I-082 | (rac)-((1R,2R,3S,4R)-2,3-dihydroxy-4-(2-(3-(2-methoxypropan-2-yl)phenyl)pyrazolo[1,5-a]pyrimidin-7-ylamino)cyclopentyl)methyl rel-sulfamate |
| I-083 | (rac)-[(1R,2R,3S,4R)-4-{[2-(3-ethynylphenyl)pyrazolo[1,5-a]pyrimidin-7-yl]amino}-2,3-dihydroxycyclopentyl]methyl rel-sulfamate |
| I-084 | (rac)-((1R,2R,3S,4R)-4-(2-(3-(2-ethoxypropan-2-yl)phenyl)pyrazolo[1,5-a]pyrimidin-7-ylamino)-2,3-dihydroxycyclopentyl)methyl rel-sulfamate |
| I-085 | (rac)-((1R,2R,3S,4R)-2,3-dihydroxy-4-(2-(9-oxo-9H-fluoren-2-yl)pyrazolo[1,5-a]pyrimidin-7-ylamino)cyclopentyl)methyl rel-sulfamate |

-continued

| cpd no. | compound name |
|---|---|
| I-086 | (rac)-((1R,2R,3S,4R)-4-(2-(benzofuran-2-yl)pyrazolo[1,5-a]pyrimidin-7-ylamino)-2,3-dihydroxycyclopentyl)methyl rel-sulfamate |
| I-087 | (rac)-((1R,2R,3S,4R)-2,3-dihydroxy-4-(2-(3-(2-oxopyrrolidin-1-yl)phenyl)pyrazolo[1,5-a]pyrimidin-7-ylamino)cyclopentyl)methyl rel-sulfamate |
| I-088 | (rac)-((1R,2R,3S,4R)-4-(2-(6-chlorobenzo[b]thiophen-2-yl)pyrazolo[1,5-a]pyrimidin-7-ylamino)-2,3-dihydroxycyclopentyl)methyl rel-sulfamate |
| I-089 | (rac)-{(1R,2R,3S,4R)-2,3-dihydroxy-4-[(6-methyl-2-phenylpyrazolo[1,5-a]pyrimidin-7-yl)amino]cyclopentyl}methyl rel-sulfamate |
| I-090 | (rac)-((1R,2R,3S,4R)-2,3-dihydroxy-4-(2-(3-(2-propoxypropan-2-yl)phenyl)pyrazolo[1,5-a]pyrimidin-7-ylamino)cyclopentyl)methyl rel-sulfamate |
| I-091 | (rac)-((1R,2R,3S,4R)-4-(2-(6-chlorobenzo[b]thiophen-3-yl)pyrazolo[1,5-a]pyrimidin-7-ylamino)-2,3-dihydroxycyclopentyl)methyl rel-sulfamate |
| I-092 | (rac)-((1R,2R,3S,4R)-4-(2-(5-chlorobenzofuran-3-yl)pyrazolo[1,5-a]pyrimidin-7-ylamino)-2,3-dihydroxycyclopentyl)methyl rel-sulfamate |
| I-093 | (rac)-((1R,2R,3S,4R)-4-(2-(dibenzo[b,d]furan-3-yl)pyrazolo[1,5-a]pyrimidin-7-ylamino)-2,3-dihydroxycyclopentyl)methyl rel-sulfamate |
| I-094 | (rac)-((1R,2R,3S,4R)-4-(2-(5-ethylbenzo[b]thiophen-3-yl)pyrazolo[1,5-a]pyrimidin-7-ylamino)-2,3-dihydroxycyclopentyl)methyl rel-sulfamate |
| I-095 | (rac)-((1R,2R,3S,4R)-4-(2-(5-ethylbenzo[b]thiophen-2-yl)pyrazolo[1,5-a]pyrimidin-7-ylamino)-2,3-dihydroxycyclopentyl)methyl rel-sulfamate |
| I-096 | (rac)-methyl rel-5-[7-({(1R,2S,3R,4R)-2,3-dihydroxy-4-[(sulfamoyloxy)methyl]cyclopentyl}amino)pyrazolo[1,5-a]pyrimidin-2-yl]-2-naphthoate |
| I-097 | (rac)-((1R,2R,3S,4R)-4-(2-(5-fluoronaphthalen-1-yl)pyrazolo[1,5-a]pyrimidin-7-ylamino)-2,3-dihydroxycyclopentyl)methyl rel-sulfamate |
| I-098 | (s.e.)-((1R,2R,3S,4R)-2,3-dihydroxy-4-{[2-(1-naphthyl)pyrazolo[1,5-a]pyrimidin-7-yl]amino}cyclopentyl)methyl sulfamate |
| I-099 | (rac)-rel-5-[7-({(1R,2S,3R,4R)-2,3-dihydroxy-4-[(sulfamoyloxy)methyl]cyclopentyl}amino)pyrazolo[1,5-a]pyrimidin-2-yl]-2-naphthoic acid |
| I-100 | (s.e.)-((1R,2R,3S,4R)-4-(2-(4-fluoronaphthalen-1-yl)pyrazolo[1,5-a]pyrimidin-7-ylamino)-2,3-dihydroxycyclopentyl)methyl sulfamate |
| I-101 | (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate |
| I-102 | (s.e)-[(1R,2R,3S,4R)-2,3-dihydroxy-4-({2-[2-methoxy-5-(trifluoromethoxy)-phenyl]pyrazolo[1,5-a]pyrimidin-7-yl}amino)cyclopentyl]methyl sulfamate |
| I-103 | (rac)-((1R,2R,3S,4R)-4-(2-(dibenzo[b,d]furan-4-yl)pyrazolo[1,5-a]pyrimidin-7-ylamino)-2,3-dihydroxycyclopentyl)methyl rel-sulfamate |
| I-104 | (s.e.)-((1R,2R,3S,4R)-4-(2-(2-methoxynaphthalen-1-yl)pyrazolo[1,5-a]pyrimidin-7-ylamino)cyclopentyl)methyl sulfamate |
| I-105 | (s.e.)-((1R,2R,3S,4R)-4-(2-(5-fluoronaphthalen-1-yl)pyrazolo[1,5-a]pyrimidin-7-ylamino)-2,3-dihydroxycyclopentyl)methyl sulfamate |
| I-106 | (s.e.)-((1R,2R,3S,4R)-2,3-dihydroxy-4-(2-(4-methoxynaphthalen-1-yl)pyrazolo[1,5-a]pyrimidin-7-ylamino)cyclopentyl)methyl sulfamate |
| I-107 | (s.e.)-((1R,2R,3S,4R)-4-(2-(4-(dimethylamino)naphthalen-1-yl)pyrazolo[1,5-a]pyrimidin-7-ylamino)-2,3-dihydroxycyclopentyl)methyl sulfamate |
| I-108 | (s.e.)-[(1R,2R,3S,4R)-4-{[2-(4-chloro-1-naphthyl)pyrazolo[1,5-a]pyrimidin-7-yl]amino}-2,3-dihydroxycyclopentyl]methyl sulfamate |
| I-109 | (s.e.)-((1R,2R,3S,4R)-2,3-dihydroxy-4-(2-(2-isopropoxynaphthalen-1-yl)pyrazolo[1,5-a]pyrimidin-7-ylamino)cyclopentyl)methyl sulfamate |
| I-110 | (s.e.)-((1R,2R,3S,4R)-4-(2-(2-(difluoromethoxy)naphthalen-1-yl)pyrazolo[1,5-a]pyrimidin-7-ylamino)-2,3-dihydroxycyclopentyl)methyl sulfamate |
| I-111 | (s.e.)-((1R,2R,3S,4R)-4-(2-(6-(difluoromethyl)naphthalen-1-yl)pyrazolo[1,5-a]pyrimidin-7-ylamino)-2,3-dihydroxycyclopentyl)methyl sulfamate |
| I-112 | (s.e.)-((1R,2R,3S,4R)-4-(2-(4-(difluoromethoxy)naphthalen-1-yl)pyrazolo[1,5-a]pyrimidin-7-ylamino)-2,3-dihydroxycyclopentyl)methyl sulfamate |
| I-113 | (s.e.)-((1R,2R,3S,4R)-4-(2-(6-fluoronaphthalen-2-yl)pyrazolo[1,5-a]pyrimidin-7-ylamino)-2,3-dihydroxycyclopentyl)methyl sulfamate |
| I-114 | (s.e.)-((1R,2R,3S,4R)-2,3-dihydroxy-4-(2-(2-methylnaphthalen-1-yl)pyrazolo[1,5-a]pyrimidin-7-ylamino)cyclopentyl)methyl sulfamate |
| I-115 | (s.e.)-((1R,2R,3S,4R)-2,3-dihydroxy-4-(2-(4-methylnaphthalen-1-yl)pyrazolo[1,5-a]pyrimidin-7-ylamino)cyclopentyl)methyl sulfamate |
| I-116 | (s.e.)-((1R,2R,3S,4R)-4-(2-(3-fluoronaphthalen-2-yl)pyrazolo[1,5-a]pyrimidin-7-ylamino)-2,3-dihydroxycyclopentyl)methyl sulfamate |
| I-117 | (s.e.)-((1R,2R,3S,4R)-4-(2-(2,4-dichloronaphthalen-1-yl)pyrazolo[1,5-a]pyrimidin-7-ylamino)-2,3-dihydroxycyclopentyl)methyl sulfamate |
| I-118 | (s.e.)-((1R,2R,3S,4R)-4-(2-(4-fluoronaphthalen-2-yl)pyrazolo[1,5-a]pyrimidin-7-ylamino)-2,3-dihydroxycyclopentyl)methyl sulfamate |
| I-119 | (s.e.)-((1R,2R,3S,4R)-4-(2-(1-fluoronaphthalen-2-yl)pyrazolo[1,5-a]pyrimidin-7-ylamino)-2,3-dihydroxycyclopentyl)methyl sulfamate |
| I-120 | (s.e.)-((1R,2R,3S,4R)-2,3-dihydroxy-4-(2-(2-methoxy-5-(trifluoromethylthio)-phenyl)pyrazolo[1,5-a]pyrimidin-7-ylamino)cyclopentyl)methyl sulfamate |
| I-121 | (rac)-((1R,2R,3S,4R)-2,3-dihydroxy-4-{[2-(6-phenylpyrazin-2-yl)pyrazolo[1,5-a]pyrimidin-7-yl]amino}cyclopentyl)methyl rel-sulfamate |
| I-122 | (rac)-[(1R,2R,3S,4R)-2,3-dihydroxy-4-({2-[3-(1-methyl-1H-pyrazol-4-yl)phenyl]pyrazolo[1,5-a]pyrimidin-7-yl}amino)cyclopentyl]methyl rel-sulfamate |

-continued

| cpd no. | compound name |
|---|---|
| I-123 | (rac)-{(1R,2R,3S,4R)-4-[(2-{3-[2-chloro-1-(hydroxymethyl)-1-methylethyl]phenyl}pyrazolo[1,5-a]pyrimidin-7-yl)amino]-2,3-dihydroxycyclopentyl}methyl rel-sulfamate |
| I-124 | (s.e.)-{(1R,2R,3S,4R)-4-[(3,6-dichloro-2-{3-[(trifluoromethyl)sulfanyl]phenyl}pyrazolo[1,5-a]pyrimidin-7-yl)amino]-2,3-dihydroxycyclopentyl}methyl sulfamate |
| I-125 | (s.e.)-{(1R,2R,3S,4R)-4-[(6-chloro-2-{3-[(trifluoromethyl)sulfanyl]phenyl}pyrazolo[1,5-a]pyrimidin-7-yl)amino]-2,3-dihydroxycyclopentyl}methyl sulfamate |

General Synthetic Methods

These and other compounds of the chemical entities of the present invention can be prepared by methods known to one of ordinary skill in the art and/or by reference to the schemes shown below and/or by reference to the procedures described in the Examples below.

Examples 1a and 1b) is transformed to a compound of formula iii by coupling with a metal substituted compound Z-M via a palladium catalyzed reaction. A compound of formula iii can also be obtained by first transforming i to a metal substituted compound of formula ii using suitable boron or tin containing reagents, and then coupling with a Scheme 1: General route for 2-substituted ((1R,2R,3S,4R)-2,3-dihydroxy-4-(pyrazolo[1,5-a]pyrimidin-7-ylamino)cyclopentyl)methyl sulfamates

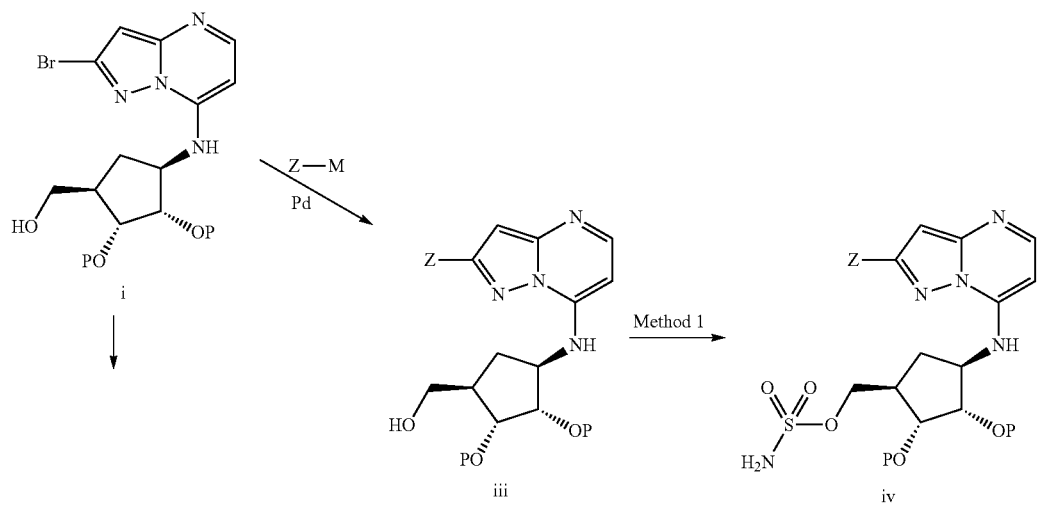

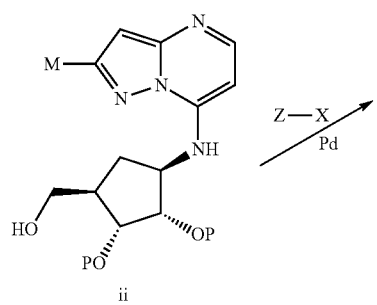

P = protecting group
M = metal

A general route for the synthesis of compounds represented by structure iv wherein Z is an optionally substituted fused or non-fused aryl or heteroaryl ring is outlined above in Scheme 1. Compound i (obtained by coupling an appropriately protected cyclopentylamine or salt thereof with 2-bromo-7-chloropyrazolo[1,5-a]pyrimidine in the presence of a suitable base as described below in the procedure of halogen substituted compound Z-X via a palladium catalyzed reaction. Compounds of formula iv are then obtained by reaction with an appropriate sulfamating reagent (for example chlorosulfonamide or see Armitage, I. et. al. U.S. Patent Application US2009/0036678, and Armitage, I. et. al. Org. Lett., 2012, 14 (10), 2626-2629) followed by appropriate deprotection conditions.

Scheme 2: General route for 5-halogen substituted, 2-substituted ((1R,2R,3S,4R)-2,3-dihydroxy-4-(pyrazolo[1,5-a]pyrimidin-7-ylamino)cyclopentyl)methyl sulfamates

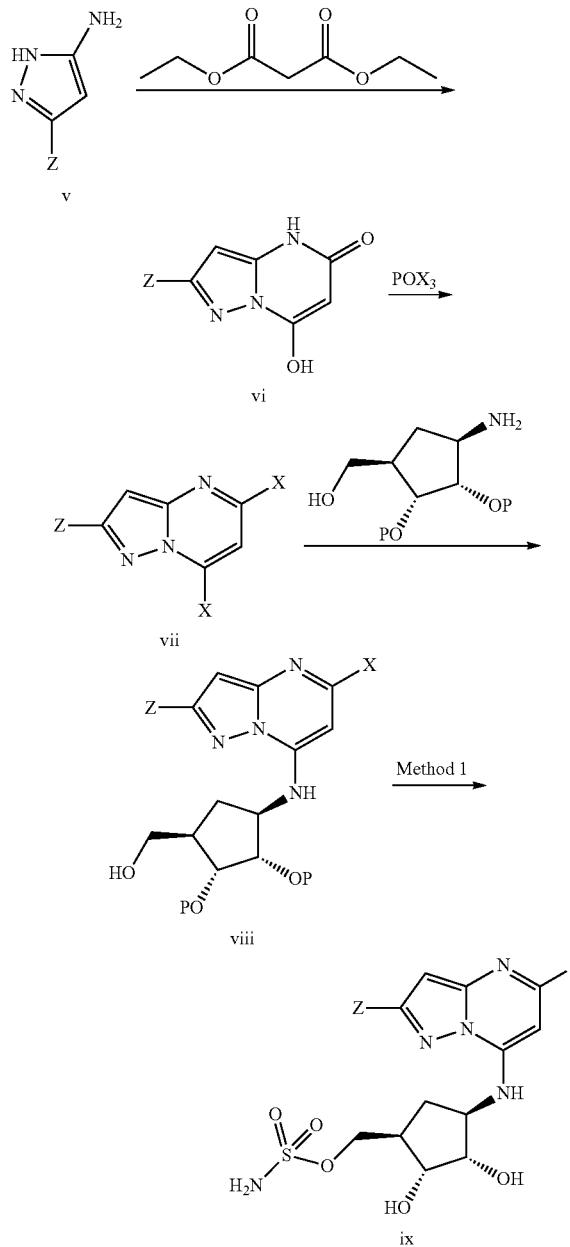

Scheme 3: General route for 5-alkyl substituted, 2-substituted ((1R,2R,3S,4R)-2,3-dihydroxy-4-(pyrazolo[1,5-a]pyrimidin-7-ylamino)cyclopentyl)methyl sulfamates

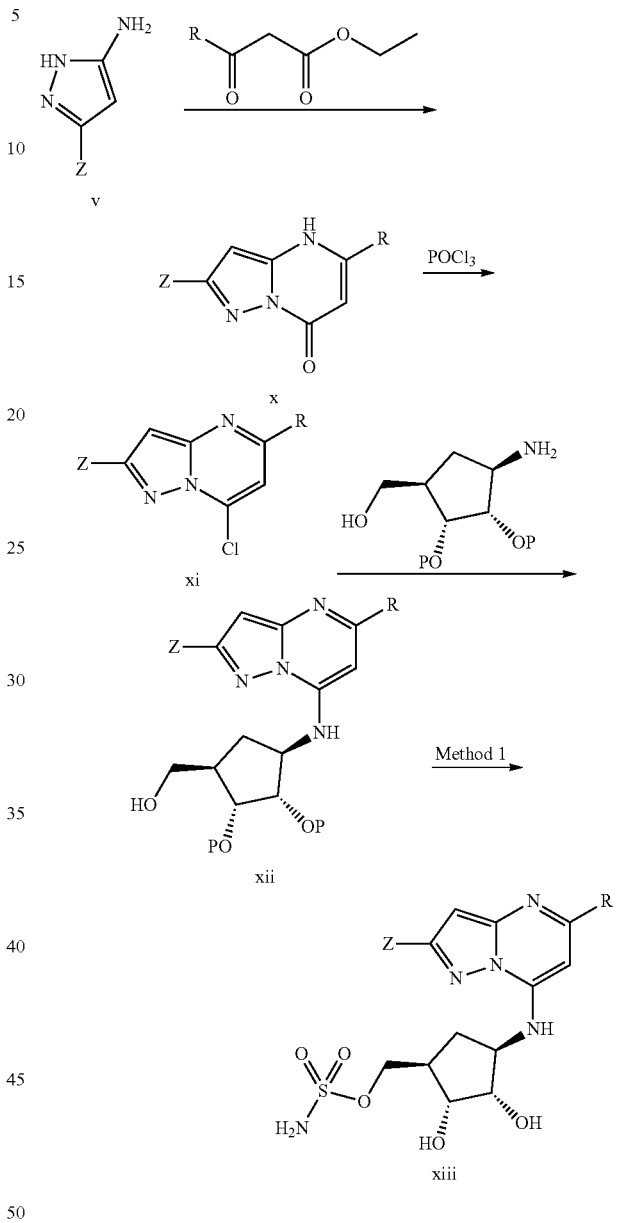

A general route for the synthesis of compounds represented by structure ix wherein Z is an optionally substituted fused or non-fused aryl or heteroaryl ring and X is a halogen is outlined above in Scheme 2. Cyclization of amino-pyrazole v with a suitable diester and an appropriate base at an elevated temperature is followed by reaction with an appropriate halogenating reagent such as $POCl_3$ at an elevated temperature to give compounds of formula vii. Compounds of formula viii are then obtained by reaction with an appropriately protected cyclopentylamine or a salt thereof in the presence of a suitable base. Sulfamation and deprotection following Method 1 as described previously provides compounds of formula ix.

A general route for the synthesis of compounds represented by structure xiii wherein Z is an optionally substituted fused or non-fused aryl or heteroaryl ring and R is an alkyl substituent is outlined above in Scheme 3. Cyclization of amino-pyrazole v with an appropriately substituted β-keto ester at an elevated temperature is followed by reaction with an appropriate halogenating reagent such as $POCl_3$ at an elevated temperature to give compounds of formula xi. Compounds of formula xii are then obtained by reaction with an appropriately protected cyclopentylamine or salt thereof in the presence of a suitable base. Sulfamation and deprotection following Method 1 as described previously provides compounds of the formula xiii.

Solid State Forms

Provided herein is an assortment of characterizing information, which is sufficient, but not all of which is necessary, to describe crystalline Form 1 anhydrous compound I-101 ((s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate ("Form 1")

FIG. 1 shows an X-ray powder diffraction (XRPD) pattern of Form 1 of compound I-101 obtained using CuKα radiation. Peaks identified in FIG. 1 include those listed in Table 1.

TABLE 1

| Angle 2-Theta ° | Intensity % |
| --- | --- |
| 13.6 | 32.4 |
| 14.8 | 57.8 |
| 15.2 | 14.2 |
| 16.4 | 64.8 |
| 17.6 | 20.1 |
| 18.0 | 74.6 |
| 19.1 | 57.0 |
| 19.4 | 24.6 |
| 20.5 | 95.0 |
| 20.7 | 100.0 |
| 21.3 | 42.7 |
| 21.6 | 23.7 |
| 22.4 | 24.9 |
| 23.6 | 54.7 |
| 23.9 | 24.3 |
| 24.6 | 43.3 |
| 27.5 | 27.4 |
| 28.0 | 17.1 |
| 28.6 | 18.1 |
| 29.3 | 25.7 |
| 31.8 | 31.6 |

In some embodiments, Form 1 is characterized by an XRPD pattern having a peak at 2θ angle 20.7°. In some embodiments, Form 1 is characterized by an XRPD pattern having peaks at 2θ angles of 20.5° and 20.7°. In some embodiments, Form 1 is characterized by an XRPD pattern having peaks at 2θ angles of 16.4°, 18.0°, 20.5° and 20.7°. In some embodiments, Form 1 is characterized by an XRPD pattern having peaks at 2θ angles of 14.8°, 16.4°, 18.0°, 19.1°, 20.5°, 20.7° and 23.6°. In some embodiments, Form 1 is characterized by an XRPD pattern having peaks at 2θ angles of 13.6°, 14.8°, 16.4°, 18.0°, 19.1°, 20.5°, 20.7°, 21.3°, 23.6°, 24.6° and 31.8°. In some embodiments, Form 1 is characterized by an XRPD pattern substantially as shown in FIG. 1.

In some embodiments, Form 1 is characterized by an XRPD pattern having a reference peak with a 2θ angle of 16.4±0.3°, and having peaks at 2θ angles of 1.6°, 4.1° and 4.3° relative to the reference peak. The term "reference peak" refers to a peak in the XRPD diffractogram that one skilled in the art considers as informing the polymorphic form of the material, i.e., differentiated from instrument noise. By "relative" it is meant that the observed 2θ angle of each peak will be the sum of the 2θ angle of the reference peak and the relative 2θ angle of that peak. For example, if the reference peak has a 2θ angle of 16.3°, the relative peaks will have 2θ angles of 17.9°, 20.4° and 20.6°; if the reference peak has a 2θ angle of 16.4°, the relative peaks will have 2θ angles of 18.0°, 20.5° and 20.7°; if the reference peak has a 2θ angle of 16.5°, the relative peaks will have 2θ angles of 18.1°, 20.6° and 20.8°; etc. In some embodiments, Form 1 is characterized by an XRPD pattern having a reference peak with a 2θ angle of 16.4±0.3°, and having peaks at 2θ angles of −1.6°, 1.6°, 2.7°, 4.1°, 4.3° and 7.2° relative to the reference peak. In some embodiments, Form 1 is characterized by an XRPD pattern having a reference peak with a 2θ angle of 16.4±0.3°, and having peaks at 2θ angles of −2.8°, −1.6°, 1.6°, 2.7°, 4.1°, 4.3°, 4.9°, 7.2°, 8.2° and 15.4° relative to the reference peak. Any of the peaks that one skilled in the art considers as informing the polymorphic form of the material can serve as the reference peak and the relative peaks can then be calculated. For example, if the reference peak has a 2θ angle of 20.7°, then the relative peaks will have 2θ angles of −4.3°, −2.7° and −0.2° relative to the reference peak.

Figure 2:
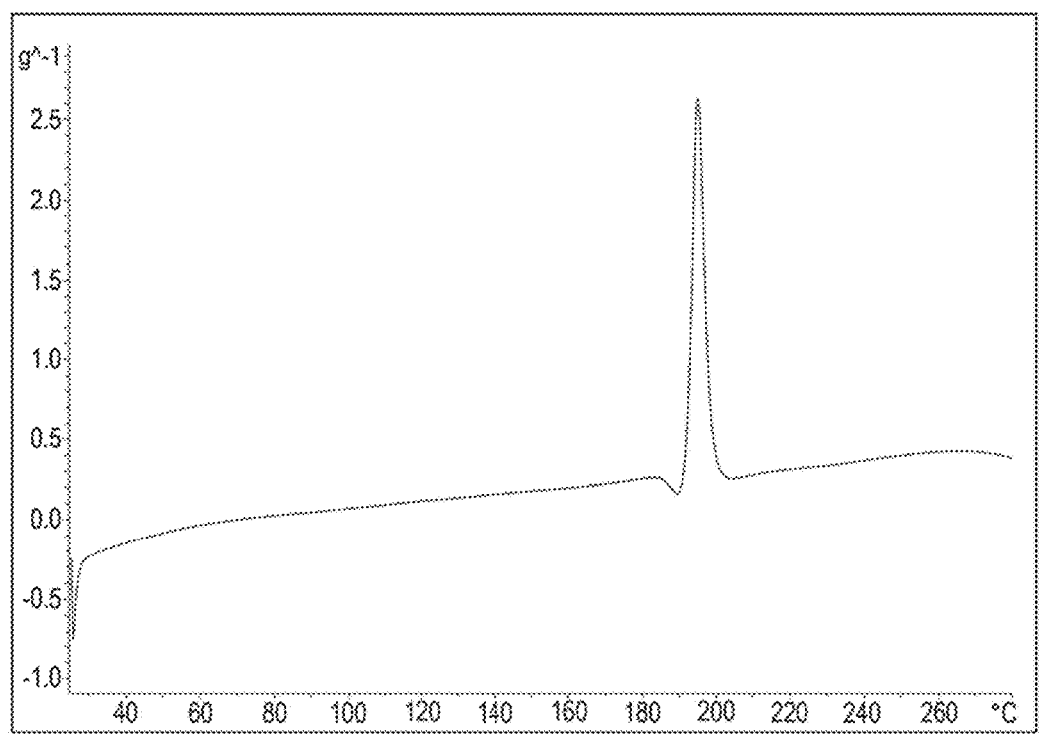
FIG. 2 shows a differential scanning calorimetry (DSC) thermogram for crystalline Form 1 anhydrous (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl) methyl sulfamate.

FIG. 2 shows a differential scanning calorimetry (DSC) profile of Form 1 of compound I-101. The DSC thermogram plots the heat flow as a function of temperature from a sample, the temperature rate change being about 10° C./min. In some embodiments, Form 1 is characterized by a DSC profile substantially as shown in FIG. 2. FIG. 2 shows an exotherm event with onset of about 192.3° C. and peak at about 195.3° C.

Figure 3:
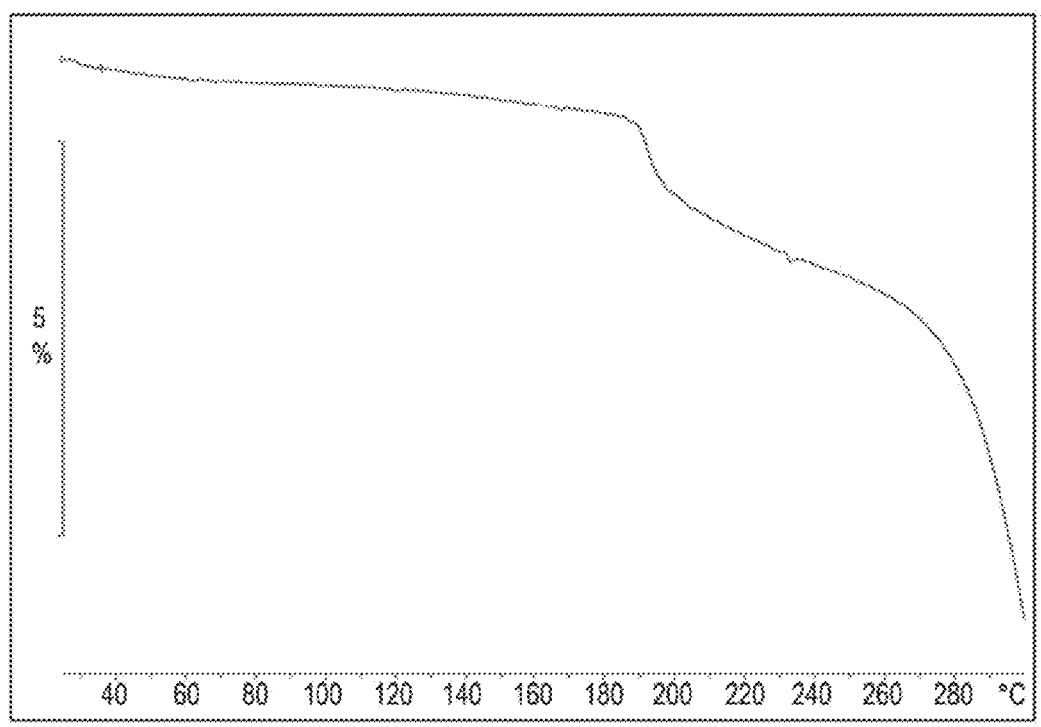
FIG. 3 shows a thermogravimetric analysis (TGA) thermogram for crystalline Form 1 anhydrous (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.

FIG. 3 shows a thermal gravimetric analysis (TGA) profile of Form 1 of compound I-101. The TGA thermogram plots the percent loss of weight of the sample as a function of temperature, the temperature rate change being about 10° C./min. FIG. 3 shows approximately 0.4% weight loss to 120° C. In some embodiments, Form 1 is characterized by a TGA profile substantially as shown in FIG. 3. Karl Fischer measurements of Form 1 show a water content of about 0.7%.

Figure 4:
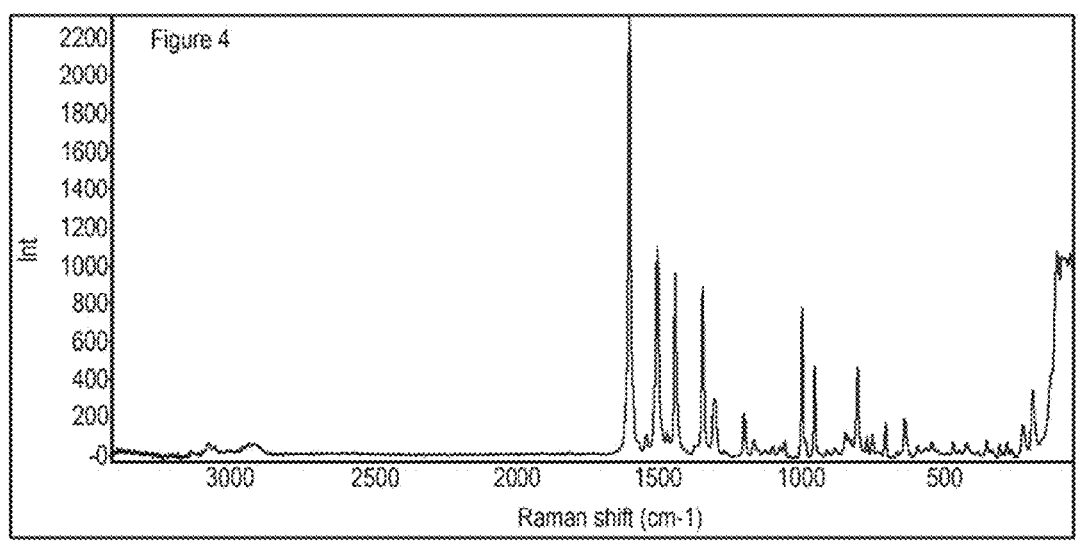
FIG. 4 shows a raman pattern for crystalline Form 1 anhydrous (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.
Figures 5A, 5B:
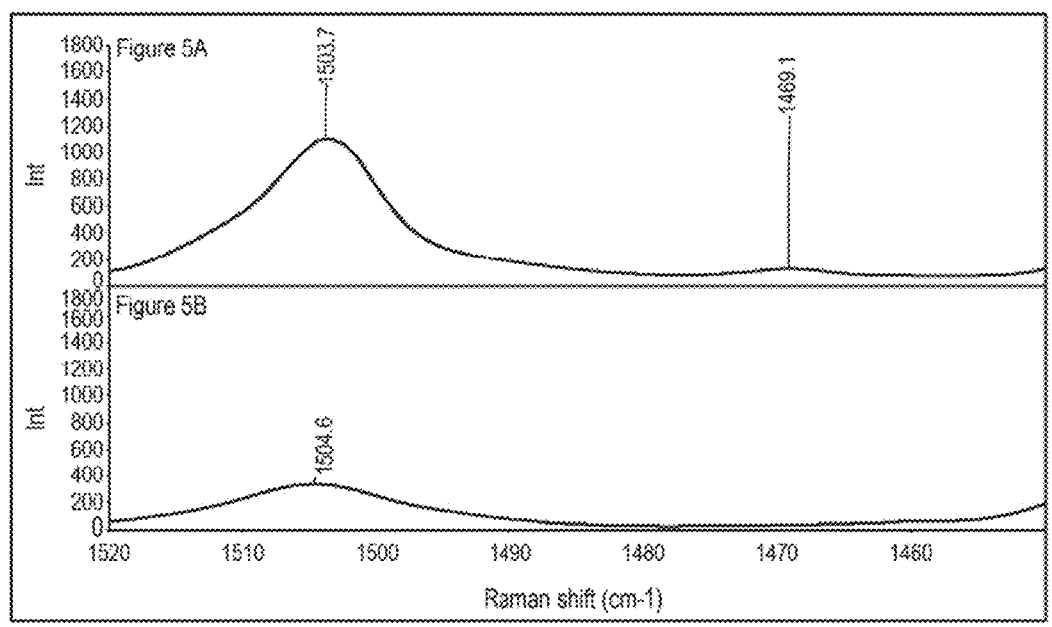
FIG. 5A shows a raman pattern in the region of 1450 cm$^{-1}$ to 1520 cm$^{-1}$ for crystalline Form 1 anhydrous (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.
FIG. 5B shows a raman pattern in the region of 1450 cm$^{-1}$ to 1520 cm$^{-1}$ for crystalline Form 2 monohydrated (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.
Figures 6A, 6B:
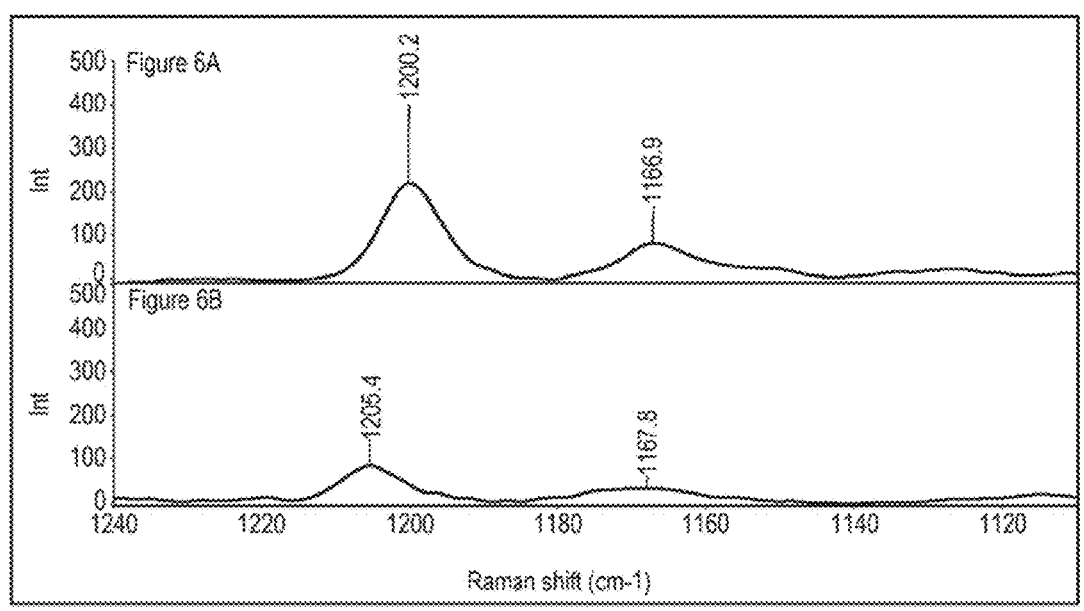
FIG. 6A shows a raman pattern in the region of 1100 cm$^{-1}$ to 1240 cm$^{-1}$ for crystalline Form 1 anhydrous (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl) methyl sulfamate.
FIG. 6B shows a raman pattern in the region of 1100 cm$^{-1}$ to 1240 cm$^{-1}$ for crystalline Form 2 monohydrated (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.
Figures 7A, 7B:
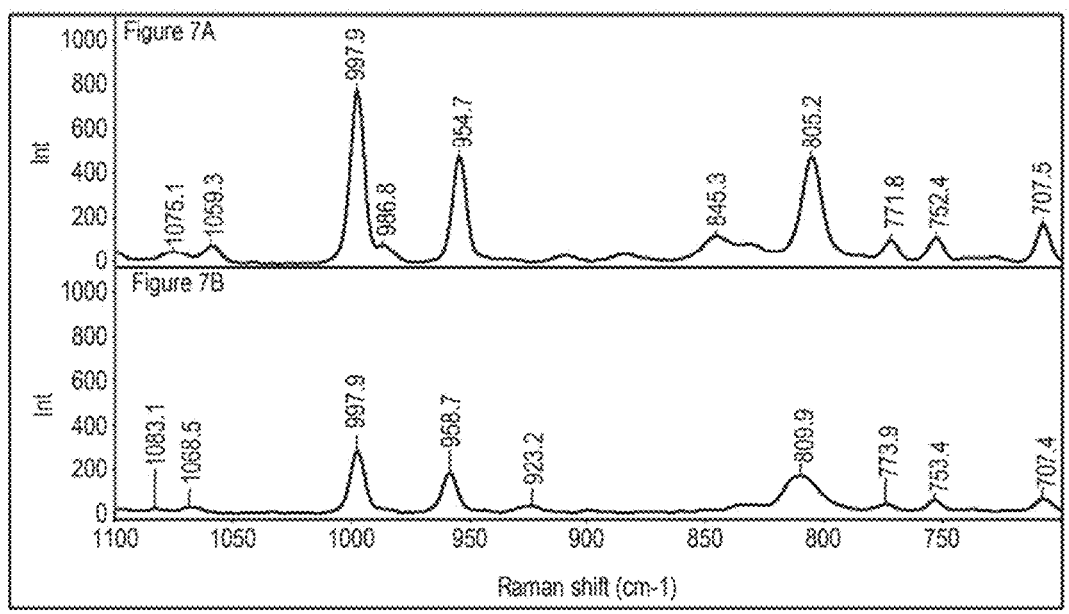
FIG. 7A shows a raman pattern in the region of about 700 cm$^{-1}$ to about 1100 cm$^{-1}$ for crystalline Form 1 anhydrous (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.
FIG. 7B shows a raman pattern in the region of about 700 cm$^{-1}$ to about 1100 cm$^{-1}$ for crystalline Form 2 monohydrated (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.

FIG. 4 shows a raman pattern of Form 1 of compound I-101. In some embodiments, Form 1 is characterized by a raman pattern substantially as shown in FIG. 4. Peaks identified in FIG. 4 in the region of 55 cm$^{-1}$ to 1800 cm$^{-1}$ include those listed in Table 2 below. FIG. 5A shows a raman pattern of Form 1 of compound I-101 in the region of 1450 cm$^{-1}$ to 1520 cm$^{-1}$. In some embodiments, Form 1 is characterized by a peak at 1469.1 cm$^{-1}$. FIG. 6A shows a raman pattern of Form 1 of compound I-101 in the region of 1100 cm$^{-1}$ to 1240 cm$^{-1}$. In some embodiments, Form 1 is characterized by a raman pattern substantially as shown in FIG. 6A. In some embodiments, Form 1 is characterized by a peak at 1200.2 cm$^{-1}$. FIG. 7A shows a raman pattern of Form 1 of compound I-101 in the region of about 700 cm$^{-1}$ to about 1100 cm$^{-1}$. In some embodiments, Form 1 is characterized by a raman pattern substantially as shown in FIG. 7A. In some embodiments, Form 1 is characterized by peaks at 1059.3, 954.7, 845.3 and 805.2 cm$^{-1}$. In some embodiments, Form 1 is characterized by peaks at 954.7 and 805.2 cm$^{-1}$.

TABLE 2

| Peak (cm$^{-1}$) | Intensity |
| --- | --- |
| 62.7 | 1057.18 |
| 93.4 | 1047.64 |
| 109.8 | 1069.98 |
| 193.2 | 340.36 |
| 226.8 | 158.25 |
| 266.3 | 26.10 |
| 283.1 | 65.41 |
| 308.3 | 51.53 |
| 353.1 | 71.31 |
| 425.3 | 61.00 |
| 469.9 | 65.13 |
| 545.2 | 64.03 |
| 595.1 | 45.09 |
| 639.9 | 188.46 |
| 707.5 | 166.50 |
| 752.4 | 105.67 |
| 771.8 | 92.90 |
| 805.2 | 466.55 |
| 845.3 | 113.29 |

TABLE 2-continued

| Peak (cm$^{-1}$) | Intensity |
|---|---|
| 954.7 | 466.61 |
| 986.8 | 70.99 |
| 997.9 | 775.23 |
| 1059.3 | 66.37 |
| 1075.1 | 34.74 |
| 1101.2 | 38.50 |
| 1166.9 | 76.42 |
| 1200.2 | 218.72 |
| 1302.3 | 295.74 |
| 1345.0 | 886.09 |
| 1440.9 | 957.45 |
| 1469.1 | 116.07 |
| 1503.7 | 1098.73 |
| 1541.6 | 98.76 |
| 1601.4 | 2315.65 |

In some embodiments, Form 1 of compound I-101 is characterized by at least one of the following features (I-i)-(I-iv):
(I-i) an XRPD pattern having peaks at 2θ angles of 16.4°, 18.0°, 20.5°, and 20.7° as shown in FIG. 1;
(I-ii) a DSC profile substantially as shown in FIG. 2;
(I-iii) a TGA profile substantially as shown in FIG. 3.
(I-iv) a raman pattern substantially as shown in FIG. 4.

In some embodiments, Form 1 is characterized by at least two of the features (I-i)-(I-iv). In some embodiments, Form 1 is characterized by at least three of the features (I-i)-(I-iv). In some embodiments, Form 1 is characterized by all four of the features (I-i)-(I-iv).

Provided herein is an assortment of characterizing information, which is sufficient, but not all of which is necessary, to describe crystalline Form 2 monohydrated compound I-101 ((s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate ("Form 2").

Figure 8:
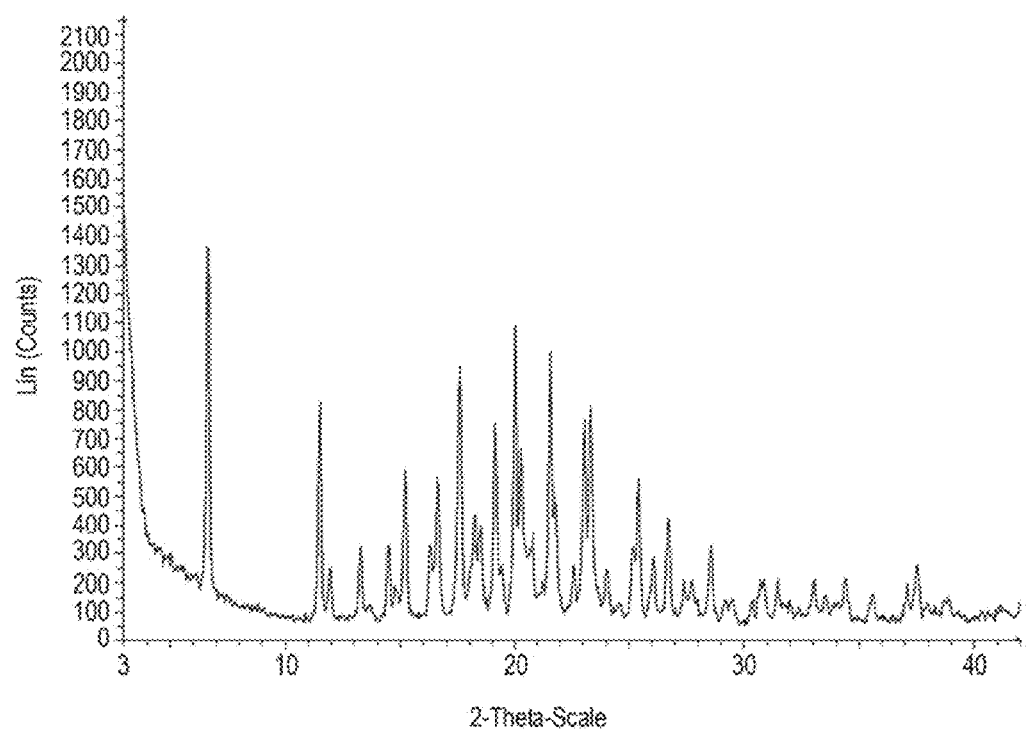
FIG. 8 shows an x-ray powder diffraction (XRPD) pattern for crystalline Form 2 monohydrated (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.

FIG. 8 shows an X-ray powder diffraction (XRPD) pattern of crystalline Form 2 monohydrated compound I-101 obtained using CuKα radiation. Peaks identified in FIG. 8 include those listed in Table 3.

TABLE 3

| Angle 2-Theta ° | Intensity % |
|---|---|
| 6.7 | 100 |
| 11.5 | 61.6 |
| 12.0 | 18.7 |
| 13.3 | 24.4 |
| 13.7 | 10.1 |
| 14.5 | 24.8 |
| 14.8 | 15.0 |
| 15.2 | 44.3 |
| 16.3 | 24.8 |
| 16.6 | 42.2 |
| 17.6 | 69.6 |
| 18.2 | 32.6 |
| 18.5 | 29.5 |
| 19.1 | 55.5 |
| 19.4 | 19.9 |
| 20.0 | 80.3 |
| 20.3 | 48.7 |
| 20.8 | 28.6 |
| 21.2 | 15.7 |
| 21.6 | 73.8 |
| 21.8 | 37.2 |
| 22.6 | 19.7 |
| 23.1 | 56.7 |
| 23.3 | 59.7 |
| 24.0 | 18.7 |
| 24.6 | 10.8 |

TABLE 3-continued

| Angle 2-Theta ° | Intensity % |
|---|---|
| 25.2 | 24.1 |
| 25.4 | 41.9 |
| 26.1 | 21.5 |
| 26.8 | 31.4 |
| 27.4 | 15.9 |
| 27.8 | 16.4 |
| 28.6 | 24.8 |
| 29.2 | 11.5 |
| 29.6 | 11.5 |
| 30.4 | 11.2 |
| 30.8 | 16.2 |
| 31.5 | 16.6 |
| 33.1 | 16.2 |
| 34.4 | 16.2 |
| 35.6 | 12.6 |
| 37.1 | 15.5 |
| 37.6 | 20.4 |

In some embodiments, Form 2 is characterized by an XRPD pattern having peaks at 2θ angles of 6.7°, 17.6°, 20.0° and 21.6°. In some embodiments, Form 2 is characterized by an XRPD pattern having peaks at 2θ angles of 6.7°, 11.5°, 17.6°, 19.1°, 20.0°, 21.6°, 23.1° and 23.3°. In some embodiments, Form 2 is characterized by an XRPD pattern having peaks at 2θ angles of 6.7°, 11.5°, 15.2°, 16.6°, 17.6°, 19.1°, 20.0°, 20.3°, 21.6°, 23.1°, 23.3° and 25.4°. In some embodiments, Form 2 is characterized by an XRPD pattern substantially as shown in FIG. 8.

In some embodiments, Form 2 is characterized by an XRPD pattern having a reference peak with a 2θ angle of 6.7±0.3°, and having peaks at 2θ angles of 10.9°, 13.3° and 14.9° relative to the reference peak. The terms "reference peak" and "relative" have the same meaning as previously described. In some embodiments, Form 2 is characterized by an XRPD pattern having a reference peak with a 2θ angle of 6.7±0.3°, and having peaks at 2θ angles of 4.8°, 10.9°, 12.4°, 13.3°, 14.9°, 16.4° and 16.6°, relative to the reference peak. In some embodiments, Form 2 is characterized by an XRPD pattern having a reference peak with a 2θ angle of 2θ angle of 6.7±0.3°, and having peaks at 2θ angles of 4.8°, 8.5°, 9.9°, 10.9°, 12.4°, 13.3°, 13.6°, 14.9°, 16.4°, 16.6° and 18.7°, relative to the reference peak. Any of the peaks that one skilled in the art considers as informing the polymorphic form of the material can serve as the reference peak and the relative peaks can then be calculated. For example, if the reference peak has a 2θ angle of 20.0°, then the relative peaks will have 2θ angles of −13.3°, −2.4° and 1.6° relative to the reference peak.

Figure 9:
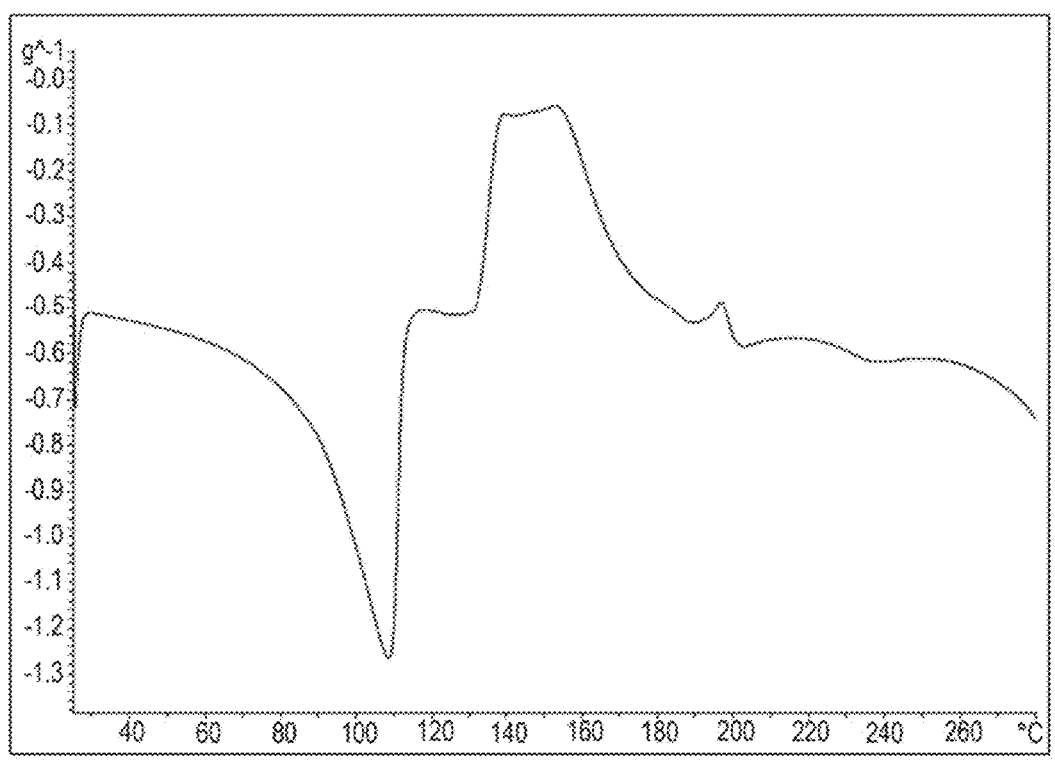
FIG. 9 shows a differential scanning calorimetry (DSC) thermogram for crystalline Form 2 monohydrated (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.

FIG. 9 shows a differential scanning calorimetry (DSC) profile of Form 2 of compound I-101. The DSC thermogram plots the heat flow as a function of temperature from a sample, the temperature rate change being about 10° C./min. In some embodiments, Form 2 is characterized by a DSC profile substantially as shown in FIG. 9. FIG. 9 shows an endotherm with onset of about 81.2° C. and a peak at about 108.3° C. corresponding to a loss of water followed by an exotherm with an onset of about 151.1° C. and peak at about 153.2° C.

Figure 10:
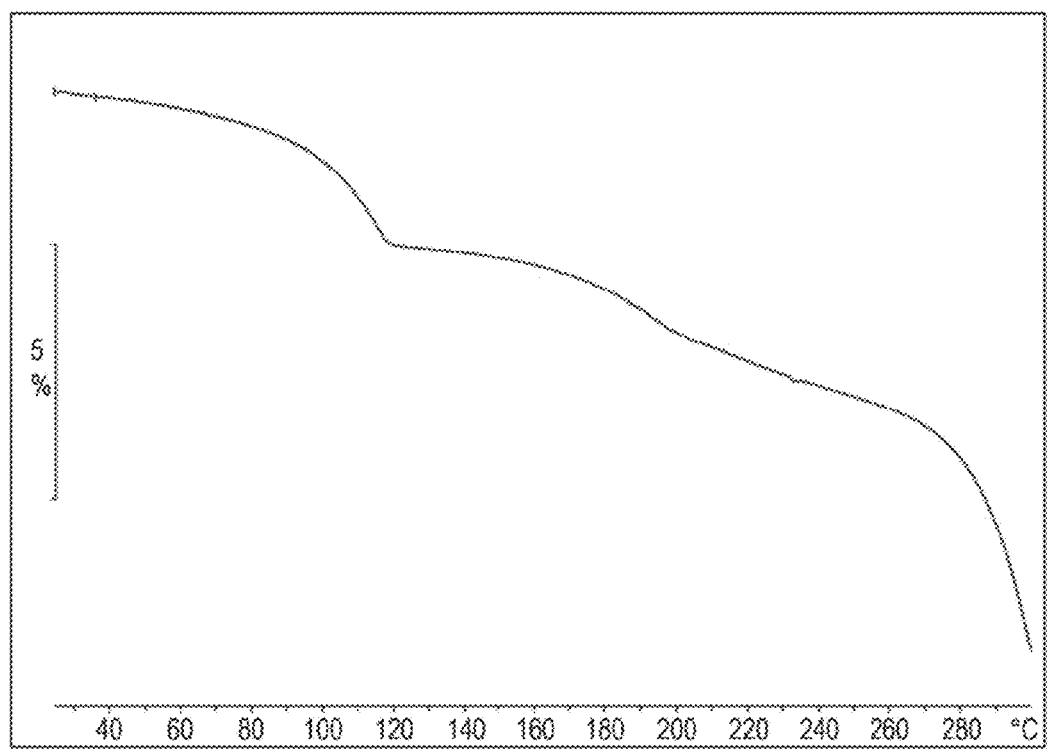
FIG. 10 shows a thermogravimetric analysis (TGA) thermogram for crystalline Form 2 monohydrated (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl) methyl sulfamate.

FIG. 10 shows a thermal gravimetric analysis (TGA) profile of Form 2 of compound I-101. The TGA thermogram plots the percent loss of weight of the sample as a function of temperature, the temperature rate change being about 10° C./min. FIG. 10 shows approximately 3.1% weight loss (w/w) to 120° C. suggesting that Form 2 is a monohydrate. In some embodiments, Form 2 of compound I-101 is characterized by a TGA profile substantially as shown in FIG. 10. Karl Fischer measurements of Form 2 of compound I-101 show a water content of about 2.9% further confirming that Form 2 is a monohydrate.

Figure 11:
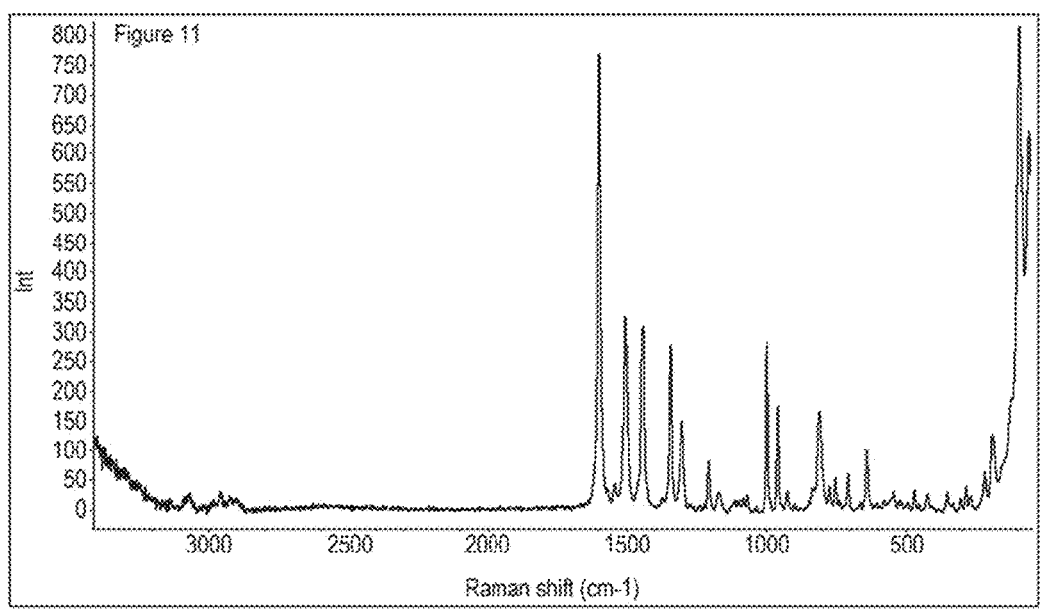
FIG. 11 shows a raman pattern for crystalline Form 2 monohydrated (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.

FIG. 11 shows a raman pattern of Form 2 of compound I-101. In some embodiments, Form 2 is characterized by a raman pattern substantially as shown in FIG. 11. Peaks identified in FIG. 11 in the region of 55 $cm^{-1}$ to 1800 $cm^{-1}$ include those listed in Table 4 below. FIG. 5B shows a raman pattern of Form 2 of compound I-101 in the region of 1450 $cm^{-1}$ to 1520 $cm^{-1}$. FIG. 6B shows a raman pattern of Form 2 of compound I-101 in the region of 1100 $cm^{-1}$ to 1240 $cm^{-1}$. In some embodiments, Form 1 is characterized by a raman pattern substantially as shown in FIG. 6B. In some embodiments, Form 1 is characterized by a peak at 1205.4 $cm^{-1}$. FIG. 7B shows a raman pattern of Form 2 of compound I-101 in the region of about 700 $cm^{-1}$ to about 1100 $cm^{-1}$. In some embodiments, Form 2 is characterized by a raman pattern substantially as shown in FIG. 7B. In some embodiments, Form 2 is characterized by peaks at 958.7 and 923.2 $cm^{-1}$.

TABLE 4

| Peak ($cm^{-1}$) | Intensity |
| --- | --- |
| 60 | 839.324 |
| 94.7 | 813.247 |
| 190.4 | 123.76 |
| 216.8 | 61.08 |
| 285.5 | 35.40 |
| 353.7 | 27.34 |
| 424.4 | 21.79 |
| 470.9 | 28.93 |
| 545.7 | 28.08 |
| 640.5 | 97.91 |
| 707.4 | 59.11 |
| 753.4 | 51.10 |
| 773.9 | 35.84 |
| 809.9 | 163.67 |
| 923.2 | 26.66 |
| 958.7 | 175.20 |
| 997.9 | 281.45 |
| 1068.5 | 22.13 |
| 1167.8 | 26.59 |
| 1205.4 | 79.16 |
| 1302.2 | 147.41 |
| 1343.7 | 278.22 |
| 1442.1 | 309.65 |
| 1504.6 | 325.60 |
| 1542.4 | 39.61 |
| 1571.0 | 34.15 |
| 1599.3 | 768.82 |

In some embodiments, Form 2 of compound I-101 is characterized by at least one of the following features (I-v)-(I-viii):

(I-v) an XRPD pattern having peaks at 2θ angles of 6.7°, 17.6°, 20.0° and 21.6° as shown in FIG. 8;
(I-vi) a DSC profile substantially as shown in FIG. 9;
(I-vii) a TGA profile substantially as shown in FIG. 10.
(I-viii) a raman pattern substantially as shown in FIG. 11.

In some embodiments, Form 2 is characterized by at least two of the features (I-v)-(I-viii). In some embodiments, Form 2 is characterized by at least three of the features (I-v)-(I-viii). In some embodiments, Form 2 is characterized by all four of the features (I-v)-(I-viii).

The chemical entities of this invention are useful inhibitors of UAE activity. Inhibitors are meant to include chemical entities which reduce the promoting effects of UAE initiated conjugation of ubiquitin to target proteins (e.g., reduction of ubiquitination), reduce intracellular signaling mediated by ubiquitin conjugation, and/or reduce proteolysis mediated by ubiquitin conjugation (e.g., inhibition of cellular ubiquitin conjugation, ubiquitin dependent signaling and ubiquitin dependent proteolysis (e.g., the ubiquitin-proteasome pathway)). Thus, the chemical entities of this invention may be assayed for their ability to inhibit UAE in vitro or in vivo, or in cells or animal models according to methods provided in further detail herein, or methods known in the art. The chemical entities may be assessed for their ability to bind or modulate UAE activity directly. Alternatively, the activity of the chemical entities may be assessed through indirect cellular assays, or assays measuring downstream effects of UAE promoted ubiquitin activation to assess inhibition of downstream effects of UAE inhibition (e.g., inhibition of ubiquitin dependent proteolysis). For example, activity may be assessed by detection of ubiquitin conjugated substrates (e.g., ubiquitin charged E2s or ubiquitinated substrates); detection of downstream protein substrate stabilization (e.g., stabilization of c-myc, stabilization of IκB); detection of inhibition of UPP activity; detection of downstream effects of UAE inhibition and substrate stabilization (e.g., reporter assays, e.g., NFκB reporter assays, p27 reporter or loss of cellular polyubiquitin assays). Assays for assessing activities are described below in the Examples section and/or are known in the art.

Derivatives

It will be appreciated that the chemical entities of this invention may be derivatized at functional groups to provide prodrug derivatives which are capable of conversion back to the parent chemical entities in vivo. Examples of such prodrugs include the physiologically acceptable and metabolically labile derivatives. More specifically, the prodrug of the chemical entity of this invention is a carbamate or amide of the —NH— group of the chemical entity, or an ether or ester of the —OH group of the chemical entity.

Such carbamate prodrugs of the —NH— group of the chemical entity include the following carbamates: 9-fluorenylmethyl, 9-(2-sulfo)fluorenylmethyl, 9-(2,7-dibromo)fluorenylmethyl, 17-tetrabenzo[a,c,g,i]fluorenylmethyl, 2-chloro-3-indenylmethyl, benz[f]inden-3-ylmethyl, 2,7-di-tert-butyl-[9-(10,10-dioxo-10,10,10,10-tetrahydrothioxanthyl)]methyl, 1,1-dioxobenzo[b]thiophene-2-yl-methyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylypethyl, 1-(3,5-di-tert-butylphenyl)-1-methylethyl, 2-(2'- and 4'-pyridyl)ethyl, 2,2-bis(4'-nitrophenyl)ethyl, N-2-pivaloylamino)-1,1-dimethylethyl, 2-[(2-nitrophenyl)dithio]-1-phenylethyl, 2-(N,N-dicyclohexylcarboxamideo)ethyl, tert-butyl, 1-adamantyl, 2-adamantyl, vinyl, allyl, 1-isopropylallyl, cinnamyl, 4-nitrocinnamyl, 3-(3'-pyridyl)prop-2-enyl, 8-quinolyl, N-hydroxypiperidinyl, alkyldithio, benzyl, para-methoxybenzyl, para-nitrobenzyl, para-bromobenzyl, para-chlorobenzyl, 2,4-dichlorobenzyl, 4-methylsulfinylbenzyl, 9-anthrylmethyl, diphenylmethyl, phenothiazinyl-(10)-carbonyl, N'-para-toluenesulfonylaminocarbonyl and N'-phenylaminothiocarbonyl.

Such amide prodrugs of the —NH— group of the chemical entity include the following amides: N-formyl, N-acetyl, N-chloroacetyl, N-trichloroacetyl, N-trifluoroacetyl, N-phenylacetyl, N-3-phenylpropionyl, N-4-pentenoyl, N-picolinoyl, N-3-pyridylcarboxamido, N-benzoylphenylalanyl, N-benzoyl and N-para-phenylbenzoyl.

Such ether prodrugs of the —OH group of the chemical entity include the following ethers: methyl, methoxymethyl, methylthiomethyl, (phenyldimethylsilyl)methoxymethyl, benzyloxymethyl, para-methoxybenzyloxymethyl, para-nitrobenzyloxymethyl, ortho-nitrobenzyloxymethyl, (4-methoxyphenoxy)methyl, guaiacolmethyl, tert-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, menthoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8,-trimethyl-4,7-methanobenzofuran-2-yl, 1-ethoxyethyl, 1-(2-chloroethoxy)ethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2,-trichloroethyl, 1,1-dianisyl-2,2,2,-trichloroethyl, 1,1,1,3,3,3-hexafluoro-2-phenylisopropyl, 2-trimethylsilylethyl, 2-(benzylthio)ethyl, 2-(phenylselenyl)ethyl, tert-butyl, allyl, propargyl, para-chlorophenyl, para-methoxyphenyl, para-nitrophenyl, 2,4-dinitrophenyl, 2,3,5,6-tetrafluoro-4-trifluoromethyl)phenyl, benzyl, para-methoxybenzyl, 3,4-dimethoxybenzyl, ortho-nitrobenzyl, para-nitrobenzyl, para-halobenzyl, 2,6-dichlorobenzyl, para-cyanobenzyl, para-phenylbenzyl, 2,6-difluorobenzyl, para-acylaminobenzyl, para-azidobenzyl, 4-azido-3-chlorobenzyl, 2-trifluoromethylbenzyl, para-(methylsulfinyl)benzyl, 2-picolyl, 4-picolyl, 3-methyl-2-picolyl N-oxide, 2-quinolinylmethyl, 1-pyrenylmethyl, diphenylmethyl, p,p'-dinitrobenzhydryl, 5-dibenzosuberyl, triphenylmethyl, alpha-naphthyldiphenylmethyl, para-methoxyphenyldiphenylmethyl, di(para-methoxyphenyl)phenyl methyl, tri(para-methoxyphenyl)methyl, 4-(4'-bromophenacyloxy)phenyldiphenylmethyl, 4,4',4"-tris(4,5-dichlorophthalimidophenyl)methyl, 4,4',4"-tri(levulinoyloxyphenyl)methyl, 4,4',4"-tri(benzoyloxyphenyl)methyl, 4,4'-dimethoxy-3"-[N-(imidazolylmethyl)trityl, 4,4'-dimethoxy-3"[N-imidazolylethyl]carbamoyl]trityl, 1.1-bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-(9-phenyl-10-oxo)anthryl, 1,3-benzodithiolan-2-yl, benzisothiazolyl 5,5-dioxido, trimethylsilyl, triethylsilyl, triisopropylsilyl, dimethylisopropylsilyl, diethylisopropylsilyl, dimethylthexylsilyl, tert-butyldimethylsilyl, tert-butyldiphenylsilyl, tribenzylsilyl, tri-para-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl and tert-butoxydiphenylsilyl.

Such ester prodrugs of the —OH group of the chemical entity include the following esters: formate, benzoylformate, acetate, chloroacetate, dichloroacetate, trichloroacetate, trifluoroacetate, methoxyacetate, triphenylmethoxyacetate, phenoxyacetate, para-chlorophenoxyacetate, phenylacetate, para-P-phenylacetate, diphenylacetate, nicotinate, 3-phenylpropionate, 4-pentenoate, 4-oxopentanoate, 4,4-(ethylenedithio)pentanoate, 5-[3-bis(4-methoxyphenyl)hydroxymethylphenoxy]levulinate, pivaloate, 1-adamantoate, crotonate, 4-methoxycrotonate, benzoate, para-phenylbenzoate and 2,4,6-trimethylbenzoate. Additionally, any physiologically acceptable equivalents of the present chemical entities, similar to the metabolically labile ether, esters of the —OH group, or carbamates or amides of the —NH— group, which are capable of producing the parent chemical entities described herein in vivo, are within the scope of this invention. See e.g., Greene and Wuts, Protective Groups in Organic Synthesis, 3$^{rd}$ Ed. John Wiley & Sons, Inc. (1999).

Compositions

Some embodiments of this invention relate to a composition comprising a chemical entity of this invention and a pharmaceutically acceptable carrier. Some embodiments of this invention relate to a composition comprising a prodrug of a chemical entity of this invention and a pharmaceutically acceptable carrier.

If a pharmaceutically acceptable salt is the chemical entity of the invention utilized in these compositions, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy,* 20th Ed., A. Gennaro (ed.), Lippincott Williams & Wilkins (2000) ("*Remington's*").

Examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of the invention preferably are in a form suitable for administration to a recipient subject, preferably a mammal, more preferably a human. The term "pharmaceutically acceptable carrier" is used herein to refer to a material that is compatible with the recipient subject, and is suitable for delivering an active agent to the target site without terminating the activity of the agent. The toxicity or adverse effects, if any, associated with the carrier preferably are commensurate with a reasonable risk/benefit ratio for the intended use of the active agent. Many such pharmaceutically acceptable carriers are known in the art. See, e.g., *Remington's; Handbook of Pharmaceutical Excipients,* 6th Ed., R. C. Rowe et al. (eds.), Pharmaceutical Press (2009).

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Pharmaceutical formulations may be prepared as liquid suspensions or solutions using a liquid, such as an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons such as mineral oil and petrolatum; and water may also be used in suspension formulations.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents may also be added. In such solid dosage forms, the active chemical entity is mixed with at least one inert, pharmaceutically acceptable excipient or carrier such as sodium citrate or dicalcium phosphate and/or a) fillers or extenders such as starches, lactose, sucrose, glucose, mannitol, micro-crystalline cellulose and silicic acid, b) binders such as, for example, carboxymethylcellulose, alginates, gelatin, sucrose, and acacia, c) humectants such as glycerol, d) disintegrating agents such as agar-agar, calcium carbonate, polyvinylpyrrolidinone, croscarmellose, sodium starch glycolate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, sodium stearyl fumarate, solid polyethylene glycols, sodium lauryl sulfate, silicon dioxide and mixtures thereof. In the case of capsules, tablets and pills, the dosage form may also comprise buffering agents.

The active chemical entity can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). The term "subject" as used herein, means an animal, preferably a mammal, more preferably a human. The term "patient" as used herein, means a human. Preferably, the composition is formulated for administration to a patient or subject having or at risk of developing or experiencing a recurrence of the relevant disorder being treated. Preferred pharmaceutical compositions of the invention are those formulated for oral, intravenous, or subcutaneous administration. However, any of the above dosage forms containing a therapeutically effective amount of a chemical entity of the invention are well within the bounds of routine experimentation and therefore, well within the scope of the instant invention. In certain embodiments, the pharmaceutical composition of the invention may further comprise another therapeutic agent. Preferably, such other therapeutic agent is one normally administered to patients with the disorder, disease or condition being treated.

By "therapeutically effective amount" is meant an amount of the chemical entity or composition sufficient, upon single or multiple dose administration, to cause a detectable decrease in UAE activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of UAE inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific chemical entity employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

Uses

In some embodiments, the invention relates to a method of inhibiting or decreasing UAE activity in a sample comprising contacting the sample with a chemical entity of this invention, or composition comprising a chemical entity of the invention. The sample, as used herein, includes sample comprising purified or partially purified UAE, cultured cells or extracts of cell cultures; biopsied cells or fluid obtained from a mammal, or extracts thereof; and body fluid (e.g., blood, serum, saliva, urine, feces, semen, tears) or extracts thereof. Inhibition of UAE activity in a sample may be carried out in vitro or in vivo, in cellulo, or in situ.

In some embodiments, the invention provides a method for treating a patient having a disorder, a symptom of a disorder, at risk of developing, or experiencing a recurrence of a disorder, comprising administering to the patient a chemical entity or pharmaceutical composition according to the invention. Treating can be to cure, heal, alleviate, relieve, alter, remedy, ameliorate, palliate, improve or affect the disorder, the symptoms of the disorder or the predisposition toward the disorder. While not wishing to be bound by theory, treating is believed to cause the inhibition of growth, ablation, or killing of a cell or tissue in vitro or in vivo, or otherwise reduce capacity of a cell or tissue (e.g., an aberrant cell, a diseased tissue) to mediate a disorder, e.g., a disorder as described herein (e.g., a proliferative disorder, e.g., a cancer, inflammatory disorder). As used herein, "inhibiting the growth" or "inhibition of growth" of a cell or tissue (e.g., a proliferative cell, tumor tissue) refers to slowing, interrupting, arresting or stopping its growth and metastases and does not necessarily indicate a total elimination of growth.

UAE represents a novel protein homeostasis target opportunity for the treatment of cancer and other human diseases where ubiquitin biology is present. Disease applications include those disorders in which inhibition of UAE activity is detrimental to survival and/or expansion of diseased cells or tissue (e.g., cells are sensitive to UAE inhibition; inhibition of UAE activity disrupts disease mechanisms; reduction of UAE activity stabilizes protein which are inhibitors of disease mechanisms; reduction of UAE activity results in inhibition of proteins which are activators of disease mechanisms). Disease applications are also intended to include any disorder, disease or condition which requires effective ubiquitination activity, which activity can be regulated by diminishing UAE activity.

For example, methods of the invention are useful in treatment of disorders involving cellular proliferation, including disorders which require effective ubiquitin ligase dependent ubiquitination and signaling or proteolysis (e.g., the ubiquitin proteasome pathway) for maintenance and/or progression of the disease state. The methods of the invention are useful in treatment of disorders mediated via proteins (e.g., KFκB activation, p27$^{Kip}$ activation, p21$^{WAF/CIP1}$ activation, p53 activation) which are regulated by UAE activity. Relevant disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease, Parkinson's disease, motor neuron disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes solid tumors and bloodborne tumors. The term "cancer" encompasses diseases of skin, tissues, organs, bone, cartilage, blood, and vessels. The term "cancer" further encompasses primary and metastatic cancers.

In some embodiments, the cancer is a solid tumor. Examples of solid tumors that can be treated by the methods of the invention include pancreatic cancer; bladder cancer; colorectal cancer; rectal cancer, breast cancer, including metastatic breast cancer; prostate cancer, including androgen-dependent and androgen-independent prostate cancer; renal cancer, including, e.g., metastatic renal cell carcinoma; hepatocellular cancer; bronchus and lung cancer, including, e.g., non-small cell lung cancer (NSCLC), squamous lung cancer, small cell lung cancer (SCLC), bronchioloalveolar carcinoma (BAC), and adenocarcinoma of the lung; ovarian cancer, including, e.g., progressive epithelial or primary peritoneal cancer; cervical cancer; endometrial cancer, bladder cancer, gastric cancer; esophageal cancer; head and neck cancer, including, e.g., squamous cell carcinoma of the head and neck, nasopharyngeal, oral cavity and pharynxthyroid cancer, melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some embodiments, the cancer is a hematologic malignancy. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); lymphomas including: Hodgkin's disease (HD); non-Hodgkin's lymphoma (NHL), including follicular lymphoma and mantle cell lymphoma; B-cell lymphoma; diffuse large B-Cell lymphoma (DLBCL), and T-cell lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the cancer is lung cancer, ovarian cancer, colon cancer, or breast cancer. In some embodiments, the cancer is acute myeloid leukemia. In some embodiments the cancer is lymphoma.

Depending on the particular disorder or condition to be treated, in some embodiments, the UAE inhibitor of the invention is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated."

The UAE inhibitor of the invention may be administered with the other therapeutic agent in a single dosage form or as a separate dosage form. When administered as a separate dosage form, the other therapeutic agent may be administered prior to, at the same time as, or following administration of the UAE inhibitor of the invention.

In some embodiments, the UAE enzyme inhibitor of the invention is administered in conjunction with a therapeutic agent selected from cytotoxic agents, radiotherapy, and immunotherapy appropriate for treatment of proliferative disorders and cancer. Examples of cytotoxic agents suitable for use in combination with the UAE inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; including, e.g., CC-5013 and CC-4047; protein tyrosine kinase inhibitors, including, e.g., imatinib mesylate and gefitinib; proteasome inhibitors, including, e.g., bortezomib; thalidomide and related analogs; antibodies, including, e.g., trastuzumab, rituximab, cetuximab, and bevacizumab; mitoxantrone; dexamethasone; prednisone; and temozolomide.

Other examples of agents the inhibitors of the invention may be combined with include anti-inflammatory agents such as corticosteroids, TNF blockers, II-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, methotrexate, and sulfasalazine; antibacterial and antiviral agents; and agents for Alzheimer's treatment such as donepezil, galantamine, memantine and rivastigmine.

In order that this invention be more fully understood, the following preparative and testing examples are set forth. These examples are for the purpose of illustration only and are not intended to be construed as limiting the scope of the invention in any way.

EXAMPLES

Abbreviations and Nomenclature

Compounds which were synthesized as racemic mixtures are specified as "(rac)-" in the corresponding name. R/S stereochemical assignments have been used to define the relative stereochemistry of molecules. It is understood that unless specifically indicated, compounds are racemic mixtures containing the compound with the designated stereochemistry along with its enantiomer. Compounds which were synthesized as single enantiomers are specified as "(s.e.)" in the corresponding name.

AA ammonium acetate
ACN acetonitrile
d doublet
dd doublet of doublets
DMF N,N-dimethylformamide
DMSO dimethylsulfoxide
EtOAc ethyl acetate
FA formic acid
J coupling constant
hr hours
Hz hertz
LAH lithium aluminum hydride
LCMS liquid chromatography mass spectrum
LDA lithium diisopropylamide
m multiplet
MeOH methanol
s singlet
t triplet
THF tetrahydrofuran
q quartet Analytical Methods LCMS data were obtained either (i) using an Agilant 1100 LC (column: Waters Symmetry, 3.5 μm C18 100×4.6 mm) and a Waters ZQ MS using the following gradients:

Method Formic Acid (FA): Composition of Mobile Phase A: 99% H$_2$O+1% ACN [+0.1% formic acid]; Composition of Mobile Phase B: 95% ACN+5% H$_2$O [+0.1% formic acid]. Linear Gradient: 5-100% B, 10 minute run at 1 mL/minute.

Method Ammonium Acetate (AA): Composition of Mobile Phase A: 99% H$_2$O+1% ACN [+10 mM ammonium acetate]; Composition of Mobile Phase B: 95% ACN+5% H$_2$O [+10 mM ammonium acetate]. Linear Gradient: 5-100% B, 10 minute run at 1 mL/minute; or (ii) using an Agilant 1100 LC (column: Luna C18(2) 100 A, 150×4.60 mm, 5 micron) and a Agilant 1100 LC/MS using the following gradient:

Method Formic Acid 2 (FA2): Composition of Mobile Phase A: 99% H$_2$O+1% ACN [+0.1% formic acid]; Composition of Mobile Phase B: 95% ACN+5% H$_2$O [+0.1% formic acid]. Linear Gradient: 5-100% B, 20 minute run at 1 mL/minute.

Preparative HPLC is performed using a Phenominex Luna C18 column.

NMR spectrum is shown by proton NMR, using a 300 MHz Bruker Avance spectrometer equipped with a 5 mm QNP probe and a 400 MHz Bruker Avance II spectrometer equipped with a 5 mm QNP probe for the measurement; δ values are expressed in ppm.

X-ray Powder Diffraction. XRPD is performed using a Bruker AXS D8 Advance X-ray Diffractometer using CuKa radiation (40 kV, 40 mA), θ-2θ goniometer, and divergence of V4 and receiving slits, a Ge monochormator and a Lynxeye detector. Samples are run under ambient conditions as flat plate specimens using powder. The sample is gently packed into a cavity cut into polished, zero-background (510) silicon wafer. The sample is rotated in its own plane during analysis. The data are collected on an angular range of 2 to 42° 2θ, with a step size of 0.05° 2θ and a collection time of 0.5 s/step. All data collection is performed using Diffrac Plus XRD Commander v2.6.1 software. Data analysis and presentation is performed using Diffrac Plus EVA v13.0.0.2 or v15.0.0.0 software.

Raman spectrum is collected using a ThermoScientific DXR Raman Microscope with the following parameters: laser 780 nm; laser power level 20.0 mW; filter 780 nm; grating 400 lines/nm; spectrograph aperture 50 μm pinhole; exposure time 30 secs; and number of exposures 2. The range of raman shift was 55.13 to 3411.62 cm$^{-1}$. Instrument control and data analysis software is OM NIC 8.3.

Thermal Analysis. The thermal events are analyzed using differential scanning calorimetry (DSC) and thermogravimetric analysis (TGA). DSC data is collected on a Mettler DSC 823E. Typically, 0.5-5.0 mg of sample in a pin-holed aluminium pan is heated at 10° C./min from 25° C. to 300° C. A nitrogen sample purge is maintained at 50 mL/min over the sample. Instrument control and data analysis software is STARe v9.20. TGA data is collected on a Mettler TGA/SDTA 851e. Typically, 5-30 mg of sample is loaded onto a pre-weighed aluminium crucible and was heated at 10° C./min from ambient temperature to 350° C. A nitrogen sample purge is maintained at 50 mL/min over the sample. Instrument control and data analysis software is STARe v9.20.

Synthetic Methods

Example 1a. Synthesis of (s.e.)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol

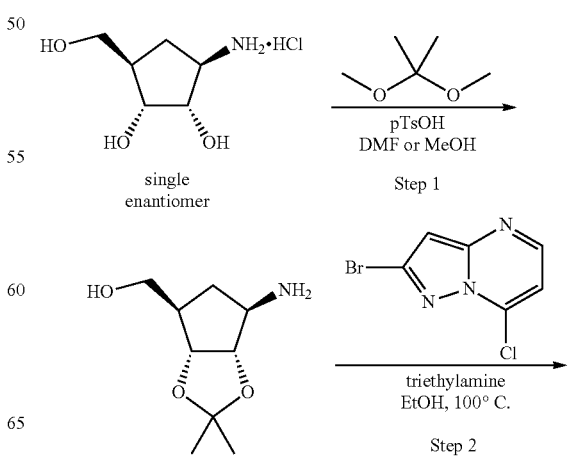

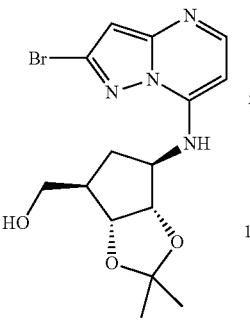

Step 1: (s.e.)-(1R,2S,3R,4R)-1-Amino-2,3-(isoproplydenyl)dihydroxy-4-hydroxymethyl cyclopentane To a mixture of (s.e.)-(1R,2S,3R,5R)-3-amino-5-(hydroxymethyl)cyclopentane-1,2-diol hydrochloride (7.00 g, 38.1 mmol; obtained as a single enantiomer by the method described in WO2008/019124) and p-toluenesulfonic acid monohydrate (8.23 g, 43.3 mmol) in methanol (43 mL) is added 2,2-dimethoxypropane (32.3 mL, 263 mmol). The mixture is stirred at room temperature overnight and then neutralized with 7 M $NH_3$/MeOH and concentrated to dryness. The residue is taken up in 2M $K_2CO_3$ (50 ml) and extracted with $EtOAc/CH_2CH_2$ 1:1 (3×50 ml). The combined organics are dried over $Na_2SO_4$, filtered, and concentrated in vacuo to give (s.e.)-(1R,2S,3R,4R)-1-amino-2,3-(isoproplydenyl)dihydroxy-4-hydroxymethyl cyclopentane (6.8 g, yield 95%). $^1H$ NMR (400 MHz, DMSO) δ 4.49-4.40 (m, 1H), 4.16-4.05 (m, 1H), 3.44-3.37 (m, 2H), 3.25-3.16 (m, 1H), 2.52-2.42 (m, 1H), 2.16-2.04 (m, 2H), 1.32 (s, 3H), 1.18 (s, 3H).

Step 2: (s.e.)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol To a suspension of (1R,2S,3R,4R)-1-amino-2,3-(isoproplydenyl)dihydroxy-4-hydroxymethyl cyclopentane (2.76 g, 14.7 mmol) in ethanol (46.5 mL) is added triethylamine (4.28 mL, 30.7 mmol) and 2-bromo-7-chloropyrazolo[1,5-a]pyrimidine (3.58 g, 15.4 mmol; obtained by the method described in J. Med. Chem. 2010, 53, 1238-1249). The reaction mixture is heated at 100° C. for 3.5 hr and then cooled to room temperature and concentrated to dryness. The residue is dissolved in chloroform and then washed with saturated sodium bicarbonate and brine. The organic layer is dried over $Na_2SO_4$, filtered and concentrated in vacuo. The solid is triturated with diethyl ether and filtered to provide (s.e.)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol (5.0 g, yield 88%). LCMS: (AA) M+383; $^1H$ NMR (400 MHz, MeOD) δ 8.14 (d, J=5.6 Hz, 1H), 6.43 (s, 1H), 6.28 (d, J=5.7 Hz, 1H), 4.64-4.56 (m, 1H), 4.55-4.48 (m, 1H), 4.15-4.05 (m, 1H), 3.75-3.61 (m, 2H), 2.63-2.53 (m, 1H), 2.41-2.31 (m, 1H), 1.88-1.78 (m, 1H), 1.51 (s, 3H), 1.30 (s, 3H).

Example 1b. Synthesis of (rac)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol

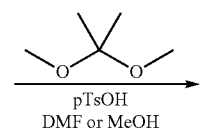

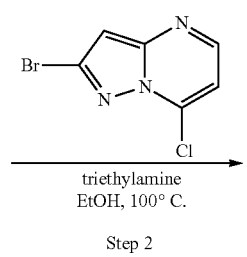

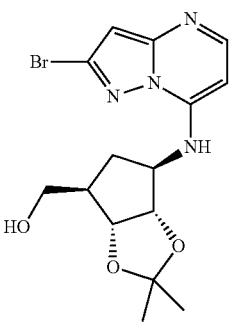

The method used to synthesize (s.e.)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol as a single enantiomer is followed to generate (rac)-rel-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol starting from (rac)-rel-(1R,2S,3R,5R)-3-amino-5-(hydroxymethyl)cyclopentane-1,2-diol hydrochloride.

Method A [Example 2]

The following procedure describes the synthesis of enantiomerically pure compounds starting from (s.e.)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol. The same procedure is used to synthesize racemic compounds starting from (rac)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol.

Example 2a. Synthesis of (s.e.)-((1R,2R,3S,4R)-2,3-dihydroxy-4-{[2-(1-naphthyl)pyrazolo[1,5-a]pyrimidin-7-yl]amino}cyclopentyl)methyl sulfamate (I-98)

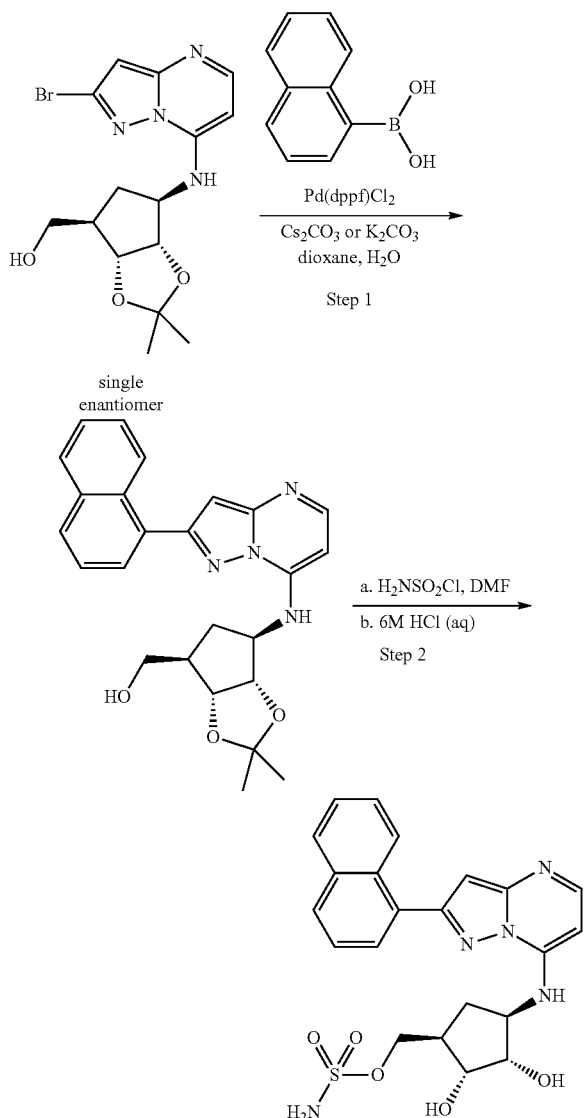

Step 1: (s.e)-((3aR,4R,6R,6aS)-2,2-dimethyl-6-{[2-(1-naphthyl)pyrazolo[1,5-a]pyrimidin-7-yl]amino}tetrahydro-3aH-cyclopenta[d][1,3]dioxol-4-yl)methanol A microwave vial is charged with {(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol (1.50 g, 3.91 mmol), 1-naphthaleneboronic acid (1.01 g, 5.87 mmol), [1,1'-bis(diphenylphosphino)ferrocene]dichloropalladium(II), complex with dichloromethane (1:1) (0.160 g, 0.196 mmol), cesium carbonate (2.55 g, 7.83 mmol) and dioxane/water (6:1, 25 mL). The reaction mixture is heated in the microwave at 120° C. for 90 minutes and then cooled to room temperature and concentrated in vacuo. The crude material is purified by column chromatography (eluent: ethyl acetate/hexane) to provide (s.e)-((3aR,4R,6R,6aS)-2,2-dimethyl-6-{[2-(1-naphthyppyrazolo[1,5-a]pyrimidin-7-yl]amino}tetrahydro-3aH-cyclopenta[d][1,3]dioxol-4-yl)methanol (1.5 g, yield 89%). LCMS: (AA) M+1 431.

Step 2: (s.e.)-((1R,2R,3S,4R)-2,3-dihydroxy-4-{[2-(1-naphthyl)pyrazolo[1,5-a]pyrimidin-7-yl]amino}cyclopentyl)methyl sulfamate (I-98)

To a vial charged with (s.e.)-((3aR,4R,6R,6aS)-2,2-dimethyl-6-{[2-(1-naphthyppyrazolo[1,5-a]pyrimidin-7-yl]amino}tetrahydro-3aH-cyclopenta[d][1,3]dioxol-4-yl)methanol (1.76 g, 4.09 mmol) in N,N-dimethylformamide (7.20 mL) is added chlorosulfonamide (1.42 g, 12.3 mmol; obtained by the method described in J. Am. Chem. Soc. 2005, 127, 15391). After 1 hr, the reaction is quenched with methanol (5 mL). 6.0 M hydrochloric acid in water (3.41 mL, 20.4 mmol) is added and the mixture is stirred for 1 hr. Solvent is removed in vacuo and the crude material is purified by preparative HPLC to provide (s.e.)-((1R,2R,3S,4R)-2,3-dihydroxy-4-{[2-(1-naphthyl)pyrazolo[1,5-a]pyrimidin-7-yl]amino}cyclopentyl)methyl sulfamate. LCMS: (AA) M+1 470; $^1$H NMR (400 MHz, MeOD) δ 8.48-8.40 (m, 1H), 8.19 (d, J=5.5 Hz, 1H), 7.99-7.90 (m, 2H), 7.81-7.75 (m, 1H), 7.60-7.47 (m, 3H), 6.69 (s, 1H), 6.37 (d, J=5.6 Hz, 1H), 4.24-4.06 (m, 3H), 4.04-3.99 (m, 1H), 3.96-3.89 (m, 1H), 2.55-2.45 (m, 1H), 2.45-2.35 (m, 1H), 1.60-1.48 (m, 1H).

Example 2b-A. Synthesis of (rac)-((1R,2R,3S,4R)-2,3-dihydroxy-4-{[2-(1-naphthyl)pyrazolo[1,5-a]pyrimidin-7-yl]amino}cyclopentyl)methyl rel-sulfamate (I-2)

The procedure of Method A is followed except (rac)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol instead of (s.e.)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol. LCMS: (AA) M+1470; $^1$H NMR (400 MHz, MeOD) δ 8.48-8.40 (m, 1H), 8.19 (d, J=5.5 Hz, 1H), 7.99-7.90 (m, 2H), 7.81-7.75 (m, 1H), 7.60-7.47 (m, 3H), 6.69 (s, 1H), 6.37 (d, J=5.6 Hz, 1H), 4.24-4.06 (m, 3H), 4.04-3.99 (m, 1H), 3.96-3.89 (m, 1H), 2.55-2.45 (m, 1H), 2.45-2.35 (m, 1H), 1.60-1.48 (m, 1H).

Method B [Example 2b-B]

Example 2b-B. Alternative Synthesis of (rac)-((1R,2R,3S,4R)-2,3-dihydroxy-4-{[2-(1-naphthyl)pyrazolo[1,5-a]pyrimidin-7-yl]amino}cyclopentyl)methyl rel-sulfamate (I-2)

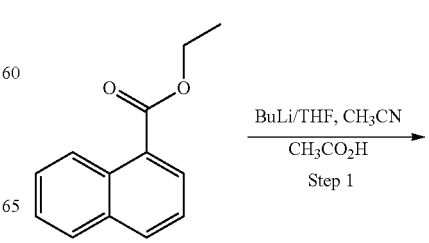

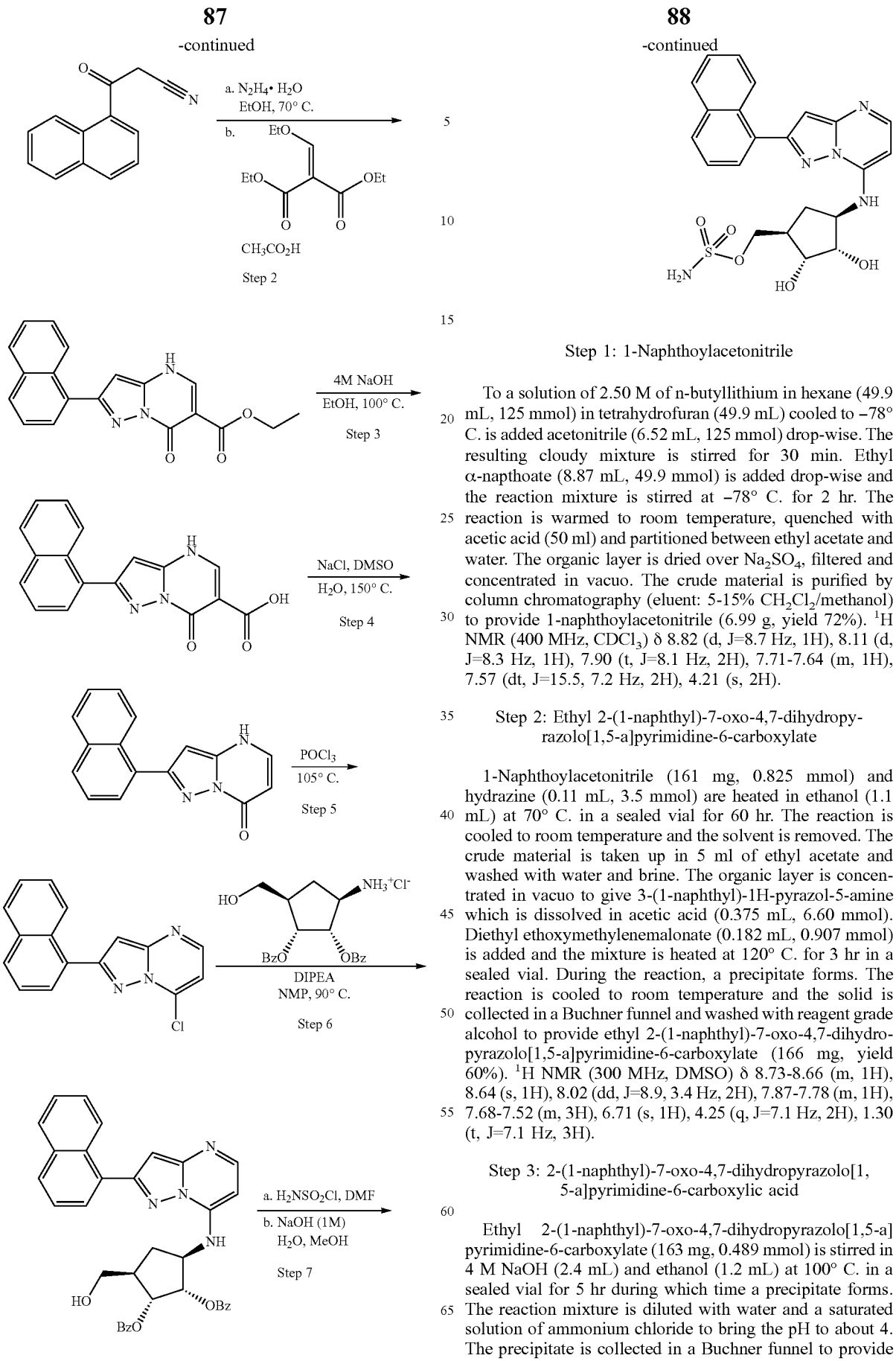

Step 1: 1-Naphthoylacetonitrile

To a solution of 2.50 M of n-butyllithium in hexane (49.9 mL, 125 mmol) in tetrahydrofuran (49.9 mL) cooled to −78° C. is added acetonitrile (6.52 mL, 125 mmol) drop-wise. The resulting cloudy mixture is stirred for 30 min. Ethyl α-napthoate (8.87 mL, 49.9 mmol) is added drop-wise and the reaction mixture is stirred at −78° C. for 2 hr. The reaction is warmed to room temperature, quenched with acetic acid (50 ml) and partitioned between ethyl acetate and water. The organic layer is dried over $Na_2SO_4$, filtered and concentrated in vacuo. The crude material is purified by column chromatography (eluent: 5-15% $CH_2Cl_2$/methanol) to provide 1-naphthoylacetonitrile (6.99 g, yield 72%). $^1$H NMR (400 MHz, $CDCl_3$) δ 8.82 (d, J=8.7 Hz, 1H), 8.11 (d, J=8.3 Hz, 1H), 7.90 (t, J=8.1 Hz, 2H), 7.71-7.64 (m, 1H), 7.57 (dt, J=15.5, 7.2 Hz, 2H), 4.21 (s, 2H).

Step 2: Ethyl 2-(1-naphthyl)-7-oxo-4,7-dihydropyrazolo[1,5-a]pyrimidine-6-carboxylate 1-Naphthoylacetonitrile (161 mg, 0.825 mmol) and hydrazine (0.11 mL, 3.5 mmol) are heated in ethanol (1.1 mL) at 70° C. in a sealed vial for 60 hr. The reaction is cooled to room temperature and the solvent is removed. The crude material is taken up in 5 ml of ethyl acetate and washed with water and brine. The organic layer is concentrated in vacuo to give 3-(1-naphthyl)-1H-pyrazol-5-amine which is dissolved in acetic acid (0.375 mL, 6.60 mmol). Diethyl ethoxymethylenemalonate (0.182 mL, 0.907 mmol) is added and the mixture is heated at 120° C. for 3 hr in a sealed vial. During the reaction, a precipitate forms. The reaction is cooled to room temperature and the solid is collected in a Buchner funnel and washed with reagent grade alcohol to provide ethyl 2-(1-naphthyl)-7-oxo-4,7-dihydro-pyrazolo[1,5-a]pyrimidine-6-carboxylate (166 mg, yield 60%). $^1$H NMR (300 MHz, DMSO) δ 8.73-8.66 (m, 1H), 8.64 (s, 1H), 8.02 (dd, J=8.9, 3.4 Hz, 2H), 7.87-7.78 (m, 1H), 7.68-7.52 (m, 3H), 6.71 (s, 1H), 4.25 (q, J=7.1 Hz, 2H), 1.30 (t, J=7.1 Hz, 3H).

Step 3: 2-(1-naphthyl)-7-oxo-4,7-dihydropyrazolo[1,5-a]pyrimidine-6-carboxylic acid Ethyl 2-(1-naphthyl)-7-oxo-4,7-dihydropyrazolo[1,5-a]pyrimidine-6-carboxylate (163 mg, 0.489 mmol) is stirred in 4 M NaOH (2.4 mL) and ethanol (1.2 mL) at 100° C. in a sealed vial for 5 hr during which time a precipitate forms. The reaction mixture is diluted with water and a saturated solution of ammonium chloride to bring the pH to about 4. The precipitate is collected in a Buchner funnel to provide 2-(1-naphthyl)-7-oxo-4,7-dihydropyrazolo[1,5-a]pyrimidine-6-carboxylic acid (145 mg, yield 97%). $^1$H NMR (400 MHz, DMSO) δ 8.74 (s, 1H), 8.72-8.64 (m, 1H), 8.03 (dd, J=11.4, 5.4 Hz, 2H), 7.86 (d, J=6.3 Hz, 1H), 7.69-7.52 (m, 3H), 6.80 (s, 1H).

Step 4: 2-(naphthalen-1-yl)pyrazolo[1,5-a]pyrimidin-7(4H)-one 2-(1-naphthyl)-7-oxo-4,7-dihydropyrazolo[1,5-a]pyrimidine-6-carboxylic acid (2.00 g, 6.55 mmol) is stirred in dimethyl sulfoxide (5.06 mL, 71.2 mol) in a 350 mL sealed reaction vessel. Sodium chloride (0.545 g, 9.33 mol) is dissolved in water (2.26 mL) and added to the reaction mixture. The reaction is heated at 150° C. for 3 days during which time an additional 8 mL of DMSO is added along with 15 mL of additional water. The resulting precipitate is collected in a Buchner funnel to provide 2-(naphthalen-1-yl)pyrazolo[1,5-a]pyrimidin-7(4H)-one (1.48 g, 87%). LCMS: (AA) M+1 262.

Step 5: 7-chloro-2-(1-naphthyl)pyrazolo[1,5-a]pyrimidine 2-(naphthalen-1-yl)pyrazolo[1,5-a]pyrimidin-7(4H)-one (4.0 g, 15 mmol) is heated in phosphoryl chloride (28 mL) in a sealed vial at 105° C. and stirred for 5 hours. The crude reaction mixture is cooled to room temperature and poured slowly over ice. The resulting solid is collected on a Buchner funnel to provide 7-chloro-2-(1-naphthyl)pyrazolo[1,5-a]pyrimidine (4.3 g, yield 100%). LCMS: (AA) M+1 280.

Step 6: (rac)-(1S,2R,3R,5R)-3-(hydroxymethyl)-5-{[2-(1-naphthyl)pyrazolo[1,5-a]pyrimidin-7-yl]amino}cyclopentane-1,2-diyl reldi-benzoate A mixture of (rac)-(1R,2S,3R,5R)-3-amino-5-(hydroxymethyl)cyclopentane-1,2-diyl reldi-benzoate hydrochloride (0.300 g, 0.767 mmol; obtained as the racemic mixture utilizing the method described in PCT Publication No. WO2008/019124), 7-chloro-2-(1-naphthyl)pyrazolo[1,5-a]pyrimidine (0.165 g, 0.590 mmol) and N,N-diisopropylethylamine (0.360 mL, 2.06 mmol) in N-methylpyrrolidine (0.80 mL) is heated in a sealed reaction vial at 90° C. and stirred for 2 hr. The reaction mixture is cooled to room temperature and partitioned between ethyl acetate and water. The organic layer is dried over Na$_2$SO$_4$, filtered and concentrated in vacuo. The residue is purified by column chromatography (eluent: 0-60% ethyl acetate/hexanes) to provide (rac)-(1S,2R,3R,5R)-3-(hydroxymethyl)-5-{[2-(1-naphthyl)pyrazolo[1,5-a]pyrimidin-7-yl]amino}cyclopentane-1,2-diyl reldi-benzoate (0.086 g, yield 24%). LCMS: (AA) M+1 599; $^1$H NMR (300 MHz, CDCl$_3$) δ 8.69-8.57 (m, 1H), 8.29 (d, J=5.2 Hz, 1H), 8.09-7.98 (m, 2H), 7.97-7.84 (m, 4H), 7.83-7.78 (m, 1H), 7.63-7.32 (m, 10H), 6.82 (s, 1H), 6.34 (d, J=5.3 Hz, 1H), 5.76-5.66 (m, 1H), 5.65-5.57 (m, 1H), 4.41-4.28 (m, 1H), 3.97-3.84 (m, 1H), 3.80-3.66 (m, 1H), 3.19-3.07 (m, 1H), 2.75-2.59 (m, 2H), 1.92-1.80 (m, 1H).

Step 7: (rac)-((1R,2R,3S,4R)-2,3-dihydroxy-4-{[2-(1-naphthyl)pyrazolo[1,5-a]pyrimidin-7-yl]amino}cyclopentyl)methyl rel-sulfamate (I-2)

To a solution of (1S,2R,3R,5R)-3-(hydroxymethyl)-5-{[2-(1-naphthyl)pyrazolo[1,5-a]pyrimidin-7-yl]amino}cyclopentane-1,2-diyl reldi-benzoate (0.243 g, 0.406 mmol) in N,N-dimethylformamide (2.4 mL) cooled to 0° C. is added chlorosulfonamide (141 mg, 1.22 mmol) The reaction mixture is stirred for 1 hr and then concentrated in vacuo. 1.0 M NaOH (2 mL) and methanol (2 mL) are added and the reaction is stirred at room temperature until benzoate hydrolysis is complete. The reaction mixture is concentrated in vacuo and the residue suspended in methanol and filtered through a syringe filter. The crude materiel is purified by column chromatography (eluent: 0-8% MeOH:CH$_2$Cl$_2$) to provide (rac)-((1R,2R,3S,4R)-2,3-dihydroxy-4-{[2-(1-naphthyl)pyrazolo[1,5-a]pyrimidin-7-yl]amino}cyclopentyl)methyl rel-sulfamate (59 mg, yield 31%). LCMS: (AA) M+1 470; $^1$H NMR (400 MHz, MeOD) δ 8.48-8.40 (m, 1H), 8.19 (d, J=5.5 Hz, 1H), 7.99-7.90 (m, 2H), 7.81-7.75 (m, 1H), 7.60-7.47 (m, 3H), 6.69 (s, 1H), 6.37 (d, J=5.6 Hz, 1H), 4.24-4.06 (m, 3H), 4.04-3.99 (m, 1H), 3.96-3.89 (m, 1H), 2.55-2.45 (m, 1H), 2.45-2.35 (m, 1H), 1.60-1.48 (m, 1H).

Method C [Example 3]

Example 3. Synthesis of (s.e.)-[(1R,2R,3S,4R)-4-{[2-(4-chloro-1-naphthyl)pyrazolo[1,5-a]pyrimidin-7-yl]amino}-2,3-dihydroxycyclopentyl]methyl sulfamate (I-108)

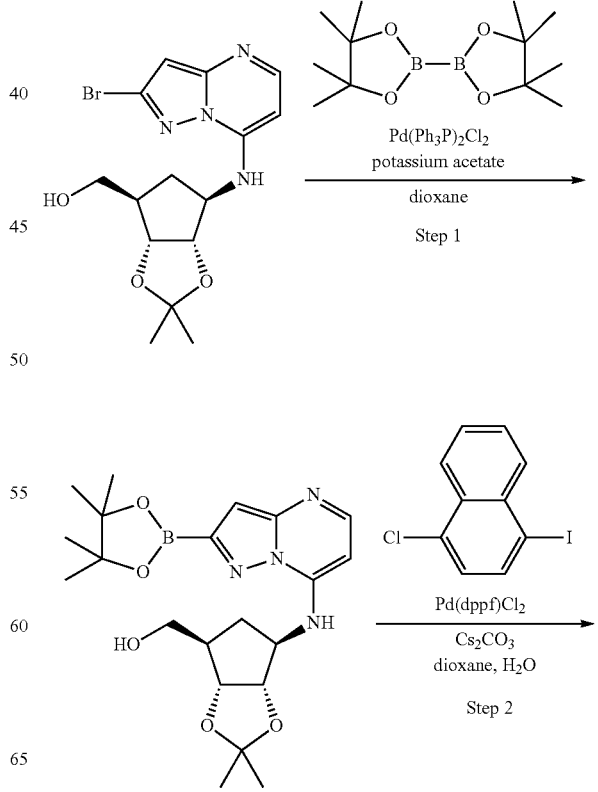

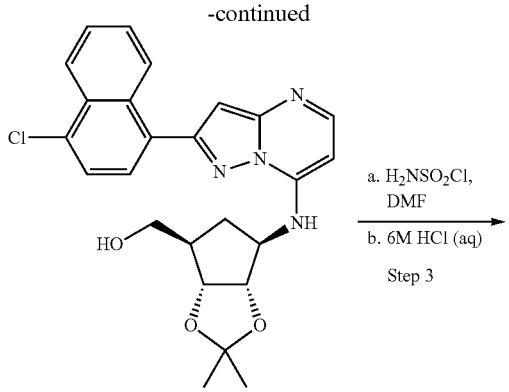

Step 1: (s.e.)-((3aR,4R,6R,6aS)-2,2-dimethyl-6-{[2-(4,4,5,5-tetramethyl-1,3,2-dioxaborolan-2-yl)pyrazolo[1,5-a]pyrimidin-7-yl]amino}tetrahydro-3aH-cyclopenta[d][1,3]dioxol-4-yl)methanol To a solution of (s.e.)-{(3aR,4R,6R,6aS)-6-[(2-bromopyrazolo[1,5-a]pyrimidin-7-yl)amino]-2,2-dimethyltetrahydro-3aH-cyclopenta[d][1,3]dioxol-4-yl}methanol (500 mg, 1.30 mmol) in 1,4-dioxane (8.0 mL) is added bis(pinacolato)diboron (663 mg, 2.61 mol), bis(triphenylphosphine)palladium(II) chloride (102 mg, 1.46 mmol) and potassium acetate (630 mg, 6.40 mmol) The mixture is heated at 100° C. for 20 hr during which time additional bis(triphenylphosphine)palladium(II) chloride (114 mg) is added in two portions. The reaction mixture is cooled to room temperature, diluted with ethyl acetate and filtered through celite to provide (s.e.)-((3aR,4R,6R,6aS)-2,2-dimethyl-6-{[2-(4,4,5,5-tetramethyl-1,3,2-dioxaborolan-2-yl)pyrazolo[1,5-a]pyrimidin-7-yl]amino}tetrahydro-3aH-cyclopenta[d][1,3]dioxol-4-yl)methanol (2 g) which is used without purification.

Step 2: (s.e.)-[(3aR,4R,6R,6aS)-6-{[2-(4-chloro-1-naphthyl)pyrazolo[1,5-a]pyrimidin-7-yl]amino}-2,2-dimethyltetrahydro-3aH-cyclopenta[d][1,3]dioxol-4-yl]methanol A microwave vial is charged with ((3aR,4R,6R,6aS)-2,2-dimethyl-6-{[2-(4,4,5,5-tetramethyl-1,3,2-dioxaborolan-2-yl)pyrazolo[1,5-a]pyrimidin-7-yl]amino}tetrahydro-3aH-cyclopenta[d][1,3]dioxol-4-yl)methanol (0.25 g, 0.58 mmol), 1-chloro-4-iodo-naphthalene (0.38 g, 1.30 mmol), [1,1'-bis(diphenylphosphino)ferrocene]dichloropalladium (II), complex with dichloromethane (1:1) (29 mg, 0.036 mmol), cesium carbonate (0.70 g, 2.2 mmol) 1,4-dioxane (4.0 mL, 50 mmol) and water (0.60 mL, 30 mmol). The reaction mixture is heated in the microwave at 110° C. for 30 minutes and then cooled to room temperature. The reaction mixture is diluted with ethyl acetate and was washed successively with water, saturated sodium bicarbonate solution and brine. The organic layer is dried over sodium sulfate, filtered and concentrated in vacuo. The crude material is purified by column chromatography (0-80% ethyl acetate/hexanes) to provide (s.e.)-[(3aR,4R,6R,6aS)-6-{[2-(4-chloro-1-naphthyl)pyrazolo[1,5-a]pyrimidin-7-yl]amino}-2,2-dimethyltetrahydro-3aH-cyclopenta[d][1,3]dioxol-4-yl]methanol (0.450 g, yield 167%). LCMS: (AA) M+1 465.

Step 3: (s.e.)-[(1R,2R,3S,4R)-4-{[2-(4-chloro-1-naphthyl)pyrazolo[1,5-a]pyrimidin-7-yl]amino}-2,3-dihydroxycyclopentyl]methyl sulfamate (I-108)

The title compound is synthesized from (s.e.)-[(3aR,4R,6R,6aS)-6-{[2-(4-chloro-1-naphthyl)pyrazolo[1,5-a]pyrimidin-7-yl]amino}-2,2-dimethyltetrahydro-3aH-cyclopenta[d][1,3]dioxol-4-yl]methanol following Step 2 of Method A. LCMS: (AA) M+1 504; $^1$H NMR (400 MHz, MeOD) δ 8.54 (d, J=7.8 Hz, 1H), 8.36 (d, J=8.5 Hz, 1H), 8.21 (d, J=5.5 Hz, 1H), 7.79-7.58 (m, 4H), 6.70 (s, 1H), 6.40 (d, J=5.6 Hz, 1H), 4.26-4.10 (m, 3H), 4.06-3.99 (m, 1H), 3.98-3.91 (m, 1H), 2.56-2.46 (m, 1H), 2.46-2.35 (m, 1H), 1.61-1.50 (m, 1H).

Method D [Example 4]

Example 4. Synthesis of (rac)-((1R,2R,3S,4R)-4-{[5-chloro-2-(1-naphthyl)pyrazolo[1,5-a]pyrimidin-7-yl]amino}-2,3-dihydroxycyclopentyl)methyl rel-sulfamate (I-9)

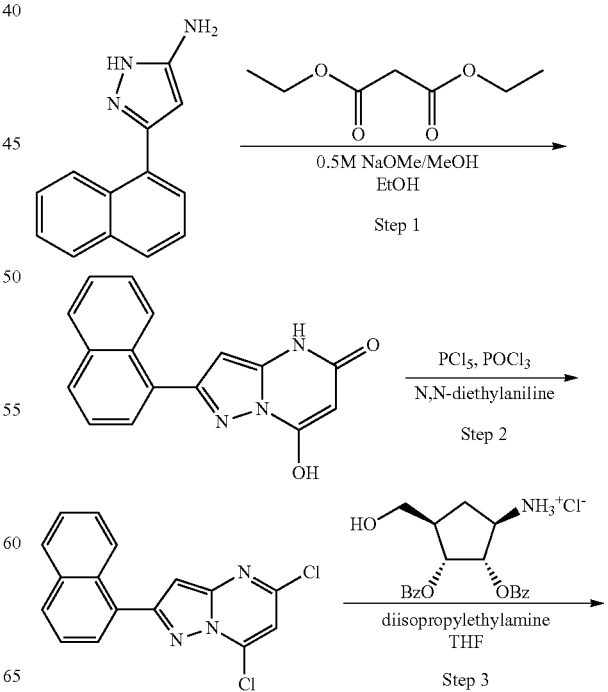

Step 1: 7-hydroxy-2-(1-naphthyl)pyrazolo[1,5-a]pyrimidin-5(4H)-one

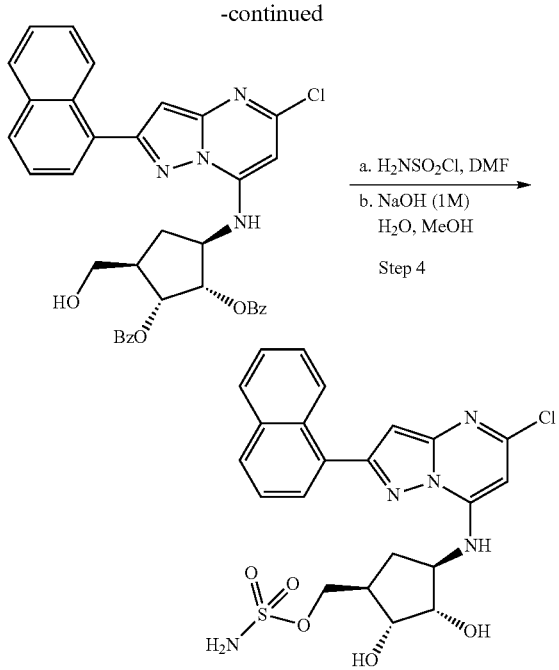

To a solution of 3-(1-naphthyl)-1H-pyrazol-5-amine (654 mg, 3.12 mmol) and dimethyl malonate (0.394 mL, 3.44 mmol) in anhydrous ethanol (9.44 mL, 162 mmol) is added 0.5 M sodium methoxide in methanol (12.5 mL, 6.25 mmol). The mixture is heated at 120° C. under a nitrogen atmosphere overnight. The reaction mixture is cooled to room temperature and the solvent is removed in vacuo. The residue is suspended in water and the precipitate is collected in a Buchner funnel to provide 2-(1-naphthyl)pyrazolo[1,5-a]pyrimidine,7-diol (534 mg, yield 62%). LCMS: (AA) M+1 278; $^1$H NMR (400 MHz, DMSO) δ 10.17 (s, 1H), 8.73 (dd, J=8.2, 4.8 Hz, 1H), 7.99-7.88 (m, 2H), 7.72 (dd, J=7.1, 1.1 Hz, 1H), 7.58-7.49 (m, 4H), 5.83 (s, 1H), 4.14 (s, 1H).

Step 2: 5,7-dichloro-2-(1-naphthyl)pyrazolo[1,5-a]pyrimidine

A mixture of 7-hydroxy-2-(1-naphthyl)pyrazolo[1,5-a]pyrimidin-5(4H)-one (534 mg, 1.92 mmol) N,N-diethylaniline (0.952 mL, 5.98 mmol), phosphorus pentachloride (205 mg, 0.986 mmol), and phosphoryl chloride (8.98 mL, 96.3 mmol) is stirred at 120° C. for 20 hours. The reaction mixture is cooled to room temperature and poured over ice. The precipitate is collected in a Buchner funnel to provide 5,7-dichloro-2-(1-naphthyl)pyrazolo[1,5-a]pyrimidine (538 mg, yield 89%). LCMS: (AA) M+1 314; $^1$H NMR (400 MHz, DMSO) δ 8.68-8.61 (m, 1H), 8.09-8.02 (m, 2H), 7.90 (dd, J=7.2, 1.2 Hz, 1H), 7.72 (s, 1H), 7.65 (dd, J=8.2, 7.2 Hz, 1H), 7.63-7.58 (m, 2H), 7.32 (s, 1H).

Step 3: (rac)-(1R,2S,3R,5R)-3-{[5-chloro-2-(1-naphthyl)pyrazolo[1,5-a]pyrimidin-7-yl]amino}-5-(hydroxymethyl)cyclopentane-1,2-diyl rel-di-benzoate A suspension of (rac)-(1R,2S,3R,5R)-3-amino-5-(hydroxymethyl)cyclopentane-1,2-diyl reldi-benzoate hydrochloride (150 mg, 0.382 mmol), 5,7-dichloro-2-(1-naphthyl)pyrazolo[1,5-a]pyrimidine (100 mg, 0.318 mmol), and N,N-diisopropylethylamine (0.166 mL, 0.955 mmol) in tetrahydrofuran (1.05 mL) is heated in a sealed reaction vial at 80° C. for 2.5 hr. The reaction is cooled to room temperature and the solvent is removed in vacuo. The crude material is purified by column chromatography (eluent: 0-80% ethyl acetate:hexanes) to provide (rac)-(1R,2S,3R,5R)-3-{[5-chloro-2-(1-naphthyl)pyrazolo[1,5-a]pyrimidin-7-yl]amino}-5-(hydroxymethyl)cyclopentane-1,2-diyl reldibenzoate (118 mg, yield 59%). LCMS: (AA) M+1 633; $^1$H NMR (400 MHz, CDCl$_3$) δ 8.57-8.52 (m, 1H), 8.01-7.97 (m, 2H), 7.94-7.89 (m, 2H), 7.88-7.83 (m, 2H), 7.73 (dd, J=7.1, 1.1 Hz, 1H), 7.63 (d, J=7.5 Hz, 1H), 7.58-7.49 (m, 2H), 7.48-7.32 (m, 8H), 6.71 (s, 1H), 6.33 (s, 1H), 5.66 (t, J=4.8 Hz, 1H), 5.55 (t, J=5.0 Hz, 1H), 4.27-4.18 (m, 1H), 3.85-3.79 (m, 1H), 3.59-3.52 (m, 1H), 2.57-2.49 (m, 2H), 1.77-1.64 (m, 1H).

Step 4: (rac)-((1R,2R,3S,4R)-4-{[5-chloro-2-(1-naphthyl)pyrazolo[1,5-a]pyrimidin-7-yl]amino}-2,3-dihydroxycyclopentyl)methyl rel-sulfamate (I-9)

The title compound is synthesized from (rac)-(1R,2S,3R,5R)-3-{[5-chloro-2-(1-naphthyl)pyrazolo[1,5-a]pyrimidin-7-yl]amino}-5-(hydroxymethyl)cyclopentane-1,2-diyl rel di-benzoate following Step 7 of Method B (yield 19%). LCMS: (AA) M+1 504; $^1$H NMR (400 MHz, MeOD) δ 8.48-8.42 (m, 1H), 7.99-7.91 (m, 2H), 7.81-7.76 (m, 1H), 7.61-7.50 (m, 3H), 6.65 (s, 1H), 6.43 (s, 1H), 4.25-4.06 (m, 3H), 4.01 (t, J=6.0 Hz, 1H), 3.94 (t, J=5.3 Hz, 1H), 2.54-2.34 (m, 2H), 1.57 (dt, J=12.6, 9.0 Hz, 1H).

Method E [Example 5]

Example 5. Synthesis of (rac)-{(1R,2R,3S,4R)-2,3-dihydroxy-4-[(5-methyl-2-phenylpyrazolo[1,5-a]pyrimidin-7-yl)amino]cyclopentyl}methyl rel-sulfamate (I-4)

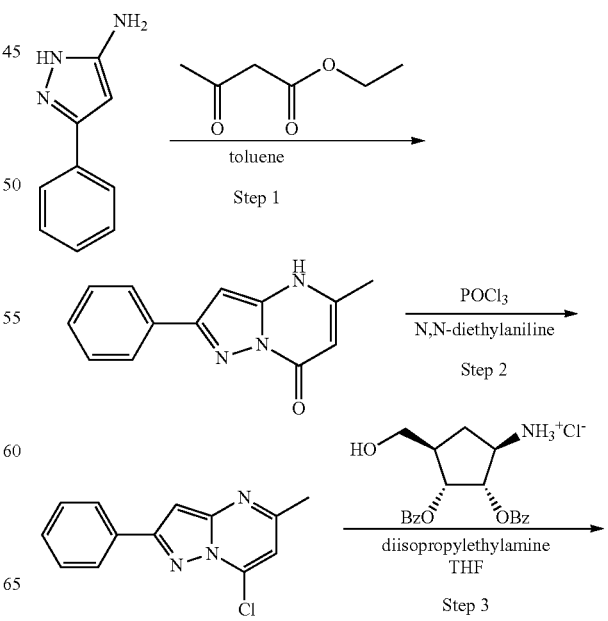

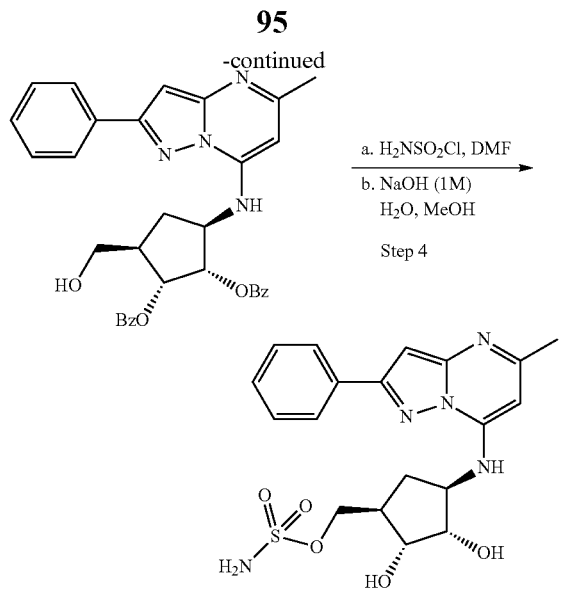

Step 4: (rac)-{(1R,2R,3S,4R)-2,3-dihydroxy-4-[(5-methyl-2-phenylpyrazolo[1,5-a]pyrimidin-7-yl)amino]cyclopentyl}methyl rel-sulfamate (I-4)

The title compound is synthesized from (rac)-(1S,2R,3R,5R)-3-(hydroxymethyl)-5-[(5-methyl-2-phenylpyrazolo[1,5-a]pyrimidin-7-yl)amino]cyclopentane-1,2-diyl reldi-benzoate following Step 7 from Method B (yield 35%). LCMS: (AA) M+1 434; $^1$H NMR (400 MHz, MeOD) δ 8.00 (d, J=7.4 Hz, 2H), 7.44 (t, J=7.5 Hz, 2H), 7.37 (t, J=7.2 Hz, 1H), 6.63 (s, 1H), 6.21 (s, 1H), 4.28-4.17 (m, 2H), 4.12-4.04 (m, 1H), 4.03-3.95 (m, 2H), 2.58-2.36 (m, 5H), 1.62-1.50 (m, 1H).

Method F [Example 6]

Example 6. Synthesis of (rac)-{(1R,2R,3S,4R)-2,3-dihydroxy-4-[(6-methyl-2-phenylpyrazolo[1,5-a]pyrimidin-7-yl)amino]cyclopentyl}methyl rel-sulfamate (I-89)

Step 1: 5-Methyl-2-phenylpyrazolo[1,5-a]pyrimidin-7(4H)-one

A mixture of 5-phenyl-1H-pyrazol-3-ylamine (501 mg, 3.15 mmol) and 3-oxobutanoic acid ethyl ester (0.433 mL, 3.39 mmol) in anhydrous toluene (2.9 mL) is heated at 120° C. in a sealed vial. After 2 hr, the reaction is cooled to room temperature. The precipitate is collected in a Buchner funnel and washed with hexanes to afford 5-methyl-2-phenylpyrazolo[1,5-a]pyrimidin-7(4H)-one (577 mg, yield 81%). LCMS: (AA) M+1 226; $^1$H NMR (400 MHz, DMSO) δ 12.35 (s, 1H), 8.01-7.92 (m, 2H), 7.49-7.43 (m, 2H), 7.42-7.37 (m, 1H), 6.57 (s, 1H), 5.60 (s, 1H), 2.29 (s, 3H).

Step 2: 7-chloro-5-methyl-2-phenylpyrazolo[1,5-a]pyrimidine

5-Methyl-2-phenylpyrazolo[1,5-a]pyrimidin-7(4H)-one (210 mg, 0.932 mmol) is heated in phosphoryl chloride (1.74 mL, 18.6 mmol) in a sealed vial at 100° C. for 2 hr. The reaction mixture is cooled to room temperature and slowly poured over ice. The resulting suspension is extracted with dichloromethane and washed with brine. The organic layer is dried over Na$_2$SO$_4$, filtered and concentrated in vacuo. The crude material is purification by column chromatography (eluent 0-100% ethyl acetate:hexanes) to provide 7-chloro-5-methyl-2-phenylpyrazolo[1,5-a]pyrimidine (123 mg, yield 54%). LCMS: (AA) M+1 244; $^1$H NMR (400 MHz, DMSO) δ 8.07-8.02 (m, 2H), 7.53-7.47 (m, 2H), 7.46-7.41 (m, 1H), 7.32 (s, 1H), 7.23 (s, 1H), 2.53 (s, 3H).

Step 3: (rac)-(1S,2R,3R,5R)-3-(hydroxymethyl)-5-[(5-methyl-2-phenylpyrazolo[1,5-a]pyrimidin-7-yl)amino]cyclopentane-1,2-diyl reldi-benzoate The title compound is synthesized from 7-chloro-5-methyl-2-phenylpyrazolo[1,5-a]pyrimidine following Step 3 from Method D except DMF is used instead of THF. LCMS: (AA) M+1 563; $^1$H NMR (400 MHz, MeOD) δ 8.06-7.97 (m, 3H), 7.88 (d, J=7.7 Hz, 2H), 7.62-7.49 (m, 2H), 7.46-7.29 (m, 8H), 6.62 (s, 1H), 6.24 (s, 1H), 5.70-5.58 (m, 2H), 4.60-4.50 (m, 1H), 3.91-3.81 (m, 1H), 3.80-3.72 (m, 1H), 2.78-2.65 (m, 2H), 2.34 (s, 3H), 1.95-1.82 (m, 1H).

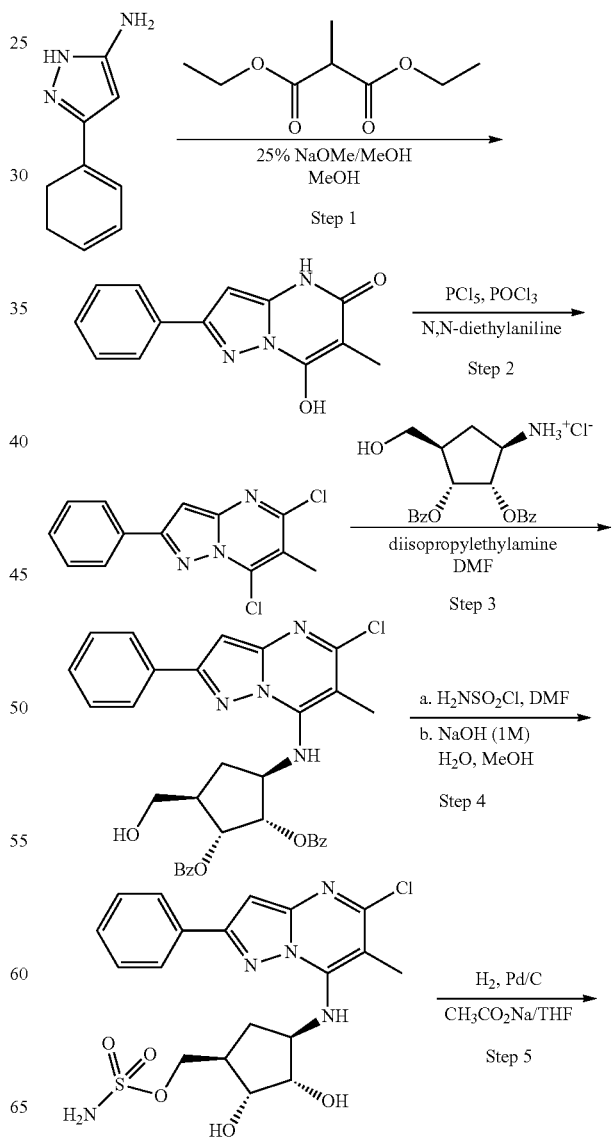

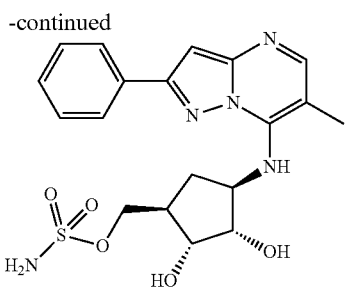

Step 1: 7-hydroxy-6-methyl-2-phenylpyrazolo[1,5-a]pyrimidin-5(4H)-one

To a solution of dimethyl methylmalonate (1.30 mL, 9.80 mmol) and 5-amino-3-phenylpyrazole (1.50 g, 9.42 mmol) in methanol (11 mL) is added 25% sodium methoxide in methanol (6.04 mL, 26.4 mmol). The reaction mixture is heated at 75° C. for 48 hr. The precipitate was collected in a Buchner funnel and washed with dichloromethane to provide 7-hydroxy-6-methyl-2-phenylpyrazolo[1,5-a]pyrimidin-5(4H)-one (2.87 g, yield 95%). LCMS: (AA) M+1 242; $^1$H NMR (400 MHz, DMSO) δ 10.39 (s, 1H), 7.92-7.86 (m, 2H), 7.41-7.33 (m, 2H), 7.32-7.26 (m, 1H), 5.92 (s, 1H), 1.75 (s, 3H).

Step 2: 5,7-dichloro-6-methyl-2-phenylpyrazolo[1,5-a]pyrimidine

The title compound is synthesized from 7-hydroxy-6-methyl-2-phenylpyrazolo[1,5-a]pyrimidin-5(4H)-one following Step 2 from Method D (yield 61%).

Step 3: (rac)-(1R,2S,3R,5R)-3-[(5-chloro-6-methyl-2-phenylpyrazolo[1,5-a]pyrimidin-7-yl)amino]-5-(hydroxymethyl)cyclopentane-1,2-diyl reldi-benzoate The title compound is synthesized from 5,7-dichloro-6-methyl-2-phenylpyrazolo[1,5-a]pyrimidine following Step 3 from Method D except DMF is used instead of THF (yield 85%). LCMS: (AA) M+1 597.

Step 4: (rac)-{(1R,2R,3S,4R)-4-[(5-chloro-6-methyl-2-phenylpyrazolo[1,5-a]pyrimidin-7-yl)amino]-2,3-dihydroxycyclopentyl}methyl rel-sulfamate The title compound is synthesized from (rac)-(1R,2S,3R,5R)-3-[(5-chloro-6-methyl-2-phenylpyrazolo[1,5-a]pyrimidin-7-yl)amino]-5-(hydroxymethyl)cyclopentane-1,2-diyl reldi-benzoate following Step 7 from Method B (yield 74%). LCMS: (AA) M+1 468.

Step 5: (rac)-{(1R,2R,3S,4R)-2,3-dihydroxy-4-[(6-methyl-2-phenylpyrazolo[1,5-a]pyrimidin-7-yl)amino]cyclopentyl}methyl rel-sulfamate (I-89)

A pressure bottle is charged with (rac)-{(1R,2R,3S,4R)-4-[(5-chloro-6-methyl-2-phenylpyrazolo[1,5-a]pyrimidin-7-yl)amino]-2,3-dihydroxycyclopentyl}methyl rel-sulfamate (111 mg, 0.237 mmol), tetrahydrofuran (1.4 mL) and Pd [10% on carbon/50% water wet; Degussa type) 76 mg, 0.036 mmol)]. The reaction is stirred at room temperature under an atmosphere of hydrogen (30 psi) for 18 hr. The reaction mixture is filtered through celite and concentrated in vacuo. The crude material is purified by preparative HPLC to provide (rac)-{(1R,2R,3S,4R)-2,3-dihydroxy-4-[(6-methyl-2-phenylpyrazolo[1,5-a]pyrimidin-7-yl)amino]cyclopentyl}methyl rel-sulfamate (15 mg, yield 13%). LCMS: (FA) M+1 434; $^1$H NMR (400 MHz, MeOD) δ 8.05-7.98 (m, 2H), 7.94 (s, 1H), 7.43 (t, J=7.4 Hz, 2H), 7.36 (t, J=7.3 Hz, 1H), 6.69 (s, 1H), 4.20 (t, J=7.8 Hz, 2H), 4.03-3.94 (m, 2H), 2.64 (s, 1H), 2.54-2.31 (m, 5H), 1.64-1.51 (m, 1H).

Example 7. Compounds Prepared by Method A

(rac)-[(1R,2R,3S,4R)-2,3-dihydroxy-4-{[2-(1H-indol-3-yl)pyrazolo[1,5-a]pyrimidin-7-yl]amino}cyclopentyl]methyl rel-sulfamate (I-32)

The title compound is prepared using {1-[tert-butyl(dimethyl)silyl]-1H-indol-3-yl}boronic acid in Step 1 instead of 1-naphthaleneboronic acid. LCMS: (AA) M+1 459; $^1$H NMR (400 MHz, MeOD) δ 8.31-8.26 (m, 1H), 8.10 (d, J=5.5 Hz, 1H), 7.86 (s, 1H), 7.46-7.40 (m, 1H), 7.22-7.14 (m, 2H), 6.70 (s, 1H), 6.28 (d, J=5.6 Hz, 1H), 4.29-4.19 (m, 2H), 4.17-4.09 (m, 1H), 4.07 (t, J=5.8 Hz, 1H), 4.00 (t, J=5.4 Hz, 1H), 2.61-2.50 (m, 1H), 2.48-2.37 (m, 1H), 1.67-1.56 (m, 1H).

(rac)-[(1R,2R,3S,4R)-4-{[2-(9H-carbazol-3-yl)pyrazolo[1,5-a]pyrimidin-7-yl]amino}-2,3-dihydroxycyclopentyl]methyl rel-sulfamate (I-37)

The title compound is prepared using 3-(4,4,5,5-tetramethyl-1,3,2-dioxaborolan-2-yl)-9H-carbazole in Step 1 instead of 1-naphthaleneboronic acid. LCMS: (AA) M+1 509; $^1$H NMR (400 MHz, MeOD) δ 8.78 (s, 1H), 8.19-8.03 (m, 3H), 7.51 (d, J=8.5 Hz, 1H), 7.46 (d, J=8.1 Hz, 1H), 7.38 (dd, J=8.1, 7.1 Hz, 1H), 7.18 (t, J=7.4 Hz, 1H), 6.82 (s, 1H), 6.29 (d, J=5.5 Hz, 1H), 4.31-4.20 (m, 2H), 4.16-3.97 (m, 3H), 2.61-2.49 (m, 1H), 2.49-2.37 (m, 1H), 1.68-1.55 (m, 1H).

(rac)-[(1R,2R,3S,4R)-2,3-dihydroxy-4-{[2-(5-methyl-2-phenyl-1,3-thiazol-4-yl)pyrazolo[1,5-a]pyrimidin-7-yl]amino}cyclopentyl]methyl rel-sulfamate (I-38)

The title compound is prepared using 5-methyl-2-phenyl-4-(4,4,5,5-tetramethyl-1,3,2-dioxaborolan-2-yl)-1,3-thiazole in Step 1 instead of 1-naphthaleneboronic acid. LCMS: (AA) M+1 517; $^1$H NMR (300 MHz, MeOD) δ 8.17 (d, J=5.5 Hz, 1H), 8.06-7.93 (m, 2H), 7.56-7.41 (m, 3H), 6.83 (s, 1H), 6.36 (d, J=5.5 Hz, 1H), 4.34-3.95 (m, 5H), 2.84 (s, 3H), 2.73-2.34 (m, 2H), 1.70-1.53 (m, 1H).

(rac)-[(1R,2R,3S,4R)-4-{[2-(5-chloro-1H-indol-3-yl)pyrazolo[1,5-a]pyrimidin-7-yl]amino}-2,3-dihydroxycyclopentyl]methyl rel-sulfamate (I-54)

The title compound is prepared using 1-boc-5-chloroindole-3-boronic acid pinacol ester in Step 1 instead of 1-naphthaleneboronic acid. LCMS: (AA) M+1 493; $^1$H NMR (300 MHz, MeOD) δ 8.28 (d, J=2.0 Hz, 1H), 8.10 (d, J=5.5 Hz, 1H), 7.91 (s, 1H), 7.41 (d, J=8.6 Hz, 1H), 7.15 (d, J=10.6 Hz, 1H), 6.68 (s, 1H), 6.28 (d, J=5.5 Hz, 1H), 4.32-3.94 (m, 5H), 2.62-2.34 (m, 2H), 1.68-1.48 (m, 1H).

(rac)-[(1R,2R,3S,4R)-4-{[2-(6-chloro-1H-indol-3-yl)pyrazolo[1,5-a]pyrimidin-7-yl]amino}-2,3-dihydroxycyclopentyl]methyl rel-sulfamate (I-55)

The title compound is prepared using 1-boc-6-chloroindole-3-boronic acid pinacol ester in Step 1 instead of 1-naphthaleneboronic acid. LCMS: (AA) M+1 493; $^1$H NMR (300 MHz, MeOD) δ 8.30 (d, J=8.5 Hz, 1H), 8.08 (d, J=5.5 Hz, 1H), 7.87 (s, 1H), 7.44 (s, 1H), 7.14 (d, J=8.6 Hz, 1H), 6.67 (s, 1H), 6.25 (d, J=5.5 Hz, 1H), 4.31-4.18 (m, 2H), 4.17-3.95 (m, 3H), 2.60-2.36 (m, 2H), 1.66-1.50 (m, 1H).

(rac)-[(1R,2R,3S,4R)-4-{[2-(9H-carbazol-2-yl)pyrazolo[1,5-a]pyrimidin-7-yl]amino}-2,3-dihydroxycyclopentyl]methyl rel-sulfamate (I-62)

The title compound is prepared using 2-(4,4,5,5-Tetramethyl-1,3, 2-dioxaborolan-2-yl)-9H-carbazole in Step 1 instead of 1-naphthaleneboronic acid. LCMS: (AA) M+1 509; $^1$H NMR (400 MHz, MeOD) δ 8.14-8.03 (m, 4H), 7.88-7.83 (m, 1H), 7.46 (d, J=8.1 Hz, 1H), 7.41-7.34 (m, 1H), 7.20-7.13 (m, 1H), 6.82 (s, 1H), 6.28 (d, J=5.6 Hz, 1H), 4.29-4.19 (m, 2H), 4.15-3.97 (m, 3H), 2.58-2.48 (m, 1H), 2.48-2.36 (m, 1H), 1.65-1.54 (m, 1H).

(rac)-[(1R,2R,3S,4R)-2,3-dihydroxy-4-{[2-(2-phenyl-1,3-oxazol-5-yl)pyrazolo[1,5-a]pyrimidin-7-yl]amino}cyclopentyl]methyl rel-sulfamate (I-67)

The title compound is prepared using 2-phenyl-5-(4,4,5, 5-tetramethyl-1,3,2-dioxaborolan-2-yl)-oxazole in Step 1 instead of 1-naphthaleneboronic acid. LCMS: (AA) M+1 487; $^1$H NMR (300 MHz, MeOD) δ 8.22-8.09 (m, 3H), 7.80 (s, 1H), 7.59-7.51 (m, 3H), 6.81 (s, 1H), 6.39 (d, J=5.6 Hz, 1H), 4.31-4.19 (m, 2H), 4.18-4.08 (m, 1H), 4.07-3.96 (m, 2H), 2.57-2.37 (m, 2H), 1.67-1.56 (m, 1H).

(s.e)-[(1R,2R,3S,4R)-2,3-dihydroxy-4-({2-[2-methoxy-5-(trifluoromethoxy)phenyl]pyrazolo[1,5-a]pyrimidin-7-yl}amino)cyclopentyl]methyl sulfamate (I-102)

The title compound is prepared using 2-Methoxy-5-(trifluoromethoxy)phenylboronic acid in Step 1 instead of 1-naphthaleneboronic acid. LCMS: (AA) M+1 534; $^1$H NMR (400 MHz, DMSO) δ 8.22 (d, J=3.1 Hz, 1H), 8.16 (d, J=5.3 Hz, 1H), 7.75 (s, 1H), 7.56-7.33 (m, 3H), 7.27 (d, J=9.2 Hz, 1H), 6.97 (s, 1H), 6.29 (d, J=5.4 Hz, 1H), 5.04 (d, J=5.4 Hz, 1H), 4.82 (s, 1H), 4.17-4.00 (m, 2H), 4.00-3.94 (m, 2H), 3.81-3.73 (m, 1H), 3.32 (s, 3H), 2.38-2.18 (m, 2H), 1.57-1.45 (m, 1H).

(rac)-((1R,2R,3S,4R)-4-(2-(dibenzo[b,d]furan-4-yl)pyrazolo[1,5-a]pyrimidin-7-ylamino)-2,3-dihydroxycyclopentyl)methyl rel-sulfamate (I-10)

The title compound is prepared using dibenzothiophene-4-boronic acid in Step 1 instead of 1-naphthaleneboronic acid. LCMS: (AA) M+1 510; $^1$H NMR (400 MHz, MeOD) δ 8.40-8.34 (m, 1H), 8.18 (d, J=5.5 Hz, 1H), 8.10-8.04 (m, 2H), 7.72 (d, J=8.2 Hz, 1H), 7.58-7.37 (m, 3H), 7.31 (s, 1H), 6.37 (d, J=5.6 Hz, 1H), 4.30-4.21 (m, 2H), 4.19-4.11 (m, 1H), 4.10-4.05 (m, 1H), 4.03-3.99 (m, 1H), 2.62-2.50 (m, 1H), 2.49-2.38 (m, 1H), 1.69-1.57 (m, 1H).

(s.e.)-((1R,2R,3S,4R)-4-(2-(dibenzo[b,d]furan-4-yl)pyrazolo[1,5-a]pyrimidin-7-ylamino)-2,3-dihydroxycyclopentyl)methyl sulfamate (I-103)

The title compound is prepared using dibenzothiophene-4-boronic acid in Step 1 instead of 1-naphthaleneboronic acid. LCMS: (AA) M+1 510; $^1$H NMR (400 MHz, MeOD) δ 8.40-8.34 (m, 1H), 8.18 (d, J=5.5 Hz, 1H), 8.10-8.04 (m, 2H), 7.72 (d, J=8.2 Hz, 1H), 7.58-7.37 (m, 3H), 7.31 (s, 1H), 6.37 (d, J=5.6 Hz, 1H), 4.30-4.21 (m, 2H), 4.19-4.11 (m, 1H), 4.10-4.05 (m, 1H), 4.03-3.99 (m, 1H), 2.62-2.50 (m, 1H), 2.49-2.38 (m, 1H), 1.69-1.57 (m, 1H).

(rac)-[(1R,2R,3S,4R)-2,3-dihydroxy-4-{[2-(1H-indol-5-yl)pyrazolo[1,5-a]pyrimidin-7-yl]amino}cyclopentyl]methyl rel-sulfamate (I-74)

The title compound is prepared using 5-indolyl boronic acid in Step 1 instead of 1-naphthaleneboronic acid. LCMS: (AA) M+1 459; $^1$H NMR (300 MHz, MeOD) δ 8.29 (s, 1H), 8.18 (d, J=7.0 Hz, 1H), 7.93-7.76 (m, 1H), 7.48 (d, J=8.5 Hz, 1H), 7.35-7.25 (m, 1H), 6.89 (s, 1H), 6.61 (d, J=7.1 Hz, 1H), 6.57-6.53 (m, 1H), 4.44-4.18 (m, 3H), 4.17-4.10 (m, 1H), 4.04-3.98 (m, 1H), 2.54-2.35 (m, 2H), 1.82-1.63 (m, 1H).

(s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl)methyl sulfamate (I-101)

The title compound is prepared using trifluoromethylthio-3-(4,4, 5,5-tetramethyl-[1,3,2]dioxaborolan-2-yl)-benzene in Step 1 instead of 1-naphthaleneboronic acid. LCMS: (AA) M+1 520; $^1$H NMR (400 MHz, MeOD) δ 8.41 (s, 1H), 8.22 (d, J=7.8 Hz, 1H), 8.14 (d, J=5.4 Hz, 1H), 7.71 (d, J=7.8 Hz, 1H), 7.65-7.54 (m, 1H), 6.83 (s, 1H), 6.34 (d, J=5.5 Hz, 1H), 4.30-3.92 (m, 5H), 2.57-2.34 (m, 2H), 1.67-1.52 (m, 1H).

(rac)-((1R,2R,3S,4R)-2,3-dihydroxy-4-(2-(3-(trifluoromethylthio)phenyl)pyrazolo[1,5-a]pyrimidin-7-ylamino)cyclopentyl)methyl rel-sulfamate (I-44)

The title compound is prepared using trifluoromethylthio-3-(4,4, 5,5-tetramethyl-[1,3,2]dioxaborolan-2-yl)-benzene in Step 1 instead of 1-naphthaleneboronic acid. LCMS: (AA) M+1 520; $^1$H NMR (400 MHz, MeOD) δ 8.41 (s, 1H), 8.22 (d, J=7.8 Hz, 1H), 8.14 (d, J=5.4 Hz, 1H), 7.71 (d, J=7.8 Hz, 1H), 7.65-7.54 (m, 1H), 6.83 (s, 1H), 6.34 (d, J=5.5 Hz, 1H), 4.30-3.92 (m, 5H), 2.57-2.34 (m, 2H), 1.67-1.52 (m, 1H).

(s.e.)-((1R,2R,3S,4R)-4-(2-(4-fluoronaphthalen-1-yl)pyrazolo[1,5-a]pyrimidin-7-ylamino)-2,3-dihydroxycyclopentyl)methyl sulfamate (I-100)

The title compound is prepared using 4-fluoronaphthalene-1-boronic acid in Step 1 instead of 1-naphthaleneboronic acid. LCMS: (AA) M+1 488; $^1$H NMR (400 MHz, MeOD) δ 8.60-8.49 (m, 1H), 8.27-8.14 (m, 2H), 7.85-7.77 (m, 1H), 7.70-7.61 (m, 2H), 7.37-7.26 (m, 1H), 6.71 (s, 1H), 6.42 (d, J=5.6 Hz, 1H), 4.28-4.12 (m, 3H), 4.08-4.03 (m, 1H), 4.01-3.96 (m, 1H), 2.62-2.36 (m, 2H), 1.65-1.51 (m, 1H).

(rac)-((1R,2R,3S,4R)-2,3-Dihydroxy-4-((2-(2-methoxy-5-(trifluoromethyl)phenyl)-pyrazolo[1,5-a]pyrimidin-7-yl)amino)cyclopentyl)methyl rel-sulfamate (I-65)

The title compound is prepared using 2-methoxy-5-(trifluoromethyl)phenylboronic acid in Step 1 instead of 1-naphthaleneboronic acid. LCMS: (FA) M+1 518; ¹H NMR (400 MHz, DMSO) δ 8.59-8.45 (m, 1H), 8.16 (d, J=5.3 Hz, 1H), 7.91-7.70 (m, 2H), 7.60-7.30 (m, 3H), 6.97 (s, 1H), 6.29 (d, J=5.4 Hz, 1H), 5.05 (s, 1H), 4.82 (s, 1H), 4.22-4.07 (m, 1H), 4.07-3.89 (m, 5H), 3.81-3.69 (m, 1H), 2.37-2.16 (m, 2H), 1.59-1.44 (m, 1H).

(rac)-((1R,2R,3S,4R)-2,3-Dihydroxy-4-((2-(2-methoxy-5-(trifluoromethoxy)phenyl)pyrazolo[1,5-a]pyrimidin-7-yl)amino)cyclopentyl)methyl rel-sulfamate (I-66)

The title compound is prepared using 2-methoxy-5-(trifluoromethoxy)phenylboronic acid in Step 1 instead of 1-naphthaleneboronic acid. LCMS: (FA) M+1 534; ¹H NMR (400 MHz, DMSO) δ 8.22 (d, J=3.0 Hz, 1H), 8.15 (d, J=5.3 Hz, 1H), 7.44-7.37 (m, 1H), 7.29-7.23 (m, 1H), 6.97 (s, 1H), 6.28 (d, J=5.4 Hz, 1H), 4.16-4.08 (m, 1H), 4.05-3.89 (m, 6H), 3.80-3.71 (m, 1H), 2.37-2.17 (m, 2H), 1.57-1.43 (m, 1H).

(rac)-((1R,2R,3S,4R)-4-((2-(Benzo[b]thiophen-4-yl)pyrazolo[1,5-a]pyrimidin-7-yl)amino)-2,3-dihydroxycyclopentyl)methyl rel-sulfamate (I-61)

The title compound is prepared using benzothiophene-4-boronic acid pinacol ester in Step 1 instead of 1-naphthaleneboronic acid. LCMS: (FA) M+1 476; ¹H NMR (400 MHz, DMSO) δ 8.38 (d, J=5.5 Hz, 1H), 8.20-8.15 (m, 2H), 8.07 (d, J=8.0 Hz, 1H), 7.95-7.91 (m, 1H), 7.87 (d, J=5.6 Hz, 1H), 7.77-7.69 (m, 1H), 7.58-7.41 (m, 2H), 6.93 (s, 1H), 6.31 (d, J=5.4 Hz, 1H), 4.17-4.09 (m, 1H), 4.07-3.93 (m, 4H), 3.81-3.74 (m, 2H), 2.41-2.18 (m, 2H), 1.61-1.43 (m, 1H).

(rac)-((1R,2R,3S,4R)-2,3-Dihydroxy-4-((2-(5-(trifluoromethyl)thiophen-2-yl)pyrazolo[1,5-a]pyrimidin-7-yl)amino)cyclopentyl)methyl rel-sulfamate (I-60)

The title compound is prepared using 5-(trifluoromethyl)thiophen-2-ylboronic acid in Step 1 instead of 1-naphthaleneboronic acid. LCMS: (FA) M+1 494; ¹H NMR (400 MHz, DMSO) δ 8.21-8.13 (m, 1H), 7.82-7.75 (m, 2H), 7.74-7.67 (m, 1H), 7.48 (s, 2H), 6.98 (s, 1H), 6.31 (d, J=5.5 Hz, 1H), 5.06-5.00 (m, 1H), 4.84-4.77 (m, 1H), 4.17-4.07 (m, 1H), 4.06-3.89 (m, 3H), 3.80-3.71 (m, 1H), 2.37-2.17 (m, 2H), 1.53-1.42 (m, 1H).

(rac)-((1R,2R,3S,4R)-4-((2-(Dibenzo[b,d]thiophen-4-yl)pyrazolo[1,5-a]pyrimidin-7-yl)amino)-2,3-dihydroxycyclopentyl)methyl rel-sulfamate (I-56)

The title compound is prepared using dibenzo[b,d]thiophen-4-ylboronic acid in Step 1 instead of 1-naphthaleneboronic acid. LCMS: (FA) M+1 526; ¹H NMR (300 MHz, DMSO) δ 8.51-8.39 (m, 2H), 8.27-8.20 (m, 2H), 8.12-8.02 (m, 1H), 7.67 (t, J=7.7 Hz, 1H), 7.61-7.42 (m, 4H), 7.39-7.27 (m, 1H), 7.13 (s, 1H), 6.39 (d, J=5.4 Hz, 1H), 4.21-4.13 (m, 1H), 4.11-3.97 (m, 3H), 3.86-3.76 (m, 1H), 2.46-2.36 (m, 1H), 2.36-2.21 (m, 1H), 1.68-1.42 (m, 1H).

(rac)-((1R,2R,3S,4R)-4-((2-(3-(Difluoromethoxy)phenyl)pyrazolo[1,5-a]pyrimidin-7-yl)amino)-2,3-dihydroxycyclopentyl)methyl rel-sulfamate (I-50)

The title compound is prepared using 3-(difluoromethoxy)-benzeneboronic acid in Step 1 instead of 1-naphthaleneboronic acid. LCMS: (AA) M+1 486; ¹H NMR (300 MHz, DMSO) δ 8.15 (d, J=5.3 Hz, 1H), 8.00-7.93 (m, 1H), 7.92-7.87 (m, 1H), 7.77-7.66 (m, 1H), 7.58-7.49 (m, 2H), 7.25-7.18 (m, 1H), 6.97 (s, 1H), 6.28 (d, J=5.4 Hz, 1H), 5.12-4.94 (m, 1H), 4.90-4.72 (m, 1H), 4.18-4.09 (m, 1H), 4.08-3.89 (m, 3H), 3.82-3.72 (m, 1H), 2.40-2.17 (m, 2H), 1.57-1.40 (m, 1H).

(rac)-((1R,2R,3S,4R)-2,3-Dihydroxy-4-((2-(3-phenoxyphenyl)pyrazolo[1,5-a]pyrimidin-7-yl)amino)cyclopentyl)methyl rel-sulfamate (I-51)

The title compound is prepared using 4,4,5,5-tetramethyl-2-(3-phenoxyphenyl)-1,3,2-dioxaborolane in Step 1 instead of 1-naphthaleneboronic acid. LCMS: (AA) M+1 512; ¹H NMR (300 MHz, DMSO) δ 8.13 (d, J=5.3 Hz, 1H), 7.92-7.82 (m, 2H), 7.49 (t, J=7.9 Hz, 1H), 7.44-7.35 (m, 2H), 7.13 (t, J=7.4 Hz, 1H), 7.08-6.97 (m, 3H), 6.93 (s, 1H), 6.26 (d, J=5.4 Hz, 1H), 4.20-4.07 (m, 1H), 4.07-3.86 (m, 3H), 3.80-3.69 (m, 1H), 2.40-2.14 (m, 2H), 1.55-1.40 (m, 1H).

(rac)-((1R,2R,3S,4R)-4-((2-(Benzo[b]thiophen-7-yl)pyrazolo[1,5-a]pyrimidin-7-yl)amino)-2,3-dihydroxycyclopentyl)methyl rel-sulfamate (I-45)

The title compound is prepared using 1-benzothien-7-ylboronic acid in Step 1 instead of 1-naphthaleneboronic acid. LCMS: (FA) M+1 476; ¹H NMR (400 MHz, DMSO) δ 8.25 (s, 1H), 8.10 (d, J=7.3 Hz, 1H), 7.99 (d, J=7.2 Hz, 1H), 7.88 (d, J=5.5 Hz, 1H), 7.59-7.46 (m, 4H), 7.26 (d, J=7.5 Hz, 1H), 7.10 (s, 1H), 6.39 (d, J=5.2 Hz, 1H), 5.09 (d, J=5.6 Hz, 1H), 4.85 (d, J=5.3 Hz, 1H), 4.23-4.12 (m, 1H), 4.11-3.95 (m, 3H), 3.86-3.76 (m, 1H), 2.48-2.37 (m, 1H), 2.36-2.24 (m, 1H), 1.56-1.44 (m, 1H).

(rac)-((1R,2R,3S,4R)-2,3-Dihydroxy-4-((2-(3-(trifluoromethoxy)phenyl)pyrazolo[1,5-a]pyrimidin-7-yl)amino)cyclopentyl)methyl rel-sulfamate (I-40)

The title compound is prepared using m-(trifluoromethoxy)phenylboronic acid in Step 1 instead of 1-naphthaleneboronic acid. LCMS: (AA) M+1 504; ¹H NMR (300 MHz, DMSO) δ 8.20-8.04 (m, 3H), 7.67-7.58 (m, 1H), 7.44-7.36 (m, 1H), 7.03 (s, 1H), 6.29 (d, J=5.4 Hz, 1H), 5.04 (s, 1H), 4.82 (s, 1H), 4.18-4.08 (m, 1H), 4.08-3.89 (m, 3H), 3.82-3.72 (m, 1H), 2.39-2.17 (m, 2H), 1.58-1.42 (m, 1H).

(rac)-((1R,2R,3S,4R)-2,3-Dihydroxy-4-((2-(3-(pyridin-2-yl)phenyl)pyrazolo[1,5-a]pyrimidin-7-yl)amino)cyclopentyl)methyl rel-sulfamate (I-36)

The title compound is prepared using (3-pyridin-2-ylphenyl)boronic acid in Step 1 instead of 1-naphthaleneboronic acid. LCMS: (AA) M+1 497; ¹H NMR (300 MHz, DMSO) δ 8.79-8.66 (m, 2H), 8.22-7.87 (m, 6H), 7.80-7.67 (m, 1H), 7.66-7.56 (m, 1H), 7.45-7.36 (m, 1H), 7.02 (s, 1H), 6.28 (d, J=5.3 Hz, 1H), 4.20-3.95 (m, 4H), 3.82-3.74 (m, 1H), 3.40-3.34 (m, 1H), 2.42-2.19 (m, 2H), 1.60-1.44 (m, 1H).

(rac)-((1R,2R,3S,4R)-4-((2-(3-Bromophenyl)pyrazolo[1,5-a]pyrimidin-7-yl)amino)-2,3-dihydroxycyclopentyl)methyl rel-sulfamate (I-28)

The title compound is prepared using 3-bromophenylboronic acid in Step 1 instead of 1-naphthaleneboronic acid. LCMS: (AA) M+1 498; ¹H NMR (300 MHz, DMSO) δ 8.33 (s, 1H), 8.15 (d, J=5.3 Hz, 1H), 8.07 (d, J=7.8 Hz, 1H), 7.78-7.71 (m, 1H), 7.63-7.57 (m, 1H), 7.51-7.40 (m, 3H), 6.99 (s, 1H), 6.28 (d, J=5.4 Hz, 1H), 5.05-4.99 (m, 1H), 4.83-4.77 (m, 1H), 4.18-4.09 (m, 1H), 4.07-3.91 (m, 3H), 3.81-3.73 (m, 1H), 2.40-2.17 (m, 2H), 1.58-1.43 (m, 1H).

(rac)-((1R,2R,3S,4R)-4-((2-(2-Fluoro-5-(trifluoromethyl)phenyl)pyrazolo[1,5-a]pyrimidin-7-yl)amino)-2,3-dihydroxycyclopentyl)methyl rel-sulfamate (I-29)

The title compound is prepared using 2-fluoro-5-(trifluoromethyl)phenylboronic acid in Step 1 instead of 1-naphthaleneboronic acid. LCMS: (FA) M+1 506; $^1$H NMR (400 MHz, DMSO) δ 8.64-8.58 (m, 1H), 8.20 (d, J=5.3 Hz, 1H), 7.94-7.84 (m, 2H), 7.67-7.59 (m, 1H), 7.48 (s, 2H), 6.86 (d, J=4.2 Hz, 1H), 6.35 (d, J=5.4 Hz, 1H), 5.04 (d, J=5.6 Hz, 1H), 4.81 (d, J=5.2 Hz, 1H), 4.17-4.08 (m, 1H), 4.07-3.92 (m, 3H), 3.81-3.73 (m, 1H), 2.38-2.17 (m, 2H), 1.58-1.45 (m, 1H).

(rac)-((1R,2R,3S,4R)-4-((2-(2-Chloro-5-(trifluoromethyl)phenyl)pyrazolo[1,5-a]pyrimidin-7-yl)amino)-2,3-dihydroxycyclopentyl)methyl rel-sulfamate (I-30)

The title compound is prepared using 2-chloro-5-(trifluoromethyl)phenylboronic acid in Step 1 instead of 1-naphthaleneboronic acid. LCMS: (FA) M+1 522; $^1$H NMR (400 MHz, DMSO) δ 8.33-8.27 (m, 1H), 8.21 (d, J=5.3 Hz, 1H), 7.95-7.91 (m, 1H), 7.90-7.81 (m, 2H), 7.47 (s, 2H), 6.95 (s, 1H), 6.34 (d, J=5.4 Hz, 1H), 5.02 (d, J=5.5 Hz, 1H), 4.80 (d, J=5.2 Hz, 1H), 4.17-4.06 (m, 1H), 4.06-3.90 (m, 3H), 3.80-3.71 (m, 1H), 2.38-2.15 (m, 2H), 1.57-1.43 (m, 1H).

(rac)-((1R,2R,3S,4R)-2,3-Dihydroxy-4-((2-(quinolin-8-yl)pyrazolo[1,5-a]pyrimidin-7-yl)amino)cyclopentyl)methyl rel-sulfamate (I-17)

The title compound is prepared using 8-quinoline boronic acid in Step 1 instead of 1-naphthaleneboronic acid. LCMS: (FA) M+1 471; $^1$H NMR (400 MHz, DMSO) δ 9.07-9.01 (m, 1H), 8.66-8.60 (m, 1H), 8.49-8.43 (m, 1H), 8.18 (d, J=5.3 Hz, 1H), 8.10-8.03 (m, 1H), 7.79-7.70 (m, 2H), 7.65-7.57 (m, 1H), 7.48 (s, 3H), 6.28 (d, J=5.3 Hz, 1H), 5.04 (d, J=5.5 Hz, 1H), 4.81 (d, J=5.3 Hz, 1H), 4.18-4.08 (m, 1H), 4.08-3.91 (m, 3H), 3.83-3.72 (m, 1H), 2.43-2.16 (m, 2H), 1.58-1.44 (m, 1H).

(s.e.)-((1R,2R,3S,4R)-4-(2-(1-fluoronaphthalen-2-yl)pyrazolo[1,5-a]pyrimidin-7-ylamino)-2,3-dihydroxycyclopentyl)methyl sulfamate (I-119)

The title compound is prepared using 2-(1-fluoro-2-naphthyl)-4, 4,5,5-tetramethyl-1,3,2-dioxaborolane in Step 1 instead of 1-naphthaleneboronic acid. LCMS: (AA) M+1 488; $^1$H NMR (400 MHz, DMSO) δ 8.47-8.41 (m, 1H), 8.22-8.16 (m, 2H), 8.04 (d, J=7.8 Hz, 1H), 7.90 (d, J=8.7 Hz, 1H), 7.81 (s, 1H), 7.72-7.63 (m, 2H), 6.94 (d, J=4.0 Hz, 1H), 6.32 (d, J=5.4 Hz, 1H), 5.07 (s, 1H), 4.84 (s, 1H), 4.20-4.10 (m, 1H), 4.07-3.95 (m, 3H), 3.82-3.74 (m, 1H), 2.38-2.23 (m, 2H), 1.57-1.47 (m, 1H).

(s.e.)-((1R,2R,3S,4R)-4-(2-(4-fluoronaphthalen-2-yl)pyrazolo[1,5-a]pyrimidin-7-ylamino)-2,3-dihydroxycyclopentyl)methyl sulfamate (I-118)

The title compound is prepared using 2-(4-fluoro-2-naphthyl)-4, 4,5,5-tetramethyl-1,3,2-dioxaborolane in Step 1 instead of 1-naphthaleneboronic acid. LCMS: (AA) M+1 488; $^1$H NMR (400 MHz, DMSO) δ 8.51 (s, 1H), 8.16 (d, J=5.3 Hz, 1H), 8.15-8.05 (m, 3H), 7.70-7.62 (m, 2H), 7.10 (s, 1H), 6.29 (d, J=5.4 Hz, 1H), 5.75 (s, 1H), 5.05 (s, 1H), 4.14 (dd, J=9.7, 5.9 Hz, 1H), 4.07-3.93 (m, 3H), 3.81-3.75 (m, 1H), 2.39-2.21 (m, 2H), 1.58-1.48 (m, 1H).

(s.e.)-((1R,2R,3S,4R)-4-(2-(3-fluoronaphthalen-2-yl)pyrazolo[1,5-a]pyrimidin-7-ylamino)-2,3-dihydroxycyclopentyl)methyl sulfamate (I-116)

The title compound is prepared using 2-(3-fluoro-2-naphthyl)-4, 4,5,5-tetramethyl-1,3,2-dioxaborolane in Step 1 instead of 1-naphthaleneboronic acid. LCMS: (AA) M+1 488; $^1$H NMR (400 MHz, DMSO) δ 8.80 (d, J=7.7 Hz, 1H), 8.19 (d, J=5.3 Hz, 1H), 8.04 (d, J=8.0 Hz, 1H), 7.96 (d, J=8.0 Hz, 1H), 7.92-7.85 (m, 1H), 7.62-7.52 (m, 3H), 6.86 (d, J=4.2 Hz, 1H), 6.33 (d, J=5.4 Hz, 1H), 5.75 (s, 1H), 5.05 (d, J=5.2 Hz, 1H), 4.21-4.10 (m, 1H), 4.10-3.94 (m, 3H), 3.83-3.74 (m, 1H), 2.40-2.22 (m, 2H), 1.60-1.47 (m, 1H).

(s.e.)-((1R,2R,3S,4R)-4-(2-(6-fluoronaphthalen-2-yl)pyrazolo[1,5-a]pyrimidin-7-ylamino)-2,3-dihydroxycyclopentyl)methyl sulfamate (I-113)

The title compound is prepared using 2-(6-fluoro-2-naphthyl)-4, 4,5,5-tetramethyl-1,3,2-dioxaborolane in Step 1 instead of 1-naphthaleneboronic acid. LCMS: (AA) M+1 488; $^1$H NMR (400 MHz, DMSO) δ 8.66 (s, 1H), 8.32 (d, J=8.6 Hz, 1H), 8.15 (t, J=4.7 Hz, 1H), 8.11-8.05 (m, 1H), 8.02 (d, J=8.7 Hz, 1H), 7.78-7.73 (m, 1H), 7.51-7.44 (m, 2H), 7.03 (s, 1H), 6.27 (t, J=5.7 Hz, 1H), 5.75 (s, 1H), 5.05 (d, J=5.3 Hz, 1H), 4.82 (s, 1H), 4.19-4.11 (m, 1H), 4.09-3.94 (m, 3H), 3.82-3.74 (m, 1H), 2.41-2.20 (m, 2H), 1.58-1.46 (m, 1H).

(rac)-((1R,2R,3S,4R)-4-(2-(5-ethyl benzo[b]thiophen-3-yl)pyrazolo[1,5-a]pyrimidin-7-ylamino)-2,3-dihydroxycyclopentyl)methyl rel-sulfamate (I-94)

The title compound is prepared using 5-ethyl-1-benzothiophen-3-yl)boronic acid in Step 1 instead of 1-naphthaleneboronic acid. LCMS: (AA) M+1 504; $^1$H NMR (400 MHz, DMSO) δ 8.15 (t, J=5.1 Hz, 1H), 7.97 (d, J=4.1 Hz, 1H), 7.89 (d, J=8.2 Hz, 1H), 7.70 (s, 1H), 7.65 (s, 1H), 7.26 (dd, J=8.3, 1.6 Hz, 1H), 6.95 (d, J=4.8 Hz, 1H), 6.29 (d, J=5.5 Hz, 1H), 5.04 (s, 1H), 4.80 (s, 1H), 4.20-4.09 (m, 1H), 4.08-3.92 (m, 3H), 3.82-3.72 (m, 1H), 2.73 (q, J=7.5 Hz, 2H), 2.38-2.19 (m, 3H), 1.56-1.43 (m, 1H), 1.25 (t, J=7.6 Hz, 3H).

(rac)-((1R,2R,3S,4R)-4-(2-(5-ethyl benzo[b]thiophen-2-yl)pyrazolo[1,5-a]pyrimidin-7-ylamino)-2,3-dihydroxycyclopentyl)methyl rel-sulfamate (I-95)

The title compound is prepared using (5-ethyl-1-benzothiophen-2-yl)boronic acid in Step 1 instead of 1-naphthaleneboronic acid. LCMS: (AA) M+1 504; $^1$H NMR (400 MHz, DMSO) δ 8.50 (s, 1H), 8.26 (s, 1H), 8.19 (d, J=5.3 Hz, 1H), 7.96 (d, J=8.3 Hz, 1H), 7.71 (s, 1H), 7.33 (dd, J=8.3, 1.5 Hz, 1H), 6.91 (s, 1H), 6.31 (d, J=5.4 Hz, 1H), 4.19-4.09 (m, 1H), 4.05-3.92 (m, 3H), 3.78 (t, J=4.8 Hz, 1H), 2.82 (q, J=7.6 Hz, 2H), 2.41-2.19 (m, 3H), 1.55-1.43 (m, 1H), 1.28 (t, J=7.6 Hz, 3H).

(rac)-((1R,2R,3S,4R)-4-(2-(benzofuran-3-yl)pyrazolo[1,5-a]pyrimidin-7-ylamino)-2,3-dihydroxycyclopentyl)methyl rel-sulfamate (I-49)

The title compound is prepared using benzofuran-3-boronic acid in Step 1 instead of 1-naphthaleneboronic acid. LCMS: (AA) M+1 460; $^1$H NMR (300 MHz, DMSO) δ 8.65 (s, 1H), 8.57-8.46 (m, 1H), 8.16 (d, J=5.3 Hz, 1H), 7.66 (dd, J=9.2, 3.6 Hz, 2H), 7.41 (dd, J=5.9, 3.2 Hz, 3H), 6.89 (s, 1H), 6.30 (d, J=5.3 Hz, 1H), 4.22-4.11 (m, 1H), 4.09-3.95 (m, 3H), 3.85-3.73 (m, 1H), 2.39-2.22 (m, 2H), 1.60-1.48 (m, 1H).

(rac)-((1R,2R,3S,4R)-4-(2-(5-chlorobenzofuran-3-yl)pyrazolo[1,5-a]pyrimidin-7-ylamino)-2,3-dihydroxycyclopentyl)methyl rel-sulfamate (I-92)

The title compound is prepared using 5-chloro-3-(4,4,5,5-tetramethyl-1,3,2-dioxaborolan-2-yl)-1-benzofuran in Step 1 instead of 1-naphthaleneboronic acid. LCMS: (AA) M+1 494; $^1$H NMR (300 MHz, DMSO) δ 8.75 (s, 1H), 8.52 (d, J=2.1 Hz, 1H), 8.16 (d, J=5.3 Hz, 1H), 7.72 (d, J=8.8 Hz, 1H), 7.45 (dd, J=8.8, 2.1 Hz, 1H), 6.31 (d, J=5.4 Hz, 1H), 4.21-4.11 (m, 1H), 4.09-3.94 (m, 3H), 3.82-3.75 (m, 1H), 2.39-2.20 (m, 3H), 1.61-1.48 (m, 1H).

(rac)-((1R,2R,3S,4R)-4-(2-(6-chlorobenzo[b]thiophen-3-yl)pyrazolo[1,5-a]pyrimidin-7-ylamino)-2,3-dihydroxycyclopentyl)methyl rel-sulfamate (I-91)

The title compound is prepared using (6-chloro-1-benzothiophen-2-yl)boronic acid in Step 1 instead of 1-naphthaleneboronic acid. LCMS: (FA) M+1 510; $^1$H NMR (300 MHz, DMSO) δ 8.89 (d, J=8.7 Hz, 1H), 8.39 (s, 1H), 8.25 (d, J=1.9 Hz, 1H), 8.20-8.15 (m, 1H), 7.70 (d, J=8.0 Hz, 1H), 7.58-7.46 (m, 3H), 6.94 (s, 1H), 6.32 (d, J=5.5 Hz, 1H), 5.04 (s, 1H), 4.83 (s, 1H), 4.21-4.10 (m, 1H), 4.08-3.95 (m, 3H), 3.77 (s, 1H), 2.36-2.24 (m, 2H), 1.61-1.45 (m, 1H).

(rac)-((1R,2R,3S,4R)-2,3-dihydroxy-4-(2-(3-(2-propoxypropan-2-yl)phenyl)pyrazolo[1,5-a]pyrimidin-7-ylamino)cyclopentyl)methyl rel-sulfamate (I-90)

The title compound is prepared using 4,4,5,5-tetramethyl-2-[3-(2-propoxypropan-2-yl)phenyl]-1,3,2-dioxaborolane in Step 1 instead of 1-naphthaleneboronic acid. LCMS: (AA) M+1 520.

(rac)-((1R,2R,3S,4R)-2,3-dihydroxy-4-(2-(3-(2-oxopyrrolidin-1-yl)phenyl)pyrazolo[1,5-a]pyrimidin-7-ylamino)cyclopentyl)methyl rel-sulfamate (I-87)

The title compound is prepared using 1-[3-(4,4,5,5-tetramethyl-1,3,2-dioxaborolan-2-yl)phenyl]pyrrolidin-2-one in Step 1 instead of 1-naphthaleneboronic acid. LCMS: (AA) M+1 503; $^1$H NMR (300 MHz, DMSO) δ 8.21-8.08 (m, 2H), 7.91-7.82 (m, 1H), 7.80-7.70 (m, 1H), 7.53-7.41 (m, 2H), 6.89 (s, 1H), 6.31-6.23 (m, 1H), 4.18-4.08 (m, 1H), 4.06-3.90 (m, 5H), 3.81-3.73 (m, 1H), 2.61-2.51 (m, 2H), 2.38-2.18 (m, 2H), 2.15-2.05 (m, 2H), 1.71 (s, 1H), 1.54-1.43 (m, 1H). (2 pyrrolidine protons under DMSO)

(rac)-((1R,2R,3S,4R)-4-(2-(6-chlorobenzo[b]thiophen-2-yl)pyrazolo[1,5-a]pyrimidin-7-ylamino)-2,3-dihydroxycyclopentyl)methyl rel-sulfamate (I-88)

The title compound is prepared using (6-chloro-1-benzothien-3-yl)boronic acid in Step 1 instead of 1-naphthaleneboronic acid. LCMS: (FA) M+1 510; $^1$H NMR (300 MHz, DMSO) δ 8.17 (d, J=5.3 Hz, 1H), 8.04 (s, 1H), 7.89 (d, J=8.6 Hz, 1H), 7.66 (d, J=7.4 Hz, 1H), 7.54-7.40 (m, 3H), 6.96 (d, J=7.0 Hz, 1H), 6.31 (d, J=5.4 Hz, 1H), 5.04 (s, 1H), 4.80 (s, 1H), 4.19-4.09 (m, 1H), 4.08-3.91 (m, 3H), 3.82-3.72 (m, 1H), 2.35-2.20 (m, 2H), 1.60-1.43 (m, 1H).

(rac)-((1R,2R,3S,4R)-4-(2-(3-(2-ethoxypropan-2-yl)phenyl)pyrazolo[1,5-a]pyrimidin-7-ylamino)-2,3-dihydroxycyclopentyl)methyl rel-sulfamate (I-84)

The title compound is prepared using 2-[3-(1-ethoxy-1-methylethyl)phenyl]-4,4,5,5-tetramethyl-1,3,2-dioxaborolane in Step 1 instead of 1-naphthaleneboronic acid. LCMS: (AA) M+1 506; $^1$H NMR (300 MHz, DMSO) δ 8.14 (d, J=5.3 Hz, 1H), 8.02 (s, 1H), 7.99-7.94 (m, 1H), 7.45 (d, J=4.9 Hz, 2H), 6.90 (s, 1H), 6.26 (d, J=5.4 Hz, 1H), 4.17-4.10 (m, 1H), 4.07-3.93 (m, 3H), 3.80-3.73 (m, 1H), 3.23-3.15 (m, 3H), 2.39-2.19 (m, 2H), 1.53 (s, 6H), 1.10 (t, J=7.0 Hz, 3H).

(rac)-((1R,2R,3S,4R)-2,3-dihydroxy-4-(2-(3-(2-methoxypropan-2-yl)phenyl)pyrazolo[1,5-a]pyrimidin-7-ylamino)cyclopentyl)methyl rel-sulfamate (I-82)

The title compound is prepared using 2-[3-(1-methoxy-1-methylethyl)phenyl]-4,4,5,5-tetramethyl-1,3,2-dioxaborolane in Step 1 instead of 1-naphthaleneboronic acid. LCMS: (AA) M+1 492; $^1$H NMR (300 MHz, DMSO) δ 8.13 (d, J=5.3 Hz, 1H), 8.03 (s, 1H), 7.96 (d, J=6.8 Hz, 1H), 7.49-7.39 (m, 2H), 6.90 (s, 1H), 6.29-6.22 (m, 1H), 4.18-4.10 (m, 1H), 4.07-3.93 (m, 3H), 3.79-3.73 (m, 1H), 3.01 (s, 3H), 2.38-2.22 (m, 2H), 1.52 (m, 7H).

(rac)-((1R,2R,3S,4R)-4-(2-(5-fluorobenzo[b]thiophen-3-yl)pyrazolo[1,5-a]pyrimidin-7-ylamino)-2,3-dihydroxycyclopentyl)methyl rel-sulfamate (I-81)

The title compound is prepared using (5-fluoro-1-benzothien-3-yl)boronic acid in Step 1 instead of 1-naphthaleneboronic acid. LCMS: (FA) M+1 494; $^1$H NMR (300 MHz, DMSO) δ 8.71-8.64 (m, 1H), 8.21-8.09 (m, 2H), 7.85-7.79 (m, 1H), 7.52-7.45 (m, 1H), 7.39-7.31 (m, 1H), 6.95 (s, 1H), 6.34-6.29 (m, 1H), 5.03 (s, 1H), 4.82 (s, 1H), 4.19-4.11 (m, 1H), 4.08-3.94 (m, 3H), 3.81-3.75 (m, 1H), 2.39-2.21 (m, 2H), 1.60-1.50 (m, 1H).

(rac)-((1R,2R,3S,4R)-2,3-dihydroxy-4-(2-(3-morpholinophenyl)pyrazolo[1,5-a]pyrimidin-7-ylamino)cyclopentyl)methyl rel-sulfamate (I-78)

The title compound is prepared using 3-(morpholino)phenylboronic acid in Step 1 instead of 1-naphthaleneboronic acid. LCMS: (AA) M+1 505; $^1$H NMR (300 MHz, DMSO) δ 8.15-8.09 (m, 1H), 7.62 (s, 1H), 7.52 (s, 1H), 7.35-7.29 (m, 1H), 6.99-6.93 (m, 1H), 6.91 (s, 1H), 6.28-6.22 (m, 1H), 5.08 (s, 1H), 4.16-4.09 (m, 1H), 4.05-3.91 (m, 3H), 3.80-3.73 (m, 5H), 3.23-3.17 (m, 4H), 2.37-2.20 (m, 2H), 1.53-1.45 (m, 1H).

(rac)-((1R,2R,3S,4R)-2,3-dihydroxy-4-(2-(3-(piperidin-1-yl)phenyl)pyrazolo[1,5-a]pyrimidin-7-ylamino)cyclopentyl)methyl rel-sulfamate (I-77)

The title compound is prepared using 3-(piperidino)phenylboronic acid in Step 1 instead of 1-naphthaleneboronic acid. LCMS: (AA) M+1 503.

(rac)-((1R,2R,3S,4R)-4-(2-(3-benzoylphenyl)pyrazolo[1,5-a]pyrimidin-7-ylamino)-2,3-dihydroxycyclopentyl)methyl rel-sulfamate (I-73)

The title compound is prepared using 3-benzoylphenylboronic acid pinacol ester in Step 1 instead of 1-naphthaleneboronic acid. LCMS: (AA) M+1 524; $^1$H NMR (300 MHz, DMSO) δ 8.44 (s, 1H), 8.40-8.33 (m, 1H), 8.19-8.12 (m, 1H), 7.81-7.56 (m, 8H), 6.99 (s, 1H), 6.34-6.22 (m, 1H), 5.03 (s, 1H), 4.80 (s, 1H), 4.17-4.07 (m, 1H), 4.06-3.90 (m, 3H), 3.80-3.68 (m, 1H), 2.35-2.20 (m, 2H), 1.54-1.43 (m, 1H).

(rac)-((1R,2R,3S,4R)-4-(2-(5-chlorobenzo[b]thiophen-3-yl)pyrazolo[1,5-a]pyrimidin-7-ylamino)-2,3-dihydroxycyclopentyl)methyl rel-sulfamate (I-71)

The title compound is prepared using (5-chloro-1-benzothien-3-yl)boronic acid in Step 1 instead of 1-naphthaleneboronic acid. LCMS: (AA) M+1 510; $^1$H NMR (300 MHz, DMSO) δ 8.80-8.77 (m, 1H), 8.43 (s, 1H), 8.20-8.10 (m, 2H), 7.89-7.82 (m, 1H), 7.52-7.47 (m, 1H), 6.93 (s, 1H), 6.34-6.29 (m, 1H), 5.04 (s, 1H), 4.83 (s, 1H), 4.18-4.10 (m, 1H), 4.06-3.95 (m, 3H), 3.81-3.75 (m, 1H), 2.38-2.22 (m, 2H), 1.59-1.48 (m, 1H).

(rac)-((1R,2R,3S,4R)-4-(2-(3-benzyl phenyl)pyrazolo[1,5-a]pyrimidin-7-ylamino)-2,3-dihydroxycyclopentyl)methyl rel-sulfamate (I-69)

The title compound is prepared using 3-benzylphenylboronic acid pinacol ester in Step 1 instead of 1-naphthaleneboronic acid. LCMS: (AA) M+1 510.

(rac)-[(1R,2R,3S,4R)-4-{[2-(3,3-dimethyl-1,3-dihydro-2-benzofuran-5-yl)pyrazolo[1,5-a]pyrimidin-7-yl]amino}-2,3-dihydroxycyclopentyl]methyl rel-sulfamate (I-53)

The title compound is prepared using 1,1-dimethyl-6-(4,4,5,5-tetramethyl-1,3,2-dioxaborolan-2-yl)-1,3-dihydro-2-benzofuran in Step 1 instead of 1-naphthaleneboronic acid. LCMS: (AA) M+1 490; $^1$H NMR (300 MHz, DMSO) δ 8.16-8.11 (m, 1H), 8.03-7.98 (m, 1H), 7.94 (s, 1H), 7.52 (s, 1H), 7.37-7.33 (m, 1H), 6.92 (s, 1H), 6.27-6.23 (m, 1H), 5.75 (s, 1H), 5.03 (s, 1H), 4.99 (s, 2H), 4.81 (s, 1H), 4.17-4.09 (m, 1H), 4.07-3.92 (m, 3H), 3.81-3.74 (m, 1H), 2.39-2.21 (m, 2H), 1.48 (s, 6H).

(rac)-((1R,2R,3S,4R)-4-(2-(dibenzo[b,d]furan-2-yl)pyrazolo[1,5-a]pyrimidin-7-ylamino)-2,3-dihydroxycyclopentyl)methyl rel-sulfamate (I-19)

The title compound is prepared using 2-(4,4,5,5-tetramethyl-1,3, 2-dioxaborolan-2-yl)dibenzo[b,d]furan in Step 1 instead of 1-naphthaleneboronic acid. LCMS: (AA) M+1 510; $^1$H NMR (300 MHz, DMSO) δ 8.85 (s, 1H), 8.30-8.25 (m, 1H), 8.22-8.18 (m, 1H), 8.17-8.13 (m, 1H), 7.83-7.78 (m, 1H), 7.76-7.72 (m, 1H), 7.58-7.44 (m, 4H), 7.01 (s, 1H), 6.30-6.25 (m, 1H), 5.05-5.03 (m, 1H), 4.85-4.79 (m, 1H), 4.18-4.11 (m, 1H), 4.08-3.96 (m, 3H), 3.82-3.76 (m, 1H), 2.41-2.25 (m, 2H), 1.60-1.48 (m, 1H).

(rac)-((1R,2R,3S,4R)-2,3-dihydroxy-4-(2-(isoquinolin-4-yl)pyrazolo[1,5-a]pyrimidin-7-ylamino)cyclopentyl)methyl rel-sulfamate (I-18)

The title compound is prepared using 4-isoquinolineboronic acid in Step 1 instead of 1-naphthaleneboronic acid. LCMS: (AA) M+1 471; $^1$H NMR (300 MHz, DMSO) δ 9.39 (s, 1H), 8.86 (s, 1H), 8.66-8.61 (m, 1H), 8.26-8.21 (m, 2H), 7.91-7.84 (m, 1H), 7.79-7.73 (m, 1H), 6.90 (s, 1H), 6.38-6.33 (m, 1H), 4.14-4.08 (m, 1H), 4.04-3.95 (m, 3H), 3.78-3.71 (m, 1H), 2.39-2.21 (m, 2H), 1.57-1.47 (m, 1H).

(rac)-((1R,2R,3S,4R)-2,3-dihydroxy-4-(2-(3-(pyrrolidin-1-yl)phenyl)pyrazolo[1,5-a]pyrimidin-7-ylamino)cyclopentyl)methyl rel-sulfamate (I-46)

The title compound is prepared using 1-[3-(4,4,5,5-tetramethyl-1,3,2-dioxaborolan-2-yl)phenyl]pyrrolidine in Step 1 instead of 1-naphthaleneboronic acid. LCMS: (AA) M+1 489.

(rac)-((1R,2R,3S,4R)-2,3-dihydroxy-4-(2-(quinolin-2-yl)pyrazolo[1,5-a]pyrimidin-7-ylamino)cyclopentyl)methyl rel-sulfamate (I-42)

The title compound is prepared using quinoline-2-boronic acid in Step 1 instead of 1-naphthaleneboronic acid. LCMS: (AA) M+1 471; $^1$H NMR (300 MHz, DMSO) δ 8.17 (d, J=5.3 Hz, 1H), 8.04 (s, 1H), 7.89 (d, J=8.6 Hz, 1H), 7.66 (d, J=7.4 Hz, 1H), 7.54-7.40 (m, 3H), 6.96 (d, J=7.0 Hz, 1H), 6.31 (d, J=5.4 Hz, 1H), 5.04 (s, 1H), 4.80 (s, 1H), 4.19-4.09 (m, 1H), 4.08-3.91 (m, 3H), 3.82-3.72 (m, 1H), 2.35-2.20 (m, 2H), 1.60-1.43 (m, 1H).

(rac)-((1R,2R,3S,4R)-2,3-dihydroxy-4-(2-(quinolin-7-yl)pyrazolo[1,5-a]pyrimidin-7-ylamino)cyclopentyl)methyl rel-sulfamate (I-43)

The title compound is prepared using quinolin-7-ylboronic acid in Step 1 instead of 1-naphthaleneboronic acid. LCMS: (AA) M+1 471; $^1$H NMR (300 MHz, DMSO) δ 8.96-8.93 (m, 1H), 8.74 (s, 1H), 8.44-8.35 (m, 2H), 8.19-8.16 (m, 1H), 8.13-8.06 (m, 1H), 7.57-7.48 (m, 2H), 7.15 (s, 1H), 6.34-6.28 (m, 1H), 5.06-5.03 (m, 1H), 4.81 (s, 1H), 4.18-4.11 (m, 1H), 4.08-3.96 (m, 3H), 3.79 (s, 1H), 3.17-3.14 (m, 1H), 2.40-2.22 (m, 2H), 1.60-1.48 (m, 1H).

(rac)-((1R,2R,3S,4R)-4-(2-(7-chloroquinolin-4-yl)pyrazolo[1,5-a]pyrimidin-7-ylamino)-2,3-dihydroxycyclopentyl)methyl rel-sulfamate (I-39)

The title compound is prepared using 7-chloroquinoline-4-boronic acid pinacol ester in Step 1 instead of 1-naphthaleneboronic acid. LCMS: (AA) M+1 505; $^1$H NMR (300 MHz, DMSO) δ 9.07-9.02 (m, 1H), 8.84-8.78 (m, 1H), 8.28-8.23 (m, 1H), 8.20-8.15 (m, 1H), 7.92 (d, J=4.5 Hz, 1H), 7.75-7.68 (m, 1H), 7.00 (s, 1H), 6.41-6.36 (m, 1H), 4.16-4.08 (m, 1H), 4.06-3.95 (m, 3H), 3.79-3.72 (m, 1H), 2.39-2.20 (m, 2H), 1.57-1.46 (m, 1H).

(rac)-((1R,2R,3S,4R)-2,3-dihydroxy-4-(2-(quinolin-6-yl)pyrazolo[1,5-a]pyrimidin-7-ylamino)cyclopentyl)methyl rel-sulfamate (I-34)

The title compound is prepared using quinoline-6-boronic acid in Step 1 instead of 1-naphthaleneboronic acid. LCMS: (AA) M+1 471; $^1$H NMR (300 MHz, DMSO) δ 8.94-8.90 (m, 1H), 8.68 (s, 1H), 8.57-8.49 (m, 1H), 8.47-8.39 (m, 1H), 8.19-8.09 (m, 2H), 7.62-7.53 (m, 2H), 7.08 (s, 1H), 6.33-6.26 (m, 1H), 5.04 (s, 1H), 4.17-4.10 (m, 1H), 4.08-3.94 (m, 3H), 3.81-3.76 (m, 1H), 2.40-2.21 (m, 2H), 1.59-1.47 (m, 1H).

(rac)-((1R,2R,3S,4R)-2,3-dihydroxy-4-(2-(5-(trifluoromethyl)quinolin-8-yl)pyrazolo[1,5-a]pyrimidin-7-ylamino)cyclopentyl)methyl rel-sulfamate (I-33)

The title compound is prepared using 5-trifluoromethylquinoline-8-boronic acid in Step 1 instead of 1-naphthaleneboronic acid. LCMS: (AA) M+1 539; $^1$H NMR (300 MHz, DMSO) δ 9.22-9.16 (m, 1H), 8.79-8.70 (m, 1H), 8.58 (d, J=8.7 Hz, 1H), 8.26-8.15 (m, 2H), 7.88-7.78 (m, 1H), 7.54 (s, 2H), 6.36-6.28 (m, 1H), 5.03 (s, 1H), 4.20-4.09 (m, 1H), 4.08-3.91 (m, 3H), 3.85-3.73 (m, 1H), 2.39-2.20 (m, 2H), 1.60-1.45 (m, 1H).

(rac)-((1R,2R,3S,4R)-2,3-dihydroxy-4-(2-(isoquinolin-5-yl)pyrazolo[1,5-a]pyrimidin-7-ylamino)cyclopentyl)methyl rel-sulfamate (I-27)

The title compound is prepared using isoquinolin-5-ylboronic acid in Step 1 instead of 1-naphthaleneboronic acid. LCMS: (AA) M+1 471; $^1$H NMR (300 MHz, DMSO) δ 9.40 (s, 1H), 8.61-8.49 (m, 2H), 8.25-8.15 (m, 3H), 7.82-7.78 (m, 1H), 7.45 (s, 1H), 6.87 (s, 1H), 6.38-6.30 (m, 1H), 5.04-5.00 (m, 1H), 4.79 (m, 1H), 4.18-4.08 (m, 1H), 4.05-3.93 (m, 3H), 3.75 (s, 1H), 2.40-2.21 (m, 2H), 1.59-1.45 (m, 1H).

(rac)-((1R,2R,3S,4R)-2,3-dihydroxy-4-(2-(quinolin-3-yl)pyrazolo[1,5-a]pyrimidin-7-ylamino)cyclopentyl)methyl rel-sulfamate (I-25)

The title compound is prepared using 3-quinolineboronic acid in Step 1 instead of 1-naphthaleneboronic acid. LCMS: (FA) M+1 471; $^1$H NMR (300 MHz, DMSO) δ 9.67 (s, 1H), 8.99 (s, 1H), 8.21-8.17 (m, 1H), 8.11-8.03 (m, 2H), 7.84-7.77 (m, 2H), 7.62 (s, 1H), 7.49 (s, 2H), 7.19-7.11 (m, 1H), 6.39-6.27 (m, 1H), 5.06-5.02 (m, 1H), 4.90-4.75 (m, 1H), 4.21-4.11 (m, 1H), 4.08-3.92 (m, 3H), 3.85-3.75 (m, 1H), 2.36-2.27 (m, 1H), 1.63-1.46 (m, 1H).

(rac)-((1R,2R,3S,4R)-4-(2-(benzo[b]thiophen-3-yl)pyrazolo[1,5-a]pyrimidin-7-ylamino)-2,3-dihydroxycyclopentyl)methyl rel-sulfamate (I-22)

The title compound is prepared using thianaphthene-3-boronic acid in Step 1 instead of 1-naphthaleneboronic acid. (FA) M+1 476; $^1$H NMR (300 MHz, DMSO) δ 8.89-8.81 (m, 1H), 8.34 (s, 1H), 8.24-8.13 (m, 1H), 8.10-8.02 (m, 1H), 7.66 (s, 1H), 7.55-7.44 (m, 3H), 6.93 (s, 1H), 6.35-6.24 (m, 1H), 5.10-5.00 (m, 1H), 4.80 (s, 1H), 4.19-4.09 (m, 1H), 4.09-3.94 (m, 3H), 3.84-3.72 (m, 1H), 2.39-2.22 (m, 2H), 1.63-1.45 (m, 1H).

(rac)-((1R,2R,3S,4R)-2,3-dihydroxy-4-(2-(naphthalen-2-yl)pyrazolo[1,5-a]pyrimidin-7-ylamino)cyclopentyl)methyl rel-sulfamate (I-16)

The title compound is prepared using 2-naphthaleneboronic acid in Step 1 instead of 1-naphthaleneboronic acid. LCMS: (AA) M+1 470; $^1$H NMR (300 MHz, DMSO) δ 8.63 (s, 1H), 8.30-8.26 (m, 1H), 8.17-8.14 (m, 1H), 8.06-7.93 (m, 3H), 7.60-7.53 (m, 2H), 7.52-7.45 (m, 1H), 7.05 (s, 1H), 6.32-6.26 (m, 1H), 5.06-5.02 (m, 1H), 4.85-4.76 (m, 1H), 4.20-4.11 (m, 1H), 4.09-3.96 (m, 3H), 3.83-3.75 (m, 1H), 2.39-2.25 (m, 2H), 1.63-1.46 (m, 1H).

(rac)-((1R,2R,3S,4R)-2,3-dihydroxy-4-(2-(2-methoxyphenyl)pyrazolo[1,5-a]pyrimidin-7-ylamino)cyclopentyl)methyl rel-sulfamate (I-72)

The title compound is prepared using 2-methoxyphenylboronic acid in Step 1 instead of 1-naphthaleneboronic acid. LCMS: (AA) M+1 450; $^1$H NMR (400 MHz, DMSO) δ 8.26-8.21 (m, 1H), 8.13 (d, J=5.3 Hz, 1H), 7.74-7.60 (m, 1H), 7.45-7.35 (m, 1H), 7.15 (d, J=7.8 Hz, 1H), 7.09-7.02 (m, 1H), 6.89 (s, 1H), 6.24 (d, J=5.4 Hz, 1H), 4.17-4.08 (m, 1H), 4.07-3.99 (m, 1H), 3.98-3.93 (m, 2H), 3.91 (s, 3H), 3.79-3.72 (m, 1H), 2.39-2.27 (m, 1H), 2.27-2.16 (m, 1H), 1.55-1.42 (m, 1H).

(rac)-((1R,2R,3S,4R)-2,3-dihydroxy-4-(2-(2-phenoxyphenyl)pyrazolo[1,5-a]pyrimidin-7-ylamino)cyclopentyl)methyl rel-sulfamate (I-68)

The title compound is prepared using (2-phenoxyphenyl)boranediol in Step 1 instead of 1-naphthaleneboronic acid. LCMS: (AA) M+1 512; $^1$H NMR (400 MHz, DMSO) δ 8.39-8.32 (m, 1H), 8.10 (d, J=5.3 Hz, 1H), 7.51-7.43 (m, 1H), 7.39-7.30 (m, 3H), 7.13-7.03 (m, 2H), 6.96 (d, J=7.8 Hz, 2H), 6.72 (s, 1H), 6.25 (d, J=5.4 Hz, 1H), 4.19-4.08 (m, 1H), 4.08-3.99 (m, 1H), 3.98-3.89 (m, 2H), 3.81-3.71 (m, 1H), 2.38-2.18 (m, 2H), 1.55-1.41 (m, 1H).

(rac)-((1R,2R,3S,4R)-4-(2-(3,3-dimethyl-2,3-dihydro-1H-inden-5-yl)pyrazolo[1,5-a]pyrimidin-7-ylamino)-2,3-dihydroxycyclopentyl)methyl rel-sulfamate (I-41)

The title compound is prepared using 2-(3,3-dimethyl-2,3-dihydro-1H-inden-5-yl)-4,4,5,5-tetramethyl-1,3,2-dioxaborolane in Step 1 instead of 1-naphthaleneboronic acid. LCMS: (AA) M+1 488; $^1$H NMR (400 MHz, DMSO) δ 8.12 (d, J=5.3 Hz, 1H), 7.90-7.84 (m, 2H), 7.27 (d, J=8.3 Hz, 1H), 6.87 (s, 1H), 6.24 (d, J=5.4 Hz, 1H), 4.19-4.08 (m, 1H), 4.09-4.00 (m, 1H), 4.01-3.91 (m, 2H), 3.82-3.73 (m, 1H), 2.93-2.81 (m, 2H), 2.39-2.28 (m, 1H), 2.28-2.17 (m, 1H), 1.97-1.88 (m, 2H), 1.56-1.43 (m, 1H), 1.29 (s, 6H).

(rac)-((1R,2R,3S,4R)-4-(2-(5-chloro-2-(trifluoromethoxy)phenyl)pyrazolo[1,5-a]pyrimidin-7-ylamino)-2,3-dihydroxycyclopentyl)methyl rel-sulfamate (I-57)

The title compound is prepared using 5-chloro-2-(trifluoromethoxy)phenylboronic acid in Step 1 instead of 1-naphthaleneboronic acid. LCMS: (AA) M+1 538; $^1$H NMR (400 MHz, DMSO) δ 8.39 (d, J=2.7 Hz, 1H), 8.20 (d, J=5.3 Hz, 1H), 7.96-7.83 (m, 1H), 7.67-7.61 (m, 1H), 7.61-7.54 (m, 1H), 6.76 (s, 1H), 6.35 (d, J=5.4 Hz, 1H), 5.18-4.70 (m, 2H), 4.21-4.09 (m, 1H), 4.07-4.00 (m, 1H), 4.00-3.90 (m, 2H), 3.81-3.70 (m, 1H), 2.39-2.16 (m, 2H), 1.59-1.44 (m, 1H).

(rac)-((1R,2R,3S,4R)-4-(2-(3,3-dimethyl-2,3-dihydrobenzofuran-5-yl)pyrazolo[1,5-a]pyrimidin-7-ylamino)-2,3-dihydroxycyclopentyl)methyl rel-sulfamate (I-26)

The title compound is prepared using 3,3-dimethyl-5-(4,4,5,5-tetramethyl-1,3,2-dioxaborolan-2-yl)-2,3-dihydro-1-benzofuran in Step 1 instead of 1-naphthaleneboronic acid. LCMS: (AA) M+1 490; $^1$H NMR (400 MHz, DMSO) δ 8.10 (d, J=5.3 Hz, 1H), 7.94-7.88 (m, 1H), 7.88-7.81 (m, 1H), 7.65-7.57 (m, 1H), 7.54-7.44 (m, 2H), 6.85 (d, J=8.3 Hz, 1H), 6.80 (s, 1H), 6.22 (d, J=5.4 Hz, 1H), 5.19-4.93 (m, 1H), 4.95-4.69 (m, 1H), 4.27 (s, 2H), 4.19-4.07 (m, 1H), 4.07-3.99 (m, 1H), 3.99-3.89 (m, 2H), 3.85-3.70 (m, 1H), 2.39-2.28 (m, 1H), 2.28-2.17 (m, 1H), 1.59-1.43 (m, 1H), 1.36 (s, 6H).

(rac)-((1R,2R,3S,4R)-4-(2-(3,3-dimethyl-2,3-dihydrobenzofuran-7-yl)pyrazolo[1,5-a]pyrimidin-7-ylamino)-2,3-dihydroxycyclopentyl)methyl rel-sulfamate (I-23)

The title compound is prepared using 3,3-dimethyl-7-(4,4,5,5-tetramethyl-1,3,2-dioxaborolan-2-yl)-2,3-dihydro-1-benzofuran in Step 1 instead of 1-naphthaleneboronic acid. LCMS: (AA) M+1 490; $^1$H NMR (400 MHz, DMSO) δ 8.13 (d, J=5.3 Hz, 1H), 8.09-8.04 (m, 1H), 7.69-7.60 (m, 1H), 7.52-7.44 (m, 2H), 7.26-7.21 (m, 1H), 7.03-6.96 (m, 1H), 6.86 (s, 1H), 6.26 (d, J=5.4 Hz, 1H), 5.08-4.96 (m, 1H), 4.85-4.66 (m, 1H), 4.39 (s, 2H), 4.19-4.07 (m, 1H), 4.08-3.99 (m, 1H), 3.98-3.91 (m, 2H), 3.82-3.69 (m, 1H), 2.40-2.28 (m, 1H), 2.28-2.17 (m, 1H), 1.56-1.42 (m, 1H), 1.34 (s, 6H).

(rac)-[(1R,2R,3S,4R)-2,3-dihydroxy-4-{[2-(1H-indol-2-yl)pyrazolo[1,5-a]pyrimidin-7-yl]amino}cyclopentyl]methyl rel-sulfamate (I-24)

The title compound is prepared using 2-pinacolateboryl indole in Step 1 instead of 1-naphthaleneboronic acid. LCMS: (AA) M+1 459; $^1$H NMR (400 MHz, DMSO) δ 11.56 (s, 1H), 8.16 (d, J=5.3 Hz, 1H), 7.62-7.54 (m, 1H), 7.49-7.36 (m, 2H), 7.17-7.08 (m, 1H), 7.06-6.97 (m, 2H), 6.88 (s, 1H), 6.30 (d, J=5.4 Hz, 1H), 5.17-4.99 (m, 1H), 4.99-4.74 (m, 1H), 4.20-4.09 (m, 1H), 4.09-4.01 (m, 1H), 4.01-3.87 (m, 2H), 3.84-3.68 (m, 1H), 2.44-2.33 (m, 1H), 2.32-2.19 (m, 1H), 1.52-1.35 (m, 1H).

(rac)-((1R,2R,3S,4R)-4-(2-(5-chloro-2-methoxyphenyl)pyrazolo[1,5-a]pyrimidin-7-ylamino)-2,3-dihydroxycyclopentyl)methyl rel-sulfamate (I-20)

The title compound is prepared using (5-chloro-2-methoxyphenyl)boronic acid in Step 1 instead of 1-naphthaleneboronic acid. LCMS: (AA) M+1 484; $^1$H NMR (400 MHz, DMSO) δ 8.35-8.25 (m, 1H), 8.14 (d, J=5.3 Hz, 1H), 7.83-7.72 (m, 1H), 7.52-7.46 (m, 2H), 7.46-7.39 (m, 1H), 7.19 (d, J=9.0 Hz, 1H), 6.94 (s, 1H), 6.27 (d, J=5.4 Hz, 1H), 5.09-4.96 (m, 1H), 4.88-4.71 (m, 1H), 4.19-4.08 (m, 1H), 4.07-4.00 (m, 1H), 4.01-3.95 (m, 2H), 3.94 (s, 3H), 3.81-3.66 (m, 1H), 2.37-2.18 (m, 2H), 1.56-1.40 (m, 1H).

(rac)-((1R,2R,3S,4R)-4-(2-(5-chloro-2-methylphenyl)pyrazolo[1,5-a]pyrimidin-7-ylamino)-2,3-dihydroxycyclopentyl)methyl rel-sulfamate (I-21)

The title compound is prepared using 5-chloro-2-methylphenylboronic acid in Step 1 instead of 1-naphthaleneboronic acid. LCMS: (AA) M+1 468; $^1$H NMR (400 MHz, DMSO) δ 8.17 (d, J=5.3 Hz, 1H), 7.84-7.69 (m, 2H), 7.52-7.42 (m, 2H), 7.41-7.33 (m, 2H), 6.72 (s, 1H), 6.29 (d, J=5.4 Hz, 1H), 5.08-4.92 (m, 1H), 4.86-4.66 (m, 1H), 4.17-4.06 (m, 1H), 4.06-3.98 (m, 1H), 3.98-3.89 (m, 2H), 3.79-3.63 (m, 1H), 3.33 (s, 3H), 2.36-2.17 (m, 2H), 1.55-1.39 (m, 1H).

(rac)-((1R,2R,3S,4R)-2,3-dihydroxy-4-(2-(3-(trimethylsilyl)phenyl)pyrazolo[1,5-a]pyrimidin-7-ylamino)cyclopentyl)methyl rel-sulfamate (I-35)

The title compound is prepared using 3-trimethylsilylphenylboronic acid in Step 1 instead of 1-naphthaleneboronic acid. LCMS: (AA) M+1 492.3; $^1$H NMR (400 MHz, DMSO) δ 8.18-8.12 (m, 2H), 8.11-8.06 (m, 1H), 7.68 (d, J=7.8 Hz, 1H), 7.55 (d, J=7.3 Hz, 1H), 7.51-7.42 (m, 3H), 6.94 (s, 1H), 6.26 (d, J=5.4 Hz, 1H), 5.03 (d, J=5.6 Hz, 1H), 4.81 (d, J=5.2 Hz, 1H), 4.13 (dd, J=9.7, 6.0 Hz, 1H), 4.06-3.89 (m, 3H), 3.77 (dd, J=10.0, 5.0 Hz, 1H), 2.39-2.17 (m, 2H), 1.56-1.42 (m, 1H), 0.31 (s, 9H).

(rac)-{(1R,2R,3S,4R)-4-[(2-{3-[(cyclopropylmethyl)sulfanyl]phenyl}pyrazolo[1,5-a]pyrimidin-7-yl)amino]-2,3-dihydroxycyclopentyl}methyl rel-sulfamate (I-76)

The title compound is prepared using 3-(cyclopropylmethyl)thiophenylboronic acid in Step 1 instead of 1-naphthaleneboronic acid. LCMS: (AA) M+506; $^1$H NMR (400 MHz, MeOD) δ 8.13 (d, J=5.5 Hz, 1H), 8.07 (s, 1H), 7.90-7.73 (m, 1H), 7.45-7.30 (m, 2H), 6.77 (s, 1H), 6.32 (d, J=5.6 Hz, 1H), 4.28-4.06 (m, 3H), 4.05-3.90 (m, 2H), 2.99-2.83 (m, 2H), 2.55-2.29 (m, 2H), 1.63-1.44 (m, 1H), 1.13-0.96 (m, 1H), 0.60-0.47 (m, 2H), 0.37-0.18 (m, 2H).

(rac)-[(1R,2R,3S,4R)-2,3-dihydroxy-4-{[2-(1H-indol-4-yl)pyrazolo[1,5-a]pyrimidin-7-yl]amino}cyclopentyl]methyl rel-sulfamate (I-75)

The title compound is prepared using 4-(4,4,5,5-tetramethyl-1,3,2-dioxaborolan-2-yl)-1H-indole in Step 1 instead of 1-naphthaleneboronic acid. LCMS: (AA) M+459; $^1$H NMR (400 MHz, MeOD) δ 8.15 (d, J=5.5 Hz, 1H), 7.68-7.59 (m, 1H), 7.51-7.43 (m, 1H), 7.36 (d, J=3.2 Hz, 1H), 7.25-7.17 (m, 1H), 7.14-7.09 (m, 1H), 6.85 (s, 1H), 6.33 (d, J=5.6 Hz, 1H), 4.31-4.18 (m, 2H), 4.18-4.09 (m, 1H), 4.09-4.02 (m, 1H), 4.02-3.95 (m, 1H), 2.61-2.49 (m, 1H), 2.49-2.36 (m, 1H), 1.69-1.54 (m, 1H).

(rac)-((1R,2R,3S,4R)-4-(2-(4-fluoro-2-methoxyphenyl)pyrazolo[1,5-a]pyrimidin-7-ylamino)-2,3-dihydroxycyclopentyl)methyl rel-sulfamate (I-70)

The title compound is prepared using 4-fluoro-2-methoxyphenylboronic acid in Step 1 instead of 1-naphthaleneboronic acid. LCMS: (AA) M+468; $^1$H NMR (300 MHz, MeOD) δ 8.27-8.16 (m, 1H), 8.12 (d, J=5.5 Hz, 1H), 6.97-6.86 (m, 2H), 6.84-6.72 (m, 1H), 6.30 (d, J=5.6 Hz, 1H), 4.31-4.17 (m, 2H), 4.15-3.91 (m, 6H), 2.61-2.33 (m, 2H), 1.69-1.50 (m, 1H).

(rac)-((1R,2R,3S,4R)-2,3-dihydroxy-4-(2-(2-(trifluoromethyl)pyridin-4-yl)pyrazolo[1,5-a]pyrimidin-7-ylamino)cyclopentyl)methyl rel-sulfamate (I-59)

The title compound is prepared using 2-(trifluoromethyl)pyridine-4-boronic acid in Step 1 instead of 1-naphthaleneboronic acid. LCMS: (AA) M+489; $^1$H NMR (300 MHz, MeOD) δ 8.78 (d, J=5.1 Hz, 1H), 8.62-8.46 (m, 1H), 8.35-8.22 (m, 1H), 8.19 (d, J=5.5 Hz, 1H), 7.05 (s, 1H), 6.40 (d, J=5.6 Hz, 1H), 4.35-3.88 (m, 5H), 2.60-2.35 (m, 2H), 1.73-1.51 (m, 1H).

(s.e.)-((1R,2R,3S,4R)-2,3-dihydroxy-4-(2-(2-methoxy-5-(trifluoromethylthio)-phenyl)pyrazolo[1,5-a]pyrimidin-7-ylamino)cyclopentyl)methyl sulfamate (I-120)

The title compound is prepared using {2-methoxy-5-[(trifluoromethyl)sulfanyl]phenyl}boronic acid in Step 1 instead of 1-naphthaleneboronic acid. LCMS: (AA) M+1 550; $^1$H NMR (400 MHz, MeOD) δ 8.58 (d, J=2.4 Hz, 1H), 8.17 (d, J=5.5 Hz, 1H), 7.82-7.61 (m, 1H), 7.29 (d, J=8.7 Hz, 1H), 7.02 (s, 1H), 6.36 (d, J=5.5 Hz, 1H), 4.31-4.11 (m, 3H), 4.10-4.03 (m, 4H), 4.02-3.96 (m, 1H), 2.64-2.34 (m, 2H), 1.71-1.51 (m, 1H).

(s.e.)-((1R,2R,3S,4R)-4-(2-(2,4-dichloronaphthalen-1-yl)pyrazolo[1,5-a]pyrimidin-7-ylamino)-2,3-dihydroxycyclopentyl)methyl sulfamate (I-117)

The title compound is prepared using 2-(2,4-dichloro-1-naphthyl)-4,4,5,5-tetramethyl-1,3,2-dioxaborolane in Step 1 instead of 1-naphthaleneboronic acid. LCMS: (AA) M+1 538; $^1$H NMR (400 MHz, MeOD) δ 8.31 (d, J=8.5 Hz, 1H), 8.23 (d, J=5.5 Hz, 1H), 7.81 (s, 1H), 7.70-7.58 (m, 2H), 7.56-7.48 (m, 1H), 6.56 (s, 1H), 6.41 (d, J=5.6 Hz, 1H), 4.23-4.07 (m, 3H), 4.02-3.95 (m, 1H), 3.95-3.87 (m, 1H), 2.56-2.31 (m, 2H), 1.55-1.42 (m, 1H).

Example 8. Compounds Prepared by Method B (rac)-((1R,2R,3S,4R)-4-(2-(biphenyl-3-yl)pyrazolo[1,5-a]pyrimidin-7-ylamino)-2,3-dihydroxycyclopentyl)methyl rel-sulfamate (I-3)

The title compound is prepared using methyl biphenyl-3-carboxylate in Step 1 instead of ethyl α-napthoate. LCMS: (AA) M+1 496; $^1$H NMR (300 MHz, MeOD) δ 8.39-8.30 (m, 1H), 8.13 (d, J=5.5 Hz, 1H), 8.04-7.95 (m, 2H), 7.72-7.28 (m, 9H), 6.85 (s, 1H), 6.31 (d, J=5.6 Hz, 1H), 4.27-4.04 (m, 3H), 4.01-3.87 (m, 2H), 2.56-2.30 (m, 2H), 1.59-1.43 (m, 1H).

(rac)-((1R,2R,3S,4R)-2,3-dihydroxy-4-(2-phenylpyrazolo[1,5-a]pyrimidin-7-ylamino)cyclopentyl)methyl rel-sulfamate (I-1)

The title compound is prepared starting from 5-amino-3-phenylpyrazole and following Step 2b to Step 7. LCMS: (AA) M+1 420; $^1$H NMR (300 MHz, MeOD) δ 8.12 (d, J=5.5 Hz, 1H), 8.07-7.99 (m, 2H), 7.49-7.36 (m, 3H), 6.76 (s, 1H), 6.31 (d, J=5.6 Hz, 1H), 4.28-3.91 (m, 5H), 2.59-2.33 (m, 2H), 1.67-1.51 (m, 1H).

(rac)-((1R,2R,3S,4R)-4-((2-(3-(tert-Butyl)phenyl)pyrazolo[1,5-a]pyrimidin-7-yl)amino)-2,3-dihydroxycyclopentyl)methyl rel-sulfamate (I-15)

The title compound is prepared using 3-tert-butylbenzoic acid ethyl ester in Step 1 instead of ethyl α-naphthoate. LCMS: (FA) M+1 476; $^1$H NMR (400 MHz, DMSO) δ 8.13 (d, J=5.3 Hz, 1H), 8.04 (s, 1H), 7.90 (d, J=7.3 Hz, 1H), 7.65 (d, J=8.0 Hz, 1H), 7.46-7.36 (m, 3H), 6.92 (s, 1H), 6.26 (d, J=5.3 Hz, 1H), 5.04 (s, 1H), 4.82 (s, 1H), 4.18-4.08 (m, 1H), 4.08-3.88 (m, 3H), 3.81-3.73 (m, 1H), 2.39-2.18 (m, 3H), 1.57-1.43 (m, 1H), 1.36 (s, 9H).

(rac)-((1R,2R,3S,4R)-4-((2-(3-Chlorophenyl)pyrazolo[1,5-a]pyrimidin-7-yl)amino)-2,3-dihydroxycyclopentyl)methyl rel-sulfamate (I-5)

The title compound is prepared using ethyl 3-chlorobenzoate in Step 1 instead of ethyl α-napthoate. LCMS: (FA) M+1 454.

(rac)-((1R,2R,3S,4R)-2,3-Dihydroxy-4-((2-(3-(trifluoromethyl)phenyl)pyrazolo[1,5-a]pyrimidin-7-yl)amino)cyclopentyl)methyl rel-sulfamate (I-7)

The title compound is prepared using 3-(trifluoromethyl)benzoic acid in Step 1 instead of ethyl α-napthoate. LCMS: M+1 488; $^1$H NMR (400 MHz, MeOD) δ 8.40 (s, 1H), 8.32-8.24 (m, 1H), 8.19-8.11 (m, 1H), 7.73-7.61 (m, 2H), 6.87 (s, 1H), 6.35 (d, J=5.5 Hz, 1H), 4.28-4.18 (m, 2H), 4.18-4.09 (m, 1H), 4.08-4.03 (m, 1H), 4.01-3.96 (m, 1H), 2.58-2.35 (m, 2H), 1.67-1.54 (m, 1H).

(rac)-[(1R,2R,3S,4R)-4-{[2-(2,4-dichlorophenyl)pyrazolo[1,5-a]pyrimidin-7-yl]amino}-2,3-dihydroxycyclopentyl]methyl rel-sulfamate (I-13)

The title compound is prepared starting from 5-(2,4-dichloro-phenyl)2H-pyrazol-3-ylamine hydrochloride and following Step 2b to Step 7. LCMS: (AA) M+1 488; $^1$H NMR (400 MHz, MeOD) δ 8.17 (s, 1H), 8.03 (d, J=8.5 Hz, 1H), 7.60 (d, J=2.0 Hz, 1H), 7.46-7.40 (m, 1H), 6.90 (s, 1H), 6.37 (d, J=5.4 Hz, 1H), 4.27-4.17 (m, 2H), 4.16-4.07 (m, 1H), 4.05-4.00 (m, 1H), 3.99-3.94 (m, 1H), 2.57-2.47 (m, 1H), 2.46-2.35 (m, 1H), 1.65-1.51 (m, 1H).

Example 9. Compounds Prepared by Method C (s.e.)-((1R,2R,3S,4R)-2,3-dihydroxy-4-(2-(2-isopropoxynaphthalen-1-yl)pyrazolo[1,5-a]pyrimidin-7-ylamino)cyclopentyl)methyl sulfamate (I-109)

The title compound is prepared using 1-bromo-2-isopropoxynaphthalene 1-bromo-2-naphthyl isopropyl in Step 2 instead of 1-chloro-4-iodo-naphthalene. LCMS: (AA) M+1 528; $^1$H NMR (400 MHz, MeOD) δ 8.20 (d, J=5.5 Hz, 1H), 7.95 (d, J=9.0 Hz, 1H), 7.87-7.80 (m, 1H), 7.71-7.63 (m, 1H), 7.45 (d, J=9.1 Hz, 1H), 7.38-7.31 (m, 2H), 6.54 (s, 1H), 6.37 (d, J=5.6 Hz, 1H), 4.67-4.59 (m, 1H), 4.23-4.06 (m, 3H), 4.02-3.95 (m, 1H), 3.94-3.89 (m, 1H), 2.58-2.46 (m, 1H), 2.45-2.34 (m, 1H), 1.56-1.44 (m, 1H), 1.20 (d, J=6.1 Hz, 6H).

(rac)-((1R,2R,3S,4R)-4-(2-(dibenzo[b,d]furan-3-yl)pyrazolo[1,5-a]pyrimidin-7-ylamino)-2,3-dihydroxycyclopentyl)methyl rel-sulfamate (I-93)

The title compound is prepared using 3-bromodibenzo[b,d]furan in Step 2 instead of 1-chloro-4-iodo-naphthalene. LCMS: (AA) M+1 510; $^1$H NMR (400 MHz, DMSO) δ 8.29 (d, J=7.9 Hz, 1H), 8.25 (d, J=5.3 Hz, 1H), 7.82-7.78 (m, 1H), 7.73 (d, J=8.2 Hz, 1H), 7.71-7.67 (m, 1H), 7.66-7.60 (m, 1H), 7.56-7.50 (m, 1H), 7.34-7.25 (m, 1H), 6.85 (s, 1H), 6.37 (d, J=5.5 Hz, 1H), 4.15-4.05 (m, 1H), 4.02-3.90 (m, 3H), 3.78-3.71 (m, 1H), 2.41-2.31 (m, 1H), 2.29-2.19 (m, 1H), 1.54-1.42 (m, 1H).

(rac)-((1R,2R,3S,4R)-4-{[2-(5-tert-butyl-2-methoxyphenyl)pyrazolo[1,5-a]pyrimidin-7-yl]amino}-2,3-dihydroxycyclopentyl)methyl rel-sulfamate (I-63)

The title compound is prepared using 4-tert-butyl-2-iodo-1-methoxybenzene in Step 2 instead of 1-chloro-4-iodo-naphthalene. LCMS: (AA) M+1 506; $^1$H NMR (400 MHz, DMSO+D20) δ 8.12 (d, J=5.3 Hz, 1H), 8.06-8.01 (m, 1H), 7.43-7.37 (m, 1H), 7.06 (d, J=8.8 Hz, 1H), 6.82 (s, 1H), 6.24 (d, J=5.4 Hz, 1H), 4.17-4.07 (m, 1H), 4.07-3.98 (m, 1H), 3.99-3.89 (m, 2H), 3.85 (s, 3H), 3.79-3.70 (m, 1H), 2.37-2.28 (m, 1H), 2.28-2.18 (m, 1H), 1.52-1.42 (m, 1H), 1.31 (s, 9H).

(rac)-((1R,2R,3S,4R)-2,3-dihydroxy-4-(2-(9-oxo-9H-fluoren-2-yl)pyrazolo[1,5-a]pyrimidin-7-ylamino)cyclopentyl)methyl rel-sulfamate (I-85)

The title compound is prepared using 2-Bromofluoren-9-one in Step 2 instead of 1-chloro-4-iodo-naphthalene.

LCMS: (AA) M+1 522; ¹H NMR (400 MHz, DMSO) δ 8.42-8.36 (m, 1H), 8.35-8.29 (m, 1H), 8.15 (d, J=5.3 Hz, 1H), 7.93 (d, J=7.8 Hz, 1H), 7.90-7.84 (m, 1H), 7.84-7.77 (m, 1H), 7.69-7.62 (m, 2H), 7.58-7.44 (m, 2H), 7.45-7.36 (m, 1H), 7.05 (s, 1H), 6.29 (d, J=5.4 Hz, 1H), 5.16-4.97 (m, 1H), 4.94-4.70 (m, 1H), 4.20-4.08 (m, 1H), 4.08-3.92 (m, 3H), 3.85-3.71 (m, 1H), 2.40-2.19 (m, 2H), 1.59-1.45 (m, 1H).

(rac)-(1R,2R,3S,4R)-4-(2-(3-cyclopentenylphenyl) pyrazolo[1,5-a]pyrimidin-7-ylamino)-2,3-dihydroxy-cyclopentyl)methyl rel-sulfamate (I-47)

The title compound is prepared using 1-bromo-3-cyclopent-1-en-1-ylbenzene in Step 2 instead of 1-chloro-4-iodo-naphthalene. LCMS: (AA) M+1 486; ¹H NMR (400 MHz, DMSO) δ 8.21-8.09 (m, 2H), 7.99-7.91 (m, 1H), 7.74-7.64 (m, 1H), 7.51-7.41 (m, 3H), 6.96 (s, 1H), 6.47-6.36 (m, 1H), 6.30-6.22 (m, 1H), 5.14-4.97 (m, 1H), 4.91-4.73 (m, 1H), 4.19-4.09 (m, 1H), 4.08-3.89 (m, 3H), 3.83-3.72 (m, 1H), 2.76 (d, m, 2H), 2.39-2.18 (m, 2H), 2.10-1.94 (m, 2H), 1.61-1.41 (m, 1H).

(rac)-((1R,2R,3S,4R)-2,3-dihydroxy-4-(2-(3-(1,1,1-trifluoro-2-methylpropan-2-yl)phenyl)pyrazolo[1,5-a]pyrimidin-7-ylamino)cyclopentyl)methyl rel-sulfamate (I-58)

The title compound is prepared using 1-iodo-3-(2,2,2-trifluoro-1,1-dimethylethyl)benzene in Step 2 instead of 1-chloro-4-iodo-naphthalene. LCMS: (AA) M+1 530; ¹H NMR (400 MHz, DMSO) δ 8.18-8.12 (m, 2H), 8.12-8.06 (m, 1H), 7.71-7.62 (m, 1H), 7.61-7.55 (m, 1H), 7.55-7.48 (m, 2H), 7.00 (s, 1H), 6.28 (d, J=5.4 Hz, 1H), 5.13-4.94 (m, 1H), 4.93-4.70 (m, 1H), 4.20-4.08 (m, 1H), 4.08-4.00 (m, 1H), 4.00-3.90 (m, 2H), 3.82-3.66 (m, 1H), 2.40-2.29 (m, 1H), 2.28-2.16 (m, 1H), 1.64 (s, 6H), 1.54-1.41 (m, 1H).

(s.e.)-((1R,2R,3S,4R)-4-(2-(2-(difluoromethoxy) naphthalen-1-yl)pyrazolo[1,5-a]pyrimidin-7-ylamino)-2,3-dihydroxycyclopentyl)methyl sulfamate (I-110)

The title compound is prepared using 1-bromo-2-(difluoromethoxy)naphthalene in Step 2 instead of 1-chloro-4-iodo-naphthalene. LCMS: (AA) M+1 536; ¹H NMR (400 MHz, MeOD) δ 8.23 (d, J=5.5 Hz, 1H), 8.06 (d, J=9.0 Hz, 1H), 8.01-7.89 (m, 1H), 7.83-7.71 (m, 1H), 7.59-7.40 (m, 3H), 6.83 (t, J=74.5 Hz, 1H), 6.59 (s, 1H), 6.42 (d, J=5.7 Hz, 1H), 4.24-4.08 (m, 3H), 4.03-3.96 (m, 1H), 3.95-3.88 (m, 1H), 2.57-2.45 (m, 1H), 2.45-2.32 (m, 1H), 1.59-1.41 (m, 1H).

(s.e.)-((1R,2R,3S,4R)-2,3-dihydroxy-4-(2-(4-methyl-naphthalen-1-yl)pyrazolo[1,5-a]pyrimidin-7-ylamino)cyclopentyl)methyl sulfamate (I-115)

The title compound is prepared using 1-bromo-4-methylnaphthalene in Step 2 instead of 1-chloro-4-iodo-naphthalene. LCMS: (AA) M+1 484; ¹H NMR (300 MHz, MeOD) δ 8.50-8.40 (m, 1H), 8.20 (d, J=5.5 Hz, 1H), 8.15-8.03 (m, 1H), 7.67 (d, J=7.2 Hz, 1H), 7.62-7.48 (m, 2H), 7.46-7.38 (m, 1H), 6.66 (s, 1H), 6.38 (d, J=5.6 Hz, 1H), 4.29-4.08 (m, 3H), 4.05-3.99 (m, 1H), 3.98-3.90 (m, 1H), 2.75 (s, 3H), 2.61-2.32 (m, 2H), 1.63-1.46 (m, 1H).

(s.e.)-((1R,2R,3S,4R)-2,3-dihydroxy-4-(2-(2-methyl-naphthalen-1-yl)pyrazolo[1,5-a]pyrimidin-7-ylamino)cyclopentyl)methyl sulfamate (I-114)

The title compound is prepared using 1-bromo-2-methylnaphthalene in Step 2 instead of 1-chloro-4-iodo-naphthalene. LCMS: (AA) M+1 484; ¹H NMR (400 MHz, MeOD) δ 8.19 (d, J=5.5 Hz, 1H), 7.93-7.79 (m, 2H), 7.52-7.36 (m, 3H), 7.36-7.26 (m, 1H), 6.47 (s, 1H), 6.36 (d, J=5.6 Hz, 1H), 4.22-4.03 (m, 3H), 4.01-3.93 (m, 1H), 3.93-3.83 (m, 1H), 2.54-2.28 (m, 5H), 1.54-1.33 (m, 1H).

(s.e.)-((1R,2R,3S,4R)-4-(2-(4-(difluoromethoxy) naphthalen-1-yl)pyrazolo[1,5-a]pyrimidin-7-ylamino)-2,3-dihydroxycyclopentyl)methyl sulfamate (I-112)

The title compound is prepared using 1-(difluoromethoxy)-4-iodonaphthalene in Step 2 instead of 1-chloro-4-iodo-naphthalene. LCMS: (AA) M+1 536; ¹H NMR (400 MHz, MeOD) δ 8.56-8.47 (m, 1H), 8.30-8.23 (m, 1H), 8.20 (d, J=5.5 Hz, 1H), 7.78 (d, J=8.0 Hz, 1H), 7.69-7.56 (m, 2H), 7.33 (d, J=7.9 Hz, 1H), 7.09 (t, J=73.8 Hz, 1H), 6.69 (s, 1H), 6.38 (d, J=5.5 Hz, 1H), 4.26-4.08 (m, 3H), 4.07-3.99 (m, 1H), 3.99-3.90 (m, 1H), 2.58-2.35 (m, 2H), 1.62-1.47 (m, 1H).

(s.e.)-((1R,2R,3S,4R)-4-(2-(6-(difluoromethyl)naph-thalen-1-yl)pyrazolo[1,5-a]pyrimidin-7-ylamino)-2,3-dihydroxycyclopentyl)methyl sulfamate (I-111)

The title compound is prepared using 1-bromo-6-(difluoromethyl)naphthalene in Step 2 instead of 1-chloro-4-iodo-naphthalene. LCMS: (AA) M+1 520; ¹H NMR (400 MHz, MeOD) δ 8.64 (d, J=8.9 Hz, 1H), 8.21 (d, J=5.5 Hz, 1H), 8.17-8.12 (m, 1H), 8.06 (d, J=8.2 Hz, 1H), 7.95-7.87 (m, 1H), 7.73-7.63 (m, 2H), 6.94 (t, J=56.1 Hz, 1H), 6.73 (s, 1H), 6.40 (d, J=5.7 Hz, 1H), 4.29-4.07 (m, 3H), 4.07-4.00 (m, 1H), 3.99-3.90 (m, 1H), 2.60-2.46 (m, 1H), 2.46-2.33 (m, 1H), 1.63-1.48 (m, 1H).

(s.e.)-((1R,2R,3S,4R)-2,3-dihydroxy-4-(2-(2-methoxynaphthalen-1-yl)pyrazolo[1,5-a]pyrimidin-7-ylamino)cyclopentyl)methyl sulfamate (I-104)

The title compound is prepared using 1-bromo-2-methoxynaphthalene in Step 2 instead of 1-chloro-4-iodo-naphthalene. LCMS: (AA) M+1 500; ¹H NMR (400 MHz, MeOD) δ 8.20 (d, J=5.5 Hz, 1H), 8.00 (d, J=9.0 Hz, 1H), 7.91-7.77 (m, 1H), 7.72-7.56 (m, 1H), 7.50 (d, J=9.1 Hz, 1H), 7.40-7.23 (m, 2H), 6.51 (s, 1H), 6.40-6.28 (m, 1H), 4.28-4.05 (m, 3H), 4.01-3.95 (m, 1H), 3.95-3.89 (m, 1H), 3.87 (s, 3H), 2.59-2.45 (m, 1H), 2.45-2.35 (m, 1H), 1.57-1.41 (m, 1H).

(s.e.)-((1R,2R,3S,4R)-4-(2-(4-(dimethylamino)naphthalen-1-yl)pyrazolo[1,5-a]pyrimidin-7-ylamino)-2,3-dihydroxycyclopentyl)methyl sulfamate (I-107)

The title compound is prepared using 1-bromo-4-(dimethylamino)naphthalene in Step 2 instead of 1-chloro-4-iodo-naphthalene. LCMS: (AA) M+1 513; $^1$H NMR (400 MHz, MeOD) δ 8.50-8.39 (m, 1H), 8.36-8.26 (m, 1H), 8.19 (d, J=5.5 Hz, 1H), 7.71 (d, J=7.8 Hz, 1H), 7.58-7.41 (m, 2H), 7.21 (d, J=7.8 Hz, 1H), 6.64 (s, 1H), 6.37 (d, J=5.6 Hz, 1H), 4.28-4.08 (m, 3H), 4.07-3.99 (m, 1H), 3.99-3.91 (m, 1H), 2.93 (s, 6H), 2.58-2.47 (m, 1H), 2.47-2.32 (m, 1H), 1.62-1.47 (m, 1H).

(s.e.)-((1R,2R,3S,4R)-2,3-dihydroxy-4-(2-(4-methoxynaphthalen-1-yl)pyrazolo[1,5-a]pyrimidin-7-ylamino)cyclopentyl)methyl sulfamate (I-106)

The title compound is prepared using 1-iodo-4-methoxynaphthalene in Step 2 instead of 1-chloro-4-iodo-naphthalene. LCMS: (AA) M+1 500; $^1$H NMR (400 MHz, MeOD) δ 8.49-8.39 (m, 1H), 8.35-8.26 (m, 1H), 8.17 (d, J=5.5 Hz, 1H), 7.73 (d, J=8.0 Hz, 1H), 7.58-7.43 (m, 2H), 7.01 (d, J=8.0 Hz, 1H), 6.64 (s, 1H), 6.35 (d, J=5.5 Hz, 1H), 4.26-4.08 (m, 3H), 4.06 (s, 3H), 4.04-3.98 (m, 1H), 3.98-3.92 (m, 1H), 2.58-2.45 (m, 1H), 2.45-2.32 (m, 1H), 1.60-1.45 (m, 1H).

(s.e.)-((1R,2R,3S,4R)-4-(2-(5-fluoronaphthalen-1-yl)pyrazolo[1,5-a]pyrimidin-7-ylamino)-2,3-dihydroxycyclopentyl)methyl sulfamate (I-105)

The title compound is prepared using 1-bromo-5-fluoronaphthalene in Step 2 instead of 1-chloro-4-iodo-naphthalene. LCMS: (AA) M+1 488; $^1$H NMR (400 MHz, MeOD) δ 8.30 (d, J=8.6 Hz, 1H), 8.24-8.16 (m, 2H), 7.93-7.84 (m, 1H), 7.72-7.61 (m, 1H), 7.54-7.43 (m, 1H), 7.30-7.20 (m, 1H), 6.71 (s, 1H), 6.40 (d, J=5.5 Hz, 1H), 4.27-4.08 (m, 3H), 4.07-3.99 (m, 1H), 3.99-3.91 (m, 1H), 2.60-2.47 (m, 1H), 2.46-2.36 (m, 1H), 1.63-1.49 (m, 1H).

(rac)-methyl rel-5-[7-({(1R,2S,3R,4R)-2,3-dihydroxy-4-[(sulfamoyloxy)methyl]-cyclopentyl}amino)pyrazolo[1,5-a]pyrimidin-2-yl]-2-naphthoate (I-96)

The title compound is prepared using methyl 5-bromo-2-naphthoate in Step 2 instead of 1-chloro-4-iodo-naphthalene. LCMS: (AA) M+1 528; $^1$H NMR (300 MHz, DMSO+D$_2$O) δ 8.72 (s, 1H), 8.62 (d, J=9.0 Hz, 1H), 8.30-8.16 (m, 2H), 8.08-7.93 (m, 2H), 7.77-7.64 (m, 1H), 6.80 (s, 1H), 6.34 (d, J=5.5 Hz, 1H), 4.16-3.87 (m, 7H), 3.77-3.69 (m, 1H), 2.42-2.14 (m, 2H), 1.56-1.41 (m, 1H).

(rac)-((1R,2R,3S,4R)-4-(2-(5-fluoronaphthalen-1-yl)pyrazolo[1,5-a]pyrimidin-7-ylamino)-2,3-dihydroxycyclopentyl)methyl rel-sulfamate (I-97)

The title compound is prepared using 1-bromo-5-fluoronaphthalene in Step 2 instead of 1-chloro-4-iodo-naphthalene. LCMS: (AA) M+488; $^1$H NMR (300 MHz, DMSO) δ 8.32 (d, J=8.6 Hz, 1H), 8.27-8.11 (m, 2H), 7.93 (d, J=7.0 Hz, 1H), 7.78-7.66 (m, 1H), 7.63-7.51 (m, 1H), 7.48-7.34 (m, 1H), 6.78 (s, 1H), 6.34 (d, J=5.3 Hz, 1H), 4.19-4.07 (m, 1H), 4.07-3.92 (m, 3H), 3.81-3.67 (m, 1H), 2.44-2.13 (m, 2H), 1.61-1.14 (m, 1H).

(rac)-((1R,2R,3S,4R)-2,3-dihydroxy-4-(2-(4-(trifluoromethylthio)phenyl)pyrazolo[1,5-a]pyrimidin-7-ylamino)cyclopentyl)methyl rel-sulfamate (I-80)

The title compound is prepared using 4-bromophenyl trifluoromethyl sulfide in Step 2 instead of 1-chloro-4-iodo-naphthalene. LCMS: (AA) M+520; $^1$H NMR (400 MHz, MeOD) δ 8.25-8.10 (m, 3H), 7.77 (d, J=8.3 Hz, 2H), 6.86 (s, 1H), 6.35 (d, J=5.6 Hz, 1H), 4.30-4.18 (m, 2H), 4.17-4.08 (m, 1H), 4.07-4.02 (m, 1H), 4.02-3.95 (m, 1H), 2.59-2.35 (m, 2H), 1.67-1.53 (m, 1H).

(rac)-((1R,2R,3S,4R)-2,3-dihydroxy-4-(2-(2-(trifluoromethylthio)phenyl)pyrazolo[1,5-a]pyrimidin-7-ylamino)cyclopentyl)methyl rel-sulfamate (I-79)

The title compound is prepared using 2-bromophenyltrifluoromethylsulfide in Step 2 instead of 1-chloro-4-iodo-naphthalene. LCMS: (AA) M+520; $^1$H NMR (400 MHz, MeOD) δ 8.21 (d, J=5.8 Hz, 1H), 7.96-7.90 (m, 1H), 7.87 (d, J=7.8 Hz, 1H), 7.69-7.62 (m, 1H), 7.60-7.51 (m, 1H), 6.76 (s, 1H), 6.45 (d, J=5.9 Hz, 1H), 4.27-4.12 (m, 3H), 4.07-3.99 (m, 1H), 3.98-3.90 (m, 1H), 2.57-2.33 (m, 2H), 1.66-1.52 (m, 1H).

(rac)-((1R,2R,3S,4R)-2,3-dihydroxy-4-(2-(6-(trifluoromethyl)pyridin-2-yl)pyrazolo[1,5-a]pyrimidin-7-ylamino)cyclopentyl)methyl rel-sulfamate (I-64)

The title compound is prepared using 2-bromo-6-(trifluoromethyl)pyridine in Step 2 instead of 1-chloro-4-iodo-naphthalene. LCMS: (AA) M+489; $^1$H NMR (400 MHz, MeOD) δ 8.49 (d, J=8.0 Hz, 1H), 8.18 (d, J=5.5 Hz, 1H), 8.15-8.07 (m, 1H), 7.79 (d, J=7.7 Hz, 1H), 7.07 (s, 1H), 6.38 (d, J=5.6 Hz, 1H), 4.32-4.18 (m, 2H), 4.18-4.09 (m, 1H), 4.08-3.94 (m, 2H), 2.62-2.50 (m, 1H), 2.48-2.36 (m, 1H), 1.69-1.55 (m, 1H).

(rac)-((1R,2R,3S,4R)-4-(2-(6-tert-butylpyridin-2-yl)pyrazolo[1,5-a]pyrimidin-7-ylamino)-2,3-dihydroxycyclopentyl)methyl rel-sulfamate (I-52)

The title compound is prepared using 2-bromo-6-tert-butylpyridine in Step 2 instead of 1-chloro-4-iodo-naphthalene. LCMS: (AA) M+477; $^1$H NMR (400 MHz, MeOD) δ 8.15 (d, J=5.5 Hz, 1H), 8.10-7.95 (m, 1H), 7.85-7.71 (m, 1H), 7.48-7.35 (m, 1H), 7.03 (s, 1H), 6.34 (d, J=5.5 Hz, 1H), 4.30-4.19 (m, 2H), 4.17-4.08 (m, 1H), 4.07-3.96 (m, 2H), 2.61-2.33 (m, 2H), 1.71-1.52 (m, 1H), 1.43 (s, 9H).

(rac)-((1R,2R,3S,4R)-4-(2-(benzofuran-2-yl)pyrazolo[1,5-a]pyrimidin-7-ylamino)-2,3-dihydroxycyclopentyl)methyl rel-sulfamate (I-86)

The title compound is prepared using 2-iodo-1-benzofuran in Step 2 instead of 1-chloro-4-iodo-naphthalene. LCMS: (FA) M+1 460.2; $^1$H NMR (400 MHz, DMSO) δ 8.19 (d, J=5.3 Hz, 1H), 7.83 (d, J=7.8 Hz, 1H), 7.73 (d, J=7.1 Hz, 1H), 7.69-7.65 (m, 1H), 7.53-7.44 (m, 2H), 7.40-7.34 (m, 1H), 7.34-7.26 (m, 1H), 6.93 (s, 1H), 6.32 (d, J=5.4 Hz, 1H), 5.04 (s, 1H), 4.80 (s, 1H), 4.17-4.07 (m, 1H), 4.07-3.89 (m, 3H), 3.78 (s, 1H), 2.40-2.13 (m, 2H), 1.58-1.44 (m, 1H).

Method C with Modification [Example 10]

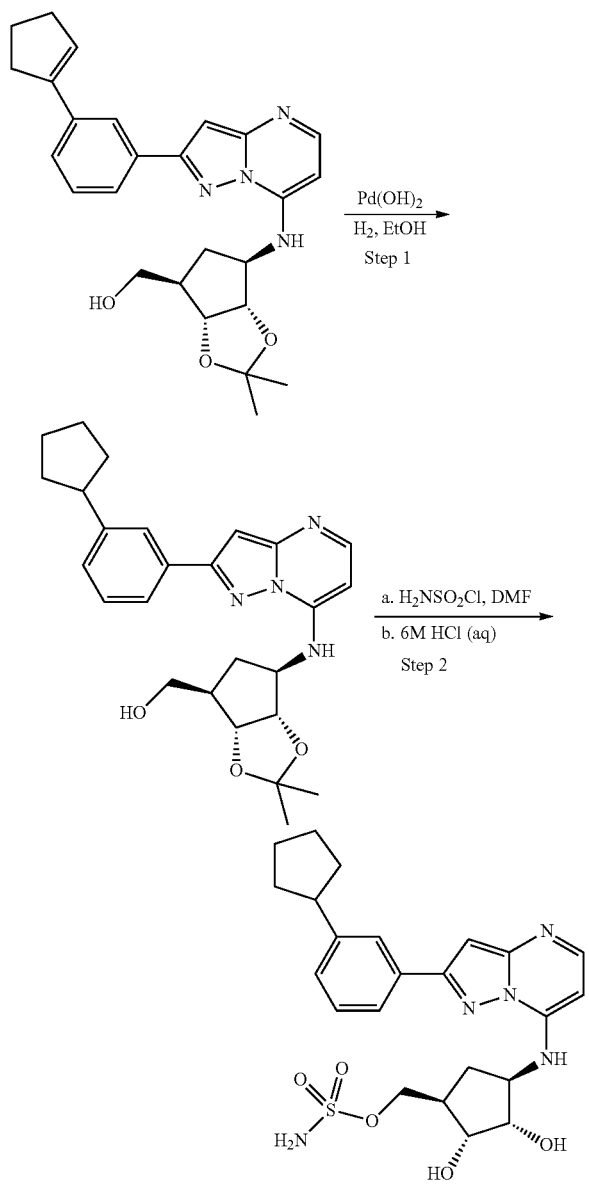

Example 10. Synthesis of (rac)-[(1R,2R,3S,4R)-4-{[2-(3-cyclopentylphenyl)pyrazolo[1,5-a]pyrimidin-7-yl]amino}-2,3-dihydroxycyclopentyl]methyl rel-sulfamate (I-48)

Step 1: (rac)-rel-[(3aR,4R,6R,6aS)-6-({2-[3-cyclopentylphenyl)pyrazolo[1,5-a]pyrimidin-7-yl]amino}-2,2-dimethyltetrahydro-3aH-cyclopenta[d][1,3]dioxol-4-yl]methanol (rac)-rel-[3aR,4R,6R,6aS)-6-({2-[3-(cyclopent-1-en-1-yl)phenyl]pyrazolo[1,5-a]pyrimidin-7-yl}amino)-2,2-dimethyltetrahydro-3aH-cyclopenta[d][1,3]dioxol-4-yl]methanol (0.039 g, 0.087 mmol) is stirred in ethanol (2.3 mL, 39 mmol). Palladium hydroxide (4.0 mg, 0.020 mmol) is added and the reaction is stirred under a balloon of hydrogen overnight. The reaction mixture is filtered through celite, rinsed with ethanol and concentrated in vacuo to provide (rac)-rel-[(3aR,4R,6R,6aS)-6-{[2-(3-cyclopentylphenyl)pyrazolo[1, 5-a]pyrimidin-7-yl]amino}-2,2-dimethyltetrahydro-3aH-cyclopenta[d][1,3]dioxol-4-yl]methanol (39 mg, yield 100%). Used in the next step without purification.

Step 2: (rac)-rel-[(1R,2R,3S,4R)-4-{[2-(3-cyclopentylphenyl)pyrazolo[1,5-a]pyrimidin-7-yl]amino}-2,3-dihydroxycyclopentyl]methyl rel-sulfamate (I-48)

The title compound is synthesized from (rac)-rel-[3aR,4R,6R,6aS)-6-{[2-(3-cyclopentylphenyl)pyrazolo[1,5-a]pyrimidin-7-yl]amino}-2,2-dimethyltetrahydro-3aH-cyclopenta[d][1,3]dioxol-4-yl]methanol following Step 2 of Method A (yield 44%). LCMS: (AA) M+1 488; $^1$H NMR (400 MHz, DMSO) δ 8.13 (d, J=5.3 Hz, 1H), 7.98-7.93 (m, 1H), 7.92-7.84 (m, 1H), 7.72-7.59 (m, 1H), 7.53-7.43 (m, 2H), 7.42-7.34 (m, 1H), 7.33-7.23 (m, 1H), 6.90 (s, 1H), 6.25 (d, J=5.4 Hz, 1H), 5.09-4.97 (m, 1H), 4.87-4.75 (m, 1H), 4.19-4.09 (m, 1H), 4.08-3.99 (m, 1H), 4.00-3.90 (m, 2H), 3.83-3.70 (m, 1H), 3.12-2.94 (m, 1H), 2.40-2.27 (m, 1H), 2.28-2.15 (m, 1H), 2.13-1.98 (m, 2H), 1.88-1.74 (m, 2H), 1.74-1.54 (m, 4H), 1.56-1.43 (m, 1H).

Method C with Modification [Example 11]

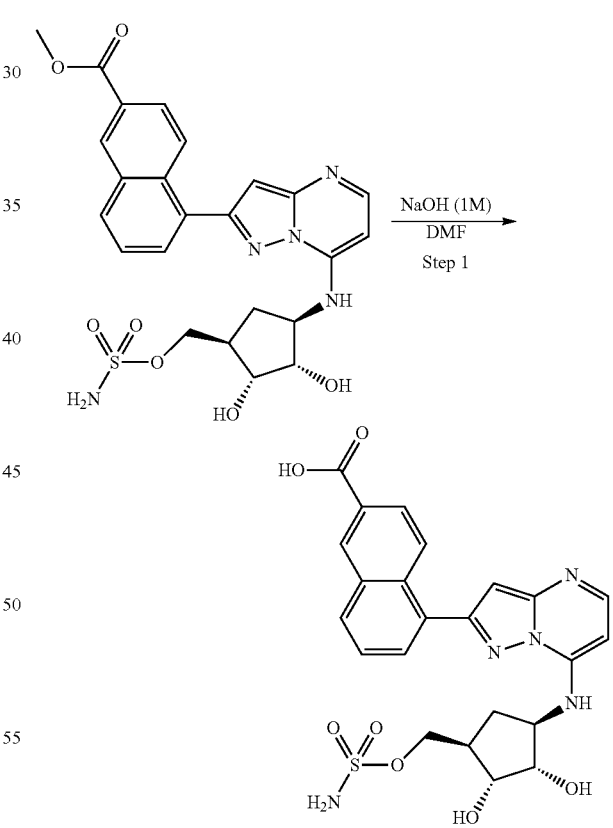

Example 11. Synthesis of (rac)-rel-5-[7-({(1R,2S,3R,4R)-2,3-dihydroxy-4-[(sulfamoyloxy)methyl]cyclopentyl}amino)pyrazolo[1,5-a]pyrimidin-2-yl]-2-naphthoic acid (I-99)

To a solution of (rac)-methyl rel-5-[7-({(1R,2S,3R,4R)-2,3-dihydroxy-4-[(sulfamoyloxy)methyl]

cyclopentyl}amino)pyrazolo[1,5-a]pyrimidin-2-yl]-2-naphthoate (0.048 g, 0.091 mmol) in DMF (2.0 mL, 26 mmol) is added 1.0 M NaOH (1.0 mL, 1.0 mmol). The mixture is stirred at room temperature for 1.5 hr and then concentrated in vacuo as an azeotropic mixture with toluene. The crude material is purified by preparative HPLC to provide (rac)-rel-5-[7-({(1R,2S,3R,4R)-2,3-dihydroxy-4-[(sulfamoyloxy)methyl]cyclopentyl}amino)pyrazolo[1,5-a]pyrimidin-2-yl]-2-naphthoic acid (4.0 mg, yield 8.5%). LCMS: (AA) M+1 514; $^1$H NMR (400 MHz, DMSO) δ 8.71-8.63 (m, 1H), 8.55 (d, J=8.9 Hz, 1H), 8.25-8.16 (m, 2H), 8.09-7.98 (m, 1H), 7.98-7.90 (m, 1H), 7.89-7.79 (m, 1H), 7.75-7.63 (m, 1H), 7.55-7.25 (m, 1H), 6.79 (s, 1H), 6.33 (d, J=5.4 Hz, 1H), 5.2-4.6 (m, 2H), 4.18-4.05 (m, 1H), 4.06-3.90 (m, 3H), 3.80-3.68 (m, 1H), 2.40-2.15 (m, 2H), 1.56-1.36 (m, 1H).

Method C with Modification [Example 12]

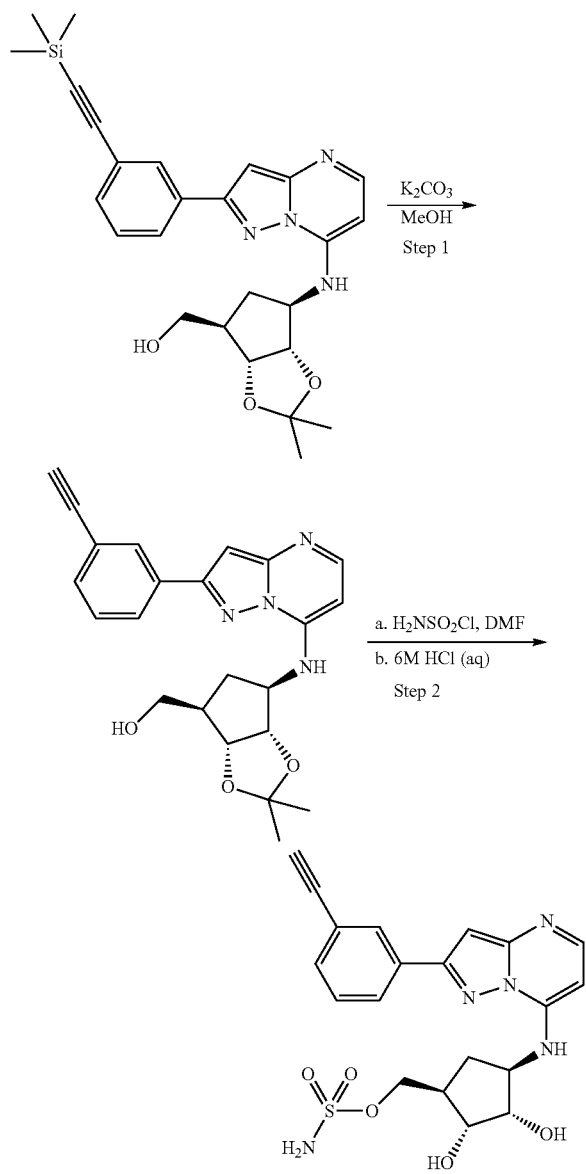

Example 12. Synthesis of (rac)-[(1R,2R,3S,4R)-4-{[2-(3-ethynylphenyl)pyrazolo[1,5-a]pyrimidin-7-yl]amino}-2,3-dihydroxycyclopentyl]methyl rel-sulfamate (I-83)

Step 1: (rac)-rel-[(3aR,4R,6R,6aS)-6-{[2-(3-ethynylphenyl)pyrazolo[1,5-a]pyrimidin-7-yl]amino}-2,2-dimethyltetrahydro-3aH-cyclopenta[d][1,3]dioxol-4-yl]methanol (rac)-rel-{(3aR,4R,6R,6aS)-2,2-dimethyl-6-[(2-{3-[(trimethylsilyl)ethynyl]phenyl}pyrazolo[1,5-a]pyrimidin-7-yl)amino]tetrahydro-3aH-cyclopenta[d][1,3]dioxol-4-yl}methanol (0.067 g, 0.00014 mol; synthesized following Step 1 in Method A except using 4,5,5-tetramethyl-[1,3,2]dioxaborolan-2-yl)-phenylethynyl-trimethylsilane instead of 1-naphthaleneboronic acid) is dissolved in methanol (0.03 mL, 0.0007 mol). Potassium carbonate (21 mg, 0.00015 mol) is added and the solution is stirred at room temperature overnight. The reaction mixture is neutralized with saturated ammonium chloride solution and extracted with dichloromethane. The organic layer is concentrated in vacuo and purified by column chromatography (0-15% MeOH/CH$_2$Cl$_2$) to provide (rac)-rel-[(3aR,4R,6R,6aS)-6-{[2-(3-ethynylphenyl)pyrazolo[1,5-a]pyrimidin-7-yl]amino}-2,2-dimethyltetrahydro-3aH-cyclopenta[d][1,3]dioxol-4-yl]methanol (0.046 g, yield 81%). LCMS: (AA) M+405; $^1$H NMR (400 MHz, DMSO) δ 8.25-8.05 (m, 4H), 7.52-7.44 (m, 2H), 7.00 (s, 1H), 6.25 (d, J=5.4 Hz, 1H), 5.25-5.17 (m, 1H), 4.59-4.48 (m, 2H), 4.27 (s, 1H), 4.16-3.99 (m, 1H), 3.65-3.44 (m, 2H), 2.48-2.38 (m, 1H), 2.28-2.19 (m, 1H), 1.87-1.72 (m, 1H), 1.46 (s, 3H), 1.24 (s, 3H).

Step 2: (rac)-[(1R,2R,3S,4R)-4-{[2-(3-ethynylphenyl)pyrazolo[1,5-a]pyrimidin-7-yl]amino}-2,3-dihydroxycyclopentyl]methyl rel-sulfamate (I-83)

The title compound is synthesized from (rac)-rel-[(3aR,4R,6R,6aS)-6-{[2-(3-ethynylphenyl)pyrazolo[1,5-a]pyrimidin-7-yl]amino}-2,2-dimethyltetrahydro-3aH-cyclopenta[d][1,3]dioxol-4-yl]methanol following Step 2 of Method A. LCMS: (AA) M+444; $^1$H NMR (400 MHz, MeOD) δ 8.22-8.16 (m, 1H), 8.13 (d, J=5.5 Hz, 1H), 8.07-7.99 (m, 1H), 7.55-7.34 (m, 2H), 6.78 (s, 1H), 6.32 (d, J=5.6 Hz, 1H), 4.28-4.17 (m, 2H), 4.16-4.07 (m, 1H), 4.07-4.02 (m, 1H), 4.01-3.94 (m, 1H), 3.55 (s, 1H), 2.60-2.29 (m, 2H), 1.67-1.47 (m, 1H).

Example 13. Compounds Prepared by Method D (rac)-{(1R,2R,3S,4R)-4-[(5-chloro-2-phenyl pyrazolo[1,5-a]pyrimidin-7-yl)amino]-2,3-dihydroxycyclopentyl}methyl rel-sulfamate (I-6)

The title compound is prepared using 5-amino-3-phenylpyrazole in Step 1 instead of 3-(1-naphthyl)-1H-pyrazol-5-amine. LCMS: (AA) M+1 454; $^1$H NMR (400 MHz, MeOD) δ 8.03 (d, J=8.5 Hz, 2H), 7.45 (t, J=7.3 Hz, 2H), 7.39 (t, J=7.3 Hz, 1H), 6.72 (s, 1H), 6.36 (s, 1H), 4.28-4.17 (m, 2H), 4.13-3.94 (m, 3H), 2.55-2.36 (m, 2H), 1.67-1.54 (m, 1H).

(rac)-[(1R,2R,3S,4R)-4-{[5-chloro-2-(4-methoxyphenyl)pyrazolo[1,5-a]pyrimidin-7-yl]amino}-2,3-dihydroxycyclopentyl]methyl rel-sulfamate (I-14)

The title compound is prepared using 5-amino-3-(4-methoxyphenyl)pyrazole in Step 1 instead of 3-(1-naphthyl)-1H-pyrazol-5-amine. LCMS: (AA) M+1 484; $^1$H NMR (300 MHz, MeOD) δ 7.94 (d, J=8.9 Hz, 2H), 7.00 (dd, J=9.3, 2.4 Hz, 2H), 6.62 (s, 1H), 6.32 (s, 1H), 4.29-4.16 (m, 2H), 4.12-3.93 (m, 3H), 3.84 (s, 3H), 2.57-2.33 (m, 2H), 1.66-1.52 (m, 1H).

(rac)-((1R,2R,3S,4R)-4-(2-(4-bromophenyl)-5-chloropyrazolo[1,5-a]pyrimidin-7-ylamino)-2,3-dihydroxycyclopentyl)methyl rel-sulfamate (I-8)

The title compound is prepared using 5-(4-bromophenyl)-2H-pyrazol-3-ylamine in Step 1 instead of 3-(1-naphthyl)-1H-pyrazol-5-amine. LCMS: (AA) M+1 532; $^1$H NMR (300 MHz, DMSO) δ 8.04 (d, J=8.5 Hz, 2H), 7.69 (d, J=8.5 Hz, 2H), 6.95 (s, 1H), 6.35 (s, 1H), 4.16-3.88 (m, 4H), 3.79-3.68 (m, 1H), 2.33-2.17 (m, 2H), 1.61-1.37 (m, 1H).

(rac)-((1R,2R,3S,4R)-4-(5-chloro-2-(pyridin-2-yl)pyrazolo[1,5-a]pyrimidin-7-ylamino)-2,3-dihydroxycyclopentyl)methyl rel-sulfamate (I-11)

The title compound is prepared using 5-pyridin-2-yl-2H-pyrazol-3-ylamine in Step 1 instead of 3-(1-naphthyl)-1H-pyrazol-5-amine. LCMS: (AA) M+1 455; $^1$H NMR (400 MHz, MeOD) δ 8.64 (d, J=4.9 Hz, 1H), 8.23 (d, J=7.9 Hz, 1H), 8.01-7.85 (m, 1H), 7.48-7.36 (m, 1H), 6.95 (s, 1H), 6.41 (s, 1H), 4.30-4.18 (m, 2H), 4.14-3.93 (m, 3H), 2.60-2.35 (m, 2H), 1.68-1.54 (m, 1H).

Method D with Modification [Example 14]

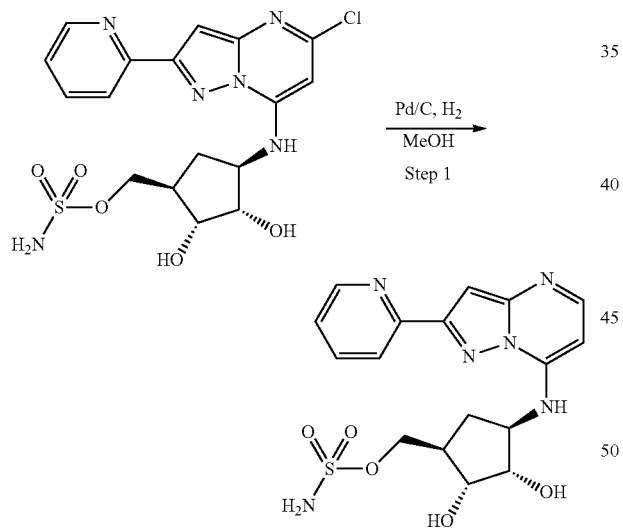

Example 14. (rac)-[(1R,2R,3S,4R)-2,3-dihydroxy-4-{[2-(pyridin-2-yl)pyrazolo[1,5-a]pyrimidin-7-yl]amino}cyclopentyl]methyl rel-sulfamate (I-12)

(rac)-[(1R,2R,3S,4R)-4-{[5-chloro-2-(pyridin-2-yl)pyrazolo[1, 5-a]pyrimidin-7-yl]amino}-2,3-dihydroxycyclopentyl]methyl rel-sulfamate (5.0 mg, 0.011 mmol; synthesized following Steps 1-4 of Method D starting from 5-pyridin-2-yl-2H-pyrazol-3-ylamine) is dissolved in methanol (1.00 mL, 0.0247 mol). Palladium on carbon (10%, 29.2 mg, 0.00275 mmol) is added and the suspension is purged with hydrogen gas and stirred for 3 days at room temperature under a balloon of hydrogen (1 atm). The reaction mixture is purged with nitrogen, filtered through celite and rinsed with methanol. The filtrate is concentrated in vacuo and purified by preparative HPLC to provide (rac)-[(1R,2R,3S, 4R)-2,3-dihydroxy-4-{[2-(pyridin-2-yl)pyrazolo[1,5-a]pyrimidin-7-yl]amino}cyclopentyl]methyl rel-sulfamate (1.0 mg, yield 22%). LCMS: (AA) M+1 421; $^1$H NMR (400 MHz, MeOD) δ 8.72-8.61 (m, 1H), 8.25 (d, J=7.8 Hz, 1H), 8.18 (d, J=4.8 Hz, 1H), 7.99-7.88 (m, 1H), 7.47-7.37 (m, 1H), 7.01 (s, 1H), 6.41-6.32 (m, 1H), 4.30-4.18 (m, 2H), 4.16-3.92 (m, 3H), 2.61-2.49 (m, 1H), 2.48-2.35 (m, 1H), 1.68-1.56 (m, 1H).

(rac)-[(1R,2R,3S,4R)-2,3-dihydroxy-4-{[2-(4-phenyl-1,3-thiazol-2-yl)pyrazolo[1,5-a]pyrimidin-7-yl]amino}cyclopentyl]methyl rel-sulfamate (I-31)

The title compound is prepared following Method D with Modification starting from (rac)-[(1R,2R,3S,4R)-4-{[5-chloro-2-(4-phenyl-1,3-thiazol-2-yl)pyrazolo[1,5-a]pyrimidin-7-yl]amino}-2,3-dihydroxycyclopentyl]methyl rel-sulfamate (synthesized following Steps 1-4 of Method D starting from 3-(4-phenylthiazol-2-yl)-1H-pyrazol-5-amine). LCMS: (AA) M+1 503; $^1$H NMR (400 MHz, MeOD) δ 8.20 (d, J=5.5 Hz, 1H), 8.06-7.99 (m, 2H), 7.90 (s, 1H), 7.46 (t, J=7.8 Hz, 2H), 7.37 (t, J=7.4 Hz, 1H), 7.02 (s, 1H), 6.42 (d, J=5.5 Hz, 1H), 4.30-4.10 (m, 3H), 4.06 (t, J=5.9 Hz, 1H), 3.99 (t, J=5.3 Hz, 1H), 2.58-2.48 (m, 1H), 2.48-2.37 (m, 1H), 1.67-1.56 (m, 1H).

Method G [Example 15]

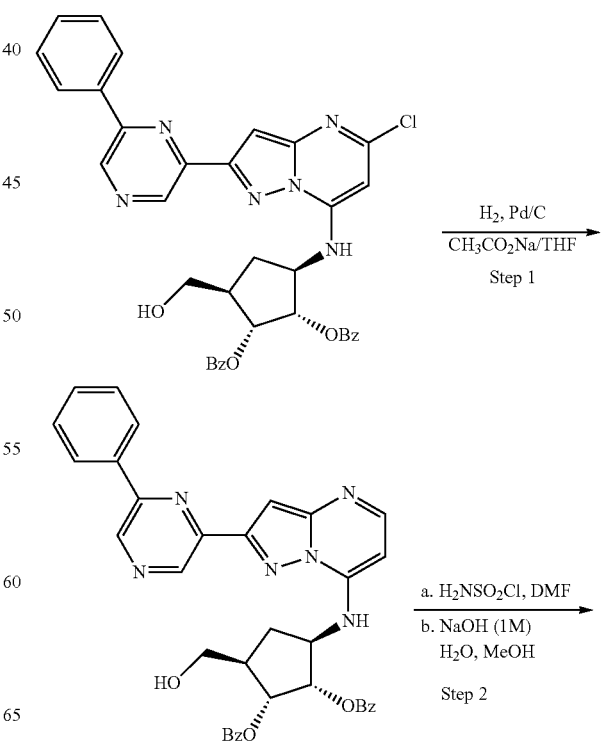

-continued

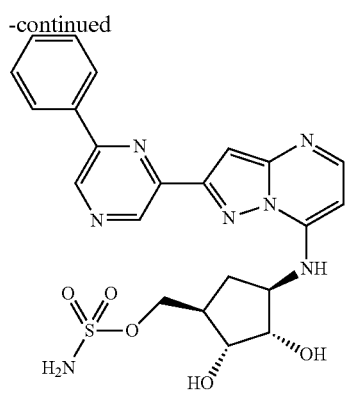

Example 15. Synthesis of (rac)-((1R,2R,3S,4R)-2,3-dihydroxy-4-{[2-(6-phenylpyrazin-2-yl)pyrazolo[1,5-a]pyrimidin-7-yl]amino}cyclopentyl)methyl rel-sulfamate (I-121)

Step 1. (rac)-(1S,2R,3R,5R)-3-(hydroxymethyl)-5-{[2-(6-phenylpyrazin-2-yl)pyrazolo[1,5-a]pyrimidin-7-yl]amino}cyclopentane-1, 2-diyl dibenzoate The title compound is prepared starting from (rac)-(1R,2S,3R,5R)-3-{[5-chloro-2-(6-phenylpyrazin-2-yl)pyrazolo[1, 5-a]pyrimidin-7-yl]amino}-5-(hydroxymethyl)cyclopentane-1,2-diyl dibenzoate (prepared from 3-(6-phenylpyrazin-2-yl)-1H-pyrazol-5-amine following Steps 1-3 of Method D) following Step 5 of Method F.

Step 2. (rac)-((1R,2R,3S,4R)-2,3-dihydroxy-4-{[2-(6-phenylpyrazin-2-yl)pyrazolo[1,5-a]pyrimidin-7-yl]amino}cyclopentyl)methyl sulfamate (I-121)

The title compound is prepared from (rac)-(1S,2R,3R,5R)-3-(hydroxymethyl)-5-{[2-(6-phenylpyrazin-2-yl)pyrazolo[1,5-a]pyrimidin-7-yl]amino}cyclopentane-1, 2-diyl dibenzoate following Step 7 of Method B. LCMS: (AA) M+1 498; $^1$H NMR (400 MHz, DMSO) δ 8.32-8.27 (m, 2H), 8.22 (d, J=5.3 Hz, 1H), 7.87 (s, 1H), 7.63-7.52 (m, 4H), 7.16 (s, 1H), 6.37 (d, J=5.4 Hz, 1H), 5.08 (s, 1H), 4.86 (s, 1H), 4.19-4.11 (m, 1H), 4.08-3.95 (m, 3H), 3.84-3.74 (m, 1H), 2.42-2.19 (m, 2H), 1.59-1.47 (m, 1H).

Also prepared by Method G:

(rac)-[(1R,2R,3S,4R)-2,3-dihydroxy-4-({2-[3-(1-methyl-1H-pyrazol-4-yl)phenyl]pyrazolo[1, 5-a]pyrimidin-7-yl}amino)cyclopentyl]methyl rel-sulfamate (I-122)

The title compound is prepared using (rac)-(1S,2R,3R,5R)-3-(hydroxymethyl)-5-({2-[3-(1-methyl-1H-pyrazol-4-yl)phenyl]pyrazolo[1,5-a]pyrimidin-7-yl}amino)cyclopentane-1,2-diyl dibenzoate in Step 1 instead of (rac)-(1R,2S,3R,5R)-3-{[5-chloro-2-(6-phenylpyrazin-2-yl)pyrazolo[1,5-a]pyrimidin-7-yl]amino}-5-(hydroxymethyl)cyclopentane-1,2-diyl dibenzoate. LCMS: (AA) M+1 500; $^1$H NMR (400 MHz, DMSO) δ 8.23 (s, 2H), 8.15 (d, J=5.3 Hz, 1H), 7.97 (s, 1H), 7.92 (d, J=7.8 Hz, 1H), 7.65 (s, 1H), 7.61-7.57 (m, 1H), 7.45 (t, J=7.7 Hz, 1H), 7.00 (s, 1H), 6.27 (d, J=5.4 Hz, 1H), 4.17-4.10 (m, 1H), 4.07-3.93 (m, 3H), 3.89 (s, 3H), 3.80-3.75 (m, 1H), 2.41-2.19 (m, 2H), 1.57-1.45 (m, 1H).

Example 16. Synthesis of (rac)-{(1R,2R,3S,4R)-4-[(2-{3-[2-chloro-1-(hydroxymethyl)-1-methylethyl]phenyl}pyrazolo[1,5-a]pyrimidin-7-yl)amino]-2,3-dihydroxycyclopentyl}methyl rel-sulfamate (I-123)

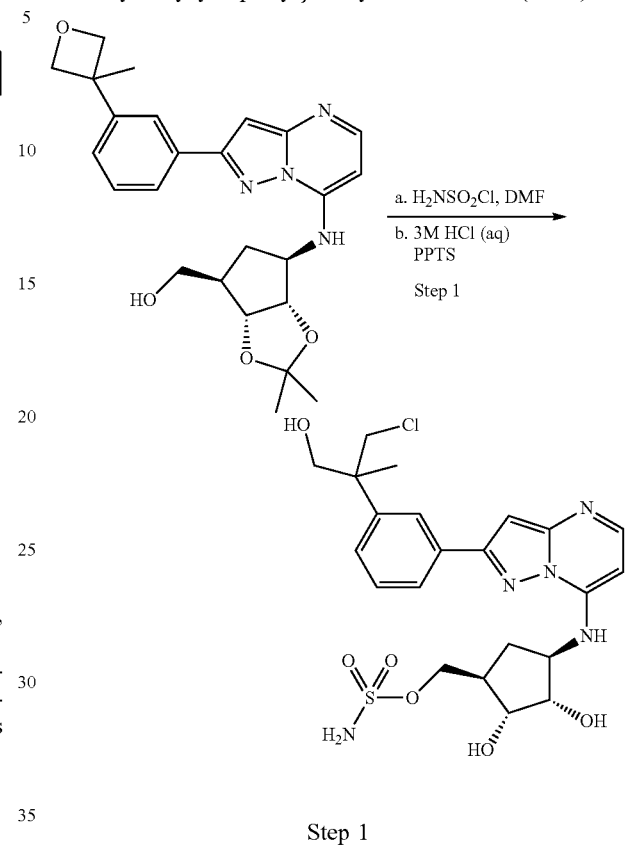

Step 1

The title compound is prepared from (rac)-[(3aR,4R,6R,6aS)-2,2-dimethyl-6-({2-[3-(3-methyloxetan-3-yl)phenyl]pyrazolo[1,5-a]pyrimidin-7-yl}amino)tetrahydro-3aH-cyclopenta[d][1,3]dioxol-4-yl]methanol following Step 2 in Method A and adding 5 equivalents of pyridinium p-toluenesulfonate after the addition of hydrochloric acid. LCMS: (AA) M+1 526.

Example 17. Synthesis of (s.e.)-{(1R,2R,3S,4R)-4-[(3,6-dichloro-2-{3-[(trifluoromethyl)sulfanyl]phenyl}pyrazolo[1,5-a]pyrimidin-7-yl)amino]-2,3-dihydroxycyclopentyl}methyl sulfamate (I-124) and (s.e.)-{(1R,2R,3S,4R)-4-[(6-chloro-2-{3-[(trifluoromethyl)sulfanyl]phenyl}pyrazolo[1,5-a]pyrimidin-7-yl)amino]-2,3-dihydroxycyclopentyl}methyl sulfamate (I-125)

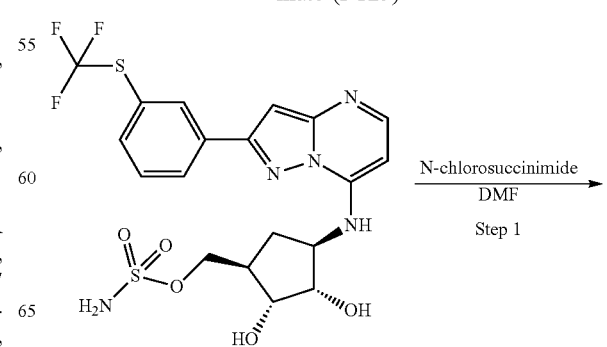

N-chlorosuccinimide
DMF
Step 1

-continued

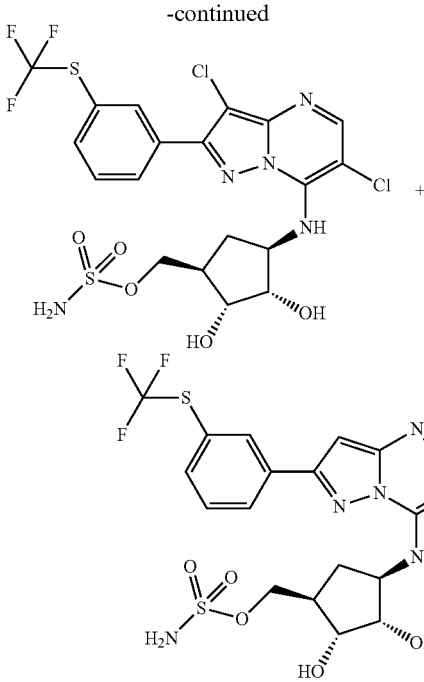

Step 1

To a vial containing (s.e.)-{(1R,2R,3S,4R)-2,3-dihydroxy-4-[(2-{3-[(trifluoromethyl)sulfanyl]phenyl}pyrazolo[1, 5-a]pyrimidin-7-yl)amino]cyclopentyl}methyl sulfamate (0.82 g, 0.0015 mol) and cooled to 0° C. is added N-chlorosuccinimide (126 mg, 0.000943 mol) as a solution in 12 mL of N,N-dimethylformamide. The reaction mixture is stirred overnight with warming to rt. Saturated sodium bicarbonate solution is added and the reaction mixture is extracted with ethyl acetate, washed with brine, dried over sodium sulfate and concentrated in vacuo. The crude material is first purified by column chromatography (eluent: methanol/methylene chloride) and then purified by HPLC to afford both the dichloro (LCMS: (FA) M+1 588) and mono chloro (LCMS: (FA) M+1 554) title compounds.

Example 18. (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl)methyl sulfamate (I-101)

The title compound is prepared following Example 2a with any of the following modifications to Step 2: (I) After the addition of 6 M hydrochloric acid in water and stirring for 1 hr, the reaction mixture is made basic by the addition of a 1.0 M sodium hydroxide solution. Solvent is removed in vacuo and methanol is added to the crude residue. The resulting suspension is filtered through syringe filter to remove inorganic salts and then concentrated in vacuo. The crude material is purified by either HPLC or column chromatography (eluent: methylene chloride/methanol). (II) After the addition of 6 M hydrochloric acid in water and stirring for 1 hr, the reaction mixture is made basic by the addition of a 1.0 M sodium hydroxide solution. Solvent is removed in vacuo and methanol is added to the crude residue. The resulting suspension is filtered through syringe filter to remove inorganic salts and then concentrated in vacuo. The crude material is purified by either HPLC or column chromatography (eluent: methylene chloride/methanol). (III) Water:tetrahydrofuran (2.6:1) is used as the solvent instead of N,N-dimethylformamide. 12 M hydrochloric acid in water is used instead of 6 M hydrochloric acid in water. Upon completion, solid sodium bicarbonate is added to neutralize the reaction mixture. The mixture is diluted with water and concentrated in vacuo to remove the THF during which time a precipitate is formed. The mixture is stirred for 30 minutes and the precipitate is collected by vacuum filtration and dried under vacuum. NMR and LCMS data correspond to data previously described for I-101.

Example 19. (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl)methyl sulfamate Form 1 anhydrous Step 1: Synthesis of tert-butyl-[({(3aR,4R,6aS)-2,2-dimethyl-6-[(2-{3-(trifluoromethylthio)phenyl}pyrazolo[1,5-a]pyrimidin-7-yl)amino]tetrahydro-3aH-cyclopenta[d][1,3]dioxol-4-yl}methoxy)sulfonyl]carbamate {(3aR,4R,6R,6aS)-2,2-dimethyl-6-[(2-{3-(trifluoromethylthio)phenyl}pyrazolo[1, 5-a]pyrimidin-7-yl)amino]tetrahydro-3aH-cyclopenta[d][1,3]dioxol-4-yl}methanol (3.4 g) was dissolved in 2-methyltetrahedrafuran (32.0 mL) and to this solution was added pyridinium p-toluenesulfonate (3.34 g). This formed a precipitate and to this white slurry was added (4-aza-1-azoniabicyclo[2.2.2]oct-1-ylsulfonyl)(tert-butoxycarbonyl)azanide-1,4-diazabicyclo[2.2.2]octane (1:1) hydrochloride (8.19 g). (prepared according to Armitage, I. et. al. U.S. Patent Application Publication US2009/0036678, and Armitage, I. et. al. *Org. Lett.*, 2012, 14 (10), 2626-2629). The mixture was stirred at ambient temperature until the HPLC showed <1% remaining starting material (about 300 minutes). To the reaction was added ethyl acetate (30 mL) and water (30 mL). After stirring for 10 minutes the phases were separated and the aqueous layer was back extracted with ethyl acetate (30 mL). The organic layers were combined and washed with 10% brine (30 mL) and the layers were separated. The organic layer was then concentrated to dryness to give an off-white solid. The solids were transferred back to the reactor with acetonitrile (35 m L) and stirred for 20 minutes. The solids were isolated by filtration and dried in a vacuum oven at full vacuum overnight (40° C., 16 hours) to give tert-butyl-[({(3aR,4R,6aS)-2,2-dimethyl-6-[(2-{3-(trifluoromethylthio)phenyl}pyrazolo[1,5-a]pyrimidin-7-yl)amino]tetrahydro-3aH-cyclopenta[d][1,3]dioxol-4-yl}methoxy)sulfonyl]carbamate (3.87 g, 88%). (LCMS: (FA2) M+1 660).

Step 2: (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl)methyl sulfamate Form 1 anhydrous To a solution of tert-butyl-[({(3aR,4R,6aS)-2,2-dimethyl-6-[(2-{3-(trifluoromethylthio)phenyl}pyrazolo[1,5-a]pyrimidin-7-yl)amino]tetrahydro-3aH-cyclopenta[d][1,3]dioxol-4-yl}methoxy)sulfonyl]carbamate (4.0 g) in acetonitrile (20.0 mL) at 0° C. was added phosphoric acid (20.0 mL) while maintaining the temperature below 10° C. This mixture was warmed to ambient temperature and stirred for 4 hours. At this time HPLC analysis showed that <1% starting material or reaction intermediates remained. To the reaction was added ethyl acetate (20 mL) and water (20 mL). After this addition was complete saturated Na₂CO₃ (80.0 mL) was added until the pH was between 6-7. After stirring for 10 minutes the phases were separated and the aqueous layer was back extracted with ethyl acetate (20 mL). The organic layers were combined and dried with Na₂SO₄. The organic layer was then concentrated to 4 vol of ethyl acetate. The solution started to precipitate within 5 minutes. This mixture was stirred for 16 hours. The resulting white solids were collected using a filter over 5 minutes. The solid was dried in a vacuum oven under full vacuum overnight (35° C., 16 hours). This yielded (s.e.)-((1R,2R, 3S,4R)-2,3-dihydroxy-4-(2-(3-(trifluoromethylthio)-phenyl)pyrazolo[1,5-a]pyrimidin-7-ylamino)cyclopentyl) methyl sulfamate anhydrous Form 1. (2.85 g, 84%). XRPD data is shown in FIG. 1; DSC data is shown in FIG. 2; TGA is shown in FIG. 3; Raman data is shown in FIGS. 4, 5A, 6A and 7A.

Form 1 can also be prepared in the following way:

To a solution of tert-butyl-[({(3aR,4R,6aS)-2,2-dimethyl-6-[(2-{3-(trifluoromethylthio)phenyl}pyrazolo[1,5-a]pyrimidin-7-yl)amino]tetrahydro-3aH-cyclopenta[d][1,3]dioxol-4-yl}methoxy)sulfonyl]carbamate (2.4 g) in acetonitrile (12.0 mL) at 0° C. was added phosphoric acid (12.0 mL) while maintaining the temperature below 10° C. This mixture was warmed to ambient temperature and stirred for 4 hours. At this time HPLC analysis showed that <1% starting material or reaction intermediates remained. To the reaction was added ethyl acetate (12 mL) and water (12 mL). After this addition was complete saturated Na₂CO₃ (48.0 mL) was added until the pH was between 6-7. After stirring for 10 minutes the phases were separated and the aqueous layer was back extracted with ethyl acetate (20 mL). The combined organic layers were then washed with water (24 mL). To the organic layer was then added acetonitrile (24 mL) and it was then concentrated to ~10 volumes. To the organic layer was then added acetonitrile (24 mL) and it was concentrated to ~10 volumes. To the organic layer was then added acetonitrile (24 mL) and it was concentrated to ~5 vol of acetonitrile. (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl)methyl sulfamate Form 1 anhydrous (prepared in Step 2 above). The solution started to precipitate within 5 minutes. This mixture was stirred for 16 hours. The resulting white solids were collected using a filter over 5 minutes. The solid was dried in a vacuum oven under full vacuum overnight (35° C., 16 hours). This yielded (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate Form 1 anhydrous (1.35 g, 71%). The analytical data is consistent with Form 1.

Form 1 can also be prepared in the following way:

To (s.e.)-((1R,2R,3S,4R)-2,3-dihydroxy-4-(2-(3-(trifluoromethylthio)phenyl)pyrazolo[1,5-a]pyrimidin-7-ylamino) cyclopentyl)methyl sulfamate Form 1 anhydrous (5.0 g) was added acetonitrile (32 mL) and water (8 mL). This mixture was heated to 50° C. at which point all the solids were in solution. To this solution was added water (40 mL) while maintaining the solution temperature at 50° C. The solution was then seeded with (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate Form 1 anhydrous (prepared in Step 2 above). The seed did not dissolve and the mixture was then cooled over 12 hours to 22° C. The resulting white solids were collected using a filter over 5 minutes. The solid was dried in a vacuum oven under full vacuum overnight (35° C., hours) to yield (s.e.)-((1R,2R, 3S,4R)-2,3-dihydroxy-4-(2-(3-(trifluoromethylthio)-phenyl)pyrazolo[1,5-a]pyrimidin-7-ylamino)cyclopentyl) methyl sulfamate Form 1 anhydrous (4.25 g, 85%). The analytical data is consistent with Form 1.

Example 20. (s.e.)-((1R,2R,3S,4R)-2,3-dihydroxy-4-(2-(3-(trifluoromethylthio)-phenyl)pyrazolo[1,5-a] pyrimidin-7-ylamino)cyclopentyl)methyl sulfamate Form 2 monohydrated To a solution of tert-butyl-[({(3aR,4R,6aS)-2,2-dimethyl-6-[(2-{3-(trifluoromethylthio)phenyl}pyrazolo[1,5-a]pyrimidin-7-yl)amino]tetrahydro-3aH-cyclopenta[d][1,3]dioxol-4-yl}methoxy)sulfonyl]carbamate (5.0 g) in acetonitrile (25.0 mL) at 0° C. was added phosphoric acid (25.0 mL) while maintaining the temperature below 10° C. This mixture was warmed to ambient temperature and stirred for 4 hours. At this time HPLC analysis showed that <1% starting material or reaction intermediates remained. To the reaction was added ethyl acetate (25 mL) and water (25 mL). After this addition was complete saturated Na₂CO₃ (100.0 mL) was added until the pH was between 6-7. After stirring for 10 minutes the phases were separated and the aqueous layer was back extracted with ethyl acetate (25 mL). The combine organics were then washed with 10% brine (50 mL). The organic layers were dried with Na₂SO₄. The organic layer was then concentrated to 4 vol of ethyl acetate. The solution started to precipitate within 5 minutes. This mixture was stirred for 16 hours. The resulting white solids were collected using a filter over 5 minutes. The solid was dried in a vacuum oven under full vacuum overnight (35° C., 16 hours). This yielded (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate Form 2 monohydrated (3.04 g, 77%). XRPD data is shown in FIG. 8; DSC data is shown in FIG. 9; TGA is shown in FIG. 10; Raman data is shown in FIGS. 11, 5B, 6B and 7B.

Form 2 can also be prepared in the following way:

(s.e.)-((1R,2R,3S,4R)-2,3-Dihydroxy-4-(2-(3-(trifluoromethylthio)phenyl)pyrazolo[1,5-a]pyrimidin-7-ylamino) cyclopentyl)methyl sulfamate Form 1 anhydrous (1.5 g) dissolved in 90:10/MeCN:water (25.0 mL) at 50° C. The solution was rapidly cooled to 5° C. To the solution was added water (20 mL) while maintaining the temperature. The reaction was then seeded with (s.e.)-((1R,2R,3S,4R)-2, 3-dihydroxy-4-(2-(3-(trifluoromethylthio)phenyl)pyrazolo [1,5-a]pyrimidin-7-ylamino)cyclopentyl)methyl sulfamate Form 2 monohydrated (prepared as above). The solution was stirred for 2 hours at 5° C. and the solution remained cloudy. Additional water (11.25 mL) was then added and the mixture was stirred for 16 hours. The slurry was then filtered and dried for 48 hours. This gave (s.e.)-((1R,2R,3S,4R)-2,3-dihydroxy-4-(2-(3-(trifluoromethylthio)phenyl)pyrazolo[1, 5-a]pyrimidin-7-ylamino)cyclopentyl)methyl sulfamate Form 2 monohydrated (1.21 g, 95%) The analytical data is consistent with Form 2.

Example 21. Competitive Slurrying Experiments

Approximately 10 mg of a 1:1 mixture of (s.e.)-((1R,2R, 3S,4R)-2,3-dihydroxy-4-(2-(3-(trifluoromethylthio)phenyl) pyrazolo[1,5-a]pyrimidin-7-ylamino)cyclopentyl)methyl sulfamate Form 1 anhydrous and (s.e.)-((1R,2R,3S,4R)-2,3-dihydroxy-4-(2-(3-(trifluoromethylthio)-phenyl)pyrazolo[1, 5-a]pyrimidin-7-ylamino)cyclopentyl)methyl sulfamate Form 2 monohydrated was placed in a vial and 100 μl of the solvents listed below in Table 5 (which had been previously saturated in Form 1) were added to the vial. The vials were agitated at the temperature shown below for 60 hours. Any solids remaining at this point were isolated by centrifugation and analysed by XRPD.

TABLE 5

Summary of Competitive Slurrying Experiments

| Temperature (° C.) | Solvent Composition | | Form present by XRPD analysis |
|---|---|---|---|
| | % MeCN | % Water | |
| 5 | 90 | 10 | Form 2 |
| 5 | 80 | 20 | Form 2 |
| 5 | 70 | 30 | Form 2 |
| ambient | 90 | 10 | Mixture |
| ambient | 80 | 20 | Mixture |
| ambient | 70 | 30 | Mixture |
| 50 | 90 | 10 | Form 1 |
| 50 | 80 | 20 | Form 1 |
| 50 | 70 | 30 | Form 1 |

In all the solvent systems studied Form 2 was isolated at 5° C. and Form 1 was isolated at 50° C. showing that isolation of the desired form can be controlled with temperature.

Example 22. Preparation of (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate solution for parenteral administration The composition of the formulation of (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate for injection (intravenous or subcutaneous) is shown in Table 6

TABLE 6

Quantitative composition of sterile solution for parenteral administration

| Component | Function | Amount (mg/mL) |
|---|---|---|
| Citric Acid anhydrous, USP | Excipient | 9.61 |
| β-Cyclodextrin Sulfobutyl Ethers, Sodium Salts (Captisol ®) (Ligand Pharmaceuticals Inc) | Excipient | 50 |
| (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate Form 1 anhydrous | | 2 |
| Sodium Hydroxide | pH adjuster | q.s. to pH 3.3 ± 0.5 |
| Water for Injection | Solvent | q.s. to 1 mL |

A batch of (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl)methyl sulfamate sterile solution for parenteral administration is prepared by performing the following steps:
1) Calculate the required amount of excipients and solvent per lot using the quantitative composition of the formulation shown in Table 3.
2) Add the calculated amount of anhydrous citric acid to 75% of the calculated amount of sterile Water for Injection and stir until citric acid is completely dissolved.
3) Add the calculated amount of Captisol® to the solution and stir until Captisol® is completely dissolved.
4) Add the calculated amount of (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate Form 1 anhydrous to the solution and stir until completely dissolved.
5) Adjust the pH of the solution to a target of 3.3±0.5 using sodium hydroxide solution.
6) Adjust the volume of the solution to a target of 2.0 mg/mL (s.e.)-((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate concentration using sterile Water for Injection.
7) Filter the compounded bulk solution using a 0.45 μM clarifying filter followed by a 0.2 μM sterilizing filter for bio-burden reduction and sterilization, respectively.
8) Aseptically fill the sterile solution in sterile and depyrogenated vials.
9) Seal the filled vials are using sterile rubber stoppers and overseal using sterile aluminum crimps with polypropylene caps.

Biological Assays
Ubiquitin Activating Enzyme (UAE) HTRF Assay

The UAE enzymatic reaction totals 50 μL and contains 50 mmol HEPES (pH 7.5), 0.05% BSA, 2.5 mM MgCl2, 0.1 uM ATP, 8 nM GST-Ubc-2, 35 nM flag-ubiquitin, 1 nM recombinant human UAE or mouse UAE. Compounds for this hUAE IC50 assay are tested at 10 point 3-fold dilution. The top concentration for this assay is 1 μM. Each compound is ordered in duplicate on the same plate. The enzymatic reaction mixture is incubated for 90 minutes at room temperature (24 degrees C.) in a 384 well plate prior to termination with a stop solution (0.1 M HEPES/0.05% Tween20, 20 mmol EDTA, 410 mM KF, 0.5 nM Eu Cryptate anti-FLAG M2-K antibody (Cis-bio International), 8 ug/mL Anti-GST XL-APC (Prozyme)). After incubation for 120 minutes, quantification of the FRET is performed on the Pherostar (BMG).

From the Pherastar raw data files, % inhibition vs. plate based controls is calculated. Dose response data is further processed in Genedata Condoseo, which performs as 4 parameter logistic fit and determines the $IC_{50}$ (intercept at 50% inhibition) for each compound. The results are shown in the following table. For compounds whose values are marked with an asterisk (*), mouse UAE was used. For all other compounds, human UAE was used.

| Compound no. | Example no. | % inhibition @0.111 μM | $IC_{50}$† |
|---|---|---|---|
| I-001 | 8 | 72* | B |
| I-002 | 2b | 100* | A |
| I-003 | 8 | 100 | A |
| I-004 | 5 | 31 | C |
| I-005 | 8 | 100* | A |
| I-006 | 13 | 23 | C |
| I-007 | 8 | 99 | A |
| I-008 | 13 | 28 | C |
| I-009 | 4 | 42 | C |
| I-010 | 7 | 100 | A |
| I-011 | 13 | 49* | C |
| I-012 | 14 | 61* | B |
| I-013 | 8 | 84 | B |
| I-014 | 13 | 30 | C |
| I-015 | 8 | 100 | A |
| I-016 | 7 | 99 | A |
| I-017 | 7 | 100 | A |
| I-018 | 7 | 100 | A |

| Compound no. | Example no. | % inhibition @0.111 μM | IC$_{50}$† |
|---|---|---|---|
| I-019 | 7 | 100 | A |
| I-020 | 7 | 100 | A |
| I-021 | 7 | 97 | A |
| I-022 | 7 | 100 | A |
| I-023 | 7 | 96 | B |
| I-024 | 7 | 98 | A |
| I-025 | 7 | 93 | B |
| I-026 | 7 | 100 | A |
| I-027 | 7 | 100 | A |
| I-028 | 7 | 99 | A |
| I-029 | 7 | 100 | A |
| I-030 | 7 | 99 | A |
| I-031 | 14 | 100 | A |
| I-032 | 7 | 100 | A |
| I-033 | 7 | 98 | A |
| I-034 | 7 | 100 | A |
| I-035 | 7 | 100 | A |
| I-036 | 7 | 100 | A |
| I-037 | 7 | 100 | A |
| I-038 | 7 | 100 | A |
| I-039 | 7 | 100 | A |
| I-040 | 7 | 100 | A |
| I-041 | 7 | 99 | A |
| I-042 | 7 | 100 | A |
| I-043 | 7 | 100 | A |
| I-044 | 7 | 100 | A |
| I-045 | 7 | 100 | A |
| I-046 | 7 | 100 | A |
| I-047 | 9 | 100 | A |
| I-048 | 10 | 100 | A |
| I-049 | 7 | 100 | A |
| I-050 | 7 | 100 | A |
| I-051 | 7 | 90 | B |
| I-052 | 9 | 100 | A |
| I-053 | 7 | 100 | A |
| I-054 | 7 | 100 | A |
| I-055 | 7 | 100 | A |
| I-056 | 7 | 100 | A |
| I-057 | 7 | 100 | A |
| I-058 | 9 | 100 | A |
| I-059 | 7 | 94 | B |
| I-060 | 7 | 89 | B |
| I-061 | 7 | 100 | A |
| I-062 | 7 | 100 | A |
| I-063 | 9 | 100 | A |
| I-064 | 9 | 96 | B |
| I-065 | 7 | 100 | A |
| I-066 | 7 | 100 | A |
| I-067 | 7 | 100 | A |
| I-068 | 7 | 95 | B |
| I-069 | 7 | 84 | B |
| I-070 | 7 | 99 | A |
| I-071 | 7 | 100 | A |
| I-072 | 7 | 100 | A |
| I-073 | 7 | 91 | B |
| I-074 | 7 | 98 | B |
| I-075 | 7 | 100 | A |
| I-076 | 7 | 100 | A |
| I-077 | 7 | 100 | A |
| I-078 | 7 | 100 | A |
| I-079 | 9 | 75 | B |
| I-080 | 9 | 80 | B |
| I-081 | 7 | 100 | A |
| I-082 | 7 | 100 | A |
| I-083 | 12 | 100 | A |
| I-084 | 7 | 100 | A |
| I-085 | 9 | 99 | A |
| I-086 | 9 | 99 | A |
| I-087 | 7 | 100 | A |
| I-088 | 7 | 97 | B |
| I-089 | 6 | 27 | C |
| I-090 | 7 | 100 | A |
| I-091 | 7 | 100* | A |
| I-092 | 7 | 100 | A |
| I-093 | 9 | 100 | A |
| I-094 | 7 | 100 | A |
| I-095 | 7 | 70 | B |
| I-096 | 9 | 100 | A |
| I-097 | 9 | 100 | A |
| I-098 | 2a | 100 | A |
| I-099 | 11 | 100 | A |
| I-100 | 7 | 100 | A |
| I-101 | 7 | 99 | A |
| I-102 | 7 | 100 | A |
| I-103 | 7 | 100 | A |
| I-104 | 9 | 100 | A |
| I-105 | 9 | 100 | A |
| I-106 | 9 | 100 | A |
| I-107 | 9 | 100 | A |
| I-108 | 3 | 100 | A |
| I-109 | 9 | 100 | A |
| I-110 | 9 | 100 | A |
| I-111 | 9 | 100 | A |
| I-112 | 9 | 100 | A |
| I-113 | 7 | 100 | A |
| I-114 | 9 | 99 | A |
| I-115 | 9 | 100 | A |
| I-116 | 7 | 100 | A |
| I-117 | 7 | 92 | B |
| I-118 | 7 | 100 | A |
| I-119 | 7 | 99 | A |
| I-120 | 7 | 100 | A |
| I-121 | 15 | 100 | A |
| I-122 | 15 | 97 | A |
| I-123 | 16 | 100 | A |
| I-124 | 17 | 20 | C |
| I-125 | 17 | 50 | C |

| † | A means | IC$_{50}$ < 10 nM |
|---|---|---|
|  | B means | 10 nM ≤ IC$_{50}$ < 100 nM |
|  | C means | 100 nM ≤ IC$_{50}$ < 1 μM |

While a number of embodiments of this invention have been described, it is apparent that the provided examples may be altered to convey other embodiments, which utilize the chemical entities and methods of this invention. It will thus be appreciated that the scope of this invention has been represented herein by way of example and is not intended to be limited by the specific embodiments described.

What is claimed is:

1. A method of treating a disease responsive to UAE inhibition in a subject in need of such treatment comprising, administering to the subject a chemical entity comprising a compound of Formula I:

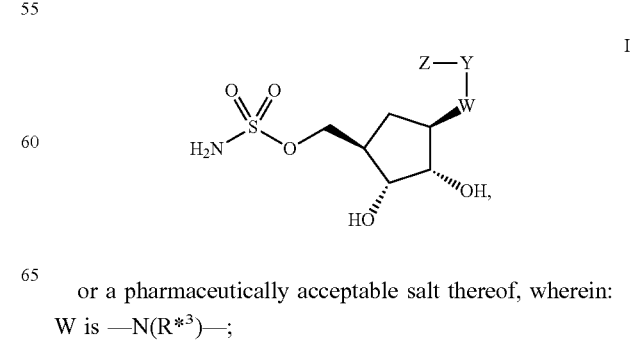

or a pharmaceutically acceptable salt thereof, wherein:

W is —N(R*³)—;

Y is

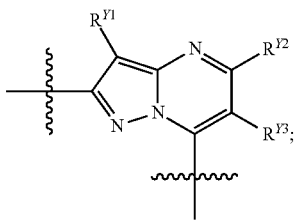

each of $R^{Y1}$, $R^{Y2}$ and $R^{Y3}$ is independently selected from —H, (a) halo, (b1) $C_{1-3}$ aliphatic, (b2) $R^{\#2-1}$, (c) —OR*³, (d) —N(R*³)₂, (e) —SR†³, (f) $C_{1-2}$ haloalkyl and (g) $C_{1-2}$ haloalkoxy;

Z is (1) optionally substituted aryl:

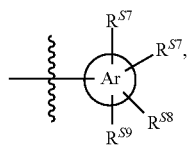

wherein

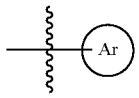

represents the aryl group;

(2) optionally substituted fused aryl:

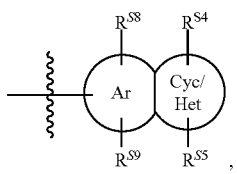

wherein

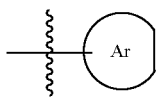

represents the aryl group, and

represents the carbocycle or heterocycle;

(3) optionally substituted heteroaryl:

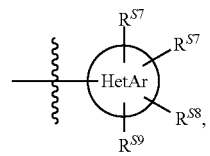

wherein

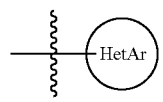

represents the heteroaryl group;
or
(4)

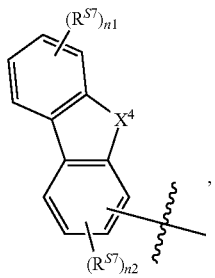

wherein
$X^4$ is —O—, —N(R*³)—, —S— or —C(O)—; and
each of n1 and n2 is independently 0, 1 or 2,
provided that n1+n2=0, 1 or 2;

each instance of $R^{S1}$ is independently selected from —H, (a) halo, (c) —OR*², (d) —N(R*²)₂ and (e) —SR†²;

each instance of $R^{S2}$ is independently selected from —H, (a) halo, (c) —OR*⁴, (d) —N(R*⁴)₂, (e) —SR†⁴, (h) —NO₂, (i) —CN, (j) —C(O)R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;

each instance of $R^{S4}$ is independently selected from —H, (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S5}$ is independently selected from —H, (a) halo, (b1) $C_{1-4}$ aliphatic, (b2) $R^{4-2}$, (c) —OR*⁴, (d) —N(R*⁴)₂, (e) —SR†⁴, (f) $C_{1-3}$ haloalkyl, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;

each instance of $R^{S7}$ is independently selected from —H, (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S8}$ is independently selected from —H, (a)halo, (b1) $C_{1-4}$ aliphatic, (b2) $R^{4-2}$, (c) —OR*⁴, (d) —N(R*⁴)₂, (e) —SR†⁴, (f) $C_{1-3}$ haloalkyl, (g1) $C_{1-3}$ haloalkoxy, (g2) $C_{1-3}$ haloalkylthio, (h) —NO₂, (i) —CN, (j) —C(O)—OR†⁴, (k) —C(O)—OR*⁴, (l) —C(O)—N(R*⁴)₂, (m) —O—C(O)—R$^{†4}$, (n) —N(R*$^4$)—C(O)—R$^{†4}$, (o) —O—C(O)—OR*$^4$, (p) —O—C(O)—N(R*$^4$)$_2$, (q) —N(R*$^4$)—C(O)—OR*$^4$ and (r) —N(R*$^4$)—C(O)—N(R*$^4$)$_2$;

each instance of R$^{S9}$ is independently selected from —H, (a) halo, (b1) C$_{1-6}$ aliphatic, (b2) R$^{\char94 6-3}$, (c) —OR*$^6$, (d) —N(R*$^6$)$_2$, (e) —SR$^{†6}$, (f) C$_{1-3}$ haloalkyl, (i) C$_{1-3}$ haloalkoxy, (g2) C$_{1-3}$ haloalkylthio, (h) —NO$_2$, (i) —CN, (j) —C(O)—R$^{†6}$, (k) —C(O)—OR*$^6$, (l) —C(O)—N(R*$^6$)$_2$, (m) —O—C(O)—R$^{†6}$, (n) —N(R*$^6$)—C(O)—R$^{†6}$, (o) —O—C(O)—OR*$^6$, (p) —O—C(O)—N(R*$^6$)$_2$, (q) —N(R*$^6$)—C(O)—OR*$^6$, (r) —N(R*$^6$)—C(O)—N(R*$^6$)$_2$, (s) —Si(R$^{†2}$)$_3$, (aa) C$_{3-8}$ carbocyclyl, (bb) -A-(C$_{3-8}$ carbocyclyl), (cc) 5- to 10-membered heterocyclyl, (dd) -A-(5- to 10-membered heterocyclyl), (ee) C$_{6-10}$ aryl, (ff) -A-(C$_{6-10}$ aryl), (gg) 5- to 10-membered heteroaryl and (hh) -A-(5- to 10-membered heteroaryl);

wherein each instance of A is independently selected from C$_{1-3}$ alkylene, C$_{0-3,0-3}$ heteroalkylene, —O—, —S—, —N(R*$^1$)— and —C(O)—;

and wherein each of (aa)-(dd) is optionally substituted with 1-3 groups independently selected from (a) halo, (b1) C$_{1-2}$ aliphatic, (b2) R$^{\#2-1}$, (c) —OR*$^2$, (d) —N(R*$^2$)$_2$ and (e) —SR$^{†2}$;

and wherein each of (ee)-(hh) is optionally substituted with 1-3 groups independently selected from (a) halo, (b1) C$_{1-4}$ aliphatic, (b2) R$^{\#4-2}$, (c) —OR*$^4$, (d) —N(R*$^4$)$_2$ and (e) —SR$^{†4}$;

each instance of R*$^6$ is independently —H or C$_{1-6}$ alkyl;
each instance of R*$^4$ is independently —H or C$_{1-4}$ alkyl;
each instance of R*$^3$ is independently —H or C$_{1-3}$ alkyl;
each instance of R*$^2$ is independently —H or C$_{1-2}$ alkyl;
each instance of R*$^1$ is independently —H or methyl;
each instance of R$^{†6}$ is independently C$_{1-6}$ alkyl;
each instance of R$^{†4}$ is independently C$_{1-4}$ alkyl;
each instance of R$^{†3}$ is independently C$_{1-3}$ alkyl;
each instance of R$^{†2}$ is independently C$_{1-2}$ alkyl;
each instance of R$^{\char94 6-3}$ is independently

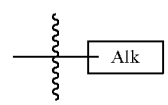

wherein

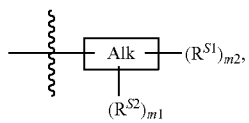

represents C$_{1-6}$ alkyl; and
  each of m1, m2 and m3 is independently 0 or 1;
each instance of R$^{\char94 4-2}$ is independently

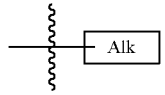

wherein

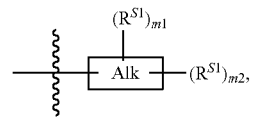

represents C$_{1-4}$ alkyl; and
  each of m1 and m2 is independently 0 or 1;
each instance of R$^{\#4-2}$ is independently

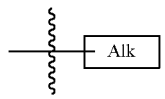

wherein

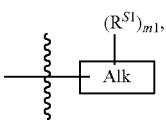

represents C$_{1-4}$ alkyl; and
  each of m1 and m2 is independently 0 or 1; and
each instance of R$^{\#2-1}$ is independently wherein represents C$_{1-2}$ alkyl; and
  m1 is 0 or 1.

2. A method of treating cancer in a subject in need of such treatment comprising, administering to the subject a therapeutically effective amount of a chemical entity comprising a compound of Formula I:

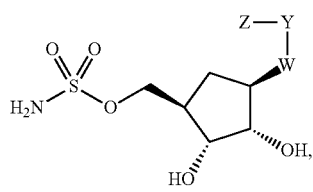

or a pharmaceutically acceptable salt thereof, wherein:
W is —N(R*$^3$)—;

Y is

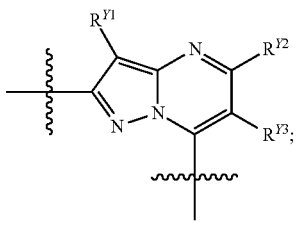

each of $R^{Y1}$, $R^{Y2}$ and $R^{Y3}$ is independently selected from —H, (a) halo, (b1) $C_{1-3}$ aliphatic, (b2) $R^{\#2-1}$, (c) —OR*³, (d) —N(R*³)₂, (e) —SR†³, (f) $C_{1-2}$ haloalkyl and (g) $C_{1-2}$ haloalkoxy;

Z is (1) optionally substituted aryl:

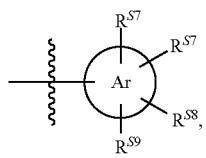

wherein

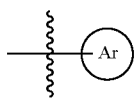

represents the aryl group;

(2) optionally substituted fused aryl:

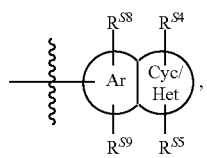

wherein

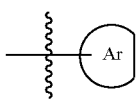

represents the aryl group, and

represents the carbocycle or heterocycle;

(3) optionally substituted heteroaryl:

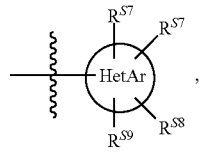

wherein

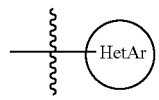

represents the heteroaryl group;

or (4)

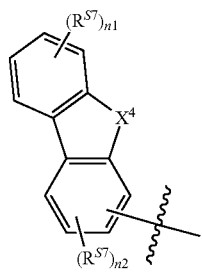

wherein $X^4$ is —O—, —N(R*³)—, —S— or —C(O)—; and
each of n1 and n2 is independently 0, 1 or 2,
provided that n1+n2=0, 1 or 2;

each instance of $R^{S1}$ is independently selected from —H, (a) halo, (c) —OR*², (d) —N(R*²)₂ and (e) —SR†²;

each instance of $R^{S2}$ is independently selected from —H, (a) halo, (c) —OR*⁴, (d) —N(R*⁴)₂, (e) —SR†⁴, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;

each instance of $R^{S4}$ is independently selected from —H, (a) halo, (b1) $C_{1-4}$ aliphatic, (b2) $R^{\#4-2}$ (c) —OR*⁴, (d) —N(R*⁴)₂ and (e) —SR†⁴;

each instance of $R^{S5}$ is independently selected from —H, (a) halo, (b1) $C_{1-4}$ aliphatic, (b2) $R^{4-2}$, (c) —OR*⁴, (d) —N(R*⁴)₂, (e) —SR†⁴, (f) $C_{1-3}$ haloalkyl, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;

each instance of $R^{S7}$ is independently selected from —H, (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S8}$ is independently selected from —H, (a) halo, (b1) $C_4$ aliphatic, (b2) $R^{4-2}$ (c) —OR*⁴, (d) —N(R*⁴)₂, (e) —SR†⁴, (f) $C_{1-3}$ haloalkyl, (g1) $C_{1-3}$ haloalkoxy, (g2) $C_{1-3}$ haloalkylthio, (h) —NO₂, (i) —CN, (j) —C(O)—R†⁴, (k) —C(O)—OR*⁴, (l) —C(O)—N(R*⁴)₂, (m) —O—C(O)—$R^{\dagger 4}$, (n) —N($R^{*4}$)—C(O)—$R^{\dagger 4}$, (o) —O—C(O)—$OR^{*4}$, (p) —O—C(O)—N($R^{*4}$)$_2$, (q) —N($R^{*4}$)—C(O)—$OR^{*4}$ and (r) —N($R^{*4}$)—C(O)—N($R^{*4}$)$_2$;

each instance of $R^{S9}$ is independently selected from —H, (a) halo, (b1) $C_{1-6}$ aliphatic, (b2) $R^{\sim 6-3}$, (c) —$OR^{*6}$, (d) —N($R^{*6}$), (e) —$SR^{\dagger 6}$, (f) $C_{1-3}$ haloalkyl, (g1) $C_{1-3}$ haloalkoxy, (g2) $C_{1-3}$ haloalkylthio, (h) —$NO_2$, (i) —CN, (j) —C(O)—$R^{\dagger 6}$, (k) —C(O)—$OR^{*6}$, (l) —C(O)—N($R^{*}$)$_2$, (m) —O—C(O)—$R^{\dagger 6}$, (n) —N($R^{*6}$)—C(O)—$R^{\dagger 6}$, (o) —O—C(O)—$OR^{*6}$, (p) —O—C(O)—N($R^{*6}$)$_2$, (q) —N($R^{*6}$)—C(O)—$OR^{*6}$, (r) —N($R^{*6}$)—C(O)—N($R^{*6}$)$_2$, (s) —Si($R^{\dagger 2}$)$_3$, (aa) $C_{3-8}$ carbocyclyl, (bb) -A-($C_{3-8}$ carbocyclyl), (cc) 5- to 10-membered heterocyclyl, (dd) -A-(5- to 10-membered heterocyclyl), (ee) $C_{6-10}$ aryl, (ff) -A-($C_{6-10}$ aryl), (gg) 5- to 10-membered heteroaryl and (hh) -A-(5- to 10-membered heteroaryl);

wherein each instance of A is independently selected from $C_{1-3}$ alkylene, $C_{0-3,0-3}$ heteroalkylene, —O—, —S—, —N($R^{*1}$)— and —C(O)—;

and wherein each of (aa)-(dd) is optionally substituted with 1-3 groups independently selected from (a) halo, (b1) $C_{1-2}$ aliphatic, (b2) $R^{\#2-1}$, (c) —$OR^{*2}$, (d) —N($R^{*2}$)$_2$ and (e) —$SR^{\dagger 2}$;

and wherein each of (ee)-(hh) is optionally substituted with 1-3 groups independently selected from (a) halo, (b1) $C_{1-4}$ aliphatic, (b2) $R^{\#4-2}$, (c) —$OR^{*4}$, (d) —N($R^{*4}$)$_2$ and (e) —$SR^{\dagger 4}$;

each instance of $R^{*6}$ is independently —H or $C_{1-6}$ alkyl;
each instance of $R^{*4}$ is independently —H or $C_{1-4}$ alkyl;
each instance of $R^3$ is independently —H or $C_{1-3}$ alkyl;
each instance of $R^{*2}$ is independently —H or $C_{1-2}$ alkyl;
each instance of $R^{*1}$ is independently —H or methyl;
each instance of $R^{\dagger 6}$ is independently $C_{1-6}$ alkyl:
each instance of $R^{\dagger 4}$ is independently $C_{1-4}$ alkyl;
each instance of $R^{\dagger 3}$ is independently $C_{1-3}$ alkyl;
each instance of $R^{\dagger 2}$ is independently $C_2$ alkyl;
each instance of $R^{\sim 6-3}$ is independently

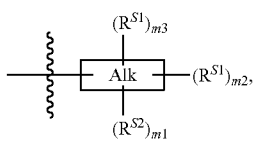

wherein

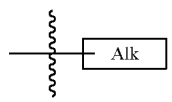

represents $C_{1-6}$ alkyl; and
each of m1, m2 and m3 is independently 0 or 1;
each instance of $R^{\sim 4-2}$ is independently

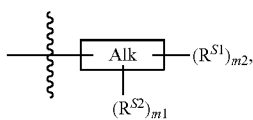

wherein

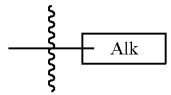

represents $C_{1-4}$ alkyl; and
each of m1 and m2 is independently 0 or 1;
each instance of $R^{\#4-2}$ is independently

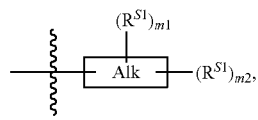

wherein

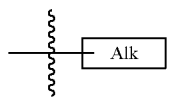

represents $C_{1-4}$ alkyl; and
each of m1 and m2 is independently 0 or 1; and
each instance of $R^{\#2-1}$ is independently

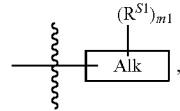

wherein

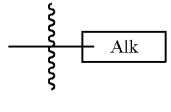

represents $C_{1-2}$ alkyl; and
m1 is 0 or 1.

3. The method of claim 2 wherein the cancer is lung cancer, ovarian cancer, colon cancer, breast cancer or lymphoma.

4. The method of claim 1, wherein the compound of Formula I is crystalline Form 1 anhydrous (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl) methyl sulfamate.

5. The method of claim 1, wherein the compound of Formula I is crystalline Form 2 monohydrated (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl) methyl sulfamate.

6. The method of claim 2, wherein the compound of Formula I is crystalline Form 1 anhydrous (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl) methyl sulfamate.

7. The method of claim 2, wherein the compound of Formula I is crystalline Form 2 monohydrated (s.e.)-((1R,2R,3S,4R)-2,3-dihydroxy-4-(2-(3-(trifluoromethylthio)-phenyl)pyrazolo[1,5-a]pyrimidin-7-ylamino)cyclopentyl) methyl sulfamate.

* * * * *